US012691177B2

(12) United States Patent
Hennessy

(10) Patent No.: US 12,691,177 B2
(45) Date of Patent: Jul. 28, 2026

(54) STABILIZED FORMULATIONS

(71) Applicant: ModernaTX, Inc., Cambridge, MA (US)

(72) Inventor: Edward J. Hennessy, Westwood, MA (US)

(73) Assignee: ModernaTX, Inc., Cambridge, MA (US)

( * ) Notice: Subject to any disclaimer, the term of this patent is extended or adjusted under 35 U.S.C. 154(b) by 1036 days.

(21) Appl. No.: 17/726,971

(22) Filed: Apr. 22, 2022

(65) Prior Publication Data

US 2022/0370616 A1 Nov. 24, 2022

Related U.S. Application Data

(60) Provisional application No. 63/229,747, filed on Aug. 5, 2021, provisional application No. 63/179,107, filed on Apr. 23, 2021.

(51) Int. Cl.
*A61K 47/22* (2006.01)
*A61J 1/14* (2023.01)
*A61K 9/00* (2006.01)
*A61K 9/127* (2025.01)
*A61K 31/7105* (2006.01)
*A61K 31/711* (2006.01)

(52) U.S. Cl.
CPC ............. *A61K 47/22* (2013.01); *A61J 1/1468* (2015.05); *A61K 9/0019* (2013.01); *A61K 9/127* (2013.01); *A61K 31/7105* (2013.01); *A61K 31/711* (2013.01)

(58) Field of Classification Search
CPC .......................... A61K 31/711; A61K 31/7105
See application file for complete search history.

(56) References Cited

U.S. PATENT DOCUMENTS

| | | | |
|---|---|---|---|
| 9,221,891 | B2 | 12/2015 | Bancel et al. |
| 9,283,287 | B2 | 3/2016 | Bancel et al. |
| 9,464,124 | B2 | 10/2016 | Bancel et al. |
| 9,512,456 | B2 | 12/2016 | Wang et al. |
| 9,872,900 | B2 | 1/2018 | Ciaramella et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,273,269 | B2 | 4/2019 | Ciaramella |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,925,958 | B2 | 2/2021 | Ciaramella |
| 11,045,540 | B2 | 6/2021 | Ciaramella |
| 11,103,578 | B2 | 8/2021 | Ciaramella et al. |
| 11,351,242 | B1 | 6/2022 | Lori et al. |
| 2013/0102034 | A1 | 4/2013 | Schrum et al. |
| 2013/0236974 | A1 | 9/2013 | De Fougerolles |
| 2013/0245103 | A1 | 9/2013 | de Fougerolles et al. |
| 2013/0259923 | A1 | 10/2013 | Bancel et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2016/0024140 | A1 | 1/2016 | Issa et al. |
| 2016/0024141 | A1 | 1/2016 | Issa et al. |
| 2016/0032273 | A1 | 2/2016 | Shahrokh et al. |
| 2016/0038612 | A1 | 2/2016 | Hoge et al. |
| 2016/0243221 | A1 | 8/2016 | Hoge et al. |
| 2017/0043037 | A1 | 2/2017 | Kariko et al. |
| 2017/0130255 | A1 | 5/2017 | Wang et al. |
| 2017/0202979 | A1 | 7/2017 | Chakraborty et al. |
| 2017/0204152 | A1 | 7/2017 | Nelson et al. |
| 2018/0000953 | A1 | 1/2018 | Almarsson et al. |
| 2018/0002393 | A1 | 1/2018 | Bancel et al. |
| 2018/0237849 | A1 | 8/2018 | Thompson |

(Continued)

FOREIGN PATENT DOCUMENTS

| | | | |
|---|---|---|---|
| WO | WO 2016/164762 | A1 | 10/2016 |
| WO | WO 2016/201377 | A1 | 12/2016 |

(Continued)

OTHER PUBLICATIONS

TATA boxes in gene transcription and poly (A) tails in mRNA stability: New perspective on the effects of berberine Yuan et al. Scientific Reports vol. 5, Article No. 18326 (2016) (Year: 2016).*
RNA targeting by small molecule alkaloids: Studies on the binding of berberine and palmatine to polyribonucleotides and comparison to ethidium Islam et al. Journal of Molecular Structure 875 (2008) 382-391 (Year: 2008).*
Molecular Aspects of Small Molecules-Poly(A) Interaction: An Approach to RNA Based Drug Design Giri et al. Current Medicinal Chemistry, 2009, 16, 965-987 (Year: 2009).*
Intelligent Intravenous Infusion Pumps to Improve Medication Administration Safety Rothschild et al. AMIA 2003 Symposium Proceedings—p. 992 (Year: 2003).*
Assessment report COVID-19 Vaccine Moderna Procedure No. EMEA/H/C/005791/0000 European Medicines Agency, Committee for Medicinal Products for Human Use (CHMP) Mar. 11, 2021 (Year: 2021).*
Photostability Issues in Pharmaceutical Dosage Forms and Photostabilization Janga et al. AAPS PharmSciTech, vol. 19, No. 1, Jan. 2018 (# 2017) (Year: 2018).*

(Continued)

*Primary Examiner* — Jeffrey S Lundgren
*Assistant Examiner* — Eric Tran
(74) *Attorney, Agent, or Firm* — Wolf, Greenfield & Sacks, P.C.

(57) ABSTRACT

Stabilized formulations of nucleic acids, including lipid nanoparticle formulations which encapsulate nucleic acids, are provided. Methods of making and of use of the formulations stabilized by chemical compounds are also provided.

23 Claims, 3 Drawing Sheets

(56) References Cited

U.S. PATENT DOCUMENTS

2018/0243225 A1 8/2018 Ciaramella
2018/0243230 A1 8/2018 Smith
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0303929 A1 10/2018 Ciaramella et al.
2018/0311336 A1 11/2018 Ciaramella et al.
2018/0311343 A1 11/2018 Huang et al.
2018/0318409 A1 11/2018 Valiante et al.
2018/0369374 A1 12/2018 Frederick et al.
2018/0371047 A1 12/2018 Ticho et al.
2019/0002890 A1 1/2019 Martini et al.
2019/0008938 A1 1/2019 Ciaramella et al.
2019/0085368 A1 3/2019 Bancel et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0275170 A1 9/2019 Benenato et al.
2019/0298657 A1 10/2019 Martini et al.
2019/0298658 A1 10/2019 Benenato
2019/0300906 A1 10/2019 Martini et al.
2019/0314292 A1 10/2019 Benenato et al.
2019/0336452 A1 11/2019 Brader
2019/0351040 A1 11/2019 Valiante et al.
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0069599 A1 3/2020 Smith et al.
2020/0071689 A1 3/2020 Miracco
2020/0085916 A1 3/2020 Martini et al.
2020/0109420 A1 4/2020 Brito et al.
2020/0129608 A1 4/2020 Ciaramella et al.
2020/0129615 A1 4/2020 Ciaramella et al.
2020/0239869 A1 7/2020 Issa et al.
2020/0254086 A1 8/2020 Hoge et al.
2020/0282047 A1 9/2020 Ciaramella et al.
2021/0046173 A1 2/2021 Ciaramella et al.
2021/0046192 A1* 2/2021 Karve .................. A61K 48/005
2021/0163919 A1 6/2021 Issa et al.
2021/0187097 A1 6/2021 Ciaramella et al.
2021/0217484 A1 7/2021 Giessel et al.
2021/0228707 A1 7/2021 Mektar et al.
2021/0268086 A1 9/2021 Zhong et al.
2021/0309976 A1 10/2021 Dousis et al.
2022/0031631 A1 2/2022 Almarsson et al.
2022/0047518 A1 2/2022 Hennessy et al.
2022/0054653 A1 2/2022 Martini et al.
2022/0062408 A1 3/2022 Kramarczyk et al.
2022/0125899 A1 4/2022 Ashburn et al.
2022/0145381 A1 5/2022 Elich et al.

FOREIGN PATENT DOCUMENTS

WO WO 2017/011773 A2 1/2017
WO WO 2017/015457 A1 1/2017
WO WO 2017/066789 A1 4/2017
WO WO 2017/070601 A1 4/2017
WO WO 2017/127750 A1 7/2017
WO WO 2017/201333 A1 11/2017
WO WO 2018/157009 A1 8/2018
WO WO 2018/232355 A1 12/2018
WO WO 2018/232357 A1 12/2018
WO WO 2019/036683 A1 2/2019
WO WO 2020/061367 A1 3/2020
WO WO 2020/146814 A1 7/2020
WO WO 2020/190750 A1 9/2020
WO WO 2020/243561 A1 12/2020
WO WO 2021/016430 A1 1/2021
WO WO 2021/030533 A1 2/2021
WO WO 2021/050864 A1 3/2021
WO WO 2021/055811 A1 3/2021
WO WO 2021/155243 A1 8/2021
WO WO 2021/159040 A2 8/2021
WO WO 2021/159130 A2 8/2021
WO WO 2021/211343 A1 10/2021
WO WO 2021/222304 A1 11/2021
WO WO 2021/231929 A1 11/2021
WO WO 2021/231963 A1 11/2021
WO WO 2021/237084 A1 11/2021
WO WO 2021/247817 A1 12/2021
WO WO 2022/067010 A1 3/2022

OTHER PUBLICATIONS

Berberine Encapsulated PLGA-PEG Nanoparticles Modulate PCSK-9 in HepG2 Cells Ochin et al. Cardiovascular & Haematological Disorders-Drug Targets, 2018, 18, 61-70 (Year: 2018).*
U.S. Appl. No. 16/036,318, filed Jul. 16, 2018, Ciaramella et al.
U.S. Appl. No. 16/144,394, filed Sep. 27, 2018, Ciaramella et al.
*U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 17/737,532, filed May 5, 2022, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/548,172, filed Dec. 10, 2021, Ciaramella et al.
U.S. Appl. No. 17/839,401, filed Jun. 13, 2022, Ciaramella et al.
U.S. Appl. No. 16/897,734, filed Jun. 10, 2020, Ciaramella et al.
U.S. Appl. No. 16/468,838, filed Jun. 12, 2019, Miracco.
U.S. Appl. No. 17/830,742, filed Jun. 2, 2022, Miracco.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.

(56) References Cited

OTHER PUBLICATIONS

U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 17/737,581, filed May 5, 2022, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/411,896, filed Aug. 25, 2021, Kramarczyk et al.
U.S. Appl. No. 17/840,478, filed Jun. 14, 2022, Kramarczyk et al.
U.S. Appl. No. 17/000,201, filed Aug. 21, 2020, Stewart-Jones et al.
U.S. Appl. No. 17/518,542, filed Nov. 3, 2021, Metkar et al.
U.S. Appl. No. 17/572,465, filed Jan. 10, 2022, Nachbagauer et al.
International Search Report and Written Opinion, mailed Aug. 2, 2022 for International Application No. PCT/US2022/025898.
Islam et al., RNA binding small molecules: studies on t-RNA binding by cytotoxic plant alkaloids berberine, palmatine and the comparison to ethidium. Biophys Chem. Feb. 2007;125(2-3):508-20. doi: 10.1016/j.bpc.2006.11.001. Epub Nov. 10, 2006.
Jia et al., Berberine-loaded solid proliposomes prepared using solution enhanced dispersion by supercritical CO2: Sustained release and bioavailability enhancement. J Drug Deliv Sci Tech. Jun. 2019;51:356-63. doi: 10.1016/j.jddst.2019.03.021.
Misik et al., Lipoxygenase inhibition and antioxidant properties of protoberberine and aporphine alkaloids isolated from Mahonia aquifolium. Planta Med. Aug. 1995;61(4):372-3. doi: 10.1055/s-2006-958107.
Schmeller et al., Biochemical activities of berberine, palmatine and sanguinarine mediating chemical defence against microorganisms and herbivores. Phytochemistry. Jan. 1997;44(2):257-66. doi: 10.1016/s0031-9422(96)00545-6.
Yu et al., Antimicrobial activity of berberine alone and in combination with ampicillin or oxacillin against methicillin-resistant *Staphylococcus aureus*. J Med Food. 2005 Winter;8(4):454-61. doi: 10.1089/jmf.2005.8.454.

* cited by examiner

STABILIZED FORMULATIONS

CROSS REFERENCE TO RELATED APPLICATIONS

The present application claims priority under 35 U.S.C. § 119(e) to each of U.S. Provisional Application No. 63/179,107, filed Apr. 23, 2021, and U.S. Provisional Application No. 63/229,747, filed Aug. 5, 2021, the contents of each of which are incorporated herein by reference in their entireties.

FIELD

Provided are formulations of nucleic acids, including lipid nanoparticle formulations which encapsulate nucleic acids, and more specifically to formulations stabilized by chemical compounds.

BACKGROUND

The use of messenger RNA as a pharmaceutical agent is of great interest for a variety of applications, including in therapeutics, vaccines, and diagnostics. Effective in vivo delivery of mRNA formulations represents a continuing challenge, as many such formulations are inherently unstable, activate an immune response, are susceptible to degradation by nucleases, or fail to reach their target organs or cells within the body due to issues with biodistribution. Each of these challenges results in loss of translational potency and therefore hinders efficacy of conventional mRNA pharmaceutical agents.

Various non-viral delivery systems, including nanoparticle formulations, present attractive opportunities to overcome many challenges associated with mRNA delivery. In particular, lipid nanoparticles (LNPs) have drawn particular attention in recent years as various LNP formulations have shown promise in a variety of pharmaceutical applications.

However, lipids have been shown to degrade nucleic acids including mRNA, and lipid nanoparticle formulations undergo rapid loss of purity when stored as refrigerated liquids. It is also evident that the stability of mRNA is poorer when encapsulated within LNPs than when stored unencapsulated.

SUMMARY

Provided, among other things, are compositions and methods for the stabilization of nucleic acids. Some aspects encompass the observation that the mixture of certain compounds with lipid nanoparticle formulations comprising nucleic acids and/or nucleic acid formulations resulted in substantially improved formulation stability.

Accordingly, in one aspect, provided herein is a stabilized pharmaceutical composition, comprising:

a nucleic acid formulation, comprising a nucleic acid, and a compound of Formula I':

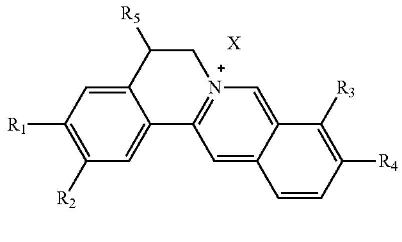

or a tautomer, solvate, or salt thereof, wherein:

each of $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R";

R' is H, or —$C_{1-4}$alkyl, wherein the —$C_{1-4}$alkyl is optionally substituted with one or more —OH;

R" is H, or —$C_{1-4}$alkyl; or

R' and R" taken together can form a 5 to 6 membered heterocycle with O or N heteroatoms, wherein the heterocycle is optionally substituted with one or more —$C_{1-4}$alkyl, or —OH; or $R_1$ and $R_2$ together with the intervening atoms form a 5-membered ring;

$R_5$ is H, —$C_{1-4}$alkyl, or $C_{3-7}$cycloalkyl; and

X is a pharmaceutically acceptable anion.

In another aspect, provided herein is a stabilized pharmaceutical composition, comprising:

a nucleic acid formulation, comprising a nucleic acid, and a compound of Formula I:

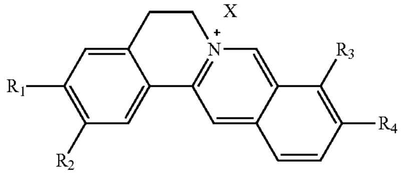

or a tautomer, solvate, or salt thereof, wherein:

each of $R_1$, $R_2$, $R_3$, and $R_4$ are independently selected from —OH, and —$OC_{1-4}$alkyl, wherein the —$OC_{1-4}$alkyl is optionally substituted with one or more —OH, —C(O)OH, —NR'R", or —C(O)NR'R";

R' is H, or —$C_{1-4}$alkyl, wherein the —$C_{1-4}$alkyl is optionally substituted with one or more —OH;

R" is H, or —$C_{1-4}$alkyl; or

R' and R" taken together can form a 5 to 6 membered heterocycle with O or N heteroatoms, wherein the heterocycle is optionally substituted with one or more —$C_{1-4}$alkyl, or —OH; and X is a pharmaceutically acceptable anion.

In some embodiments, the nucleic acid formulation comprises lipid nanoparticles. In some embodiments, the nucleic acid formulation comprises liposomes. In some embodiments, the nucleic acid formulation comprises a lipoplex. In some embodiments, the nucleic acid is encapsulated within the lipid nanoparticles, liposomes, or lipoplex.

In some embodiments, the compound of Formula I' or Formula I has a purity of at least 70%, 80%, 90%, 95%, or 99%. In some embodiments, the compound of Formula I' or Formula I contains fewer than 100 ppm of elemental metals.

In certain embodiments, the nucleic acid is coding or non-coding. In certain embodiments, the nucleic acid is DNA or RNA. In certain particular embodiments, the nucleic acid is mRNA.

In some embodiments, the composition is formulated in an aqueous solution. In some embodiments, the aqueous solution comprises lipid nanoparticles and the nucleic acid is encapsulated in the lipid nanoparticles. In some embodiments, the aqueous solution has a pH of or about 5 to 8, including pH of about 5, 5.5, 6, 6.5, 7, 7.5, or 8. In some embodiments, the aqueous solution does not comprise NaCl. In some embodiments, the aqueous solution comprises NaCl in a concentration of or about 150 mM. In some embodiments, the aqueous solution comprises a buffer. In some embodiments, the aqueous solution comprises a phosphate buffer, a tris buffer, an acetate buffer, a histidine buffer, or a citrate buffer. In some embodiments, the concentration of the buffering agent(s) is about 2-10 mM.

In some embodiments, the compound of Formula I' or Formula I is present at a concentration of less than about 10 mM. In some embodiments, the compound of Formula I' or Formula I is present at a concentration between about 0.1 mM and about 10 mM. In some embodiments, the compound of Formula I' or Formula I is present at a concentration of or about 2 mM. In some embodiments, the compound of Formula I' or Formula I is present at a concentration of or about 1 mM. In some embodiments, the compound of Formula I' or Formula I is present at a concentration of or about 0.5 mM.

In some embodiments, the lipid nanoparticle comprises a ratio of 20-60% amino lipids, 5-30% phospholipid, 10-55% structural lipid, and 0.5-15% PEG-modified lipid. In some embodiments, the lipid nanoparticle comprises a ratio of 20-60% amino lipids, 5-25% phospholipid, 25-55% structural lipid, and 0.5-15% PEG-modified lipid. In certain embodiments, the ratio is a mass ratio. In other embodiments, the ratio is a molar ratio.

In some embodiments, the nucleic acid is a lyophilized product. In some embodiments, the lyophilized product comprises lipid nanoparticles and the nucleic acid is encapsulated in the lipid nanoparticles.

According to some aspects, compositions are provided for the treatment of a disease in a subject. In some embodiments, the disease is caused by an infectious agent. In some embodiments, the disease is caused by or associated with a virus. In some embodiments, the disease is a disease caused by or associated with a malignant cell. In some embodiments, the disease is cancer. According to some aspects, compositions having properties which inhibit microbial growth are provided. In some embodiments, microbial growth in the composition is inhibited by a compound disclosed herein. In some embodiments, the composition does not comprise phenol, m-cresol, or benzyl alcohol.

According to some aspects, methods of formulating nucleic acids are provided. In some embodiments, a method of formulating a nucleic acid comprises adding to a composition comprising a nucleic acid and a lipid, a compound of Formula I' or Formula I, or a tautomer or solvate thereof, to obtain a formulated composition.

In another aspect, provided herein is the use of a composition for the treatment of a disease in a subject. In certain embodiments, the disease is caused by an infection agent, and may be, for example, caused by or associated with a virus. In certain embodiments, the disease is caused by or associated with a malignant cell, such as cancer.

In another aspect, provided herein is a method of formulating a nucleic acid, comprising: adding to a composition comprising a nucleic acid a stabilizing compound (e.g., a compound of Formula I' or Formula I, or a tautomer, solvate, or salt thereof), to obtain a formulated composition. In some embodiments, the method further comprises subsequently removing the compound of Formula I' or Formula I from the formulated composition.

According to some aspects, compositions of lipid nanoparticles and mRNA having certain mRNA purity levels are provided herein. In some embodiments, a composition comprises a lipid nanoparticle encapsulating a mRNA, wherein the composition comprises a mRNA purity level of greater than 50% main peak mRNA purity after at least thirty days of storage. In some embodiments, the composition comprises a mRNA purity level of greater than 60% main peak mRNA purity after at least thirty days of storage. In some embodiments, the composition comprises a mRNA purity level of greater than 70% main peak mRNA purity after at least thirty days of storage. In some embodiments, the composition comprises a mRNA purity level of greater than 80% main peak mRNA purity after at least thirty days of storage. In some embodiments, the composition comprises a mRNA purity level of greater than 90% main peak mRNA purity after at least thirty days of storage. In some embodiments, the composition comprises a mRNA purity level of greater than 50% main peak mRNA purity after at least six months of storage. In some embodiments, the storage is at room temperature. In some embodiments, the storage is at greater than room temperature. In some embodiments, the storage is at 4° C.

According to some aspects, compositions of lipid nanoparticles encapsulating mRNA having certain compositions of RNA fragments are provided herein. In some embodiments, a composition comprises a lipid nanoparticle encapsulating a mRNA, wherein the composition comprises less than 50% RNA fragments after at least thirty days of storage. In some embodiments, the composition comprises less than 60% RNA fragments after at least thirty days of storage. In some embodiments, the composition comprises less than 70% RNA fragments after at least thirty days of storage. In some embodiments, the composition comprises less than 80% RNA fragments after at least thirty days of storage. In some embodiments, the composition comprises less than 90% RNA fragments after at least thirty days of storage. In some embodiments, the composition comprises less than 95% RNA fragments after at least thirty days of storage.

In some embodiments, the composition is stored for at least six months.

In some embodiments, the storage is at room temperature. In some embodiments, the storage is at greater than room temperature. In some embodiments, the storage is at 4° C.

In some embodiments, the composition comprises a compound of Formula I' or Formula I, or a tautomer or solvate thereof.

In another aspect, provided herein is a method for producing a protein in a subject, comprising: administering a composition to the subject, wherein the nucleic acid is an mRNA, and wherein the mRNA encodes for the production of a protein in the subject.

In another aspect, provided herein is a pharmaceutically acceptable method of processing an mRNA-lipid nanoparticle for therapeutic injection, comprising combining an mRNA, a lipid nanoparticle, and a stabilizing compound (e.g., a compound of Formula I' or Formula i, or a tautomer, solvate, or salt thereof).

In another aspect, provided herein is a pharmaceutically acceptable method of conferring anti-microbial properties to an mRNA-lipid nanoparticle composition, comprising adding a stabilizing compound (e.g., a compound of Formula I' or Formula I. or a tautomer, solvate, or salt thereof), to the mRNA-lipid nanoparticle composition.

According to some aspects, devices enabling the use of compositions and methods disclosed herein are provided. In some embodiments, a syringe or cartridge, comprising a composition is provided. In some embodiments, an infusion pump, comprising a composition is provided. In some embodiments, a syringe or cartridge, comprising multiple doses of a composition is provided.

Other advantages and novel features will become apparent from the following detailed description of various non-limiting embodiments when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

FIG. 1A shows sized-based purity of formulation 1 over 12 months of refrigerated storage. FIG. 1B shows sized-based purity of formulation 2 over 6 months of refrigerated storage.

DETAILED DESCRIPTION

Figure 1A:
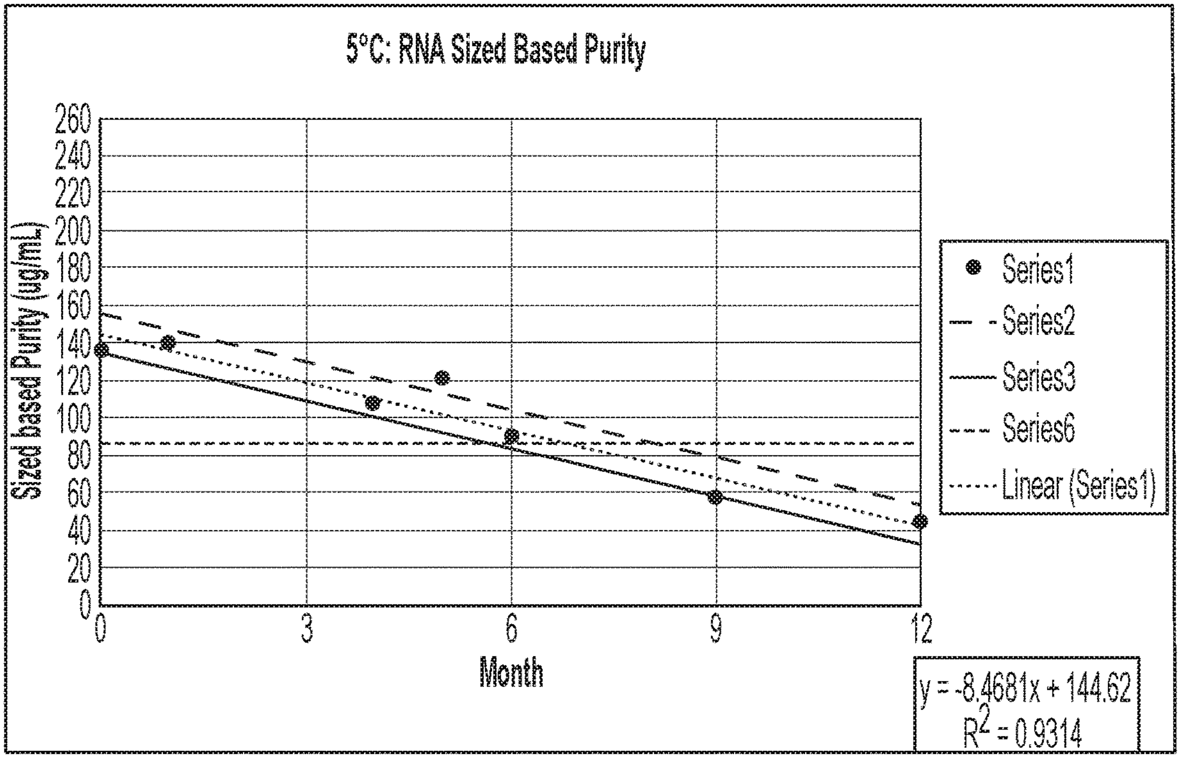
FIGS. 1A-1B show mRNA instability in lipid nanoparticle formulations at refrigerated temperature. In each case less than 9 months of refrigerated storage stability would be possible.

Lipid nanoparticle (LNP) formulations offer the opportunity to deliver various nucleic acids in vivo for applications in which unencapsulated nucleic acids would be ineffective, but their broad utility has been hindered by insufficient nucleic acid stability over relevant timeframes. Degradation of nucleic acids within LNP formulations limits the use of such formulations to applications in which frozen compositions are acceptable.

It was surprisingly found that a mixture of certain compounds with nucleic acids in LNP formulations or with LNP formulations resulted in substantially improved stability including nucleic acid stability. Accordingly nucleic acid and lipid compositions, and methods for their preparation and use are provided.

It was determined, using both accelerated and real-time conditions, that the stability of formulations can be significantly enhanced using potent stabilizing excipients or compounds provided herein. The inclusion of these compounds in formulations such as lipid based and/or nucleic acid formulations provides properties useful for preparation, storage and use of therapeutic agents. For instance, it has been demonstrated that for nucleic acid formulations, such as mRNA-lipid nanoparticle (mRNA-LNP) compositions, combination with stabilizing compounds (e.g., a compound of Formula I' or Formula I, or a tautomer, solvate, or salt thereof) dramatically inhibits the rate of purity loss of mRNA encapsulated within the LNP under a variety of storage conditions. The instability of mRNA, specifically loss of purity, is considered one of the greatest challenges to its fundamental therapeutic and commercial viability. Additionally, the instability of mRNA is significant when formulated as an LNP. Provided are stabilizing compounds that provide a solution to these problems.

The discovery that a class of compounds is able to stabilize nucleic acids within a lipid carrier such as an LNP is unexpected and unprecedented. This finding enables several significant applications, including extended refrigerated liquid shelf-life, extended in-use periods at room temperature, and extended in-use stability at physiological temperatures up to higher temperatures such as 40° C. Achieving a stable liquid formulation also enables commercially and therapeutically desirable packaging and delivery options including prefilled syringes and cartridges for patient-friendly autoinjector and infusion pump devices. The incorporation of this compound into methods of making as well as, optionally, the final drug product will provide a significant improvement in purity values of therapeutic nucleic acids, such as mRNA upon manufacture. This solves a critical problem, as current manufacturing processes and formulations experience a 5-10% purity loss during LNP formation and processing that is typical with current large-scale LNP production. The ability to stabilize solutions and pharmaceutical preparations of mRNA and other therapeutics therefore represent a valuable technology facilitating broader use of therapeutic compositions such as mRNA compositions.

In one aspect, provided herein is a stabilized pharmaceutical composition, comprising:

a nucleic acid formulation, comprising a nucleic acid, and a compound of Formula I':

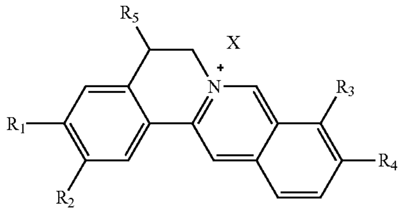

or a tautomer, solvate, or salt thereof, wherein:

each of $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R";

R' is H, or —$C_{1-4}$alkyl, wherein the —$C_{1-4}$alkyl is optionally substituted with one or more —OH;

R" is H, or —$C_{1-4}$alkyl; or

R' and R" taken together can form a 5 to 6 membered heterocycle with O or N heteroatoms, wherein the heterocycle is optionally substituted with one or more —$C_{1-4}$alkyl, or —OH; or $R_1$ and $R_2$ together with the intervening atoms form a 5-membered ring;

$R_5$ is H, —$C_{1-4}$alkyl, or $C_{3-7}$cycloalkyl; and

X is a pharmaceutically acceptable anion.

In one aspect, a stabilized pharmaceutical composition is provided, comprising: a nucleic acid formulation, comprising a nucleic acid, and a compound of Formula I:

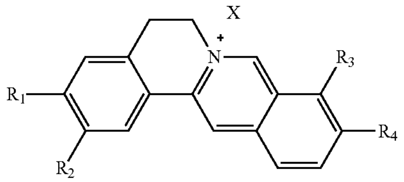

or a tautomer, solvate, or salt thereof, wherein:

each of $R_1$, $R_2$, $R_3$, and $R_4$ are independently selected from —OH, and —$OC_{1-4}$alkyl, wherein the —$OC_{1-4}$alkyl is optionally substituted with one or more —OH, —C(O)OH, —NR'R", or —C(O)NR'R";

R' is H, or —$C_{1-4}$alkyl, wherein the —$C_{1-4}$alkyl is optionally substituted with one or more —OH;

R" is H, or —$C_{1-4}$alkyl; or

R' and R" taken together can form a 5 to 6 membered heterocycle with O or N heteroatoms, wherein the heterocycle is optionally substituted with one or more —$C_{1-4}$alkyl, or —OH; and X is a pharmaceutically acceptable anion.

In some embodiments, a compound of Formula I' is of Formula I.

Certain embodiments of the composition are provided, wherein $R_1$, $R_2$, and $R_3$ are independently —$OC_{1-4}$alkyl; and $R_4$ is —OH or —$OC_{1-4}$alkyl, wherein the —$OC_{1-4}$alkyl is substituted with one or more —OH, —C(O)OH, —NR'R", or —C(O)NR'R". In certain embodiments, $R_1$, $R_2$, and $R_3$ are —$OCH_3$. In certain embodiments, $R_4$ is —OH. In certain embodiments, $R_4$ is —$OC_{1-4}$alkyl substituted with one or more —OH, —C(O)OH, —NR'R", or —C(O)NR'R".

Other embodiments of the composition are provided, wherein $R_1$, $R_2$, and $R_4$ are independently —$OC_{1-4}$alkyl; and $R_4$ is —OH or —$OC_{1-4}$alkyl, wherein the —$OC_{1-4}$alkyl is substituted with one or more —OH, —C(O)OH, —NR'R", or —C(O)NR'R". In certain embodiments, $R_1$, $R_2$, and $R_4$ are —$OCH_3$. In certain embodiments, $R_3$ is —OH. In certain embodiments, $R_3$ is —$OC_{1-4}$alkyl substituted with one or more —OH, —C(O)OH, —NR'R", or —C(O)NR'R".

Other embodiments of the composition are provided, wherein $R_1$, $R_3$, and $R_4$ are independently —$OC_{1-4}$alkyl; and $R_2$ is —OH or —$OC_{1-4}$alkyl, wherein the —$OC_{1-4}$alkyl is substituted with one or more —OH, —C(O)OH, —NR'R", or —C(O)NR'R". In certain embodiments, $R_1$, $R_3$, and $R_4$ are —$OCH_3$. In certain embodiments, $R_2$ is —OH. In certain embodiments, $R_2$ is —$OC_{1-4}$alkyl substituted with one or more —OH, —C(O)OH, —NR'R", or —C(O)NR'R".

Other embodiments of the composition are provided, wherein $R_2$, $R_3$, and $R_4$ are independently —$OC_{1-4}$alkyl; and $R_1$ is —OH or —$OC_{1-4}$alkyl, wherein the —$OC_{1-4}$alkyl is substituted with one or more —OH, —C(O)OH, —NR'R", or —C(O)NR'R". In certain embodiments, $R_2$, $R_3$, and $R_4$ are —$OCH_3$. In certain embodiments, $R_1$ is —OH. In certain embodiments, $R_1$ is —$OC_{1-4}$alkyl substituted with one or more —OH, —C(O)OH, —NR'R", or —C(O)NR'R".

Other embodiments of the composition are provided, wherein $R_1$ and $R_2$ together with the intervening atoms form a 5-membered ring (e.g., a heterocyclyl such as a cyclic acetal); and $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R". In certain embodiments, $R_3$ and $R_4$ are —$OCH_3$.

Other embodiments of the composition are provided, wherein $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R", or $R_1$ and $R_2$ together with the intervening atoms form a 5-membered ring (e.g., a heterocyclyl such as a cyclic acetal); and $R_5$ is —$C_{3-7}$cycloalkyl. In certain embodiments, $R_5$ is —$C_{3-5}$cycloalkyl. In certain embodiments, $R_5$ is cyclopropyl. In certain embodiments, $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R".

Other embodiments of the composition are provided, wherein $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R", or $R_1$ and $R_2$ together with the intervening atoms form a 5-membered ring (e.g., a heterocyclyl such as a cyclic acetal); and $R_5$ is —$C_{1-4}$alkyl. In certain embodiments, $R_5$ is methyl, ethyl, or propyl. In certain embodiments, $R_5$ is methyl or ethyl. In certain embodiments, $R_5$ is methyl. In certain embodiments. $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH. —NR'R", or —C(O)NR'R".

Other embodiments of the composition are provided, wherein $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R", or $R_1$ and $R_2$ together with the intervening atoms form a 5-membered ring (e.g., a heterocyclyl such as a cyclic acetal); and $R_5$ is H, Me, or cyclopropyl.

Other embodiments of the composition are provided, wherein at least one of $R_1$, $R_2$, $R_3$, and $R_4$ is —$OCH_3$ substituted with one or more $C_1$-$C_3$ alkyl, —OH, —C(O)OH, —NR'R", or —C(O)NR'R".

In certain embodiments, the compound of Formula I' or Formula I is a compound depicted in Table 1, or a tautomer, solvate, or salt thereof. Each compound of Table 1 further comprises a pharmaceutically acceptable anion X.

TABLE 1

| | |
|---|---|
| 1 | 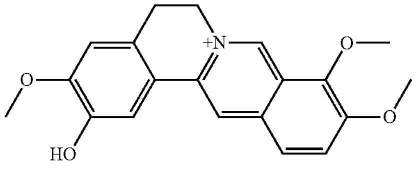 |
| 2 | 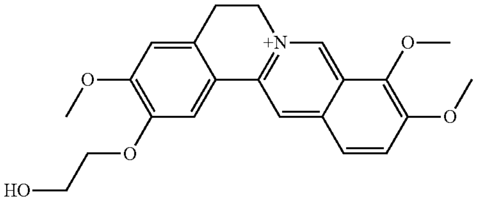 [SMILES: COc1cc2c(cc1OCCO)-c1cc3ccc(OC)c(OC)c3c[n+]1CC2] |

TABLE 1-continued
3
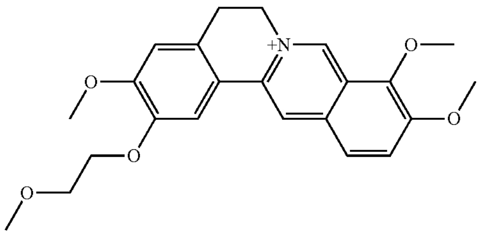
4
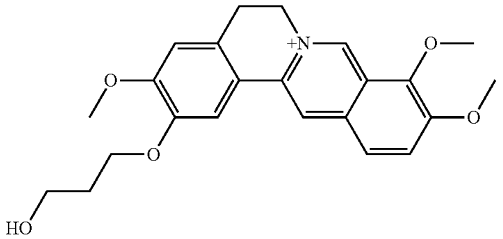 [SMILES: COc1cc2c(cc1OCCCO)-c1cc3ccc(OC)c(OC)c3c[n+]1CC2]
5
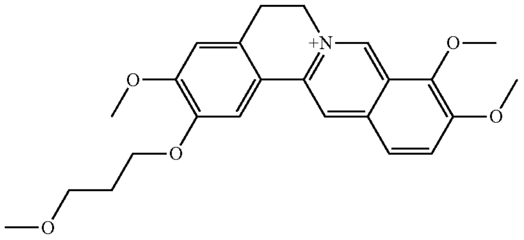
6
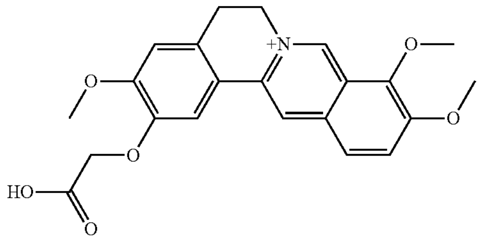 [SMILES: COc1cc2c(cc1OCC(=O)O)-c1cc3ccc(OC)c(OC)c3c[n+]1CC2]
7
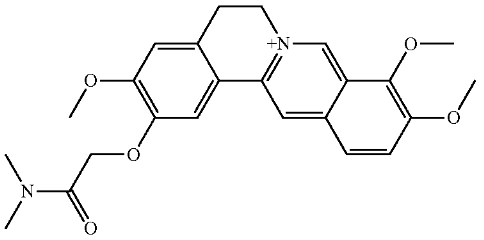
8
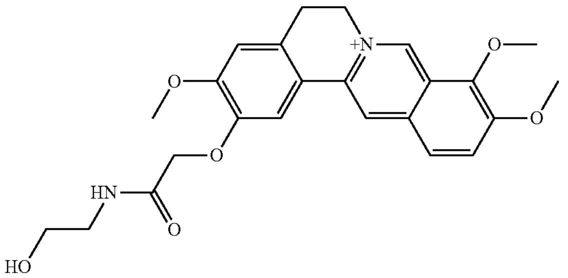 [SMILES: COc1cc2c(cc1OCC(=O)NCCO)-c1cc3ccc(OC)c(OC)c3c[n+]1CC2]

TABLE 1-continued
9
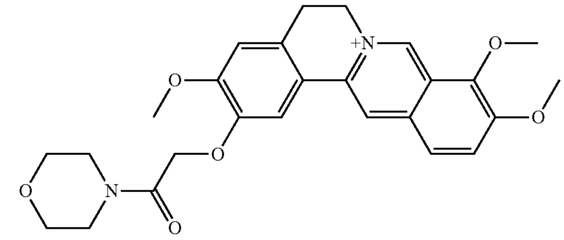 [SMILES: COc1cc2c(cc1OCC(=O)N1CCOCC1)-c1cc3ccc(OC)c(OC)c3c[n+]1CC2]
10
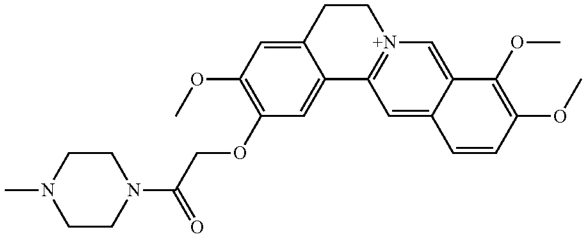
11
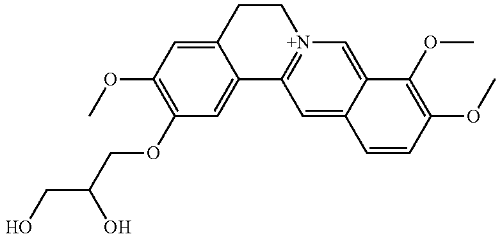 [SMILES: COc1cc2c(cc1OCC(O)CO)-c1cc3ccc(OC)c(OC)c3c[n+]1CC2]
12
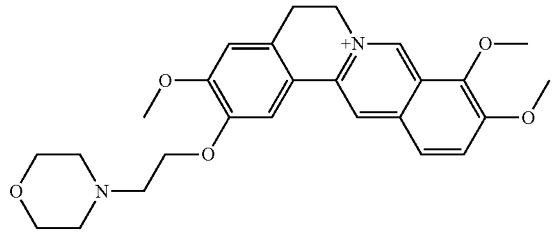 [SMILES: COc1cc2c(cc1OCCN1CCOCC1)-c1cc3ccc(OC)c(OC)c3c[n+]1CC2]
13
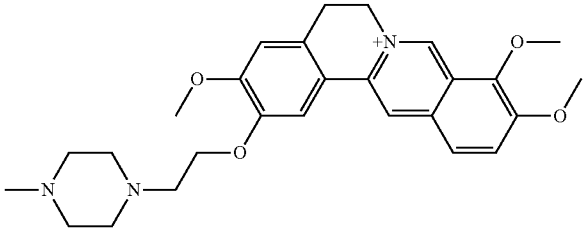
14
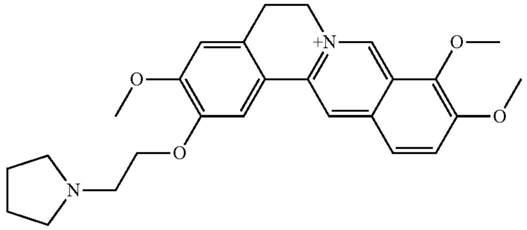 [SMILES: COc1cc2c(cc1OCCN1CCCC1)-c1cc3ccc(OC)c(OC)c3c[n+]1CC2]

TABLE 1-continued
15
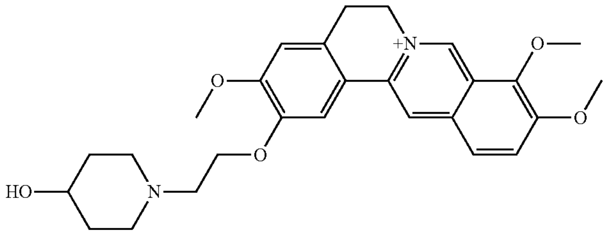 [SMILES: COc1cc2c(cc1OCCN1CCC(O)CC1)-c1cc3ccc(OC)c(OC)c3c[n+]1CC2]
16
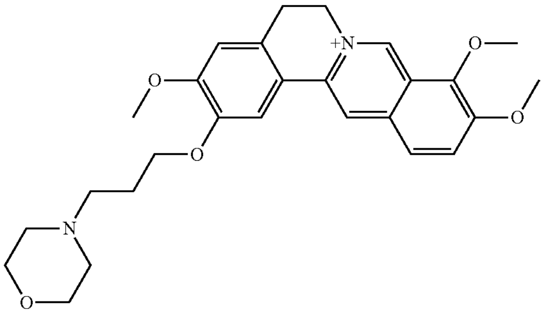 [SMILES: COc1cc2c(cc1OCCCN1CCOCC1)-c1cc3ccc(OC)c(OC)c3c[n+]1CC2]
17
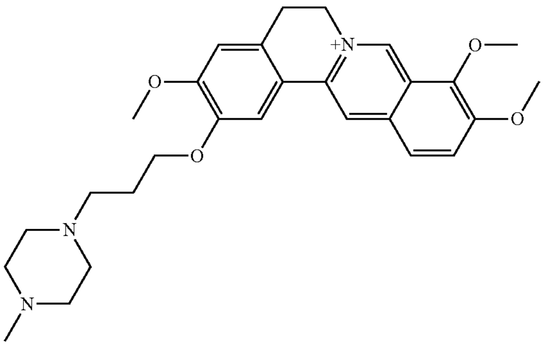 [SMILES: COc1cc2c(cc1OCCCN1CCN(C)CC1)-c1cc3ccc(OC)c(OC)c3c[n+]1CC2]
18
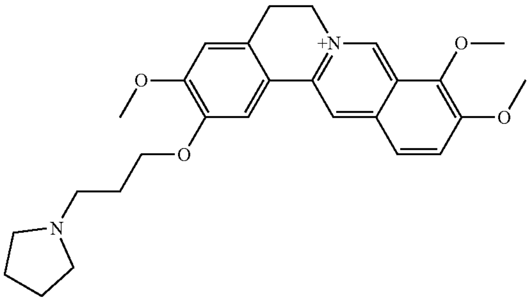 [SMILES: COc1cc2c(cc1OCCCN1CCCC1)-c1cc3ccc(OC)c(OC)c3c[n+]1CC2]
19
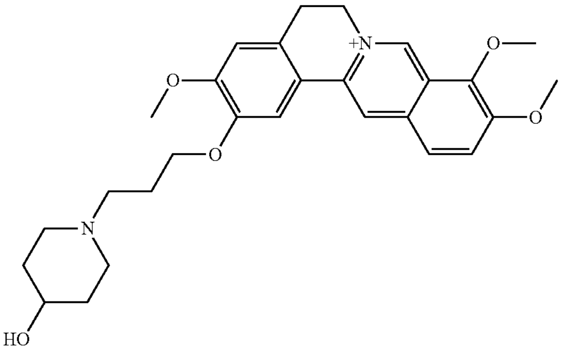 [SMILES: COc1cc2c(cc1OCCCN1CCC(O)CC1)-c1cc3ccc(OC)c(OC)c3c[n+]1CC2]

TABLE 1-continued
20
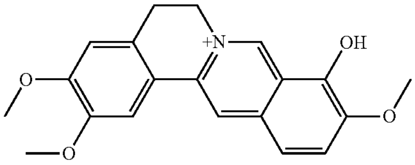
21
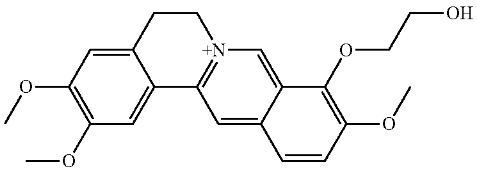
22
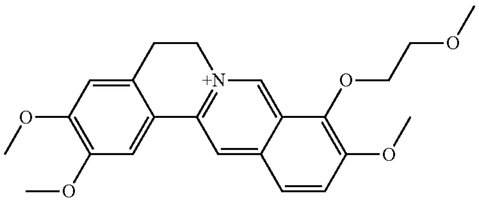
23
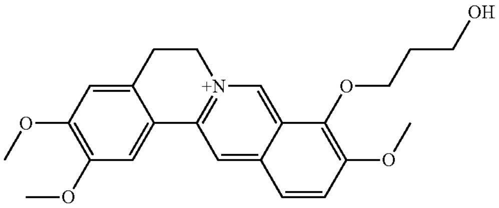 [SMILES: COc1cc2c(cc1OC)-c1cc3ccc(OC)c(OCCCO)c3c[n+]1CC2]
24
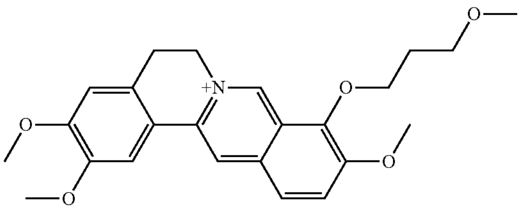
25
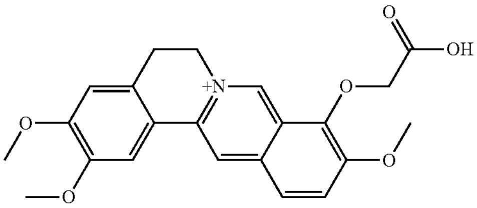 [SMILES: COc1cc2c(cc1OC)-c1cc3ccc(OC)c(OCC(=O)O)c3c[n+]1CC2]
26
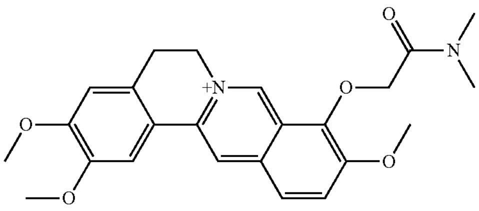

TABLE 1-continued
27
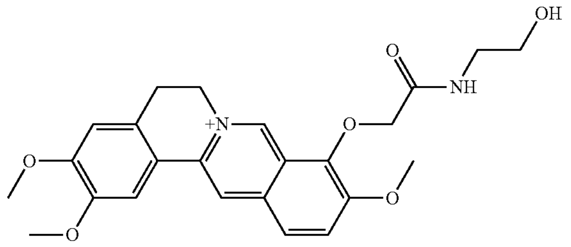 [SMILES: COc1cc2c(cc1OC)-c1cc3ccc(OC)c(OCC(=O)NCCO)c3c[n+]1CC2]
28
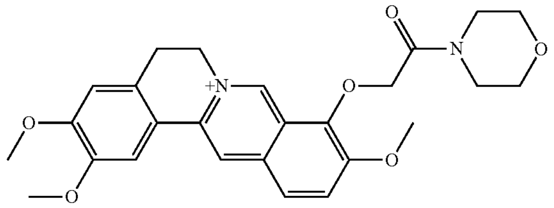 [SMILES: COc1cc2c(cc1OC)-c1cc3ccc(OC)c(OCC(=O)N4CCOCC4)c3c[n+]1CC2]
29
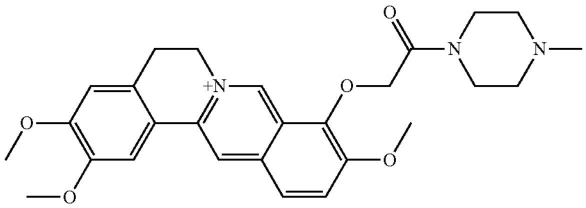
30
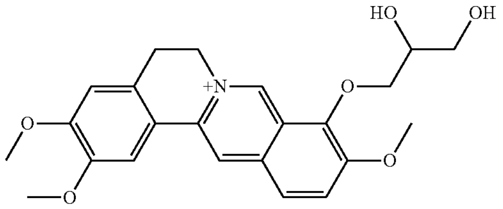 [SMILES: COc1cc2c(cc1OC)-c1cc3ccc(OC)c(OCC(O)CO)c3c[n+]1CC2]
31
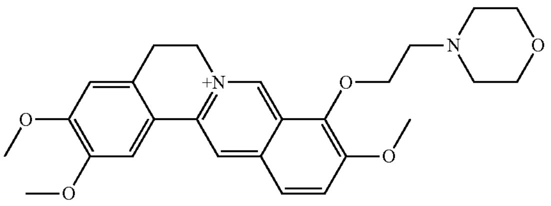 [SMILES: COc1cc2c(cc1OC)-c1cc3ccc(OC)c(OCCN4CCOCC4)c3c[n+]1CC2]
32
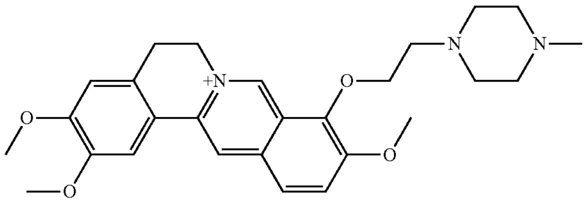
33
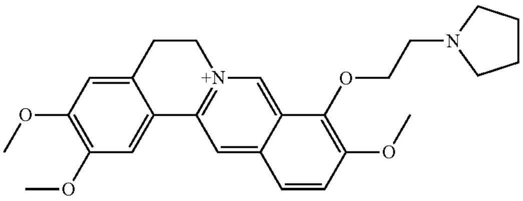 [SMILES: COc1cc2c(cc1OC)-c1cc3ccc(OC)c(OCCN4CCCC4)c3c[n+]1CC2]

TABLE 1-continued
34
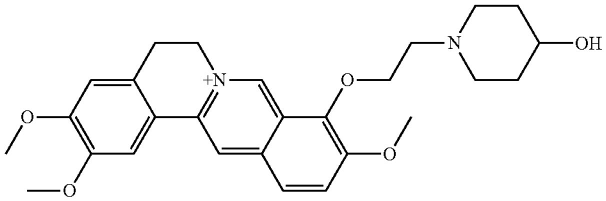 [SMILES: COc1cc2c(cc1OC)-c1cc3ccc(OC)c(OCCN4CCC(O)CC4)c3c[n+]1CC2]
35
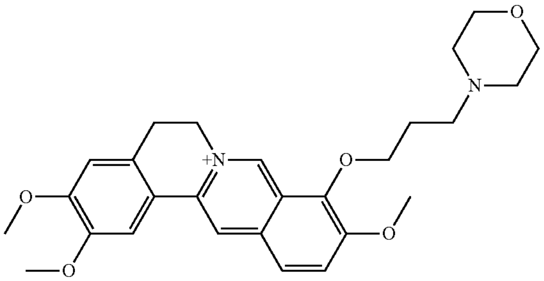 [SMILES: COc1cc2c(cc1OC)-c1cc3ccc(OC)c(OCCCN4CCOCC4)c3c[n+]1CC2]
36
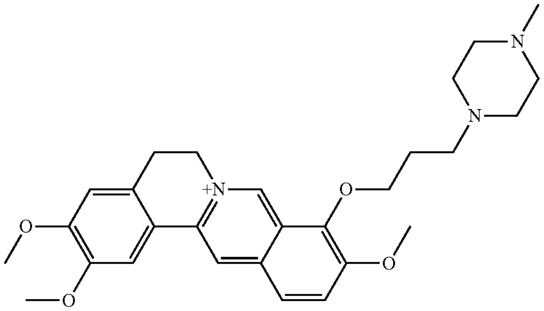
37
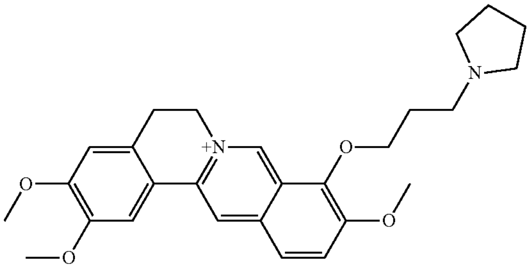 [SMILES: COc1cc2c(cc1OC)-c1cc3ccc(OC)c(OCCCN4CCCC4)c3c[n+]1CC2]
38
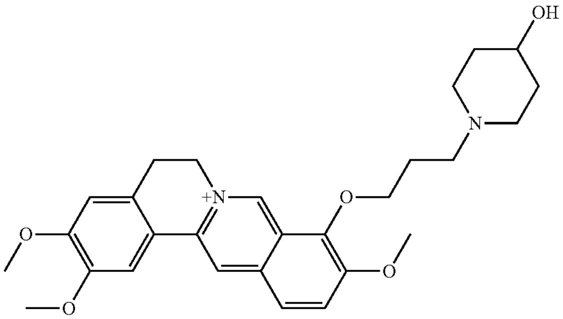 [SMILES: COc1cc2c(cc1OC)-c1cc3ccc(OC)c(OCCCN4CCC(O)CC4)c3c[n+]1CC2]
39
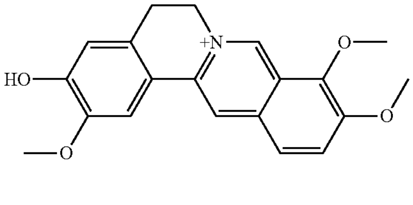 [SMILES: COc1cc2c(cc1O)CC[n+]1cc3c(OC)c(OC)ccc3cc1-2]

TABLE 1-continued
| | |
|---|---|
| 40 | 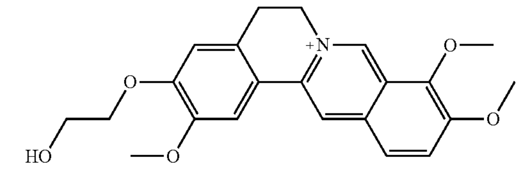 |
| 41 | 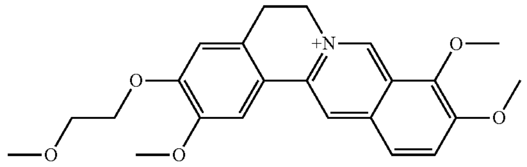 |
| 42 | 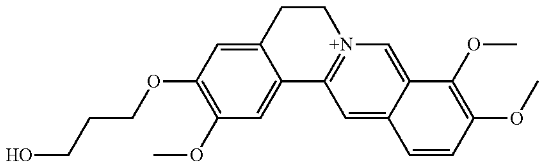 |
| 43 | 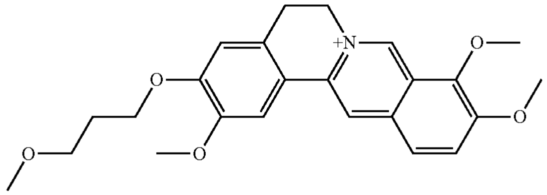 |
| 44 | 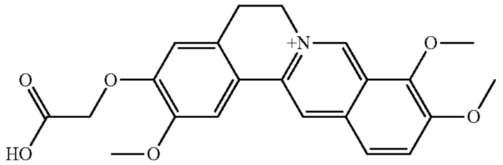 [SMILES: COc1cc2c(cc1OCC(=O)O)CC[n+]1cc3c(OC)c(OC)ccc3cc1-2] |
| 45 | 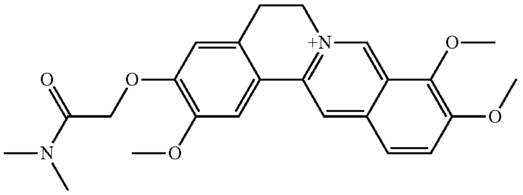 |
| 46 | 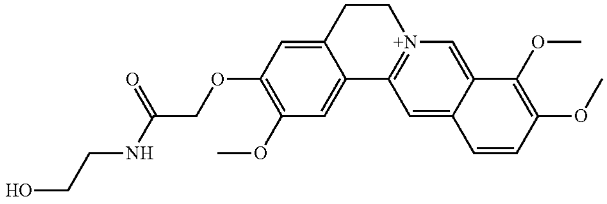 [SMILES: COc1cc2c(cc1OCC(=O)NCCO)CC[n+]1cc3c(OC)c(OC)ccc3cc1-2] |
| 47 | 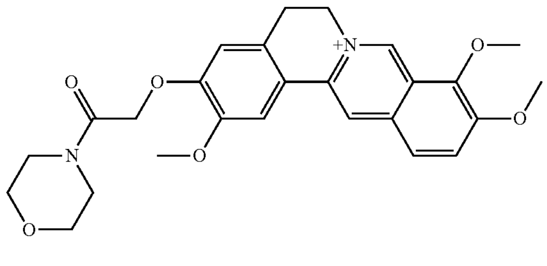 [SMILES: COc1cc2c(cc1OCC(=O)N1CCOCC1)CC[n+]1cc3c(OC)c(OC)ccc3cc1-2] |

TABLE 1-continued
48
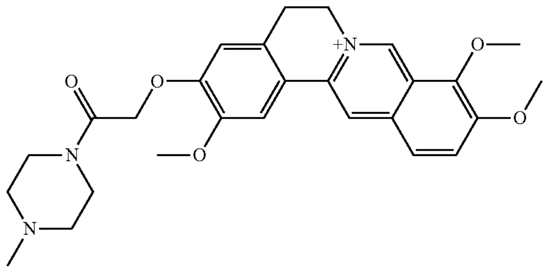
49
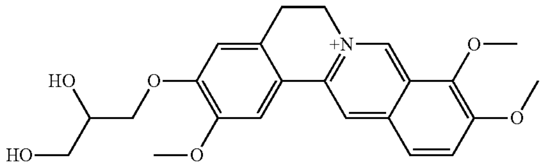
50
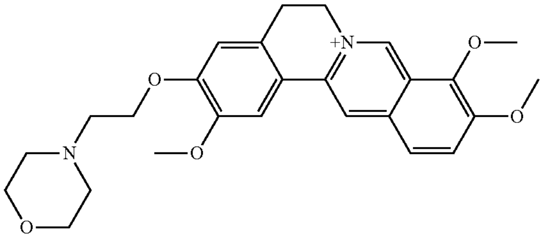 [SMILES: COc1cc2c(cc1OCCN1CCOCC1)CC[n+]1cc3c(OC)c(OC)ccc3cc1-2]
51
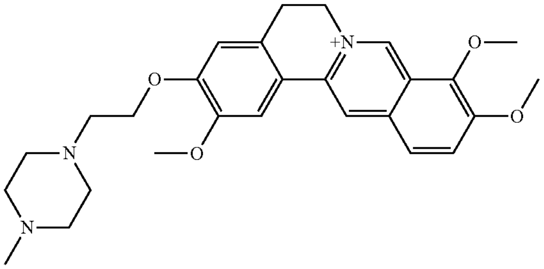 [SMILES: COc1cc2c(cc1OCCN1CCN(C)CC1)CC[n+]1cc3c(OC)c(OC)ccc3cc1-2]
52
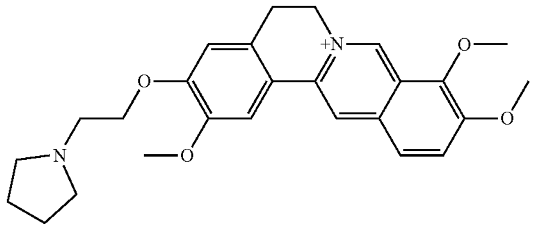 [SMILES: COc1cc2c(cc1OCCN1CCCC1)CC[n+]1cc3c(OC)c(OC)ccc3cc1-2]
53
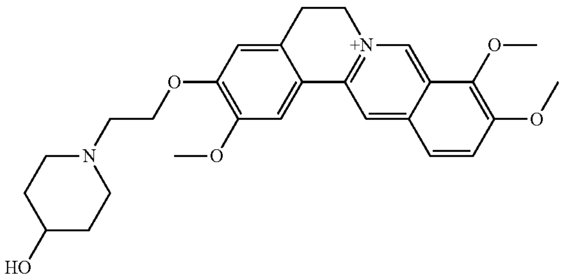 [SMILES: COc1cc2c(cc1OCCN1CCC(O)CC1)CC[n+]1cc3c(OC)c(OC)ccc3cc1-2]

TABLE 1-continued
54
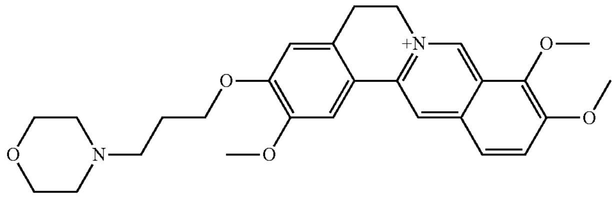 [SMILES: COc1cc2c(cc1OCCCN1CCOCC1)CC[n+]1cc3c(OC)c(OC)ccc3cc1-2]
55
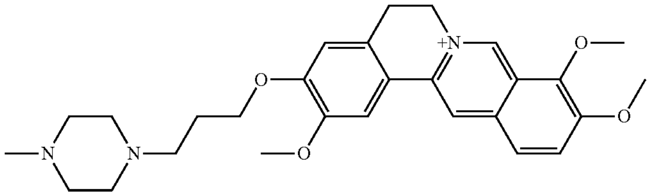
56
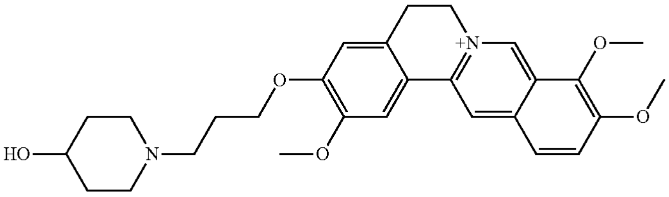 [SMILES: COc1cc2c(cc1OCCCN1CCC(O)CC1)CC[n+]1cc3c(OC)c(OC)ccc3cc1-2]
57
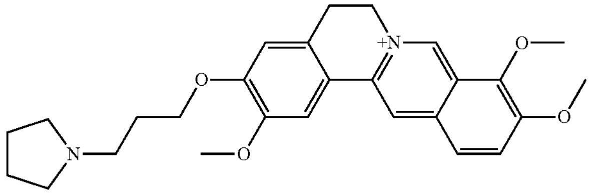 [SMILES: COc1cc2c(cc1OCCCN1CCCC1)CC[n+]1cc3c(OC)c(OC)ccc3cc1-2]
58
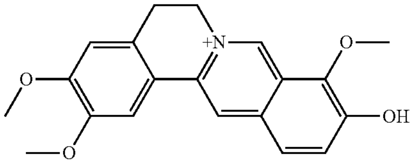
59
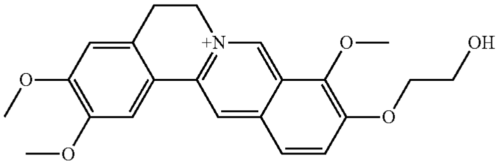 [SMILES: COc1cc2c(cc1OC)-c1cc3ccc(OCCO)c(OC)c3c[n+]1CC2]
60
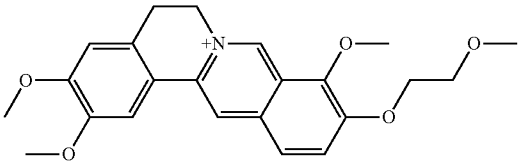
61
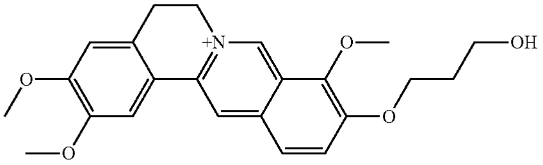 [SMILES: COc1cc2c(cc1OC)-c1cc3ccc(OCCCO)c(OC)c3c[n+]1CC2]

TABLE 1-continued
62
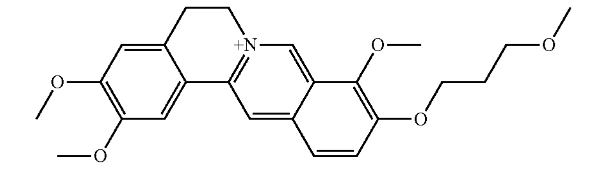
63
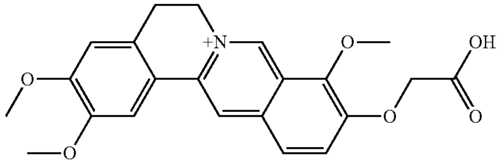 [SMILES: COc1cc2c(cc1OC)-c1cc3ccc(OCC(=O)O)c(OC)c3c[n+]1CC2]
64
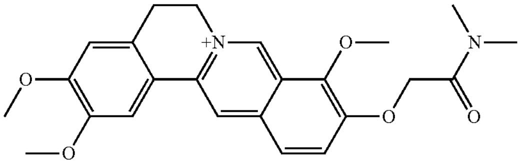
65
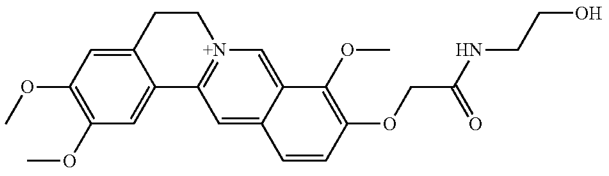 [SMILES: COc1cc2c(cc1OC)-c1cc3ccc(OCC(=O)NCCO)c(OC)c3c[n+]1CC2]
66
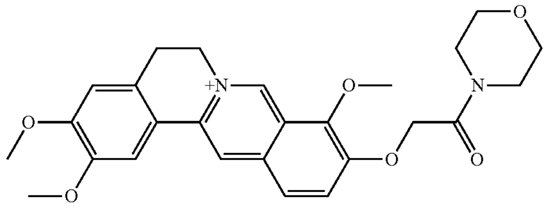 [SMILES: COc1cc2c(cc1OC)-c1cc3ccc(OCC(=O)N4CCOCC4)c(OC)c3c[n+]1CC2]
67
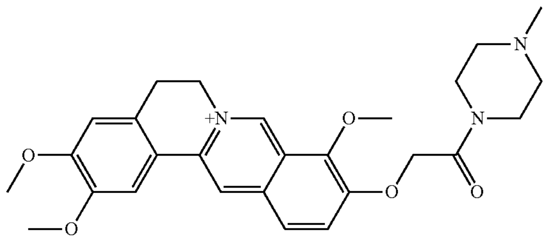
68
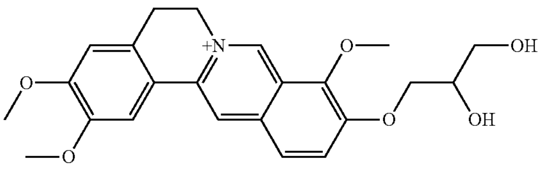 [SMILES: COc1cc2c(cc1OC)-c1cc3ccc(OCC(O)CO)c(OC)c3c[n+]1CC2]
69
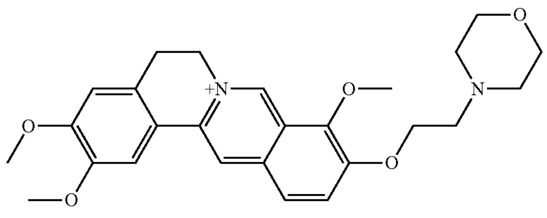 [SMILES: COc1cc2c(cc1OC)-c1cc3ccc(OCCN4CCOCC4)c(OC)c3c[n+]1CC2]

TABLE 1-continued
| | |
|---|---|
| 70 | 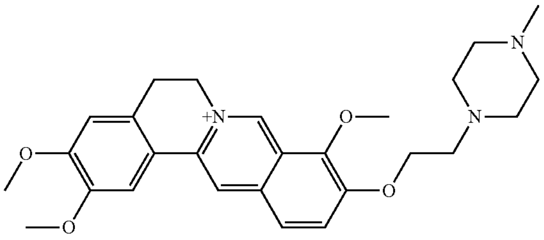 [SMILES: COc1cc2c(cc1OC)-c1cc3ccc(OCCN4CCN(C)CC4)c(OC)c3c[n+]1CC2] |
| 71 | 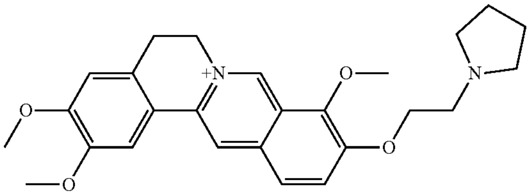 [SMILES: COc1cc2c(cc1OC)-c1cc3ccc(OCCN4CCCC4)c(OC)c3c[n+]1CC2] |
| 72 | 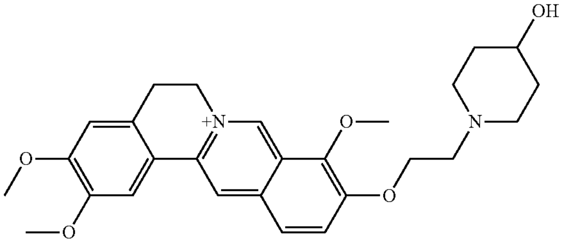 [SMILES: COc1cc2c(cc1OC)-c1cc3ccc(OCCN4CCC(O)CC4)c(OC)c3c[n+]1CC2] |
| 73 | 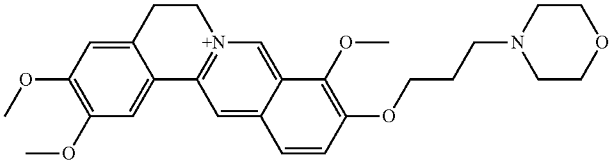 [SMILES: COc1cc2c(cc1OC)-c1cc3ccc(OCCCN4CCOCC4)c(OC)c3c[n+]1CC2] |
| 74 | 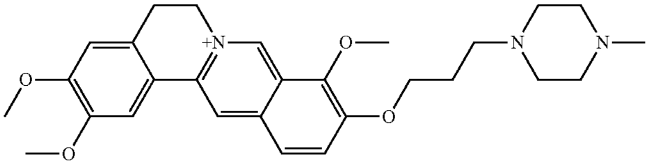 |
| 75 | 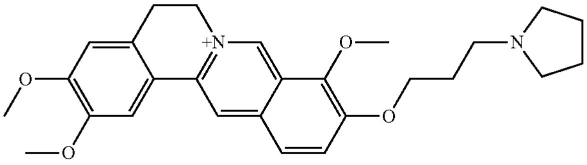 [SMILES: COc1cc2c(cc1OC)-c1cc3ccc(OCCCN4CCCC4)c(OC)c3c[n+]1CC2] |
| 76 | 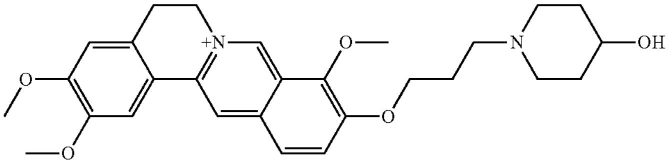 [SMILES: COc1cc2c(cc1OC)-c1cc3ccc(OCCCN4CCC(O)CC4)c(OC)c3c[n+]1CC2] |

In certain embodiments, the compound of Formula I' or Formula I is a compound depicted in Table 2, or a tautomer, solvate, or salt thereof. Each compound of Table 2 further comprises a pharmaceutically acceptable anion X.

TABLE 2

77

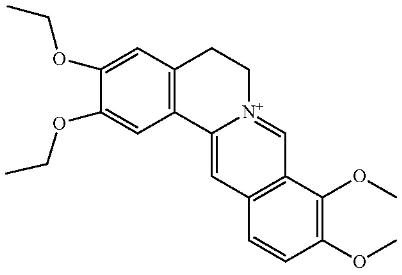 [SMILES: CCOc1cc2c(cc1OCC)-c1cc3ccc(OC)c(OC)c3c[n+]1CC2]

78

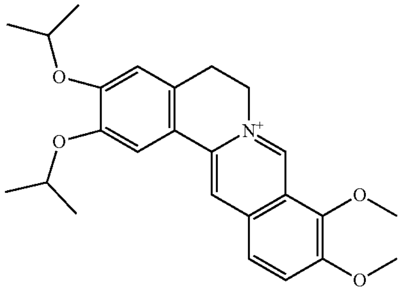 [SMILES: COc1ccc2cc3[n+](cc2c1OC)CCc1cc(OC(C)C)c(OC(C)C)cc1-3]

79

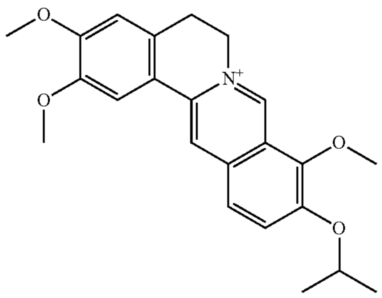 [SMILES: COc1cc2c(cc1OC)-c1cc3ccc(OC(C)C)c(OC)c3c[n+]1CC2]

80

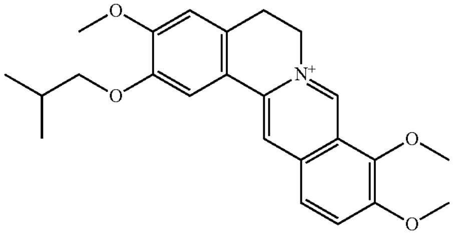 [SMILES: COc1cc2c(cc1OCC(C)C)-c1cc3ccc(OC)c(OC)c3c[n+]1CC2]

81

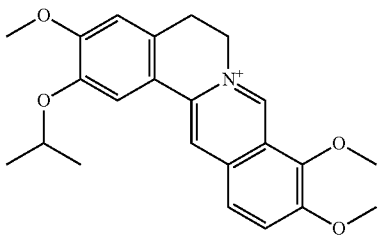

TABLE 2-continued

82

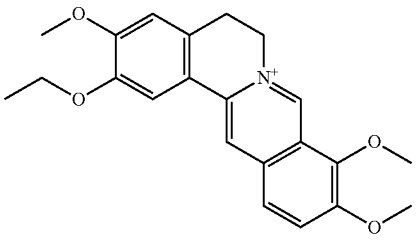 [SMILES: CCOc1cc2c(cc1OC)CC[n+]1cc3c(OC)c(OC)ccc3cc1-2]

83

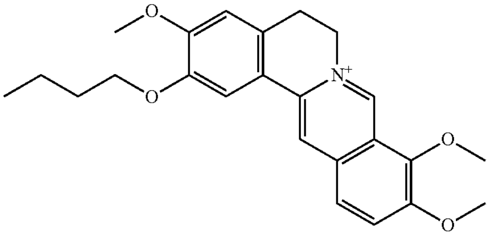 [SMILES: CCCCOc1cc2c(cc1OC)CC[n+]1cc3c(OC)c(OC)ccc3cc1-2]

84

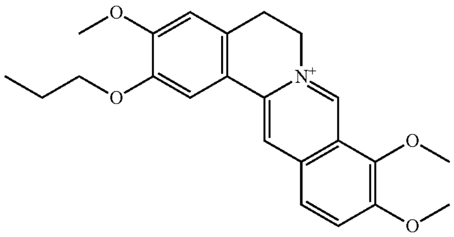

In certain embodiments, the compound of Formula I' or Formula I is a compound depicted in Table 3, or a tautomer, solvate, or salt thereof. Each compound of Table 3 further comprises a pharmaceutically acceptable anion X.

TABLE 3

85

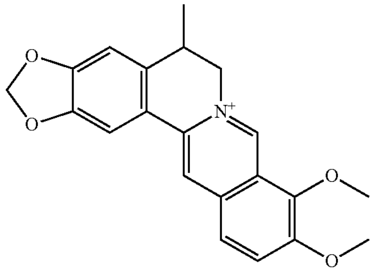 [SMILES: COc1ccc2cc3[n+](cc2c1OC)CC(C)c1cc2c(cc1-3)OCO2]

86

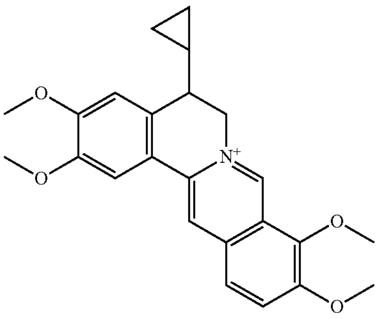

TABLE 3-continued

87

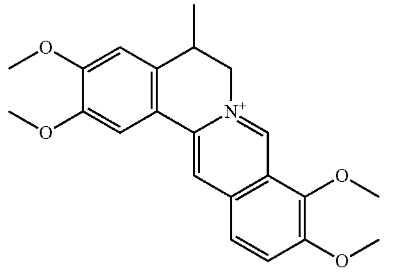

In certain embodiments, the compound of Formula I' or Formula I is a compound depicted in Table 1 or Table 2, or a tautomer, solvate, or salt thereof. In certain embodiments, the compound of Formula I' or Formula I is a compound depicted in Table 2 or Table 3, or a tautomer, solvate, or salt thereof. In certain embodiments, the compound of Formula I' or Formula I is a compound depicted in Table 1, Table 2, or Table 3, or a tautomer, solvate, or salt thereof. Each compound of Table 1, Table 2, and Table 3 further comprises a pharmaceutically acceptable anion X.

In some embodiments, the compound (e.g., a compound of Formula I' or Formula I) has a purity of at least 50%. In some embodiments, the compound has a purity of at least 55%, at least 60%, at least 65%, at least 70%, at least 75%, at least 80%, at least 85%, at least 90%, at least 95%, at least 96%, at least 97%, at least 98%, at least 99%, or at least 99.9%. Methods of determining the purity of a compound are discussed below.

In some embodiments, the composition (e.g., a nucleic acid and/or lipid composition disclosed herein) has a purity of at least 50%. The purity of a composition reflects the amount of components used to make the composition in the composition at any particular point in time. In some embodiments, the composition has a purity of at least 55%, at least 60%, at least 65%, at least 70%, at least 75%, at least 80%, at least 85%, at least 90%, at least 95%, at least 96%, at least 97%, at least 98%, at least 99%, or at least 99.9%.

The purity of a composition may be characterized based on the presence of impurities in the composition at any particular point in time. Impurities include, for instance, lipid-RNA adducts, which are typical degradation products of mRNA-LNPs or elemental metals. In some embodiments, a composition is considered to have an adequate purity if less than 10% of the RNA in a composition is in the form of a lipid-RNA adduct. In some embodiments, a composition is considered to have an adequate purity if less than 9%, 8%, 7%, 6%, 5%, 4%, 3%, 2%, 1%, 0.5%, or 0.1% of the RNA in a composition is in the form of a lipid-RNA adduct.

The purity of a composition may also be characterized based on the presence of adduct impurities that arise from the decomposition of an ionizable amine lipid (e.g., tertiary amine lipid) component of the composition. For example, an ionizable amine lipid may be converted into one or more electrophilic compounds which react with nucleic acid bases to afford covalent adducts. In particular, an ionizable amine lipid may be oxidized to the corresponding N-oxide, which is ultimately hydrolyzed to the corresponding aldehyde. The aldehyde may then react with amine residues on the bases to form covalent adducts.

In certain embodiments, oxidation of the ionizable amine is facilitated by mildly acidic conditions. In certain embodiments, oxidation of the ionizable amine is facilitated by a sensitizing compound. In some embodiments, the sensitizing compound is a triplet sensitizer. In some embodiments, the sensitizing compound is a compound of Formula I' or Formula I, or a tautomer or solvate thereof. In certain embodiments, oxidation of the ionizable amine is facilitated by exposure to light. In such embodiments, formation of covalent adducts can be reduced by reducing exposure of a composition (e.g., a lipid nanoparticle formulation) to light. In other embodiments, oxidation of the ionizable amine occurs without exposure to light.

In certain embodiments, the covalent adducts are distinguished as late-eluting peaks using reverse phase ion pair high performance liquid chromatography (RP-IP HPLC). In certain embodiments, the covalent adducts are not distinguishable using capillary electrophoresis.

The formation of covalent adducts to mRNA can abrogate the ability of the mRNA to undergo translation.

In some embodiments, the stabilizer (e.g., a compound of Formula I', Formula I, or Formula II, or a tautomer or solvate thereof) preserves the purity of the nucleic acid. In some embodiments, the stabilizer preserves the purity of the nucleic acid in a concentration dependent manner. In some embodiments, 0.01-10 mM of stabilizer preserves the purity of the nucleic acid. In some embodiments, 0.1-1 mM of stabilizer preserves the purity of the nucleic acid. In some embodiments, 0.1-1 mM of stabilizer preserves the purity of the nucleic acid at 25° C. In some embodiments, the stabilizer decreases degradation of the nucleic acid. In some embodiments, the stabilizer decreases adduct formation.

In some embodiments, the compound (e.g., a compound of Formula I' or Formula I, or a tautomer, solvate, or salt thereof) is free of elemental metals. In some embodiments, the compound contains fewer than 1000 ppm, fewer than 900 ppm, fewer than 800 ppm, fewer than 700 ppm, fewer than 600 ppm, fewer than 500 ppm, fewer than 400 ppm, fewer than 300 ppm, fewer than 200 ppm, fewer than 100 ppm, fewer than 90 ppm, fewer than 80 ppm, fewer than 70 ppm, fewer than 60 ppm, fewer than 50 ppm, fewer than 40 ppm, fewer than 30 ppm, fewer than 20 ppm, fewer than 10 ppm, fewer than 9 ppm, fewer than 8 ppm, fewer than 7 ppm, fewer than 6 ppm, fewer than 5 ppm, fewer than 4 ppm, fewer than 3 ppm, fewer than 2 ppm, fewer than 1 ppm of elemental metals.

The term "elemental metal" is given its ordinary meaning in the art. A metal is an element that readily forms positive ions (i.e., cations) and forms metallic bonds. An elemental metal refers to a metal which is not present in a salt form or otherwise within a compound. Those of ordinary skill in the art will, in general, recognize elemental metals.

Purity can be determined by any suitable method known in the art. Non-limiting examples of methods to determine the purity of a compound include melting point determination, boiling point determination, spectroscopy (e.g., UV-VIS spectroscopy), titration, chromatography (e.g., liquid chromatography or gas chromatography), mass spectroscopy, capillary electrophoresis, and optical rotation.

According to some embodiments, compositions are formulated in aqueous solutions. An aqueous solution is a solution in which components are dissolved or otherwise dispersed within water.

In some embodiments, an aqueous solution has a given pH value. In some embodiments, the pH of an aqueous solution disclosed herein is within the range of about 4.5 to about 8.5. In some embodiments, the pH of an aqueous solution is within the range of about 5 to about 8, about 6 to about 8, about 7 to about 8, about 6.5 to about 8, about 6.5 to about 7.5, about 6.5 to about 7, about 7.5 to about 8.5, or any range or combination thereof. In some embodiments, the pH of an aqueous solution is or is about 5, is or is about 5.5, is or is about 6, is or is about 6.5, is or is about 7, is or is about 7.5, or is or is about 8.

In some embodiments, an aqueous solution comprises a pH buffer component, such as a phosphate buffer, a tris buffer, an acetate buffer, a histidine buffer or a citrate buffer, among others. Such a buffer acts to modulate the pH of an aqueous solution, such as an aqueous solution having a pH of 5, 5.5, 6, 6.5, 7, 7.5 or 8. In a particular embodiment, the aqueous solution has a buffered pH of about 6. Aqueous solutions may comprise various concentrations of salts (e.g., sodium chloride, NaCl). In some embodiments, an aqueous solution may comprise a salt (e.g., NaCl) in a concentration of or about 50 mM, of or about 60 mM, of or about 70 mM, of or about 80 mM, of or about 90 mM, of or about 100 mM, of or about 110 mM, of or about 120 mM, of or about 130 mM, of or about 140 mM, of or about 150 mM, of or about 160 mM, of or about 170 mM, of or about 180 mM, of or about 190 mM, of or about 200 mM, or any intermediate concentration therein. In embodiments in which an aqueous solution comprises more than one salt, each salt may independently have a concentration of one or more of the values described above.

According to some aspects, aqueous solutions (e.g., aqueous solutions comprising nucleic acid, lipid, or nucleic acid and lipid) comprise a compound (e.g., a compound of Formula I' or Formula I, or a tautomer, solvate, or salt thereof) at a concentration of between about 0.1 mM and about 10 mM. In some embodiments, an aqueous solution (e.g., an aqueous solution comprising nucleic acid, lipid, or nucleic acid and lipid) comprises a compound (e.g., a compound of Formula I' or Formula I, or a tautomer, solvate, or salt thereof) at a concentration of between about 0.2 mM and about 10 mM, about 0.3 mM and about 10 mM, about 0.4 mM and about 10 mM, about 0.5 mM and about 10 mM, about 0.6 mM and about 10 mM, about 0.7 mM and about 10 mM, about 0.8 mM and about 10 mM, about 0.9 mM and about 10 mM, about 1 mM and about 10 mM, about 0.5 mM and about 9 mM, about 0.5 mM and about 8 mM, about 0.5 mM and about 7 mM, about 0.5 mM and about 6 mM, about 0.5 mM and about 5 mM, about 0.5 mM and about 4 mM about 0.5 mM and about 3 mM, about 0.5 mM and about 2 mM, about 0.5 mM and about 1.5 mM, about 0.5 mM and about 1 mM, or any range or combination thereof. In some embodiments, an aqueous solution (e.g., an aqueous solution comprising nucleic acid, lipid, or nucleic acid and lipid) comprises a compound (e.g., a compound of Formula I' or Formula I, or a tautomer, solvate, or salt thereof) at a concentration of or about 0.1 mM, 0.2 mM, 0.3 mM, 0.4 mM, 0.5 mM, 0.6 mM, 0.7 mM, 0.8 mM, 0.9 mM, 1 mM, 1.5 mM, 2 mM, 2.5 mM, 3 mM 4 mM, 5 mM, 6 mM, 7 mM, 8 mM, 9 mM, or of or about 10 mM. In some embodiments, an aqueous solution (e.g., an aqueous solution comprising nucleic acid, lipid, or nucleic acid and lipid) comprises a compound (e.g., a compound of Formula I' or Formula I, or a tautomer, solvate, or salt thereof) at a concentration of or about 0.5 mM, 1 mM, 1.5 mM, or of or about 2 mM. In some embodiments, an aqueous solution (e.g., an aqueous solution comprising nucleic acid, lipid, or nucleic acid and lipid) does not comprise a compound of Formula I' or Formula I, or a tautomer, solvate, or salt thereof.

According to some aspects, a composition is a lyophilized product. A lyophilized product is one from which liquid (e.g., water) has been removed by freeze drying, in which a liquid product is frozen and subsequently placed under a vacuum to remove liquid, leaving a composition substantially free of liquid. In some embodiments, a lyophilized product comprises lipids. In some embodiments, a lyophilized product comprises lipid nanoparticles. In some embodiments, a lyophilized product comprises nucleic acid. In some embodiments, a lyophilized product comprises nucleic acid encapsulated within lipid nanoparticles. In some embodiments, a lyophilized product comprises a compound of Formula I' or Formula I, or a tautomer, solvate, or salt thereof. In some embodiments, a lyophilized product comprises a compound of Formula I' or Formula I, or a tautomer, solvate, or salt thereof. In some embodiments, a lyophilized product comprises lipids, nucleic acids, a compound of Formula I' or Formula I, or a tautomer, solvate, or salt thereof, or any mixture thereof. In some embodiments, a lyophilized product is reconstituted with a solution comprising a compound of Formula I' or Formula I. or a tautomer, solvate, or salt thereof.

According to some aspects, a compound (e.g., a compound of Formula I' or Formula I, or a tautomer, solvate, or salt thereof) permeates into a lipid nanostructure (e.g., lipid nanoparticle, liposome, or lipoplex) to some extent. Permeation into a lipid nanostructure can be characterized, for example, by a partition coefficient representing the relative concentrations at equilibrium of the compound in the lipid nanostructure and in the solution in which the lipid nanostructure is comprised. The partition coefficient is a ratio of concentrations, and therefore represents the relative solubilities of the compound in the bulk solution and in the lipid nanostructure. A partition coefficient can be determined by one of skill in the art, for example by equilibrium dialysis.

In some embodiments, permeation of the compound into a lipid nanostructure (e.g., lipid nanoparticle, liposome, or lipoplex) is defined by a partition coefficient $K_{LS}$ representing the partitioning between a solution (e.g., water or an aqueous solution) and the lipid nanostructure comprised within the solution. In some embodiments, the log of the partition coefficient $K_{LS}$ (log $K_{LS}$) of a compound provided herein for a solution provided herein and a lipid nanostructure provided herein, measured at 25° C. is or is about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10. In some embodiments, the log $K_{LS}$ is defined with reference to a compound (e.g., a compound of Formula I' or Formula I. or a tautomer, solvate, or salt thereof) in water partitioning into a lipid nanostructure. In some embodiments, permeation of the compound into a lipid nanostructure (e.g., lipid nanoparticle, liposome, or lipoplex) is defined by a partition coefficient $K_{OW}$ which is defined by the ratio of concentrations of the compound in octanol and water at equilibrium. In some embodiments, the log of the partition coefficient $K_{OW}$ (log $K_{OW}$) of a compound, measured at 25° C. is or is about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10. In some embodiments, log $K_{OW}$ of a compound, measured at 25° C., is or is about 6. In some embodiments, log $K_{OW}$ of a compound, measured at 25° C., is or is about 5.85. In some embodiments, log $K_{OW}$ of a compound, measured at 25° C., is or is about 5.

In some embodiments, permeation of a compound (e.g., a compound of Formula I' or Formula I, or a tautomer, solvate, or salt thereof) into a lipid nanostructure (e.g., lipid nanoparticle, liposome, or lipoplex) is defined by the amount of the compound (e.g., by weight) present in the lipid nanostructure following incubation of the lipid nanostructure with a given concentration of the compound. In some embodiments, following incubation of a lipid nanostructure with a 1 mM solution of the compound, the lipid nanostructure comprises 0.001%, 0.005%, 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.51%, 0.52%, 0.53%, 0.54%, 0.55%, 0.56%, 0.57%, 0.58%, 0.59%, 0.6%, 0.61%, 0.62%, 0.63%, 0.64%, 0.65%, 0.66%, 0.67%, 0.68%, 0.69%, 0.7%, 0.71%, 0.72%, 0.73%, 0.74%, 0.75%, 0.76%, 0.77%, 0.78%, 0.79%, 0.8%, 0.81%, 0.82%, 0.83%, 0.84%, 0.85%, 0.86%, 0.87%, 0.88%, 0.89%, 0.9%, 0.91%, 0.92%, 0.93%, 0.94%, 0.95%, 0.96%, 0.97%, 0.98%, 0.99%, 1%, 1.1%, 1.12%, 1.14%, 1.16%, 1.18%, 1.2%, 1.22%, 1.24%, 1.26%, 1.28%, 1.3%, 1.32%, 1.34%, 1.36%, 1.38%, 1.4%, 1.42%, 1.44%, 1.46%, 1.48%, 1.5%, 1.52%, 1.54%, 1.56%, 1.58%, 1.6%, 1.62%, 1.64%, 1.66%, 1.68%, 1.7%, 1.72%, 1.74%, 1.76%, 1.78%, 1.8%, 1.82%, 1.84%, 1.86%, 1.88%, 1.9%, 1.92%, 1.94%, 1.96%, 1.98%, 2%, 2.2%, 2.4%, 2.6%, 2.8%, 3% by weight of the compound, or any range or combination thereof.

In some embodiments, permeability increases at the gel-to-liquid phase transition. In some embodiments, permeability increases with greater surface fluidity (e.g., membrane viscosity). In some embodiments, surface fluidity increases with temperature. In some embodiments, the LNPs do not undergo a phase transition. In some embodiments, surface polarity (e.g., the presence of polar molecules) increases with temperature.

In some embodiments, the surface properties of the LNP change over time in the absence of stabilizer (e.g., a compound of Formula I', Formula I, or Formula II, or a tautomer or solvate thereof). In some embodiments, the surface polarity of the LNP increases over time in the absence of stabilizer. In some embodiments, the surface fluidity of the LNP increases over time in the absence of stabilizer. In some embodiments, the surface fluidity of the LNP stays approximately constant over time in the absence of stabilizer.

In some embodiments, the surface properties of the LNP change over time in the presence of stabilizer (e.g., a compound of Formula I', Formula I, or Formula II, or a tautomer or solvate thereof). In some embodiments, the surface polarity of the LNP increases over time in the presence of stabilizer. In some embodiments, the surface polarity of the LNP increases more over time in the presence of stabilizer than in the absence of stabilizer. In some embodiments, the surface fluidity of the LNP increases over time in the presence of stabilizer. In some embodiments, the surface fluidity of the LNP increases less over time in the presence of stabilizer than in the absence of stabilizer.

In some embodiments, the nanoparticle and nucleic acid are equilibrated at 5° C. to 60° C. In some embodiments, the nanoparticle and nucleic acid are equilibrated at 5, 15, 25, 32, 40, 50, or 60° C. In some embodiments, the nanoparticle and nucleic acid are equilibrated with a stabilizer. In some embodiments, the nanoparticle and nucleic acid are equilibrated for at least 10 minutes.

In some embodiments, a stabilizing compound is incubated with the mRNA (e.g., a LNP comprising the mRNA) for a period of at least 30 minutes, such as 1 hour, 2 hours, 3 hours, 4 hours, 5 hours, 6 hours, 7 hours, 8 hours, 9 hours, 10 hours, 15 hours, 20 hours, 24 hours, 36 hours, 48 hours, 72 hours, 4 days, 5 days, 6 days, 7 days, 8 days, 9 days, 10 days or more. In some embodiments, the stabilizing compound is incubated with the mRNA (e.g., a LNP comprising the mRNA) at a temperature of 0° C. or more, such as 5° C., 10° C., 15° C., 20° C., 25° C., 30° C., 35° C., 37° C., 40° C., 45° C., or more.

In some embodiments, a stabilizing compound is water soluble. In some embodiments, the compound has a solubility in water of at least 10 mg/L (e.g., at least 100 mg/L, at least 200 mg/L, at least 300 mg/L, at least 400 mg/L, at least 500 mg/L, at least 600 mg/L, at least 700 mg/L, at least 800 mg/L, at least 900 mg/L, at least 1 g/L, at least 2 g/L, at least 3 g/L, at least 10 g/L, or more) at 25° C. In some embodiments, the compound has a solubility in water of or about 50 g/L at 25° C. In some embodiments, the compound has a solubility in water of or about 45 g/L at 25° C. In some embodiments, the compound has a solubility in water of or about 43.6 g/L at 25° C.

According to some aspects, a stabilizing compound (e.g., a compound of Formula I' or Formula I, or a tautomer, solvate, or salt thereof) has a low cytotoxicity. In some embodiments, a compound has a cytotoxicity LC50 value of at least 5 mg/L (e.g., at least 10 mg/L, at least 15 mg/L, at least 20 mg/L, at least 25 mg/L, at least 30 mg/L, at least 35 mg/L, at least 40 mg/L, at least 45 mg/L, at least 50 mg/L, or more) when measured in mammalian cells (e.g., human cells or murine cells) in culture, or when measured in test organisms (e.g., fish, such as zebrafish or *Mystus vittatus*).

In some embodiments, the stabilizing compound is a photosensitive stabilizing compound. Thus, in some embodiments the stabilizing compound is shielded from light exposure (e.g., sunlight, room light, UV light, and/or fluorescent light). Thus, in some embodiments, the stabilizing compound and/or mixtures or composition containing the stabilizing compound (e.g., mRNA compositions, LNP compositions, mRNA-encapsulated LNP compositions, and/or LNP component compositions) are protected from exposure to light. That is, in some embodiments light is inhibited or prohibited from contacting a composition comprising the stabilizing compound. In some embodiments, the composition comprising the stabilizer compound is stored in a container that inhibits or prohibits light from contacting the composition. In some embodiments, the composition is stored in a container covered mostly, or preferably entirely, with a film, foil, or coating that is light impermeable.

Nucleic Acids

Also provided are stabilized nucleic acids. In some embodiments, the nucleic acids are in contact with a stabilizing compound. Some embodiments comprise a composition comprising a nucleic acid and a stabilizing compound.

As used herein, the term "nucleic acid" refers to multiple nucleotides (i.e., molecules comprising a sugar (e.g., ribose or deoxyribose) linked to a phosphate group and to an exchangeable organic base, which is either a substituted pyrimidine (e.g., cytosine (C), thymine (T) or uracil (U)) or a substituted purine (e.g., adenine (A) or guanine (G))). As used herein, the term nucleic acid refers to polyribonucleotides as well as polydeoxyribonucleotides. The term nucleic acid also includes polynucleosides (i.e., a polynucleotide minus the phosphate) and any other organic base containing polymer. Non-limiting examples of nucleic acids include chromosomes, genomic loci, genes or gene segments that encode polynucleotides or polypeptides, coding sequences, non-coding sequences (e.g., intron, 5'-UTR, or 3'-UTR) of a gene, pri-mRNA, pre-mRNA, cDNA, mRNA, etc. In some embodiments, the nucleic acid is mRNA. A nucleic acid may include a substitution and/or modification. In some embodiments, the substitution and/or modification is in one or more bases and/or sugars. For example, in some embodiments a nucleic acid includes nucleic acids having backbone sugars that are covalently attached to low molecular weight organic groups other than a hydroxyl group at the 2' position and other than a phosphate group or hydroxy group at the 5' position. Thus, in some embodiments, a substituted or modified nucleic acid includes a 2'-O-alkylated ribose group. In some embodiments, a modified nucleic acid includes sugars such as hexose, 2'-F hexose, 2'-amino ribose, constrained ethyl (cEt), locked nucleic acid (LNA), arabinose or 2'-fluoroarabinose instead of ribose. Thus, in some embodiments, a nucleic acid is heterogeneous in backbone composition thereby containing any possible combination of polymer units linked together such as peptide-nucleic acids (which have an amino acid backbone with nucleic acid bases).

In some embodiments, a nucleic acid is DNA, RNA, PNA, cEt, LNA, ENA or hybrids including any chemical or natural modification thereof. Chemical and natural modifications are well known in the art. Non-limiting examples of modifications include modifications designed to increase translation of the nucleic acid, to increase cell penetration or sub-cellular distribution of the nucleic acid, to stabilize the nucleic acid against nucleases and other enzymes that degrade or interfere with the structure or activity of the nucleic acid, and to improve the pharmacokinetic properties of the nucleic acid.

In some embodiments, the compositions provided herein comprise a RNA having an open reading frame (ORF) encoding a polypeptide. In some embodiments, the RNA is a messenger RNA (mRNA). In some embodiments, the RNA (e.g., mRNA) further comprises a 5' UTR, 3' UTR, a poly(A) tail and/or a 5' cap analog.

Messenger RNA (mRNA) is any RNA that encodes a (at least one) protein (a naturally-occurring, non-naturally-occurring, or modified polymer of amino acids) and can be translated to produce the encoded protein in vitro, in vivo, in situ, or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences may further comprise additional elements, e.g., 5' and 3' UTRs, but that those elements, unlike the ORF, need not necessarily be present in an RNA polynucleotide of the present disclosure.

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a composition includes an RNA polynucleotide having an open reading frame encoding at least one polypeptide having at least one modification, at least one 5' terminal cap, and is formulated within a lipid nanoparticle along with the stabilizing compound (e.g., Formula I' or Formula I, or a tautomer, solvate, or salt thereof).

5' terminal caps can include endogenous caps or cap analogs. According to the present invention, a 5' terminal cap can comprise a guanine analog. Useful guanine analogs include, but are not limited to, inosine, N1-methyl-guanosine, 2' fluoro-guanosine, 7-deaza-guanosine, 8-oxo-guanosine, 2-amino-guanosine, LNA-guanosine, and 2-azido-guanosine.

Also provided herein are exemplary caps including those that can be used in co-transcriptional capping methods for ribonucleic acid (RNA) synthesis, using RNA polymerase, e.g., wild type RNA polymerase or variants thereof, e.g., such as those variants described herein. In one embodiment, caps can be added when RNA is produced in a "one-pot" reaction, without the need for a separate capping reaction. Thus, the methods, in some embodiments, comprise reacting a polynucleotide template with a RNA polymerase variant, nucleoside triphosphates, and a cap analog under in vitro transcription reaction conditions to produce RNA transcript.

In some embodiments, the cap analog binds to a polynucleotide template that comprises a promoter region comprising a transcriptional start site having a first nucleotide at nucleotide position +1, a second nucleotide at nucleotide position +2, and a third nucleotide at nucleotide position +3. In some embodiments, the cap analog hybridizes to the polynucleotide template at least at nucleotide position +1, such as at the +1 and +2 positions, or at the +1, +2, and +3 positions.

A cap analog may be, for example, a dinucleotide cap, a trinucleotide cap, or a tetranucleotide cap. In some embodiments, a cap analog is a dinucleotide cap. In some embodiments, a cap analog is a trinucleotide cap. In some embodiments, a cap analog is a tetranucleotide cap. As used here the term "cap" includes the inverted G nucleotide and can comprise additional nucleotides 3' of the inverted G, e.g., 1, 2, or more nucleotides 3' of the inverted G and 5' to the 5' UTR.

Exemplary caps comprise a sequence GG, GA, or GGA wherein the underlined, italicized G is an inverted G.

A trinucleotide cap, in some embodiments, comprises a compound of formula (I)

(I)

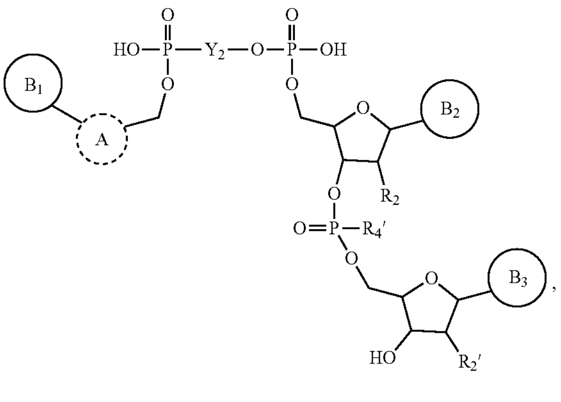

or a stereoisomer, tautomer or salt thereof, wherein

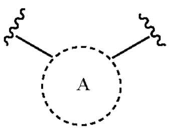

is

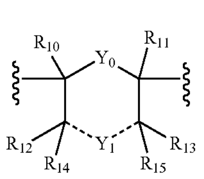

or

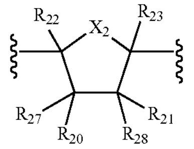

;

ring $B_1$ is a modified or unmodified Guanine;

ring $B_2$ and ring $B_3$ each independently is a nucleobase or a modified nucleobase;

$X_2$ is O, $S(O)_p$, $NR_{24}$ or $CR_{25}R_{26}$ in which p is 0, 1, or 2;

$Y_0$ is O or $CR_6R_7$;

Y1 is O, $S(O)_n$, $CR_6R_7$, or $NR_8$, in which n is 0, 1, or 2;

each --- is a single bond or absent, wherein when each --- is a single bond, Yi is O, $S(O)_n$, $CR_6R_7$, or $NR_8$; and when each --- is absent, $Y_1$ is void;

$Y_2$ is $(OP(O)R_4)_m$ in which m is 0, 1, or 2, or —O—$(CR_{40}R_{41})$u-$Q_0$-$(CR_{42}R_{43})$v-, in which $Q_0$ is a bond, O, $S(O)_r$, $NR_{44}$, or $CR_{45}R_{46}$, r is 0, 1, or 2, and each of u and v independently is 1, 2, 3 or 4;

each $R_2$ and $R_{2'}$ independently is halo, LNA, or $OR_3$;

each $R_3$ independently is H, $C_1$-$C_6$ alkyl, $C_2$-$C_6$ alkenyl, or $C_2$-$C_6$ alkynyl and $R_3$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

each $R_4$ and $R_{4'}$ independently is H, halo, $C_1$-$C_6$ alkyl, OH, SH, SeH, or $BH_3^-$;

each of $R_6$, $R_7$, and $R_8$, independently, is -$Q_1$-$T_1$, in which $Q_1$ is a bond or $C_1$-$C_3$ alkyl linker optionally substituted with one or more of halo, cyano, OH and $C_1$-$C_6$ alkoxy, and $T_1$ is H, halo, OH, COOH, cyano, or $R_{s1}$, in which $R_{s1}$ is $C_1$-$C_3$ alkyl, $C_2$-$C_6$ alkenyl, $C_2$-$C_6$ alkynyl, $C_1$-$C_6$ alkoxyl, C(O)O—$C_1$-$C_6$ alkyl, $C_3$-$C_8$ cycloalkyl, $C_6$-$C_{10}$ aryl, $NR_{31}R_{32}$, $(NR_{31}R_{32}R_{33})^+$, 4 to 12-membered heterocycloalkyl, or 5- or 6-membered heteroaryl, and $R_{s1}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, $NR_{31}R_{32}$, $(NR_{31}R_{32}R_{33})^+$, $C_3$-$C_8$ cycloalkyl, $C_6$-$C_{10}$ aryl, 4 to 12-membered heterocycloalkyl, and 5- or 6-membered heteroaryl;

each of $R_{10}$, $R_{11}$, $R_{12}$, $R_{13}$ $R_{14}$, and $R_{15}$, independently, is -$Q_2$-$T_2$, in which $Q_2$ is a bond or $C_1$-$C_3$ alkyl linker optionally substituted with one or more of halo, cyano, OH and $C_1$-$C_6$ alkoxy, and $T_2$ is H, halo, OH, $NH_2$, cyano, $NO_2$, $N_3$, $R_{s2}$, or $OR_{s2}$, in which $R_{s2}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl. NHC(O)—$C_1$-$C_6$ alkyl, $NR_{31}R_{32}$, $(NR_{31}R_{32}R_{33})^+$, 4 to 12-membered heterocycloalkyl, or 5- or 6-membered heteroaryl, and $R_{s2}$ is optionally substituted with one or more substituents selected from the group consisting of halo, OH, oxo, $C_1$-$C_6$ alkyl, COOH, C(O)O—$C_1$-$C_6$ alkyl, cyano. $C_1$-$C_6$ alkoxyl, $NR_{31}R_{32}$, $(NR_{31}R_{32}R_{33})^+$, $C_3$-$C_8$ cycloalkyl, $C_6$-$C_{10}$ aryl, 4 to 12-membered heterocycloalkyl, and 5- or 6-membered heteroaryl; or alternatively $R_{12}$ together with $R_{14}$ is oxo, or $R_{13}$ together with $R_{15}$ is oxo, each of $R_{20}$, $R_{21}$, $R_{22}$, and $R_{23}$ independently is -$Q_3$-$T_3$, in which $Q_3$ is a bond or $C_1$-$C_3$ alkyl linker optionally substituted with one or more of halo, cyano, OH and $C_1$-$C_6$ alkoxy, and $T_3$ is H, halo, OH, $NH_2$, cyano, $NO_2$, $N_3$, $R_{S3}$, or $OR_{S3}$, in which $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl. NHC(O)—$C_1$-$C_6$ alkyl, mono-$C_1$-$C_6$ alkylamino, di-$C_1$-$C_6$ alkylamino, 4 to 12-membered heterocycloalkyl, or 5- or 6-membered heteroaryl, and $Rs_3$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_{24}$, $R_{25}$, and $R_{26}$ independently is H or $C_1$-$C_6$ alkyl;

each of $R_{27}$ and $R_{28}$ independently is H or $OR_{29}$; or $R_{27}$ and $R_{28}$ together form O—$R_{30}$—O; each $R_{29}$ independently is H, $C_1$-$C_6$ alkyl, $C_2$-$C_6$ alkenyl, or $C_2$-$C_6$ alkynyl and $R_{29}$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

$R_{30}$ is $C_1$-$C_6$ alkylene optionally substituted with one or more of halo, OH and $C_1$-$C_6$ alkoxyl;

each of $R_{31}$, $R_{32}$, and $R_{33}$, independently is H, $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl;

each of $R_{40}$, $R_{41}$, $R_{42}$, and $R_{43}$ independently is H, halo, OH, cyano, $N_3$, $OP(O)R_{47}R_{48}$, or $C_1$-$C_6$ alkyl optionally substituted with one or more $OP(O)R_{47}R_{48}$, or one $R_{41}$ and one $R_{43}$, together with the carbon atoms to which they are attached and $Q_0$, form $C_4$-$C_{10}$ cycloalkyl, 4- to 14-membered heterocycloalkyl, $C_6$-$C_{10}$ aryl, or 5- to 14-membered heteroaryl, and each of the cycloalkyl, heterocycloalkyl, phenyl, or 5- to 6-membered heteroaryl is optionally substituted with one or more of OH, halo, cyano, $N_3$, oxo, $OP(O)R_{47}R_{48}$, $C_1$-$C_6$ alkyl, $C_1$-$C_6$ haloalkyl, COOH, C(O)O—$C_1$-$C_6$ alkyl, $C_1$-$C_6$ alkoxyl, $C_1$-$C_6$ haloalkoxyl, amino, mono-$C_1$-$C_6$ alkylamino, and di-$C_1$-$C_6$ alkylamino;

$R_{44}$ is H, $C_1$-$C_6$alkyl, or an amine protecting group;

each of $R_{45}$ and $R_{46}$ independently is H, $OP(O)R_{47}R_{48}$, or $C_1$-$C_6$ alkyl optionally substituted with one or more $OP(O)R_{47}R_{48}$, and each of $R_{47}$ and $R_{48}$, independently is H, halo, $C_1$-$C_6$ alkyl, OH, SH, SeH, or $BH_3$.

It should be understood that a cap analog, as provided herein, may include any of the cap analogs described in international publication WO 2017/066797, published on 20 Apr. 2017, incorporated by reference herein in its entirety.

In some embodiments, the $B_2$ middle position can be a non-ribose molecule, such as arabinose.

In some embodiments $R_2$ is ethyl-based.

Thus, in some embodiments, a trinucleotide cap comprises the following structure:

(II)

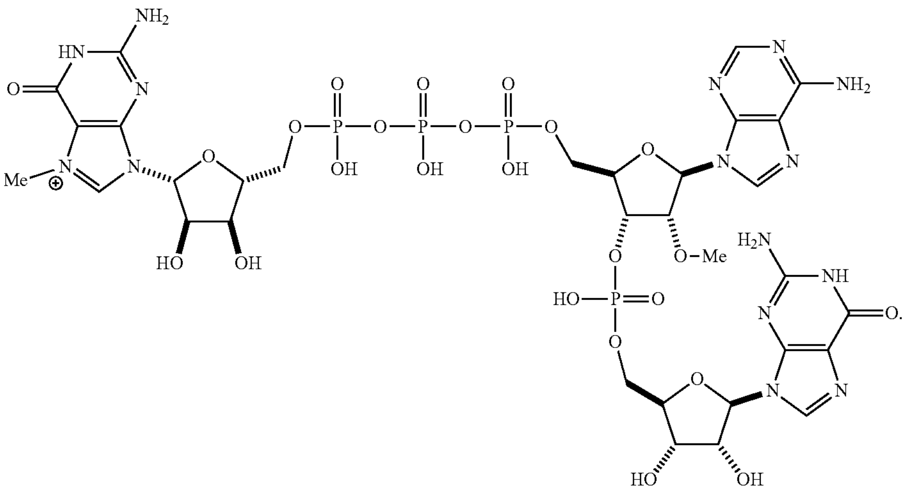

In yet other embodiments, a trinucleotide cap comprises the following structure:

(III)

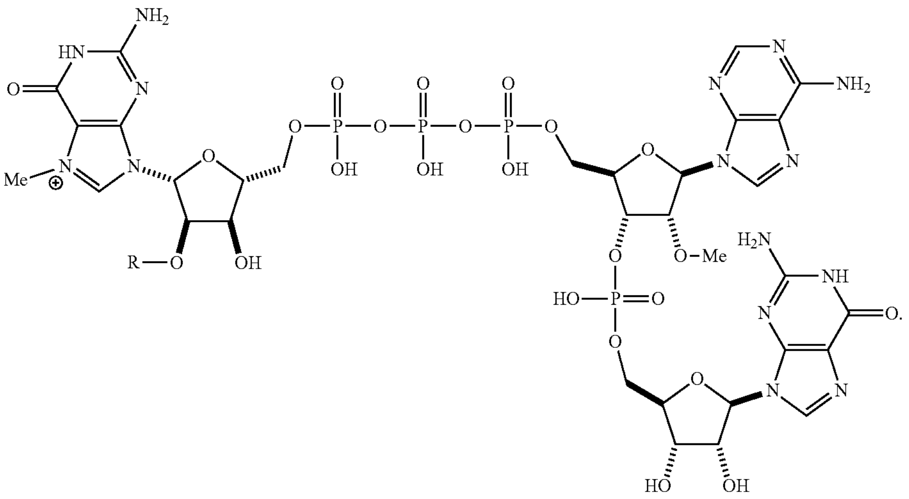

In still other embodiments, a trinucleotide cap comprises the following structure:

(IV)

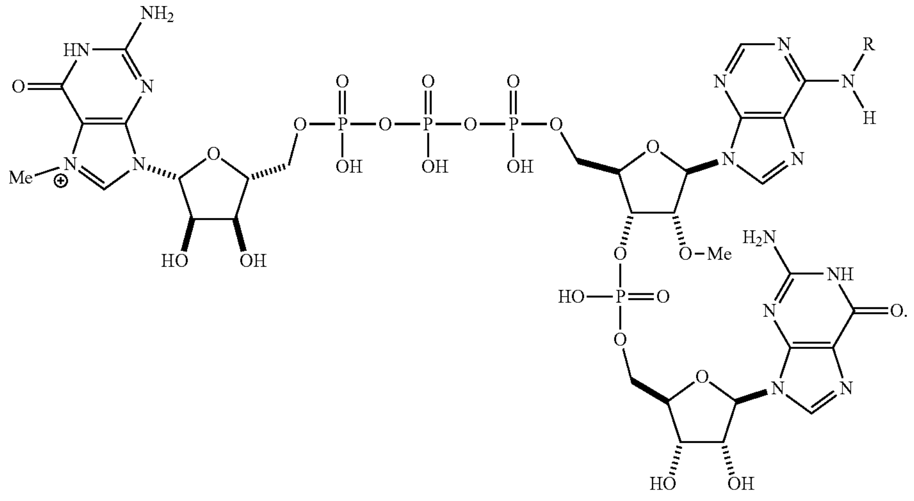

In some embodiments, R is an alkyl (e.g., $C_1$-$C_6$ alkyl). In some embodiments. R is a methyl group (e.g., $C_1$ alkyl). In some embodiments, R is an ethyl group (e.g., $C_2$ alkyl).

A trinucleotide cap, in some embodiments, comprises a sequence selected from the following sequences: GAA, GAC, GAG, GAU, GCA, GCC, GCG, GCU, GGA, GGC, GGGG, GUG, GUA, GUC, GUG, and GUU. In some embodiments, a trinucleotide cap comprises GAA. In some embodiments, a trinucleotide cap comprises GAC. In some embodiments, a trinucleotide cap comprises GAG. In some embodiments, a trinucleotide cap comprises GAU. In some embodiments, a trinucleotide cap comprises GCA. In some embodiments, a trinucleotide cap comprises GCC. In some embodiments, a trinucleotide cap comprises GCG. In some embodiments, a trinucleotide cap comprises GCU. In some embodiments, a trinucleotide cap comprises GGA. In some embodiments, a trinucleotide cap comprises GGC. In some embodiments, a trinucleotide cap comprises GGG. In some embodiments, a trinucleotide cap comprises GGU. In some embodiments, a trinucleotide cap comprises GUA. In some embodiments, a trinucleotide cap comprises GUC. In some embodiments, a trinucleotide cap comprises GUG. In some embodiments, a trinucleotide cap comprises GUU.

In some embodiments, a trinucleotide cap comprises a sequence selected from the following sequences: m$^7$GpppApA, m$^7$GpppApC, m$^7$GpppApG, m$^7$GpppApU, m$^7$GpppCpA, m$^7$GpppCpC, m$^7$GpppCpG, m$^7$GpppCpU, m$^7$GpppGpA, m$^7$GpppGpC, m$^7$GpppGpG, m$^7$GpppGpU, m$^7$GpppUpA, m$^7$GpppUpC, m$^7$GpppUpG, and m$^7$GpppUpU.

In some embodiments, a trinucleotide cap comprises m$^7$GpppApA. In some embodiments, a trinucleotide cap comprises m$^7$GpppApC. In some embodiments, a trinucleotide cap comprises m$^7$GpppApG. In some embodiments, a trinucleotide cap comprises m$^7$GpppApU. In some embodiments, a trinucleotide cap comprises m$^7$GpppCpA. In some embodiments, a trinucleotide cap comprises m$^7$GpppCpC. In some embodiments, a trinucleotide cap comprises m$^7$GpppCpG. In some embodiments, a trinucleotide cap comprises m$^7$GpppCpU. In some embodiments, a trinucleotide cap comprises m$^7$GpppGpA. In some embodiments, a trinucleotide cap comprises m$^7$GpppGpC. In some embodiments, a trinucleotide cap comprises m$^7$GpppGpG. In some embodiments, a trinucleotide cap comprises m$^7$GpppGpU. In some embodiments, a trinucleotide cap comprises m$^7$GpppUpA. In some embodiments, a trinucleotide cap comprises m$^7$GpppUpC. In some embodiments, a trinucleotide cap comprises m$^7$GpppUpG. In some embodiments, a trinucleotide cap comprises m$^7$GpppUpU.

A trinucleotide cap, in some embodiments, comprises a sequence selected from the following sequences: m$^7$G$_{3'OMe}$pppApA, m$^7$G$_{3'OMe}$pppApC, m$^7$G$_{3'OMe}$pppApG, m$^7$G$_{3'OMe}$pppApU, m$^7$G$_{3'OMe}$pppCpA, m$^7$G$_{3'OMe}$pppCpC, m$^7$G$_{3'OMe}$pppCpG, m$^7$G$_{3'OMe}$pppCpU, m$^7$G$_{3'OMe}$pppGpA, m$^7$G$_{3'OMe}$pppGpC, m$^7$G$_{3'OMe}$pppGpG, m$^7$G$_{3'OMe}$pppGpU, m$^7$G$_{3'OMe}$pppUpA, m$^7$G$_{3'OMe}$pppUpC, m$^7$G$_{3'OMe}$pppUpG, and m$^7$G$_{3'OMe}$pppUpU.

In some embodiments, a trinucleotide cap comprises m$^7$G$_{3'OMe}$pppApA. In some embodiments, a trinucleotide cap comprises m$^7$G$_{3'OMe}$pppApC. In some embodiments, a trinucleotide cap comprises m$^7$G$_{3'OMe}$pppApG. In some embodiments, a trinucleotide cap comprises m$^7$G$_{3'OMe}$pppApU. In some embodiments, a trinucleotide cap comprises m$^7$G$_{3'OMe}$pppCpA. In some embodiments, a trinucleotide cap comprises m$^7$G$_{3'OMe}$pppCpC. In some embodiments, a trinucleotide cap comprises m$^7$G$_{3'OMe}$pppCpG. In some embodiments, a trinucleotide cap comprises m$^7$G$_{3'OMe}$pppCpU. In some embodiments, a trinucleotide cap comprises m$^7$G$_{3'OMe}$pppGpA. In some embodiments, a trinucleotide cap comprises m$^7$G$_{3'OMe}$pppGpC. In some embodiments, a trinucleotide cap comprises m$^7$G$_{3'OMe}$pppGpG. In some embodiments, a trinucleotide cap comprises m$^7$G$_{3'OMe}$pppGpU. In some embodiments, a trinucleotide cap comprises m$^7$G$_{3'OMe}$pppUpA. In some embodiments, a trinucleotide cap comprises m$^7$G$_{3'OMe}$pppUpC. In some embodiments, a trinucleotide cap comprises m$^7$G$_{3'OMe}$pppUpG. In some embodiments, a trinucleotide cap comprises m$^7$G$_{3'OMe}$pppUpU.

A trinucleotide cap, in other embodiments, comprises a sequence selected from the following sequences: m$^7$G$_{3'OMe}$pppA$_{2'OMe}$pA, m$^7$G$_{3'OMe}$pppA$_{2'OMe}$pC, m$^7$G$_{3'OMe}$pppA$_{2'OMe}$pG, m$^7$G$_{3'OMe}$pppA$_{2'OMe}$pU, m$^7$G$_{3'OMe}$pppC$_{2'OMe}$pA, m$^7$G$_{3'OMe}$pppC$_{2'OMe}$pC, m$^7$G$_{3'OMe}$pppC$_{2'OMe}$pG, m$^7$G$_{3'OMe}$pppC$_{2'OMe}$pU, m$^7$G$_{3'OMe}$pppG$_{2'OMe}$pA, m$^7$G$_{3'OMe}$pppG$_{2'OMe}$pC, m$^7$G$_{3'OMe}$pppG$_{2'OMe}$pG, m$^7$G$_{3'OMe}$pppG$_{2'OMe}$pU, $m^7G_{3'OMe}pppU_{2'OMe}pA$, $m^7G_{3'OMe}pppU_{2'OMe}pC$, $m^7G_{3'OMe}pppU_{2'OMe}pG$, and $m^7G_{3'OMe}pppU_{2'OMe}pU$.

In some embodiments, a trinucleotide cap comprises $m^7G_{3'OMe}pppA_{2'OMe}pA$. In some embodiments, a trinucleotide cap comprises $m^7G_{3'OMe}pppA_{2'OMe}pC$. In some embodiments, a trinucleotide cap comprises $m^7G_{3'OMe}pppA_{2'OMe}pG$. In some embodiments, a trinucleotide cap comprises $m^7G_{3'OMe}pppA_{2'OMe}pU$. In some embodiments, a trinucleotide cap comprises $m^7G_{3'OMe}pppC_{2'OMe}pA$. In some embodiments, a trinucleotide cap comprises $m^7G_{3'OMe}pppC_{2'OMe}pC$. In some embodiments, a trinucleotide cap comprises $m^7G_{3'OMe}pppC_{2'OMe}pG$. In some embodiments, a trinucleotide cap comprises $m^7G_{3'OMe}pppC_{2'OMe}pU$. In some embodiments, a trinucleotide cap comprises $m^7G_{3'OMe}pppG_{2'OMe}pA$. In some embodiments, a trinucleotide cap comprises $m^7G_{3'OMe}pppG_{2'OMe}pC$. In some embodiments, a trinucleotide cap comprises $m^7G_{3'OMe}pppG_{2'OMe}pG$. In some embodiments, a trinucleotide cap comprises $m^7G_{3'OMe}pppG_{2'OMe}pU$. In some embodiments, a trinucleotide cap comprises $m^7G_{3'OMe}pppU_{2'OMe}pA$. In some embodiments, a trinucleotide cap comprises $m^7G_{3'OMe}pppU_{2'OMe}pC$. In some embodiments, a trinucleotide cap comprises $m^7G_{3'OMe}pppU_{2'OMe}pG$. In some embodiments, a trinucleotide cap comprises $m^7G_{3'OMe}pppU_{2'OMe}pU$.

A trinucleotide cap, in still other embodiments, comprises a sequence selected from the following sequences: $m^7GpppA_{2'OMe}pA$, $m^7GpppA_{2'OMe}pC$, $m^7GpppA_{2'OMe}pG$, $m^7GpppA_{2'OMe}pU$, $m^7GpppC_{2'OMe}pA$, m $GpppC_{2'OMe}pC$, $m^7GpppC_{2'OMe}pG$, $m^7GpppC_{2'OMe}pU$, $m^7GpppG_{2'OMe}pA$, $m^7GpppG_{2'OMe}pC$, $m^7GpppG_{2'OMe}pG$, $m^7GpppG_{2'OMe}pU$, $m^7GpppU_{2'OMe}pA$, $m^7GpppU_{2'OMe}pC$, $m^7GpppU_{2'OMe}pG$, and $m^7GpppU_{2'OMe}pU$.

In some embodiments, a trinucleotide cap comprises $m^7GpppA_{2'OMe}pA$. In some embodiments, a trinucleotide cap comprises $m^7GpppA_{2'OMe}pC$. In some embodiments, a trinucleotide cap comprises $m^7GpppA_{2'OMe}pG$. In some embodiments, a trinucleotide cap comprises $m^7GpppA_{2'OMe}pU$. In some embodiments, a trinucleotide cap comprises $m^7GpppC_{2'OMe}pA$. In some embodiments, a trinucleotide cap comprises $m^7GpppC_{2'OMe}pC$. In some embodiments, a trinucleotide cap comprises $m^7GpppC_{2'OMe}pG$. In some embodiments, a trinucleotide cap comprises $m^7GpppC_{2'OMe}pU$. In some embodiments, a trinucleotide cap comprises $m^7GpppG_{2'OMe}pA$. In some embodiments, a trinucleotide cap comprises $m^7GpppG_{2'OMe}pC$. In some embodiments, a trinucleotide cap comprises $m^7GpppG_{2'OMe}pG$. In some embodiments, a trinucleotide cap comprises $m^7GpppG_{2'OMe}pU$. In some embodiments, a trinucleotide cap comprises $m^7GpppU_{2'OMe}pA$. In some embodiments, a trinucleotide cap comprises $m^7GpppU_{2'OMe}pC$. In some embodiments, a trinucleotide cap comprises $m^7GpppU_{2'OMe}pG$. In some embodiments, a trinucleotide cap comprises $m^7GpppU_{2'OMe}pU$.

In some embodiments, a trinucleotide cap comprises $m^7Gpppm^6A_{2'OMe}pG$. In some embodiments, a trinucleotide cap comprises $m^7Gpppe^6A_{2'OMe}pG$.

In some embodiments, a trinucleotide cap comprises GAG. In some embodiments, a trinucleotide cap comprises GCG. In some embodiments, a trinucleotide cap comprises GUG. In some embodiments, a trinucleotide cap comprises GGG.

In some embodiments, a trinucleotide cap comprises any one of the following structures:

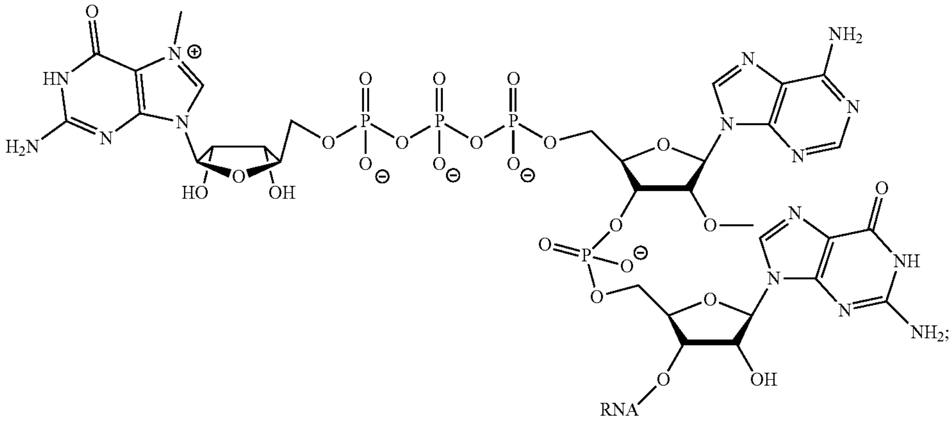

(V)

-continued (VI)

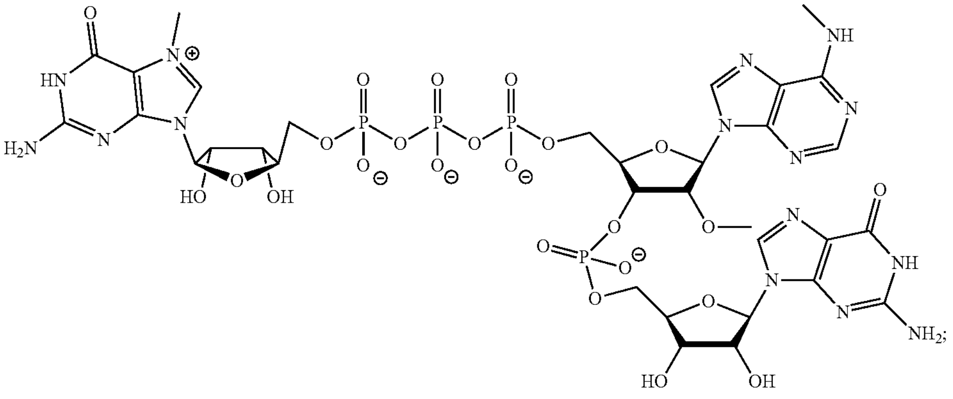

or (VII)

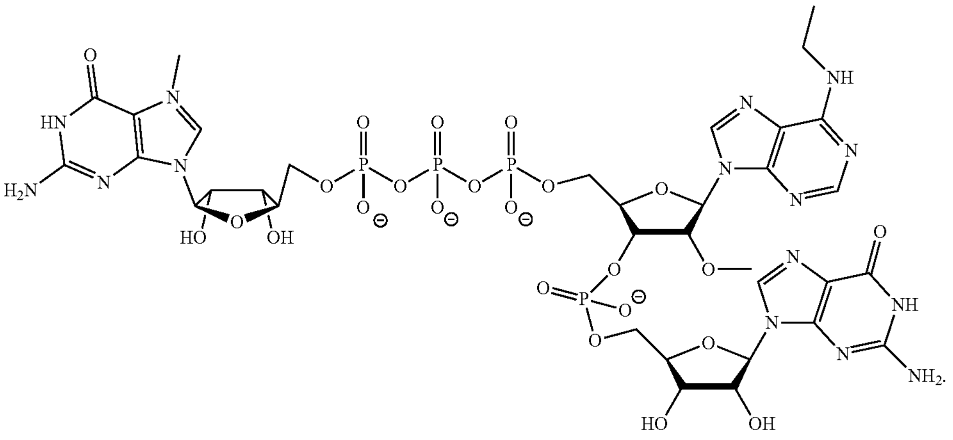

In some embodiments, the cap analog comprises a tetranucleotide cap. In some embodiments, the tetranucleotide cap comprises a trinucleotide as set forth above. In some embodiments, the tetranucleotide cap comprises $^{m7}GpppN_1N_2N_3$, where $N_1$, $N_2$, and $N_3$ are optional (i.e., can be absent or one or more can be present) and are independently a natural, a modified, or an unnatural nucleoside base. In some embodiments, $^{m7}G$ is further methylated, e.g., at the 3' position. In some embodiments, the $^{m7}G$ comprises an O-methyl at the 3' position. In some embodiments $N_1$, $N_2$, and $N_3$ if present, optionally, are independently an adenine, a uracil, a guanidine, a thymine, or a cytosine. In some embodiments, one or more (or all) of $N_1$, $N_2$, and $N_3$, if present, are methylated. e.g., at the 2' position. In some embodiments, one or more (or all) of $N_1$, $N_2$, and $N_3$, if present have an O-methyl at the 2' position.

In some embodiments, the tetranucleotide cap comprises the following structure:

(VIII)

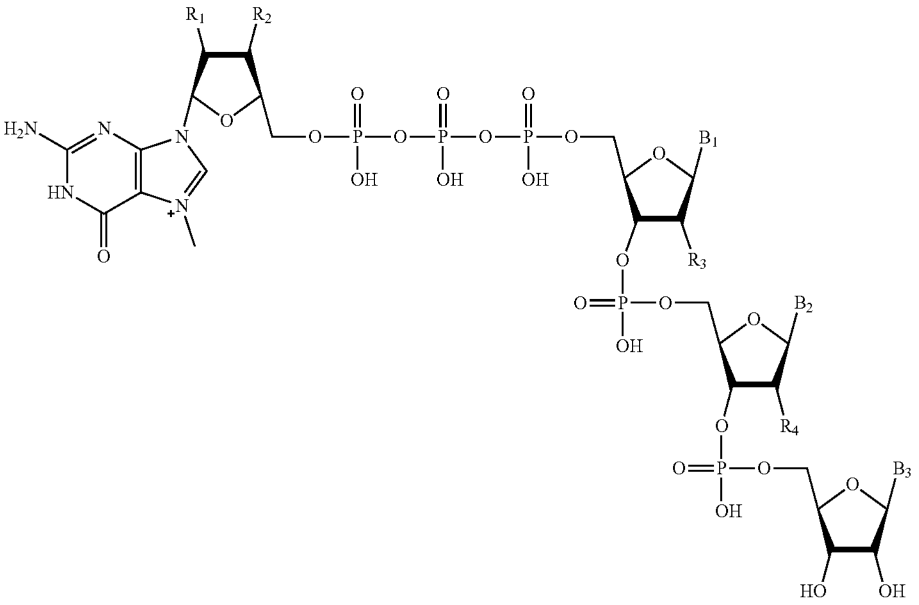

wherein $B_1$, $B_2$, and $B_3$ are independently a natural, a modified, or an unnatural nucleoside based; and $R_1$, $R_2$, $R_3$, and $R_4$, are independently OH or O-methyl. In some embodiments, $R_3$ is O-methyl and $R_4$ is OH. In some embodiments, $R_3$ and $R_4$ are O-methyl. In some embodiments, $R_4$ is O-methyl. In some embodiments, $R_1$ is OH, $R_2$ is OH, $R_3$ is O-methyl, and $R_4$ is OH. In some embodiments, $R_1$ is OH. $R_2$ is OH, $R_3$ is O-methyl and $R_4$ is O-methyl. In some embodiments, at least one of $R_1$ and $R_2$ is O-methyl. $R_3$ is O-methyl, and $R_4$ is OH. In some embodiments, at least one of $R_1$ and $R_2$ is O-methyl, $R_3$ is O-methyl, and $R_4$ is O-methyl.

In some embodiments, $B_1$, $B_3$, and $B_3$ are natural nucleoside bases. In some embodiments, at least one of $B_1$, $B_2$, and $B_3$ is a modified or unnatural base. In some embodiments, at least one of $B_1$, $B_2$, and $B_3$ is $N_6$-methyladenine. In some embodiments, $B_1$ is adenine, cytosine, thymine, or uracil. In some embodiments, $B_1$ is adenine, $B_2$ is uracil, and $B_3$ is adenine. In some embodiments, $R_1$ and $R_2$ are OH, $R_3$ and $R_4$ are O-methyl, $B_1$ is adenine, $B_2$ is uracil, and $B_3$ is adenine.

In some embodiments the tetranucleotide cap comprises a sequence selected from the following sequences: GAAA, GACA, GAGA, GAUA, GCAA, GCCA, GCGA, GCUA, GGAA, GGCA, GGGA, GGUA, GUCA, and GUUA. In some embodiments the tetranucleotide cap comprises a sequence selected from the following sequences: GAAG. GACG, GAGG, GAUG, GCAG, GCCG, GCGG, GCUG, GGAG, GGCG, GGGG, GGUG, GUCG, GUGG, and GUUG. In some embodiments the tetranucleotide cap comprises a sequence selected from the following sequences: GAAU, GACU, GAGU, GAUU, GCAU, GCCU. GCGU, GCUU, GGAU, GGCU, GGGU, GGUU, GUAU, GUCU, GUGU, and GUUU. In some embodiments the tetranucleotide cap comprises a sequence selected from the following sequences: GAAC, GACC, GAGC, GAUC, GCAC, GCCC, GCGC, GCUC, GGAC, GGCC, GGGC, GGUC, GUAC, GUCC, GUGC, and GUUC.

A tetranucleotide cap, in some embodiments, comprises a sequence selected from the following sequences: $m^7G_{3'OMe}pppApApN$, $m^7G_{3'OMe}pppApCpN$, $m^7G_{3'OMe}pppApGpN$, $m^7G_{3'OMe}pppApUpN$, $m^7G_{3'OMe}pppCpApN$, $m^7G_{3'OMe}pppCpCpN$, $m^7G_{3'OMe}pppCpGpN$, $m^7G_{3'OMe}pppCpUpN$, $m^7G_{3'OMe}pppGpApN$, $m^7G_{3'OMe}pppGpCpN$, $m^7G_{3'OMe}pppGpGpN$, $m^7G_{3'OMe}pppGpUpN$, $m^7G_{3'OMe}pppUpApN$, $mG_{3'OMe}pppUpCpN$, $m^7G_{3'OMe}pppUpGpN$, and $m^7G_{3'OMe}pppUpUpN$, where N is a natural, a modified, or an unnatural nucleoside base.

A tetranucleotide cap, in other embodiments, comprises a sequence selected from the following sequences: $m^7G_{3'OMe}pppA_{2'OMe}pApN$, $m^7G_{3'OMe}pppA_{2'OMe}pCpN$, $m^7G_{3'OMe}pppA_{2'OMe}pGpN$, $m^7G_{3'OMe}pppA_{2'OMe}pUpN$, $m^7G_{3'OMe}pppC_{2'OMe}pApN$, $m^7G_{3'OMe}pppC_{2'OMe}pCpN$, $m^7G_{3'OMe}pppC_{2'OMe}pGpN$, $m^7G_{3'OMe}pppC_{2'OMe}pUpN$, $m^7G_{3'OMe}pppG_{2'OMe}pApN$, $m^7G_{3'OMe}pppG_{2'OMe}pCpN$, $m^7G_{3'OMe}pppG_{2'OMe}pGpN$, $m^7G_{3'OMe}pppG_{2'OMe}pUpN$, $m^7G_{3'OMe}pppU_{2'OMe}pApN$, $m^7G_{3'OMe}pppU_{2'OMe}pCpN$, $m^7G_{3'OMe}pppU_{2'OMe}pGpN$, and $m^7G_{3'OMe}pppU_{2'OMe}pUpN$, where N is a natural, a modified, or an unnatural nucleoside base.

A tetranucleotide cap, in still other embodiments, comprises a sequence selected from the following sequences: $m^7GpppA_{2'OMe}pApN$, $m^7GpppA_{2'OMe}pCpN$, $m^7GpppA_{2'OMe}pGpN$, $m^7GpppA_{2'OMe}pUpN$, $m^7GpppC_{2'OMe}pApN$, $m^7GpppC_{2'OMe}pCpN$, $m^7GpppC_{2'OMe}pGpN$, $m^7GpppC_{2'OMe}pUpN$, $m^7GpppG_{2'OMe}pApN$, $m^7GpppG_{2'OMe}pCpN$, $m^7GpppG_{2'OMe}pGpN$, $m^7GpppG_{2'OMe}pUpN$, $m^7GpppU_{2'OMe}pApN$, $m^7GpppU_{2'OMe}pCpN$, $m^7GpppU_{2'OMe}pGpN$, and $m^7GpppU_{2'OMe}pUpN$, where N is a natural, a modified, or an unnatural nucleoside base.

A tetranucleotide cap, in other embodiments, comprises a sequence selected from the following sequences: $m^7G_{3'OMe}pppA_{2'OMe}pA_{2'OMe}pN$, $m^7G_{3'OMe}pppA_{2'OMe}pC_{2'OMe}pN$, $m^7G_{3'OMe}pppA_{2'OMe}pG_{2'OMe}pN$, $m^7G_{3'OMe}pppA_{2'OMe}pU_{2'OMe}pN$, $m^7G_{3'OMe}pppC_{2'OMe}pA_{2'OMe}pN$, $m^7G_{3'OMe}pppC_{2'OMe}pC_{2'OMe}pN$, $m^7G_{3'OMe}pppC_{2'OMe}pG_{2'OMe}pN$, $m^7G_{3'OMe}pppC_{2'OMe}pU_{2'OMe}pN$, $m^7G_{3'OMe}pppG_{2'OMe}pA_{2'OMe}pN$, $m^7G_{3'OMe}pppG_{2'OMe}pC_{2'OMe}pN$, $m^7G_{3'OMe}pppG_{2'OMe}pG_{2'OMe}pN$, $m^7G_{3'OMe}pppG_{2'OMe}pU_{2'OMe}pN$, $m^7G_{3'OMe}pppU_{2'OMe}pA_{2'OMe}pN$, $m^7G_{3'OMe}pppU_{2'OMe}pC_{2'OMe}pN$, $m^7G_{3'OMe}pppU_{2'OMe}pG_{2'OMe}pN$, and $m^7G_{3'OMe}pppU_{2'OMe}pU_{2'OMe}pN$, where N is a natural, a modified, or an unnatural nucleoside base.

A tetranucleotide cap, in still other embodiments, comprises a sequence selected from the following sequences: $m^7GpppA_{2'OMe}pA_{2'OMe}pN$, $m^7GpppA_{2'OMe}pC_{2'OMe}pN$, $m^7GpppA_{2'OMe}pG_{2'OMe}pN$, $m^7GpppA_{2'OMe}pU_{2'OMe}pN$, $m^7GpppC_{2'OMe}pA_{2'OMe}pN$, $m^7GpppC_{2'OMe}pC_{2'OMe}pN$, $m^7GpppC_{2'OMe}pG_{2'OMe}pN$, $m^7GpppC_{2'OMe}pU_{2'OMe}pN$, $m^7GpppG_{2'OMe}pA_{2'OMe}pN$, $m^7GpppG_{2'OMe}pC_{2'OMe}pN$, $m^7GpppG_{2'OMe}pG_{2'OMe}pN$, $m^7GpppG_{2'OMe}pU_{2'OMe}pN$, $m^7GpppU_{2'OMe}pA_{2'OMe}pN$, $m^7GpppU_{2'OMe}pC_{2'OMe}pN$, $m^7GpppU_{2'OMe}pG_{2'OMe}pN$, and $m^7GpppU_{2'OMe}pU_{2'OMe}pN$, where N is a natural, a modified, or an unnatural nucleoside base.

In some embodiments, a tetranucleotide cap comprises GGAG. In some embodiments, a tetranucleotide cap comprises the following structure:

(A) tail may be an essential element with respect to the stability of the individual mRNA.

In some embodiments, a composition comprises an RNA (e.g., mRNA) having an ORF that encodes a signal peptide fused to the expressed polypeptide. Signal peptides, usually comprising the N-terminal 15-60 amino acids of proteins, are typically needed for the translocation across the membrane on the secretory pathway and, thus, universally control the entry of most proteins both in eukaryotes and prokaryotes to the secretory pathway. A signal peptide may have a length of 15-60 amino acids.

In some embodiments, an ORF encoding a polypeptide is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions, insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust (IX)

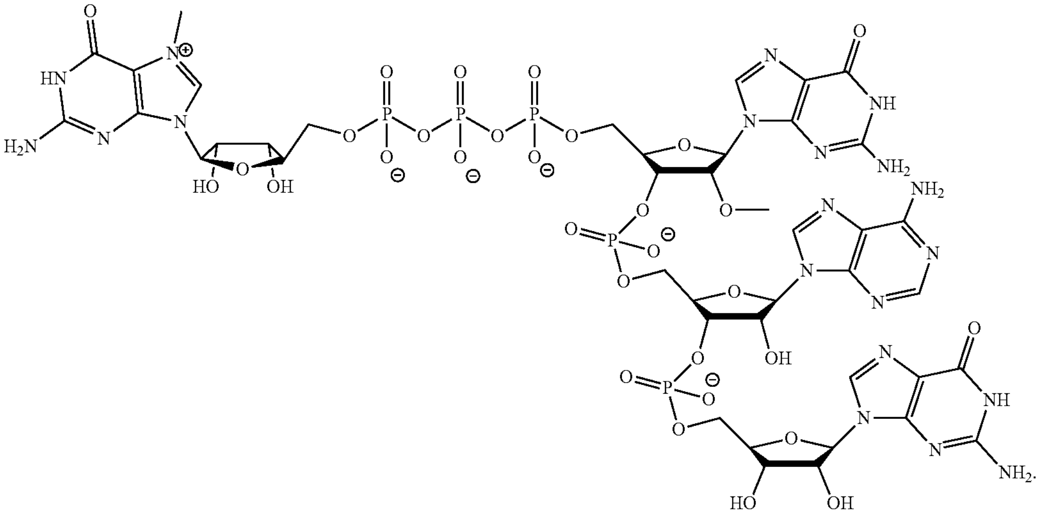

The capping efficiency of a post-transcriptional or co-transcriptional capping reaction may vary. As used herein "capping efficiency" refers to the amount (e.g., expressed as a percentage) of mRNAs comprising a cap structure relative to the total mRNAs in a mixture (e.g., a post-translational capping reaction or a co-transcriptional calling reaction). In some embodiments, the capping efficiency of a capping reaction is at least 60%, 70%, 80%, 90%, 95%, 99%, or 99.9% (e.g., after the capping reaction at least 60%, 70%, 80%, 90%, 95%, 99%, or 99.9% of the input mRNAs comprise a cap). In some embodiments, multivalent co-IVT reactions described herein do not affect the capping efficiency of the mRNAs resulting from the IVT reaction.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, an RNA (e.g., mRNA) is not chemically modified and comprises the standard ribonucleotides consisting of adenosine, guanosine, cytosine and uridine. In some embodiments, nucleotides and nucleosides comprise standard nucleoside residues such as those present in transcribed RNA (e.g. A, G, C, or U). In some embodiments, nucleotides and nucleosides comprise standard deoxyribonucleosides such as those present in DNA (e.g. dA, dG, dC, or dT).

The compositions comprise, in some embodiments, an RNA having an open reading frame encoding a polypeptide, wherein the nucleic acid comprises nucleotides and/or nucleosides that can be standard (unmodified) or modified as is known in the art. In some embodiments, nucleotides and nucleosides comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide is one as is generally known or recognized in the art. Non-limiting examples of such naturally occurring modified nucleotides and nucleotides can be found, inter alia, in the widely recognized MODOMICS database.

Also provided are modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, I-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a mRNA comprises 1-methyl-pseudouridine (m1ψ) substitutions at one or more or all uridine positions of the nucleic acid.

In some embodiments, a mRNA comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, a mRNA comprises pseudouridine (ψ) substitutions at one or more or all uridine positions of the nucleic acid.

In some embodiments, a mRNA comprises pseudouridine (ψ) substitutions at one or more or all uridine positions of the nucleic acid and 5-methyl cytidine substitutions at one or more or all cytidine positions of the nucleic acid.

In some embodiments, a mRNA comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids may be partially or fully modified along the entire length of the molecule. For example, one or more or all or a given type of nucleotide (e.g., purine or pyrimidine, or any one or more or all of A, G, U, C) may be uniformly modified in a nucleic acid, or in a predetermined sequence region thereof (e.g., in the mRNA including or excluding the poly(A) tail). In some embodiments, all nucleotides X in a nucleic acid (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The mRNAs disclosure may comprise one or more regions or parts which act or function as an untranslated region. Where mRNAs are designed to encode at least one polypeptide of interest, the nucleic may comprise one or more of these untranslated regions (UTRs). Wild-type untranslated regions of a nucleic acid are transcribed but not translated. In mRNA, the 5' UTR starts at the transcription start site and continues to the start codon but does not include the start codon; whereas the 3' UTR starts immediately following the stop codon and continues until the transcriptional termination signal. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

According to some aspects, a stabilizing compound (e.g., Formula I' or Formula I, or a tautomer, solvate, or salt thereof) disclosed herein interacts with a nucleic acid. In some embodiments, the compound interacts with a nucleic acid comprised within a lipid nanostructure (e.g., a lipid nanoparticle, liposome, or lipoplex). In some embodiments, the compound intercalates with a nucleic acid. In some embodiments, the compound intercalates with a nucleic acid comprised within a lipid nanostructure. In some embodiments, the compound binds with a nucleic acid. In some embodiments, the compound reversibly binds with a nucleic acid. In some embodiments, the compound binds with a nucleic acid comprised within a lipid nanostructure.

In some embodiments, a stabilizing compound (e.g., a compound of Formula I', Formula I, or Formula II, or a tautomer or solvate thereof) binds with a nucleic acid externally. In some embodiments, a stabilizing compound interacts with a nucleic acid via pi-pi stacking. In some embodiments, a stabilizing compound interacts with the bases a nucleic acid via pi-pi stacking. In some embodiments, a stabilizing compound interacts with a nucleic acid and changes backbone helicity of the nucleic acid. In some embodiments, a stabilizing compound self-associates. In some embodiments, a stabilizing compound self-associates via pi-pi stacking.

In some embodiments, a stabilizing compound (e.g., a compound of Formula I', Formula I, or Formula II, or a tautomer or solvate thereof) has a similar proportion of nucleic acid contacts to self-contacts. In some embodiments, a stabilizing compound has a higher proportion of self-contacts to nucleic acid contacts. In some embodiments, a stabilizing compound binds to nucleic acid ribose contacts or to nucleic acid base contacts. In some embodiments, a stabilizing compound self-associates, binds to nucleic acid ribose contacts, or binds to nucleic acid base contacts. In some embodiments, a stabilizing compound self-associates, binds to nucleic acid ribose contacts, or binds to nucleic acid base contacts preferentially over binding to nucleic acid phosphate contacts. In some embodiments, a stabilizing compound does not substantially bind to nucleic acid phosphate contacts.

In some embodiments, a stabilizing compound (e.g., a compound of Formula I', Formula I, or Formula II, or a tautomer or solvate thereof) is positively charged. In some embodiments, the positive charge contributes to nucleic acid binding.

In some embodiments, a stabilizing compound (e.g., a compound of Formula I', Formula I, or Formula II, or a tautomer or solvate thereof) interacts with a nucleic acid and provides shielding from solvent. In some embodiments, a stabilizing compound shields ribose from water. In some embodiments, a stabilizing compound shields ribose from water more than the compound shields the phosphate groups of a nucleic acid. In some embodiments, a stabilizing compound reduces solvent exposure of ribose. In some embodiments, a stabilizing compound reduces solvent exposure of phosphate groups of a nucleic acid. In some embodiments, a stabilizing compound reduces solvent exposure of ribose more than it reduces the solvent exposure of phosphate groups of a nucleic acid. In some embodiments, the solvent exposure is measured by the solvent accessible surface area (SASA). In some embodiments, a stabilizing compound decreases the solvent accessible area of ribose to about 5-10 $nm^2$. In some embodiments, a stabilizing compound decreases the solvent accessible area of ribose to about 6-8 $nm^2$. In some embodiments, a stabilizing compound decreases the solvent accessible area of phosphate to about 9-12 $nm^2$. In some embodiments, a stabilizing compound decreases the solvent accessible area of phosphate to about 10-11 $nm^2$.

In some embodiments, a stabilizing compound (e.g., Formula I' or Formula I, or a tautomer, solvate, or salt thereof) interacts with a nucleic acid (e.g., an mRNA) with a binding affinity defined by a particular equilibrium dissociation constant. In some embodiments, the equilibrium dissociation constant is less than $10^{-3}$ M (e.g., less than $10^{-4}$ M, less than $10^{-5}$ M, less than $10^{-5}$ M, less than $10^{-7}$ M, less than $10^{-8}$ M, or less than $10^{-9}$ M). In some embodiments, the equilibrium dissociation constant is between $10^{-3}$ M and $10^{-4}$ M, between $10^{-3}$ M and $10^{-5}$ M, between $10^{-3}$ M and $10^{-6}$ M, between $10^{-3}$ M and $10^{-7}$ M, between $10^{-3}$ M and $10^{-8}$ M, between $10^{-3}$ M and $10^{-9}$ M, between $10^{-3}$ M and $10^{-10}$ M, between $10^{-4}$ M and $10^{-5}$ M, between $10^{-4}$ M and $10^{-6}$ M, between $10^{-4}$ M and $10^{-7}$ M, between $10^{-4}$ M and $10^{-8}$ M, between $10^{-4}$ M and $10^{-9}$ M, between $10^{-4}$ M and $10^{-10}$ M, between $10^{-5}$ M and $10^{-6}$ M, between $10^{-5}$ M and $10^{-7}$ M, between $10^{-5}$ M and $10^{-8}$ M, between $10^{-5}$ M and $10^{-9}$ M, between $10^{-5}$ M and $10^{-10}$ M, between $10^{-6}$ M and $10^{-7}$ M, between $10^{-6}$ M and $10^{-8}$ M, between $10^{-6}$ M and $10^{-9}$ M, between $10^{-6}$ M and $10^{-10}$ M, between $10^{-7}$ M and $10^{-8}$ M, between $10^{-7}$ M and $10^{-9}$ M, between $10^{-7}$ M and $10^{-10}$ M, between $10^{-8}$ M and $10^{-9}$ M, between $10^{-8}$ M and $10^{-10}$ M, or between $10^{-9}$ M and $10^{-10}$ M. In some embodiments, the equilibrium dissociation constant is between $10^{-3}$ M and $10^{-4}$ M or between $10^{-3}$ M and $10^{-5}$ M.

mRNA molecules that are conformationally stabilized by compounds provided herein can exhibit thermal unfolding temperatures (measured by circular dichroism or DSC, for example) that are higher than in the absence of such stabilizing compound. In some embodiments, a stabilizing compound (e.g., Formula I' or Formula I, or a tautomer, solvate, or salt thereof) confers increased stability to a nucleic acid (e.g., an mRNA) in a folded structure. In some embodiments, the compound confers increased stability to a folded structure of a nucleic acid (e.g., an mRNA) relative to its unfolded or less folded (i.e., more linear) form. Changes in stability of a folded structure of a nucleic acid can be identified by one of ordinary skill in the art, for example, by circular dichroism. Such changes in stability of a folded structure may, for example, result in changes in the amplitude of peaks in circular dichroism spectra. In some embodiments, the compound enhances the thermal stability of a nucleic acid (e.g., an mRNA) in a folded state. Changes in thermal stability of a folded state of a nucleic acid can be identified by one of ordinary skill in the art, for example, by differential scanning calorimetry. Such changes in thermal stability may, for example, result in shifts of differential scanning calorimetry thermograms.

In some embodiments, a stabilizing compound (e.g., Formula I' or Formula I, or a tautomer, solvate, or salt thereof) causes compaction of a nucleic acid molecule (e.g., an mRNA) upon interacting with the nucleic acid molecule. In some embodiments, the compound causes a decrease in the hydrodynamic radius of a nucleic acid molecule (e.g. an mRNA) upon interaction with the nucleic acid molecule. In some embodiments, the compound causes compaction or a decrease in the hydrodynamic radius of a nucleic acid molecule by 5%, 10%, 15%, 20%, 25%, 30%, 35%, 40%, 45%, 50%, 55%, 60%, or more. In some embodiments, the compound causes compaction or a decrease in the hydrodynamic radius of a nucleic acid molecule when the compound is in a concentration of 1 μM, 2 M, 3 M, 4 μM, 5 μM, 6 μM, 7 μM 8 μM, 9 μM, 10 μM, 15 μM, 20 μM 25 μM, 30 μM, 35 μM 40 μM, 45 μM, 50 μM 60 μM, 70 μM, 80 μM 90 μM, or 100 μM. In some embodiments, the compound causes compaction or a decrease in the hydrodynamic radius of a nucleic acid molecule when the compound is in a concentration of 10 μM. In some embodiments, the compound causes compaction of a nucleic acid molecule (e.g., an mRNA) within a lipid nanostructure (e.g., a lipid nanoparticle, liposome, or lipoplex) disclosed herein. In some embodiments, the compound causes compaction of a nucleic acid molecule within a lipid nanostructure without changing the size of the lipid nanostructure. Compaction of a nucleic acid molecule or a decrease in its hydrodynamic radius can be measured by one of ordinary skill in the art, for example, via dynamic light scattering or transmission electron microscopy measurements. However, such compaction cannot be directly measured within a lipid nanoparticle.

Lipid Nanoparticle Formulations

A lipid nanoparticle (LNP) refers to a nanoscale construct (e.g., a nanoparticle, typically less than 100 nm in diameter) comprising lipid molecules arranged in a substantially spherical (e.g., spheroid) geometry, sometimes encapsulating one or more additional molecular species. In some embodiments, the LNP contains a bleb region, e.g., as described in Brader et al., Biophysical Journal 120: 1-5 (2021). A LNP may comprise or one or more types of lipids, including but not limited to amino lipids (e.g., ionizable amino lipids), neutral lipids, non-cationic lipids, charged lipids, PEG-modified lipids, phospholipids, structural lipids and sterols. In some embodiments, a LNP may further comprise one or more cargo molecules, including but not limited to nucleic acids (e.g., mRNA, plasmid DNA, DNA or RNA oligonucleotides, siRNA, shRNA, snRNA, snoRNA, lncRNA, etc.), small molecules, proteins and peptides. A LNP may have a unilamellar structure (i.e., having a single lipid layer or lipid bilayer surrounding a central region) or a multilamellar structure (i.e., having more than one lipid layer or lipid bilayer surrounding a central region). In some embodiments, a lipid nanoparticle may be a liposome. A liposome is a nanoparticle comprising lipids arranged into one or more concentric lipid bilayers around a central region. The central region of a liposome may comprise an aqueous solution, suspension, or other aqueous composition.

In some embodiments, nucleic acids are formulated as lipid nanoparticle (LNP) compositions. Lipid nanoparticles typically comprise amino lipid, phospholipid, structural lipid and PEG lipid components along with the nucleic acid cargo of interest. The lipid nanoparticles can be generated using components, compositions, and methods as are generally known in the art, see for example PCT/US2016/052352; PCT/US2016/068300; PCT/US2017/037551; PCT/US2015/027400; PCT/US2016/047406; PCT/US2016/000129; PCT/US2016/014280; PCT/US2017/038426; PCT/US2014/027077; PCT/US2014/055394; PCT/US2016/052117; PCT/US2012/06%10; PCT/US2017/027492; PCT/US2016/059575; PCT/US2016/069491; PCT/US2016/069493; and PCT/US2014/066242, all of which are incorporated by reference herein in their entirety.

In some embodiments, a LNP comprises an N:P ratio of from about 2:1 to about 30:1.

In some embodiments, a LNP comprises an N:P ratio of about 6:1.

In some embodiments, a LNP comprises an N:P ratio of about 3:1, 4:1, or 5:1.

In some embodiments, a LNP comprises a wt/wt ratio of the ionizable amino lipid component to the RNA of from about 10:1 to about 100:1.

In some embodiments, a LNP comprises a wt/wt ratio of the ionizable amino lipid component to the RNA of about 20:1.

In some embodiments, a LNP comprises a wt/wt ratio of the ionizable amino lipid component to the RNA of about 10:1.

In some embodiments, a LNP has a mean diameter from about 30 nm to about 150 nm.

In some embodiments, a LNP has a mean diameter from about 60 nm to about 120 nm.

In some embodiments, the lipid nanoparticle has a diameter of at most 80 nm, at most 70 nm, at most 60 nm, at most 50 nm, at most 40 nm, at most 30 nm, or at most 20 nm.

In some embodiments, the lipid nanoparticle has a diameter of at most 30 nm.

In some embodiments, the lipid nanoparticle has a diameter of at most 20 nm.

In some embodiments, the LNPs have one or more regions having a lamellar structure. In some embodiments, the lamellar structure diminishes with increasing temperature in the absence of stabilizer. In some embodiments, the LNP size increases with increasing time in the absence of stabilizer. In some embodiments, the LNP size increases with diminished lamellar structure in the absence of stabilizer. In some embodiments, loss of lamellar structure is not reversible in the absence of stabilizer. In some embodiments, loss of lamellar structure is not reversible at higher temperatures (e.g., 40° C.) in the absence of stabilizer.

In some embodiments, the lamellar structure diminishes with increasing temperature in the presence of stabilizer. In some embodiments, the lamellar structure is preserved at low temperature in the presence of stabilizer. In some embodiments, the lamellar structure is preserved at 5° C. in the presence of stabilizer.

In some embodiments, a lipid nanoparticle may comprise two or more components (e.g., amino lipid and nucleic acid, PEG-lipid, phospholipid, structural lipid). For instance, a lipid nanoparticle may comprise an amino lipid and a nucleic acid. Compositions comprising the lipid nanoparticles may be used for a wide variety of applications, including the stealth delivery of therapeutic payloads with minimal adverse innate immune response.

Ionizable Amino Lipids

In some embodiments, the lipid nanoparticles comprise one or more of ionizable molecules, polynucleotides, and optional components, such as structural lipids, sterols, neutral lipids, phospholipids and a molecule capable of reducing particle aggregation (e.g., polyethylene glycol (PEG), PEG-modified lipid), such as those described above.

In some embodiments, a LNP described herein may include one or more ionizable molecules (e.g., amino lipids or ionizable lipids). The ionizable molecule may comprise a charged group and may have a certain pKa. In certain embodiments, the pKa of the ionizable molecule may be greater than or equal to about 6, greater than or equal to about 6.2, greater than or equal to about 6.5, greater than or equal to about 6.8, greater than or equal to about 7, greater than or equal to about 7.2, greater than or equal to about 7.5, greater than or equal to about 7.8, greater than or equal to about 8. In some embodiments, the pKa of the ionizable molecule may be less than or equal to about 10, less than or equal to about 9.8, less than or equal to about 9.5, less than or equal to about 9.2, less than or equal to about 9.0, less than or equal to about 8.8, or less than or equal to about 8.5. Combinations of the above referenced ranges are also possible (e.g., greater than or equal to 6 and less than or equal to about 8.5). Other ranges are also possible. In embodiments in which more than one type of ionizable molecule are present in a particle, each type of ionizable molecule may independently have a pKa in one or more of the ranges described above.

In general, an ionizable molecule comprises one or more charged groups. In some embodiments, an ionizable molecule may be positively charged or negatively charged. For instance, an ionizable molecule may be positively charged. For example, an ionizable molecule may comprise an amine group. As used herein, the term "ionizable molecule" has its ordinary meaning in the art and may refer to a molecule or matrix comprising one or more charged moiety. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule and/or matrix may be selected as desired.

In some cases, an ionizable molecule (e.g., an amino lipid or ionizable lipid) may include one or more precursor moieties that can be converted to charged moieties. For instance, the ionizable molecule may include a neutral moiety that can be hydrolyzed to form a charged moiety, such as those described above. As a non-limiting specific example, the molecule or matrix may include an amide, which can be hydrolyzed to form an amine, respectively. Those of ordinary skill in the art will be able to determine whether a given chemical moiety carries a formal electronic charge (for example, by inspection, pH titration, ionic conductivity measurements, etc.), and/or whether a given chemical moiety can be reacted (e.g., hydrolyzed) to form a chemical moiety that carries a formal electronic charge.

The ionizable molecule (e.g., amino lipid or ionizable lipid) may have any suitable molecular weight. In certain embodiments, the molecular weight of an ionizable molecule is less than or equal to about 2,500 g/mol, less than or equal to about 2,000 g/mol, less than or equal to about 1,500 g/mol, less than or equal to about 1,250 g/mol, less than or equal to about 1,000 g/mol, less than or equal to about 900 g/mol, less than or equal to about 800 g/mol, less than or equal to about 700 g/mol, less than or equal to about 600 g/mol, less than or equal to about 500 g/mol, less than or equal to about 400 g/mol, less than or equal to about 300 g/mol, less than or equal to about 200 g/mol, or less than or equal to about 100 g/mol. In some instances, the molecular weight of an ionizable molecule is greater than or equal to about 100 g/mol, greater than or equal to about 200 g/mol, greater than or equal to about 300 g/mol, greater than or equal to about 400 g/mol, greater than or equal to about 500 g/mol, greater than or equal to about 600 g/mol, greater than or equal to about 700 g/mol, greater than or equal to about 1000 g/mol, greater than or equal to about 1,250 g/mol, greater than or equal to about 1,500 g/mol, greater than or equal to about 1,750 g/mol, greater than or equal to about 2,000 g/mol, or greater than or equal to about 2,250 g/mol. Combinations of the above ranges (e.g., at least about 200 g/mol and less than or equal to about 2,500 g/mol) are also possible. In embodiments in which more than one type of ionizable molecules are present in a particle, each type of ionizable molecule may independently have a molecular weight in one or more of the ranges described above.

In some embodiments, the percentage (e.g., by weight, or by mole) of a single type of ionizable molecule (e.g., amino lipid or ionizable lipid) and/or of all the ionizable molecules within a particle may be greater than or equal to about 15%, greater than or equal to about 16%, greater than or equal to about 17%, greater than or equal to about 18%, greater than or equal to about 19%, greater than or equal to about 20%, greater than or equal to about 21%, greater than or equal to about 22%, greater than or equal to about 23%, greater than or equal to about 24%, greater than or equal to about 25%, greater than or equal to about 30%, greater than or equal to about 35%, greater than or equal to about 40%, greater than or equal to about 42%, greater than or equal to about 45%, greater than or equal to about 48%, greater than or equal to about 50%, greater than or equal to about 52%, greater than or equal to about 55%, greater than or equal to about 58%, greater than or equal to about 60%, greater than or equal to about 62%, greater than or equal to about 65%, or greater than or equal to about 68%. In some instances, the percentage (e.g., by weight, or by mole) may be less than or equal to about 70%, less than or equal to about 68%, less than or equal to about 65%, less than or equal to about 62%, less than or equal to about 60%, less than or equal to about 58%, less than or equal to about 55%, less than or equal to about 52%, less than or equal to about 50%, or less than or equal to about 48%. Combinations of the above referenced ranges are also possible (e.g., greater than or equal to 20% and less than or equal to about 60%, greater than or equal to 40% and less than or equal to about 55%, etc.). In embodiments in which more than one type of ionizable molecule is present in a particle, each type of ionizable molecule may independently have a percentage (e.g., by weight, or by mole) in one or more of the ranges described above. The percentage (e.g., by weight, or by mole) may be determined by extracting the ionizable molecule(s) from the dried particles using, e.g., organic solvents, and measuring the quantity of the agent using high pressure liquid chromatography (i.e., HPLC), liquid chromatography-mass spectrometry (LC-MS), nuclear magnetic resonance (NMR), or mass spectrometry (MS). Those of ordinary skill in the art would be knowledgeable of techniques to determine the quantity of a component using the above-referenced techniques. For example, HPLC may be used to quantify the amount of a component, by, e.g., comparing the area under the curve of a HPLC chromatogram to a standard curve.

It should be understood that the terms "charged" or "charged moiety" does not refer to a "partial negative charge" or "partial positive charge" on a molecule. The terms "partial negative charge" and "partial positive charge" are given their ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the lipid nanoparticle comprises at least one ionizable amino lipid, at least one non-cationic lipid, at least one sterol, and/or at least one polyethylene glycol (PEG)-modified lipid.

In some embodiments, the lipid nanoparticle comprises 40-50 mol % ionizable lipid, optionally 45-50 mol %, for example, 45-46 mol %, 46-47 mol %, 47-48 mol %, 48-49 mol %, or 49-50 mol % for example about 45 mol %, 45.5 mol %, 46 mol %, 46.5 mol %, 47 mol %, 47.5 mol %, 48 mol %, 48.5 mol %, 49 mol %, or 49.5 mol %.

In some embodiments, the lipid nanoparticle comprises 20-60 mol % ionizable amino lipid. For example, the lipid nanoparticle may comprise 20-50 mol %, 20-40 mol %, 20-30 mol %, 30-60 mol %, 30-50 mol %, 30-40 mol %, 40-60 mol %, 40-50 mol %, or 50-60 mol % ionizable amino lipid. In some embodiments, the lipid nanoparticle comprises 20 mol %, 30 mol %, 40 mol %, 50 mol %, or 60 mol % ionizable amino lipid. In some embodiments, the lipid nanoparticle comprises 35 mol %, 36 mol %, 37 mol %, 38 mol %, 39 mol %, 40 mol %, 41 mol %, 42 mol %, 43 mol %, 44 mol %, 45 mol %, 46 mol %, 47 mol %, 48 mol %, 49 mol %, 50 mol %, 51 mol %, 52 mol %, 53 mol %, 54 mol %, or 55 mol % ionizable amino lipid.

In some embodiments, the lipid nanoparticle comprises 45-55 mole percent (mol %) ionizable amino lipid. For example, lipid nanoparticle may comprise 45, 46, 47, 48, 49, 50, 51, 52, 53, 54, or 55 mol % ionizable amino lipid.

In some embodiments, the ionizable amino lipid is a compound of Formula (AI):

(AI)

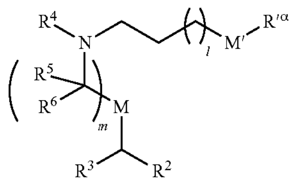

or its N-oxide, or a salt or isomer thereof, wherein $R'^{a}$ is $R'^{branched}$; wherein $R'^{branched}$ is:

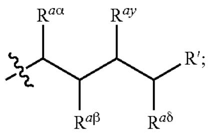

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$, wherein n is selected from the group consisting of 1, 2, 3, 4, and 5, and

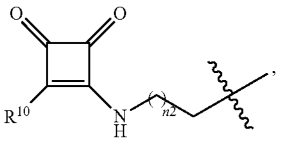

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments of the compounds of Formula (AI), $R'^{a}$ is $R'^{branched}$; $R'^{branched}$ is

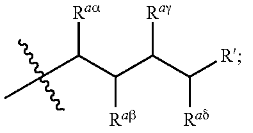

denotes a point of attachment; $R^{a\alpha}$, $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; l is 5; and m is 7.

In some embodiments of the compounds of Formula (AI), $R'^{a}$ is $R'^{branched}$; $R'^{branched}$ is

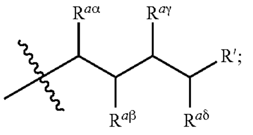

denotes a point of attachment; $R^{a\alpha}$, $R^{a\beta}$, $R^{a\gamma}$, and $R^{a\delta}$ are each H; $R^2$ and $R_3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; l is 3; and m is 7.

In some embodiments of the compounds of Formula (AI), $R'^{a}$ is $R'^{branched}$; $R'^{branched}$ is

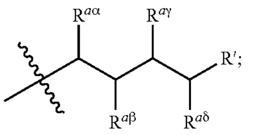

denotes a point of attachment; $R^{a\alpha}$ is $C_{2-12}$ alkyl; $R^{a\beta}$, $R^{a\gamma}$, and $R^{a\delta}$ are each H; $R^2$ and $R^3$ are each $C_{1-14}$ alkyl; $R^4$ is

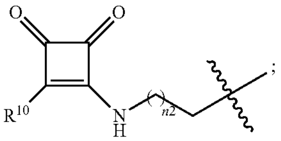

$R^{10}$NH($C^{1-6}$ alkyl); n2 is 2; $R^5$ is H; each $R^6$ is H; M and M' are each —C(O)O—; R' is a $C_{1-12}$ alkyl; l is 5; and m is 7.

In some embodiments of the compounds of Formula (I), $R'^{a}$ is $R'^{branched}$; $R'^{branched}$ is

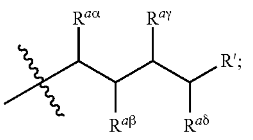

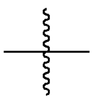

denotes a point of attachment; $R^{a\alpha}$, $R^{a\beta}$, and $R^{a\delta}$ are each H; $R^{a\gamma}$ is $C_{2-12}$ alkyl; $R^2$ and $R^3$ are each $C_{1-14}$ alkyl; $R^4$ is $—(CH_2)_nOH$; n is 2, each $R^5$ is H; each $R^6$ is H; M and M' are each —C(O)O—; R' is a $C_{1-12}$ alkyl; l is 5; and m is 7.

In some embodiments, the compound of Formula (I) is selected from:

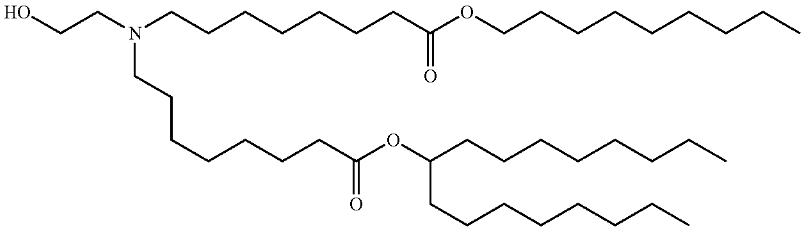

,

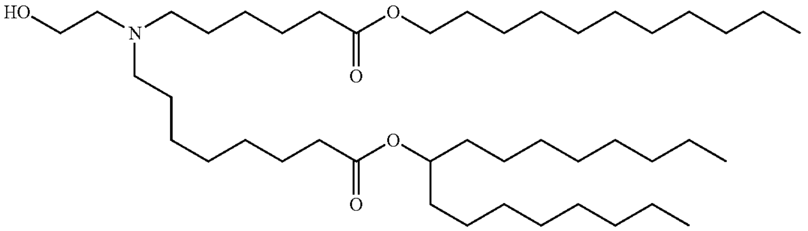

,

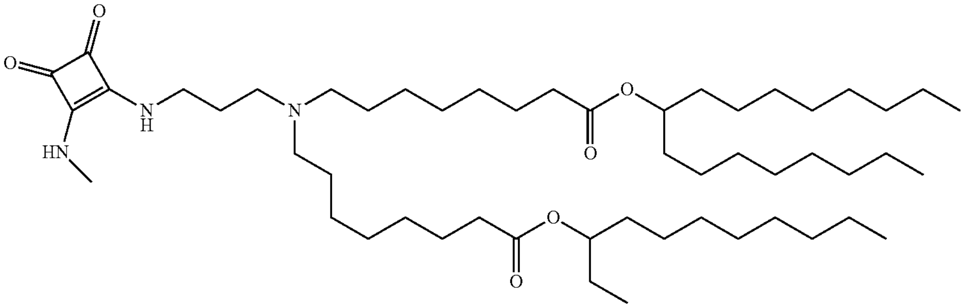

, and

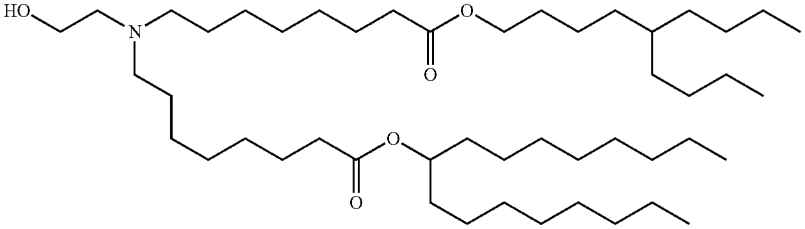

.

In some embodiments, the ionizable amino lipid is a compound of Formula (AIa):

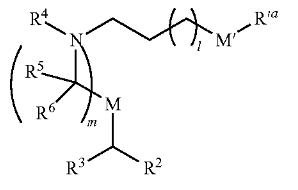

(AIa) or its N-oxide, or a salt or isomer thereof, wherein $R'^{a}$ is $R'^{branched}$; wherein $R'^{branched}$ is:

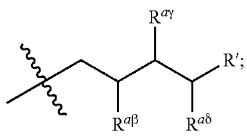

;

wherein

denotes a point of attachment;

wherein $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

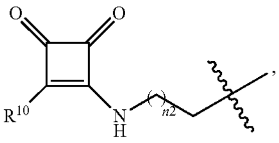

, wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments, the ionizable amino lipid is a compound of Formula (AIb):

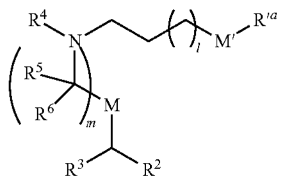

(AIb) or its N-oxide, or a salt or isomer thereof, wherein $R'^{a}$ is $R'^{branched}$; wherein $R'^{branched}$ is:

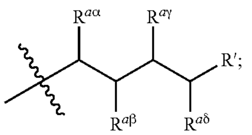

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is $-(CH_2)_nOH$, wherein n is selected from the group consisting of 1, 2, 3, 4, and 5;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments of Formula (AI) or (AIb), $R'^{a}$ is $R'^{branched}$; $R'^{branched}$ is

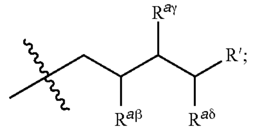 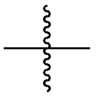

denotes a point of attachment; $R^{a\beta}$, $R^{a\gamma}$, and $R^{a\delta}$ are each H; $R^2$ and $R^3$ are each $C_{1-14}$ alkyl; $R^4$ is $-(CH_2)_nOH$; n is 2; each $R^5$ is H; each $R^6$ is H; M and M' are each —C(O)O—; R' is a $C_{1-12}$ alkyl; l is 5; and m is 7.

In some embodiments of Formula (AI) or (AIb), $R'^{a}$ is $R'^{branched}$; $R'^{branched}$ is

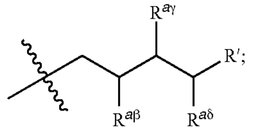 

denotes a point of attachment, $R^{a\beta}$, $R^{a\gamma}$, and $R^{a\delta}$ are each H; $R^2$ and $R^3$ are each $C_{1-14}$ alkyl; $R^4$ is $-(CH_2)_nOH$; n is 2; each $R^5$ is H; each $R^6$ is H; M and M' are each $-C_2(O)O-$; R' is a $C_{1-12}$ alkyl; l is 3; and m is 7.

In some embodiments of Formula (AI) or (AIb), $R'^{a}$ is $R'^{branched}$; $R'^{branched}$ is

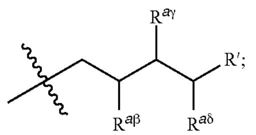 

denotes a point of attachment; $R^{a\beta}$ and $R^{a\delta}$ are each H; $R^{a\gamma}$ is $C_{2-12}$ alkyl; $R^2$ and $R^3$ are each $C_{1-14}$ alkyl; $R^4$ is $-(CH_2)_nOH$; n is 2; each $R^5$ is H; each $R^6$ is H; M and M' are each —C(O)O—; R' is a $C_{1-12}$ alkyl; l is 5; and m is 7.

In some embodiments the ionizable amino lipid is a compound of Formula (AIc):

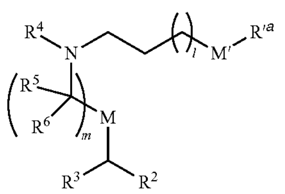

or its N-oxide, or a salt or isomer thereof, wherein $R'^{a}$ is $R'^{branched}$; wherein $R'^{branched}$ is:

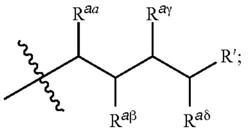

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is

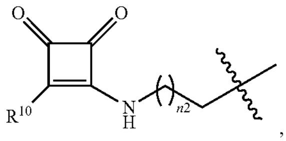, wherein

denotes a point of attachment; wherein $R^{10}$ is $N(R)_2$; each R is independently selected from the group consisting of $C_{1-6}$ alkyl, $C_{2-3}$ alkenyl, and H; n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments, $R'^{a}$ is $R'^{branched}$; $R'^{branched}$ is

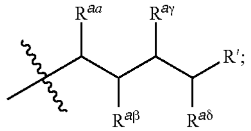 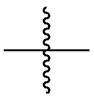

denotes a point of attachment; $R^{a\beta}$, $R^{a\gamma}$, and $R^{a\delta}$ are each H; $R^{a\alpha}$ is $C_{2-12}$ alkyl; $R^2$ and $R^3$ are each $C_{1-14}$ alkyl; $R^4$ is

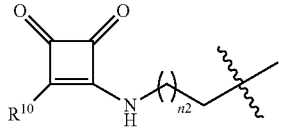; 

denotes a point of attachment; $R^{10}$ is NH($C_{1-6}$ alkyl); n2 is 2; each $R^5$ is H; each $R^6$ is H; M and M' are each —C(O)O—; R' is a $C_{1-12}$ alkyl; l is 5; and m is 7.

In some embodiments, the compound of Formula (AIc) is:

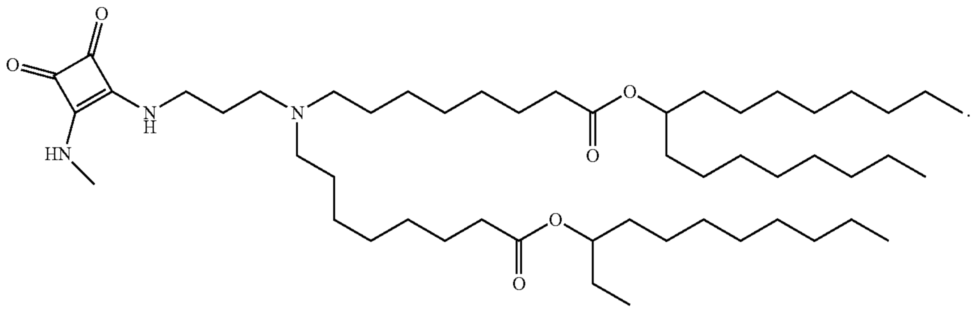 [SMILES: CCCCCCCCC(CC)OC(=O)CCCCCCCN(CCCCCCCC(=O)OC(CCCCCCCC)CCCCCCCC)CCCNc1c(NC)c(=O)c1=O].

In some embodiments, the ionizable amino lipid is a compound of Formula (AII):

(AII)

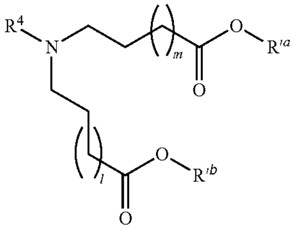

or its N-oxide, or a salt or isomer thereof, wherein $R'^{a}$ is $R'^{branched}$ or $R'^{cyclic}$; wherein $R'^{branched}$ is:

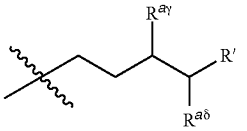

and $R'^{cyclic}$ is:

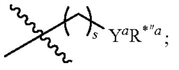

and $R'^{branched}$ is:

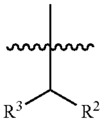

or

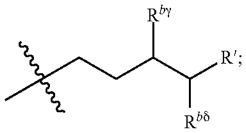

wherein

denotes a point of attachment;

$R^{a\gamma}$ and $R^{a\delta}$ are each independently selected from the group consisting of H, $C_{1-12}$ alkyl, and $C_{2-12}$ alkenyl, wherein at least one of $R^{a\gamma}$ and $R^{a\delta}$ is selected from the group consisting of $C_{1-12}$ alkyl and $C_{2-12}$ alkenyl;

$R^{b\gamma}$ and $R^{b\delta}$ are each independently selected from the group consisting of H, $C_{1-12}$ alkyl, and $C_{2-12}$ alkenyl, wherein at least one of $R^{b\gamma}$ and $R^{b\delta}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

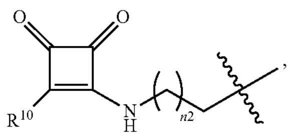, wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

$Y^a$ is a $C_{3-6}$ carbocycle;

$R^{*''a}$ is selected from the group consisting of $C_{1-15}$ alkyl and $C_{2-15}$ alkenyl; and s is 2 or 3;

m is selected from 1, 2, 3, 4, 5, 6, 7, 8, and 9;

l is selected from 1, 2, 3, 4, 5, 6, 7, 8, and 9.

In some embodiments, the ionizable amino lipid is a compound of Formula (AII-a):

(AII-a)

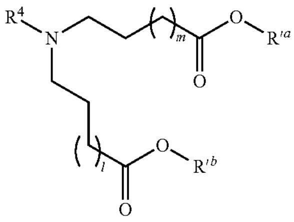

or its N-oxide, or a salt or isomer thereof, wherein $R'^{a}$ is $R'^{branched}$ or $R'^{cyclic}$; wherein $R'^{branched}$ is:

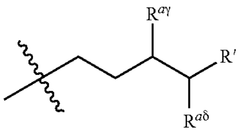

and $R'^{b}$ is:

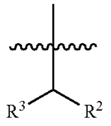

or

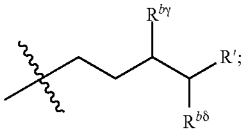

wherein

denotes a point of attachment;

$R^{a\gamma}$ and $R^{a\delta}$ are each independently selected from the group consisting of H, $C_{1-12}$ alkyl, and $C_{2-12}$ alkenyl, wherein at least one of $R^{a\gamma}$ and $R^{a\delta}$ is selected from the group consisting of $C_{1-12}$ alkyl and $C_{2-12}$ alkenyl;

$R^{b\gamma}$ and $R^{b\delta}$ are each independently selected from the group consisting of H, $C_{1-12}$ alkyl, and $C_{2-12}$ alkenyl, wherein at least one of $R^{b\gamma}$ and $R^{b\delta}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

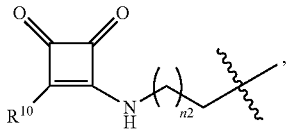

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid is a compound of Formula (AII-b):

(AII-b)

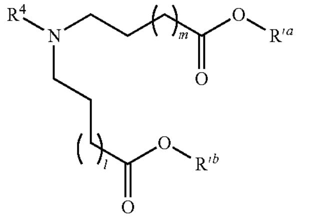

or its N-oxide, or a salt or isomer thereof, wherein $R'^{a}$ is $R'^{branched}$ or $R'^{cyclic}$; wherein $R'^{branched}$ is:

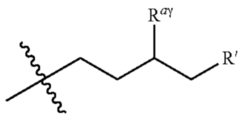

and $R'^{b}$ is:

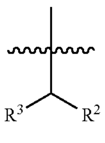

or

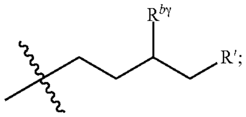

wherein

denotes a point of attachment;

$R^{a\gamma}$ and $R^{b\gamma}$ are each independently selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4, and 5, and

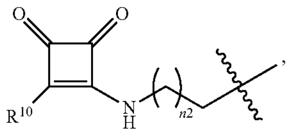

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-2}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid is a compound of Formula (AII-c):

(AII-c)

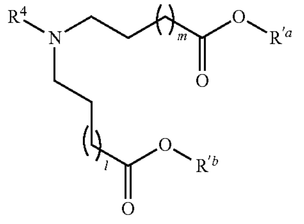

or its N-oxide, or a salt or isomer thereof, wherein $R'^{a}$ is $R'^{branched}$ or $R'^{cyclic}$; wherein $R'^{branched}$ is:

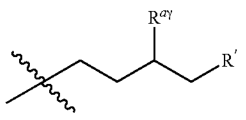

and $R'^{b}$ is: 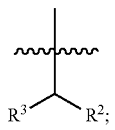

wherein

denotes a point of attachment;

wherein $R^{a\gamma}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

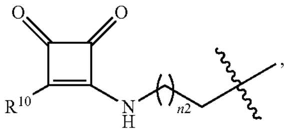

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

R' is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid is a compound of Formula (AII-d):

(AII-d)

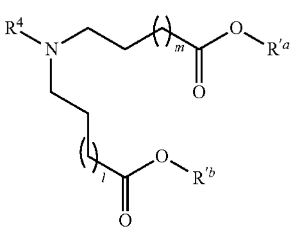

or its N-oxide, or a salt or isomer thereof, wherein $R'^{a}$ is $R'^{branched}$ or $R'^{cyclic}$; wherein $R'^{branched}$ is:

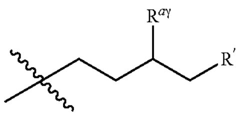

and $R'^{b}$ is:

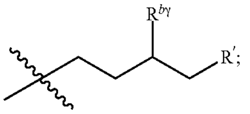

wherein

denotes a point of attachment;

wherein $R^{a\gamma}$ and $R^{b\gamma}$ are each independently selected from the group consisting of $C_{1-12}$ alkyl and $C_{2-12}$ alkenyl;

$R^4$ is selected from the group consisting of $—(CH_2)_nOH$ wherein n is selected from the group consisting of 1, 2, 3, 4, and 5, and

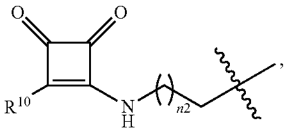

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid is a compound of Formula (AII-e):

(AII-e)

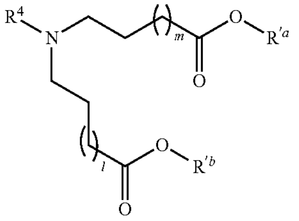

or its N-oxide, or a salt or isomer thereof, wherein $R'^{a}$ is $R'^{branched}$ or $R'^{cyclic}$; wherein $R'^{branched}$ is:

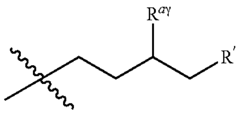

and $R'^{b}$ is:

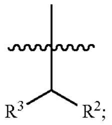

wherein

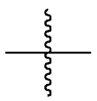

denotes a point of attachment;

wherein $R^{a\gamma}$ is selected from the group consisting of $C_{1-12}$ alkyl and $C_{2-12}$ alkenyl;

$R^2$ and $R^3$ are each independently selected from the group consisting of $C_{1-4}$ alkyl and $C_{2-14}$ alkenyl;

$R^4$ is $—(CH_2)_nOH$ wherein n is selected from the group consisting of 1, 2, 3, 4, and 5;

R' is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments of the compound of Formula (AII), (AII-a), (AII-b), (AII-c), (AII-d), or (AII-e), m and l are each independently selected from 4, 5, and 6. In some embodiments of the compound of Formula (AII), (AII-a), (AII-b), (AII-c), (AII-d), or (AII-e), m and l are each 5.

In some embodiments of the compound of Formula (AII), (AII-a), (AII-b), (AII-c), (AII-d), or (AII-e), each R' independently is a $C_{1-12}$ alkyl. In some embodiments of the compound of Formula (AII), (AII-a), (AII-b), (AII-c), (AII-d), or (AII-e), each R' independently is a $C_{2-5}$ alkyl.

In some embodiments of the compound of Formula (AII), (AII-a), (AII-b), (AII-c), (AII-d), or (AII-e), $R'^{b}$ is:

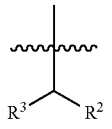

and $R^2$ and $R^3$ are each independently a $C_{1-14}$ alkyl. In some embodiments of the compound of Formula (AII), (AII-a), (AII-b), (AII-c), (AII-d), or (AII-e), $R'^{b}$ is:

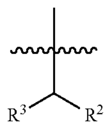

and $R^2$ and $R^3$ are each independently a $C_{6-10}$ alkyl. In some embodiments of the compound of Formula (AII), (AII-a), (AII-b), (AII-c), (AII-d), or (AII-e), $R'^{b}$ is:

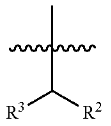

and $R^2$ and $R^3$ are each a $C_8$ alkyl.

In some embodiments of the compound of Formula (AII), (AII-a). (AII-b), (AII-c), (AII-d), or (AII-e), $R'^{branched}$ is:

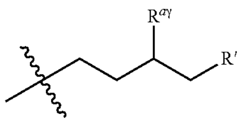

and $R'^{b}$ is:

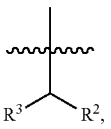

$R^{a\gamma}$ is a $C_{1-12}$ alkyl and $R^2$ and $R^3$ are each independently a $C_{6-10}$ alkyl. In some embodiments of the compound of Formula (AII), (AII-a), (AII-b), (AII-c), (AII-d), or (AII-e), $R'^{branched}$ is:

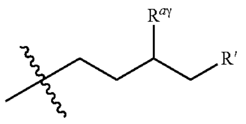

and $R'^{b}$ is:

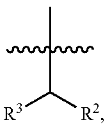

$R^{a\gamma}$ is a $C_{2-6}$ alkyl and $R^2$ and $R^3$ are each independently a $C_{6-10}$ alkyl. In some embodiments of the compound of Formula (AII), (AII-a), (AII-b), (AII-c), (AII-d), or (AII-e), $R'^{branched}$ is:

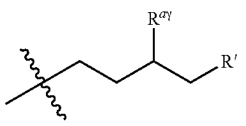

and $R'^{b}$ is:

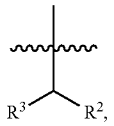

$R^{a\gamma}$ is a $C_{2-6}$ alkyl, and $R^2$ and $R^3$ are each a $C_8$ alkyl.

In some embodiments of the compound of Formula (AII), (AII-a), (AII-b), (AII-c), (AII-d), or (AII-e), $R'^{branched}$ is

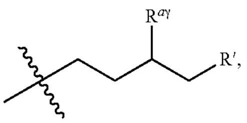

$R'^{b}$ is:

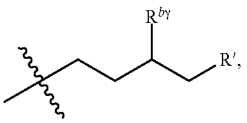

and $R^{a\gamma}$ and $R^{b\gamma}$ are each a $C_{1-12}$ alkyl. In some embodiments of the compound of Formula (AII), (AII-a), (AII-b), (AII-c), (AII-d), or (AII-e), $R'^{branched}$ is:

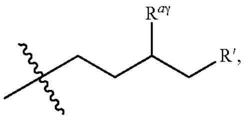

$R'^{b}$ is:

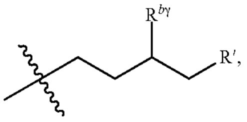

and $R^{a\gamma}$ and $R^{b\gamma}$ are each a $C_{2-6}$ alkyl.

In some embodiments of the compound of Formula (AII), (AII-a), (AII-b), (AII-c), (AII-d), or (AII-e), m and l are each independently selected from 4, 5, and 6 and each R' independently is a $C_{1-12}$ alkyl. In some embodiments of the compound of Formula (AII), (AII-a), (AII-b), (AII-c), (AII-d), or (AII-e), m and l are each 5 and each R' independently is a $C_{2-5}$ alkyl.

In some embodiments of the compound of (AII), (AII-a), (AII-b), (AII-c). (AII-d), or (AII-e), $R'^{branched}$ is:

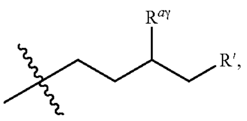

$R'^{b}$ is:

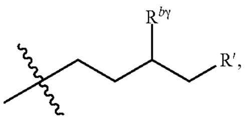

m and l are each independently selected from 4, 5, and 6, each R' independently is a $C_{1-12}$ alkyl, and $R^{a\gamma}$ and $R^{b\gamma}$ are each a $C_{1-12}$ alkyl. In some embodiments of the compound of Formula (AII), (AII-a), (AII-b), (AII-c), (AII-d), or (AII-e), $R'^{branched}$ is:

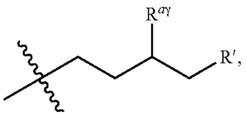

$R'^{b}$ is:

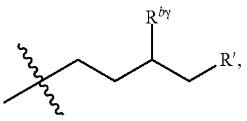

m and l are each 5, each R' independently is a $C_{2-5}$ alkyl, and $R^{a\gamma}$ and $R^{b\gamma}$ are each a $C_{2-6}$ alkyl.

In some embodiments of the compound of Formula (AII), (AII-a), (AII-b), (AII-c), (AII-d), or (AII-e), $R'^{branched}$ is:

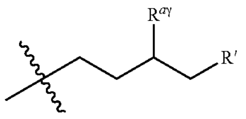

and $R'^{b}$ is:

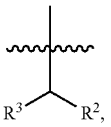

m and l are each independently selected from 4, 5, and 6. R' is a $C_{1-12}$ alkyl, $R^{a\gamma}$ is a $C_{1-12}$ alkyl and $R^2$ and $R^3$ are each independently a $C_{6-10}$ alkyl.

In some embodiments of the compound of Formula (AII), (AII-a), (AII-b), (AII-c), (AII-d), or (AII-e), $R'^{branched}$ is:

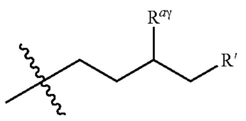

and $R'^b$ is:

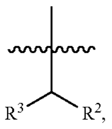

m and l are each 5, R' is a $C_{2-5}$ alkyl. $R^{a\gamma}$ is a $C_{2-6}$ alkyl, and $R^2$ and $R^3$ are each a $C_8$ alkyl.

In some embodiments of the compound of (AII), (AII-a), (AII-b), (AII-c), (AII-d), or (AII-e), $R^4$ is

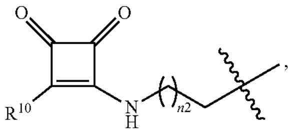

wherein $R^{10}$ is NH($C_{1-6}$ alkyl) and n2 is 2. In some embodiments of the compound of Formula (AII), (AII-a), (AII-b), (AII-c), (AII-d), or (AII-e). $R^4$ is

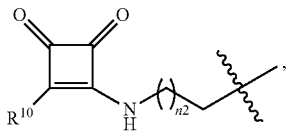

wherein $R^{10}$ is NH($CH_3$) and n2 is 2.

In some embodiments of the compound of Formula (AII), (AII-a), (AII-b), (AII-c), (AII-d), or (AII-e). $R'^{branched}$ is:

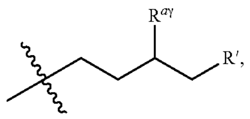

$R'^b$ is:

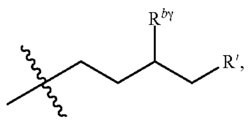

m and l are each independently selected from 4, 5, and 6, each R' independently is a $C_{1-12}$ alkyl, $R^{a\gamma}$ and $R^{b\gamma}$ are each a $C_{1-12}$ alkyl, and $R_4$ is

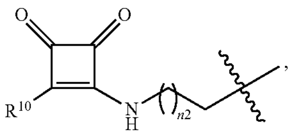

wherein $R^{10}$ is NH($C_{1-6}$ alkyl), and n2 is 2. In some embodiments of the compound of Formula (AI), (AII-a), (AII-b), (AII-c), (AII-d), or (AII-e), $R'^{branched}$ is:

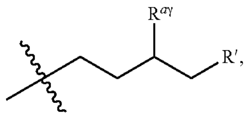

$R'^b$ is:

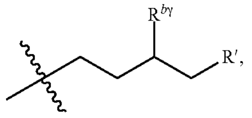

m and l are each 5, each R' independently is a $C_{2-5}$ alkyl, $R^{a\gamma}$ and $R^{b\gamma}$ are each a $C_{2-6}$ alkyl, and $R^4$ is

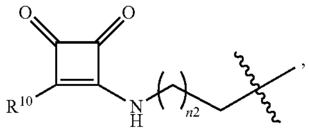

wherein $R^{10}$ is NH($CH_3$) and n2 is 2.

In some embodiments of the compound of Formula (AII), (AII-a), (AII-b), (AII-c), (AII-d), or (AII-e), $R'^{branched}$ is:

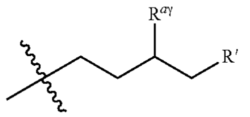

and $R'^b$ is:

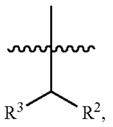

m and l are each independently selected from 4, 5, and 6. R' is a $C_{1-12}$ alkyl, $R^2$ and $R^3$ are each independently a $C_{6-10}$ alkyl, R" is a $C_{1-12}$ alkyl, and $R^4$ is

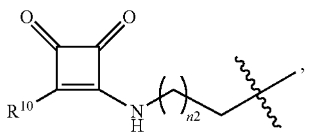

wherein $R^{10}$ is NH($C_{1-6}$ alkyl) and n2 is 2. In some embodiments of the compound of Formula (AII), (AII-a), (AII-b), (AII-c), (AII-d), or (AII-e), $R'^{branched}$ is:

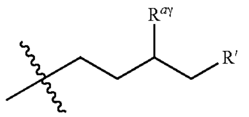

and $R'^{b}$ is:

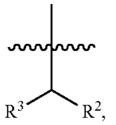

m and l are each 5, R' is a $C_{2-5}$ alkyl. $R^{a\gamma}$ is a $C_{2-6}$ alkyl, $R^2$ and $R^3$ are each a $C_8$ alkyl, and $R^4$ is

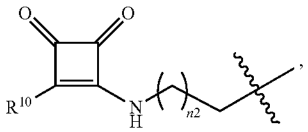

wherein $R^{10}$ is $NH(CH_3)$ and n2 is 2.

In some embodiments of the compound of Formula (AII), (AII-a), (AII-b), (AII-c), (AII-d), or (AII-e), $R^4$ is —$(CH_2)_nOH$ and n is 2, 3, or 4. In some embodiments of the compound of Formula (AII), (AII-a), (AII-b), (AII-c), (AII-d), or (AII-e), $R^4$ is —$(CH_2)_nOH$ and n is 2.

In some embodiments of the compound of Formula (AII), (AII-a), (AII-b), (AII-c), (AII-d), or (AII-e), $R'^{branched}$ is:

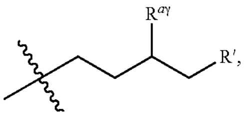

$R'^{b}$ is:

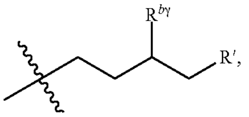

m and l are each independently selected from 4, 5, and 6, each R' independently is a $C_{1-12}$ alkyl, $R^{a\gamma}$ and $R^{b\gamma}$ are each a $C_{1-12}$ alkyl, $R^4$ is —$(CH_2)_nOH$, and n is 2, 3, or 4. In some embodiments of the compound of Formula (AII), (AII-a), (AII-b), (AII-c), (AII-d), or (AII-e), $R'^{branched}$ is:

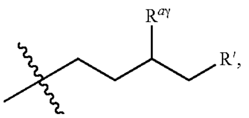

$R'^{b}$ is:

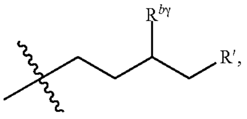

m and l are each 5, each R' independently is a $C_{2-5}$ alkyl, $R^{a\gamma}$ and $R^{b\gamma}$ are each a $C_{2-6}$ alkyl, $R^4$ is —$(CH_2)_nOH$, and n is 2.

In some embodiments, the ionizable amino lipids compound of Formula (AII-f):

(AII-f)

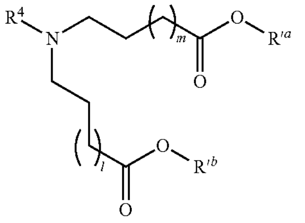

or its N-oxide, or a salt or isomer thereof, wherein $R'^{a}$ is $R'^{branched}$ or $R'^{cyclic}$; wherein $R'^{branched}$ is:

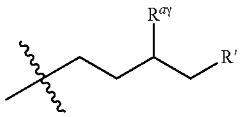

and $R'^{b}$ is:

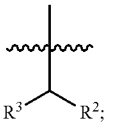

wherein

denotes a point of attachment;

$R^{a\gamma}$ is a $C_{1-12}$ alkyl;

$R^2$ and $R^3$ are each independently a $C_{1-14}$ alkyl;

$R^4$ is —$(CH_2)_nOH$ wherein n is selected from the group consisting of 1, 2, 3, 4, and 5; R' is a $C_{1-12}$ alkyl;

m is selected from 4, 5, and 6; and l is selected from 4, 5, and 6.

In some embodiments of the compound of Formula (AII-f), m and l are each 5, and n is 2, 3, or 4.

In some embodiments of the compound of Formula (AII-f) R' is a $C_{2-5}$ alkyl, $R^{a\gamma}$ is a $C_{2-6}$ alkyl, and $R^2$ and $R^3$ are each a $C_{6-10}$ alkyl.

In some embodiments of the compound of Formula (AII-f), m and l are each 5, n is 2, 3, or 4, R' is a $C_{2-5}$ alkyl, $R^{a\gamma}$ is a $C_{2-6}$ alkyl, and $R^2$ and $R_3$ are each a $C_{6-10}$ alkyl.

In some embodiments, the ionizable amino lipid is a compound of Formula (AII-g):

(AII-g)

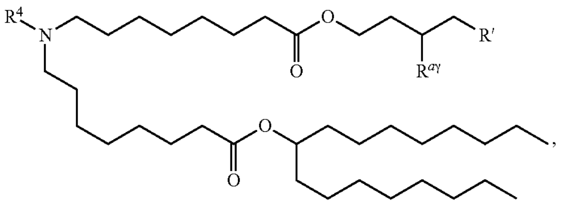

wherein $R^{a\gamma}$ is a $C_{2-6}$ alkyl;

R' is a $C_{2-5}$ alkyl; and $R^4$ is selected from the group consisting of $—(CH_2)_nOH$ wherein n is selected from the group consisting of 3, 4, and 5, and

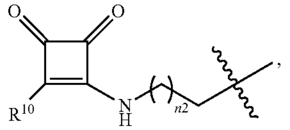

wherein

denotes a point of attachment, $R^{10}$ is $NH(C_{1-6}$ alkyl), and n2 is selected from the group consisting of 1, 2, and 3.

In some embodiments, the ionizable amino lipid is a compound of Formula (AII-h):

(AII-h)

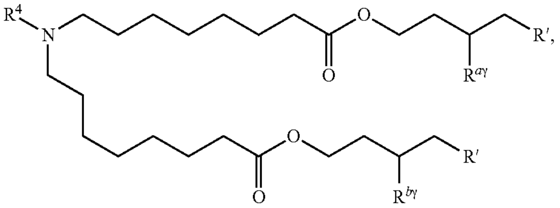

$R^{a\gamma}$ and $R^{b\gamma}$ are each independently a $C_{2-6}$ alkyl;

each R' independently is a $C_{2-5}$ alkyl; and $R^4$ is selected from the group consisting of $—(CH_2)_nOH$ wherein n is selected from the group consisting of 3, 4, and 5, and

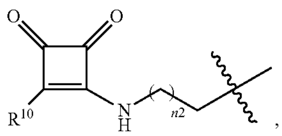

wherein

denotes a point of attachment, $R^{10}$ is $NH(C_{1-6}$ alkyl), and n2 is selected from the group consisting of 1, 2, and 3.

In some embodiments of the compound of Formula (AII-g) or (AII-h). $R^4$ is

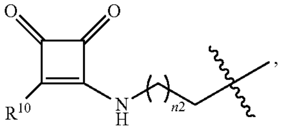

wherein $R^{10}$ is $NH(CH_3)$ and n2 is 2.

In some embodiments of the compound of Formula (AII-g) or (AII-h), $R^4$ is $—(CH_2)_2OH$.

In some embodiments, the ionizable amino lipids may be one or more of compounds of Formula (VI):

(VI)

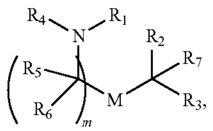

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R^2$ and $R^3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R_4$ is selected from the group consisting of hydrogen, a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—N(R)S(O)_2R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —OC(O)-M"-C(O)O—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, another subset of compounds of Formula (VI) includes those in which:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (VI) includes those in which:

$R_1$ is selected from the group consisting of $C_{5-30}$ alkyl, $C_{5-20}$ alkenyl, —R*YR", —YR", and —R"M'R';

$R^2$ and $R^3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R_4$ is selected from the group consisting of a $C_{3-6}$ carbocycle, $—(CH_2)_nQ$, $(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$. $—N(OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (VI) includes those in which:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)R$, —C(O)N(R)OR, and —$C(=NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R' is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (VI) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R' is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (VI) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group:

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In certain embodiments, a subset of compounds of Formula (VI) includes those of Formula (VI-A):

(VI-A)

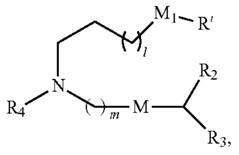

or its N-oxide, or a salt or isomer thereof, wherein l is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R^2$ and $R^3$ are independently selected from the group consisting of H, $C_{1-14}$ alkyl, and $C_{2-4}$ alkenyl. For example, m is 5, 7, or 9. For example, Q is OH, $—NHC(S)N(R)_2$, or $—NHC(O)N(R)_2$. For example, Q is —N(R)C(O)R, or $—N(R)S(O)_2R$.

In certain embodiments, a subset of compounds of Formula (VI) includes those of Formula (VI-B):

(VI-B)

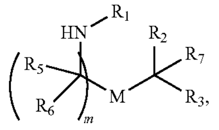

or its N-oxide, or a salt or isomer thereof in which all variables are as defined herein. For example, m is selected from 5, 6, 7, 8, and 9; $R_4$ is hydrogen, unsubstituted $C_{1-3}$ alkyl, or $—(CH_2)_nQ$, in which Q is H, $—NHC(S)N(R)_2$, $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—. —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, $—NHC(S)N(R)_2$, or $—NHC(O)N(R)_2$. For example, Q is —N(R)C(O)R, or $—N(R)S(O)_2R$.

In certain embodiments, a subset of compounds of Formula (VI) includes those of Formula (VII):

(VII)

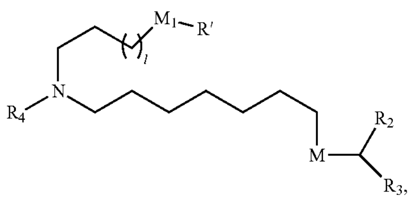

or its N-oxide, or a salt or isomer thereof, wherein l is selected from 1, 2, 3, 4, and 5; $M_1$ is a bond or M'; $R_4$ is hydrogen, unsubstituted $C_{1-3}$ alkyl, or $—(CH_2)_nQ$, in which n is 2, 3, or 4, and Q is OH, $—NHC(S)N(R)_2$. $—NHC(O)N(R)_2$, —N(R)C(O)R, $—N(R)S(O)_2R$, $—N(R)R_8$, $—NHC({=}NR_9)N(R)_2$, $—NHC({=}CHR_9)N(R)_2$, $—OC(O)N(R)_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In one embodiment, the compounds of Formula (VI) are of Formula (VIIa), (VIIa)

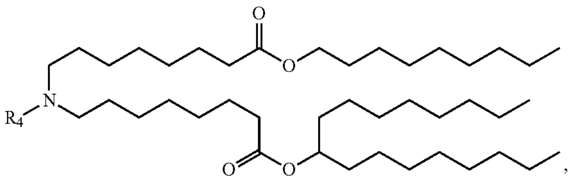

or their N-oxides, or salts or isomers thereof, wherein $R_4$ is as described herein.

In another embodiment, the compounds of Formula (VI) are of Formula (VIIb), (VIIb)

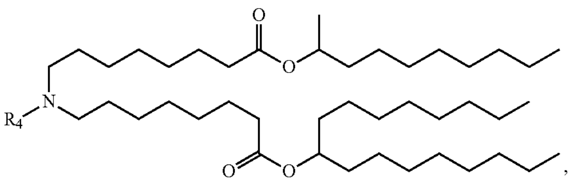

or their N-oxides, or salts or isomers thereof, wherein $R_4$ is as described herein.

In another embodiment, the compounds of Formula (VI) are of Formula (VIIc) or (VIIe):

(VIIc)

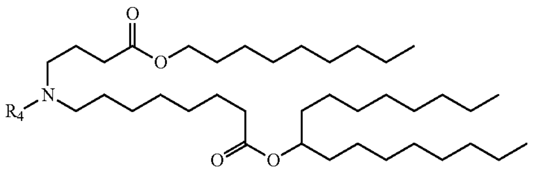

or (VIIe)

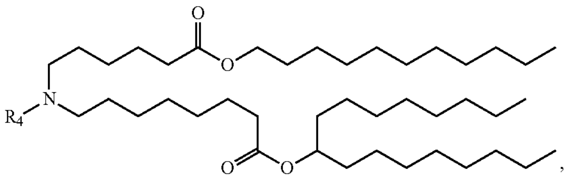

or their N-oxides, or salts or isomers thereof, wherein $R_4$ is as described herein.

In another embodiment, the compounds of Formula (VI) are of Formula (VIIf):

(VIIf)

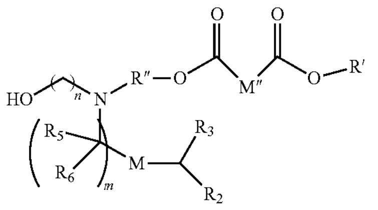

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{3-14}$ alkyl and $C_{5-14}$ alkenyl, and n is selected from 2, 3, and 4.

In a further embodiment, the compounds of Formula (VI) are of Formula (VIId), (VIId)

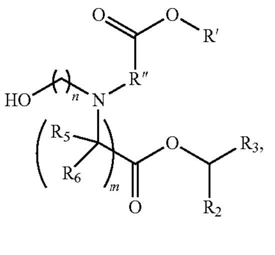

or their N-oxides, or salts or isomers thereof, wherein n is 2, 3, or 4; and m, R, R", and $R_2$ through R are as described herein. For example, each of $R_2$ and $R_3$ may be independently selected from the group consisting of $C_{5-14}$ alkyl and $C_{5-14}$ alkenyl.

In some embodiments, an ionizable amino lipid of the disclosure comprises a compound having structure:

(Compound I)

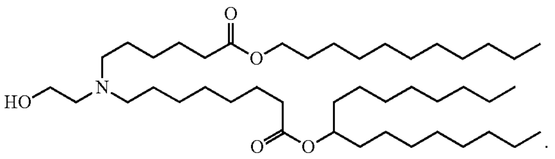

In some embodiments, an ionizable amino lipid of the disclosure comprises a compound having structure:

(Compound II)

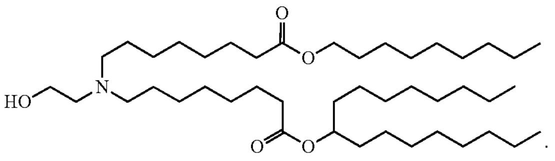

In a further embodiment, the compounds of Formula (VI) are of Formula (VIIg), (VIIg)

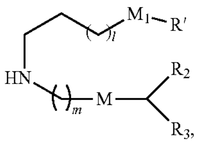

or their N-oxides, or salts or isomers thereof, wherein 1 is selected from 1, 2, 3, 4, and 5; m is selected from 5, 6, 7, 8, and 9; M, is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M" is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable amino lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

The central amine moiety of a lipid according to Formula (VI), (VI-A), (VI-B), (VII), (VIIa), (VIIb), (VIIc), (VIId), (VIIe), (VIIf), or (VIIg) may be protonated at a physiological pH. Thus, a lipid may have a positive or partial positive charge at physiological pH. Such amino lipids may be referred to as cationic lipids, ionizable lipids, cationic amino lipids, or ionizable amino lipids. Amino lipids may also be zwitterionic, i.e., neutral molecules having both a positive and a negative charge.

In some embodiments, the ionizable amino lipids of the present disclosure may be one or more of compounds of formula (VIII), (VIII)

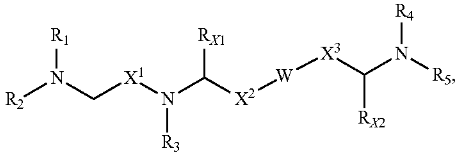

or salts or isomers thereof, wherein

W is

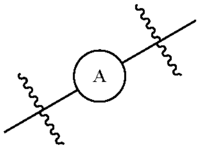

or

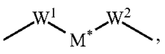

ring A is

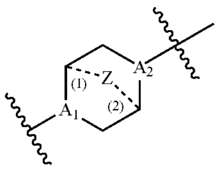

or

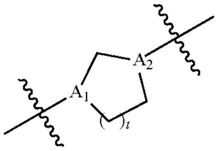

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

$R_{X1}$ and $R_{X2}$ are each independently H or $C_{1-3}$ alkyl;

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —$S(O)_2$—, —C(O)S—, —SC(O)—, an aryl group, and a heteroaryl group;

M* is $C_1$-$C_6$ alkyl, $W^1$ and $W^2$ are each independently selected from the group consisting of —O— and —$N(R_6)$—;

each $R_6$ is independently selected from the group consisting of H and $C_{1-5}$ alkyl;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —$(CH_2)_n$—C(O)—, —C(O)—$(CH_2)_n$—, —$(CH_2)_n$—C(O)O—, —OC(O)—$(CH_2)_n$—, —$(CH_2)_n$—OC(O)—, —C(O)O—$(CH_2)_n$—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H;

each R" is independently selected from the group consisting of $C_{3-12}$ alkyl, $C_{3-12}$ alkenyl and —R*MR'; and n is an integer from 1-6;

wherein when ring A is

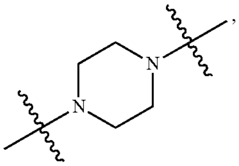 [SMILES: *N1CCN(*)CC1]

, then i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of formulae (VIIIa1)-(VIIIa8):

(VIIIa1)

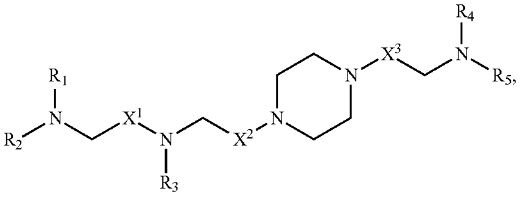

(VIIIa2)

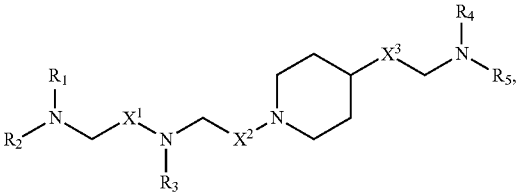

(VIIIa3)

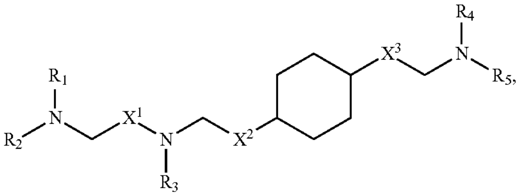

(VIIIa4)

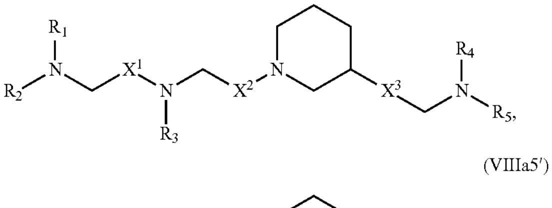

(VIIIa5')

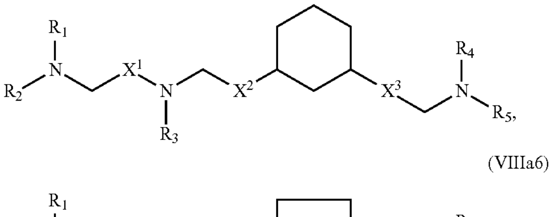

(VIIIa6)

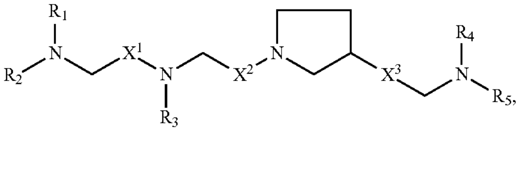

-continued (VIIIa7)

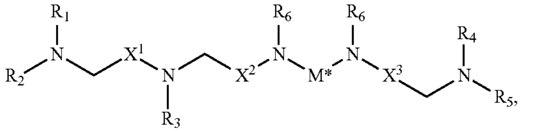

or (VIIIa8)

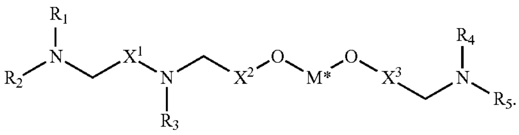

In some embodiments, the ionizable amino lipid is

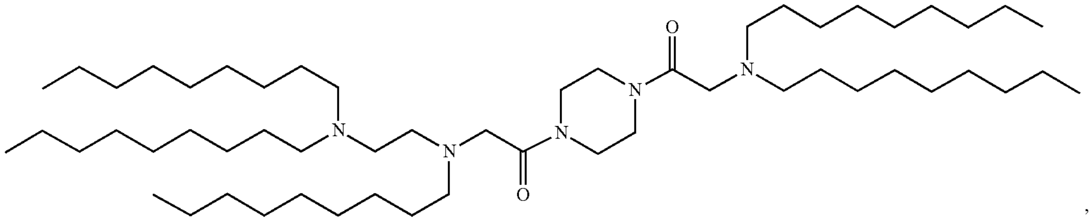 [SMILES: CCCCCCCCCN(CCCCCCCCC)CCN(CCCCCCCCC)CC(=O)N1CCN(C(=O)CN(CCCCCCCCC)CCCCCCCCC)CC1]

, or a salt thereof.

The central amine moiety of a lipid according to Formula (VIII), (VIIIa1), (VIIIa2), (VIIIa3), (VIIIa4), (VIIIa5), (VIIIa6), (VIIIa7), or (VIIIa8) may be protonated at a physiological pH. Thus, a lipid may have a positive or partial positive charge at physiological pH.

In some embodiments, the lipid nanoparticle comprises a lipid having the structure:

(III-L)

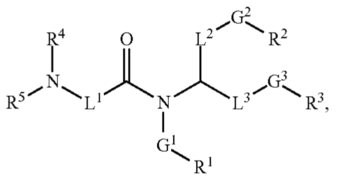

or a pharmaceutically acceptable salt, tautomer, or stereoisomer thereof, wherein:

$R^1$ is optionally substituted $C_1$-$C_{24}$ alkyl or optionally substituted $C_2$-$C_{24}$ alkenyl;

$R^2$ and $R^3$ are each independently optionally substituted $C_1$-$C_{36}$ alkyl;

$R^4$ and $R^5$ are each independently optionally substituted $C_1$—C(alkyl, or $R^4$ and $R^5$ join, along with the N to which they are attached, to form a heterocyclyl or heteroaryl;

$L^1$, $L^2$, and $L^3$ are each independently optionally substituted $C_1$-$C_{18}$ alkylene;

$G^1$ is a direct bond, $—(CH_2)_nO(C{=}O)—$, $—(CH_2)_n(C{=}O)O—$, or $—(C{=}O)—$;

$G^2$ and $G^3$ are each independently $—(C{=}O)O—$ or $—O(C{=}O)—$; and n is an integer greater than 0.

In some embodiments, the lipid nano article comprises a lipid having the structure:

(IV-L)

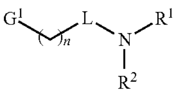

or a pharmaceutically acceptable salt, tautomer, or stereoisomer thereof, wherein:

$G^1$ is $—N(R^3)R^4$ or —OR;

$R^1$ is optionally substituted branched, saturated or unsaturated $C_{12}$-$C_{36}$ alkyl;

$R^2$ is optionally substituted branched or unbranched, saturated or unsaturated $C_{12}$-$C_{36}$ alkyl when L is $—C({=}O)—$; or $R^2$ is optionally substituted branched or unbranched, saturated or unsaturated $C_4$-$C_{36}$ alkyl when L is $C_6$-$C_{12}$ alkylene, $C_6$-$C_{12}$ alkenylene, or $C_2$-$C_6$ alkynylene;

$R^3$ and $R^4$ are each independently H, optionally substituted branched or unbranched, saturated or unsaturated $C_1$-$C_6$ alkyl; or $R^3$ and $R^4$ are each independently optionally substituted branched or unbranched, saturated or unsaturated $C_1$-$C_6$ alkyl when L is $C_6$-$C_{12}$ alkylene, $C_6$-$C_{12}$alkenylene, or $C_2$-$C_6$ alkynylene; or $R^3$ and $R^4$, together with the nitrogen to which they are attached, join to form a heterocyclyl;

$R^5$ is H or optionally substituted $C_1$-$C_6$ alkyl;

L is $—C({=}O)—$, $C_6$-$C_{12}$ alkylene, $C_6$-$C_{12}$ alkenylene, or $C_2$-$C_6$ alkynylene; and n is an integer from 1 to 12.

In some embodiments, the lipid nanoparticle comprises a lipid having the structure:

(V-L)

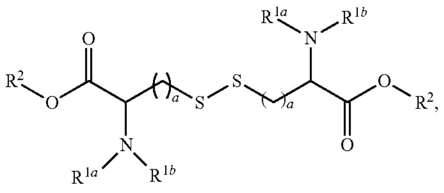

or a pharmaceutically acceptable salt thereof, wherein:

each $R^{1a}$ is independently hydrogen, $R^{1c}$, or $R^{1d}$;

each $R^{1b}$ is independently $R^{1c}$ or $R^{1d}$;

each $R^{1c}$ is independently $—[CH_2]_2C(O)X^1R^3$;

each $R^{1d}$ Is independently $—C(O)R^4$;

each $R^2$ is independently $—[C(R^{2a})_2]_cR^{2b}$;

each $R^{2a}$ is independently hydrogen or $C_1$-$C_6$ alkyl;

$R^{2b}$ is $—N(L_1\text{-}B)_2$; $—(OCH_2CH_2)_6OH$; or $—(OCH_2CH_2)_bOCH_3$;

each $R_3$ and $R^4$ is independently $C_6$-$C_{30}$ aliphatic;

each $L_3$ is independently $C_1$-$C_{10}$ alkylene;

each B is independently hydrogen or an ionizable nitrogen-containing group;

each $X^1$ is independently a covalent bond or O;

each a is independently an integer of 1-10;

each b is independently an integer of 1-10; and each c is independently an integer of 1-10.

In some embodiments, the lipid nanoparticle comprises a lipid having the structure:

(VI-L)

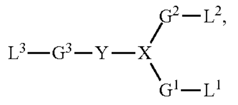

or a pharmaceutically acceptable salt, prodrug or stereoisomer thereof, wherein:

X is N, and Y is absent; or X is CR, and Y is NR;

$L^1$ is —O(C—O)R', —(C═O)OR', —C(═O)R', —OR', —$S(O)_x$R', —S—SR'. —C(═O)SR', —SC(═O)$R^1$, —$NR^a$C(═O)$R^1$, —C(═O)$NR^bR^c$, —$NR^a$C(═O)$NR^bR^c$, —OC(═O)$NR^bR^c$, or —$NR^a$C(═O)O$R^1$;

$L^2$ is —O(C═O)$R^2$, —(C═O)O$R^2$, —C(═O)$R^2$, —O$R^2$, —$S(O)_x R^2$, —S—S$R^2$, —C(═O)SR', —SC(═O)$R^2$, —$NR^d$C(═O)$R^2$, —C(═O)$NR^eR^f$, —$NR^d$C(═O)$NR^eR^f$, —OC(═O)$NR^eR^f$; —$NR^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

In some embodiments, the lipid nanoparticle comprises a lipid having the structure:

(VII-L)

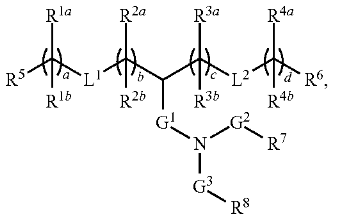

or a pharmaceutically acceptable salt, tautomer, prodrug or stereoisomer thereof, wherein:

$L^1$ and $L^2$ are each independently —O(C═O)—, —(C═))O—, —C(═O)—, —O—, —S(O)x-$_s$ —S—S—, —C(═O)S—, —SC(═O)—, —$NR^a$C(═O)—, —C(═O)$NR^a$—, —$NR^a$C(═O)$NR^a$—, —OC(═O)$NR^a$—, —$NR^a$C(═O)O— or a direct bond;

$G^1$ is C, —$C_2$ alkylene, —(C═O)—, —O(C═O)—, —SC(═O)—, —$NR^8$C(═O)— or a direct bond;

$G^2$ is —C(O)—, —(CO)O—, —C(═O)S—, —C(═O)$NR^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond;

$R^{4A}$ and $R^{4B}$ are, at each occurrence, independently either: (a) H or $C_1$-$C_{12}$ alkyl; or (b) $R^{4A}$ is H or $C_1$-$C_{12}$ alkyl, and $R^{4B}$ together with the carbon atom to which it is bound is taken together with an adjacent $R^{4B}$ and the carbon atom to which it is bound to form a carbon-carbon double bond;

$R^5$ and $R^6$ are each independently H or methyl;

$R^7$ is H or C, —$C_{20}$ alkyl;

$R^8$ is OH, —N($R^9$)(C═O)$R^{10}$, —(C═O)$NR^9$R'°, —$NR^9R^{10}$, —(C═O)OR"$^1$ or —O(C═O)R", provided that $G^3$ is $C_4$-$C_6$ alkylene when $R^8$ is —$NR^9R^{10}$, $R^9$ and $R^{10}$ are each independently H or $C_1$-$C_{12}$ alkyl;

R" is aralkyl;

a, b, c and d are each independently an integer from 1 to 24; and x is 0, 1 or 2, wherein each alkyl, alkylene and aralkyl is optionally substituted.

In some embodiments, the lipid nanoparticle comprises a lipid having the structure:

(VIII-L)

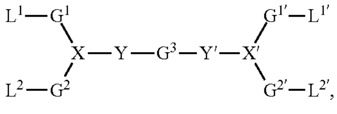

or a pharmaceutically acceptable salt, prodrug or stereoisomer thereof, wherein:

X and X' are each independently N or CR;

Y and Y' are each independently absent, —O(C═O)—, —(C═O)O— or NR, provided that:

a) Y is absent when X is N;

b) Y' is absent when X is N;

c) Y is —O(C═O)—, —(C═O)O— or NR when X is CR; and d) Y' is —O(C═O)—, —(C═O)O— or NR when X' is CR, $L^1$ and $L^{1'}$ are each independently —O(C═O)R', —(C═O)OR', —C(═O)R', —OR', —$S(O)_z$R', —S—

SR', —C(═O)SR', —SC(═O)R', —$NR^aC$(═O)R', —C(═O)$NR^bR^c$, —$NR^aC$(═O)$NR^bR^c$, —OC(═O)$NR^bR^c$ or —$NR^aC$(═O)OR;

$L^2$ and $L^{2'}$ are each independently —O(C═O)$R^2$, —C(═O)$OR^2$, —C(═O)$R^2$, —$OR^2$, —$S(O)_zR^2$, —S—$SR^2$, —C(═O)$SR^2$, —SC(═O)$R^2$, —$NR^dC$(═O)$R^2$, —C(═O)$NR^eR^f$, —$NR^dC$(═O)$NR^eR^f$, —OC(═O)$NR^eR^f$; —$NR^dC$(═O)$OR^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

G is $C_2$-$C_{24}$ heteroalkylene or $C_2$-$C_{24}$ heteroalkenylene;

$R^a$, $R^b$, $R^d$ and $R^e$ are, at each occurrence, independently H, $C_1$-$C_{12}$ alkyl or $C_2$-$C_{12}$ alkenyl;

$R^c$ and $R^f$ are, at each occurrence, independently $C_1$-$C_{12}$ alkyl or $C_2$-$C_{12}$ alkenyl;

R is, at each occurrence, independently H or $C_1$-$C_2$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, heteroalkylene and heteroalkenylene is independently substituted or unsubstituted unless otherwise specified.

In some embodiments, the lipid nanoparticle comprises a lipid having the structure:

(IX-L)

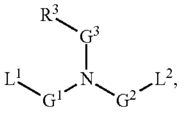

or a pharmaceutically acceptable salt, prodrug or stereoisomer thereof, wherein:

$L^1$ is —O(C═O)R', —(C═O)OR', —C(═O)R', —OR', —$S(O)_xR'$, —S—SR', —C(═O)SR', —SC(═O)R', —$NR^aC$(═O)$R^1$, —C(═O)$NR^bR^c$, —$NR^aC$(═O)$NR^bR^c$, —OC(═O)$NR^bR^c$ or —$NR^aC$(═O)$OR^1$;

$L^2$ is —O(C═O)$R^2$, —(C═O)$OR^2$, —C(═O)$R^2$, —$OR^2$, —$S(O)_xR^2$, —S—$SR^2$, —C(═O)$SR^2$, —SC(═O)$R^2$, —$NR^dC$(═O)$R^2$, —C(═O)$NR^eR^f$, —$NR^dC$(═O)$NR^eR^f$, —OC(═O)$NR^eR^f$; —$NR^dC$(═O)$OR^2$ or a direct bond to $R^2$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_2$ alkenyl;

$R^1$ and $R^2$ are each independently branched $C_6$-$C_{24}$ alkyl or branched $C_6$-$C_{24}$alkenyl;

$R^3$ is —$N(R^4)R^5$;

$R^4$ is $C_1$-$C_{12}$ alkyl;

$R^5$ is substituted $C_1$-$C_{12}$ alkyl; and x is 0, 1 or 2, and wherein each alkyl, alkenyl, alkylene, alkenylene, cycloalkylene, cycloalkenylene, aryl and aralkyl is independently substituted or unsubstituted unless otherwise specified.

In some embodiments, the lipid nanoparticle comprises a lipid having the structure:

(Xa-L)

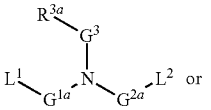

or (Xb-L)

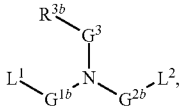

or a pharmaceutically acceptable salt, prodrug or stereoisomer thereof, wherein:

$L^1$ is —O(C═O)R', —(C═O)OR', —C(═O)R', —OR', —$S(O)_xR'$, —S—SR', —C(═O)SR', —SC(═O)R', —$NR^aC$(═O)R', —C(═O)$NR^bR^c$, —$NR^aC$(═O)$NR^bR^c$, —OC(═O)$NR^bR^c$ or —$NR^aC$(═O)OR';

$L^2$ is —O(C═O)$R^2$, —(C═O)$OR^2$, —C(═O)$R^2$, —$OR^2$, —$S(O)_xR^2$, —S—$SR^2$, —C(═O)$SR^2$, —SC(═O)$R^2$, —$NR^dC$(═O)R—, —C(═O)$NR^eR^f$, —$NR^dC$(═O)$NR^eR^f$, —OC(═O)$NR^eR^f$; —$NR^dC$(═O)$OR^2$ or a direct bond to $R^2$;

$G^{1a}$ and $G^{2b}$ are each independently $C_2$-$C_{12}$ alkylene or $C_2$-$C_{12}$ alkenylene;

$G^{1b}$ and $G^{2b}$ are each independently $C_1$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3a}$ is —C(═O)$N(R^{4a})R^{5a}$ or —C(═O)$OR^6$;

$R^{3b}$ is —$NR^{4b}C$(═O)$R^{5b}$;

$R^{4a}$ is $C_1$-$C_{12}$ alkyl;

$R^{4b}$ is H, $C_1$-$C_{12}$ alkyl or $C_2$-$C_{12}$ alkenyl;

$R^{5a}$ is H, $C_1$-$C_8$ alkyl or $C_2$-$C_8$ alkenyl;

$R^{5b}$ is $C_1$-$C_{12}$ alkyl or $C_2$-$C_{12}$ alkenyl when $R^{4b}$ is H; or $R^{5b}$ is $C_1$-$C_{12}$ alkyl or $C_2$-$C_{12}$ alkenyl when $R^4$ is $C_1$-$C_{12}$ alkyl or $C_2$-$C_{12}$ alkenyl;

$R^6$ is H, aryl or aralkyl; and x is 0, 1 or 2, and wherein each alkyl, alkenyl, alkylene, alkenylene, cycloalkylene, cycloalkenylene, aryl and aralkyl is independently substituted or unsubstituted.

In some embodiments, the lipid nanoparticle comprises a lipid having the structure:

(XI-L)

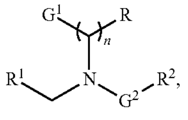

or a pharmaceutically acceptable salt, prodrug or stereoisomer thereof, wherein:

$G^1$ is —OH, —$R^3R_4$, —(C═O)$R^5$ or —$R^3$(C═O)$R^5$;

$G^2$ is —$CH_2$— or —(C═O)—;

R is, at each occurrence, independently H or OH;

$R^1$ and $R^2$ are each independently optionally substituted branched, saturated or unsaturated $C_{12}$-$C_{36}$ alkyl;

$R^3$ and $R^4$ are each independently H or optionally substituted straight or branched, saturated or unsaturated $C_1$-$C_6$ alkyl;

$R^5$ is optionally substituted straight or branched, saturated or unsaturated $C_1$-$C_6$ alkyl; and n is an integer from 2 to 6.

In some embodiments, the lipid nanoparticle comprises a lipid having the structure:

(XII-L)

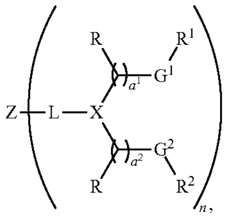

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —S(O), —S—S—. —C(═O)S—, SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O—, and the other of $G^1$ or $G^2$ is, at each occurrence, —O(C═O)—, —(C═O)O—, —C(═O)—, —O—, —S(O), —S—S—, —C(═O)S—, —SC(═O)—, —N($R^a$)C(═O)—, —C(═O)N($R^a$)—, —N($R^a$)C(═O)N($R^a$)—, —OC(═O)N($R^a$)— or —N(R)C(═O)O— or a direct bond;

L is, at each occurrence, ~O(C═O)—, wherein ~ represents a covalent bond to X; X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

$R^1$

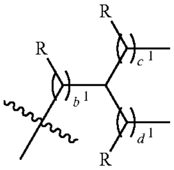

and

-continued $R^2$

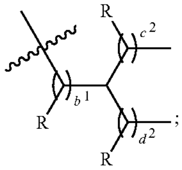

;

$a^1$ and $a^2$ are, at each occurrence, independently an integer from 3 to 12; $b^1$ and $b^2$ are, at each occurrence, independently 0 or 1;

$c^1$ and $c^2$ are, at each occurrence, independently an integer from 5 to 10; $d^1$ and $d^2$ are, at each occurrence, independently an integer from 5 to 10; y is, at each occurrence, independently an integer from 0 to 2; and n is an integer from 1 to 6, wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

In some embodiments, the lipid nanoparticle comprises a lipid having the structure:

(XIII-L)

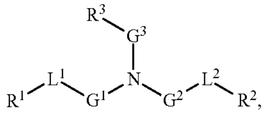

or a pharmaceutically acceptable salt, prodrug or stereoisomer thereof, wherein:

one of $L^1$ or $L^2$ is —O(C═O)—, —(C═O)O—, —C(═O)—, —O—, —S(O)$_x$—, —S—S—, —C(═O)S—, —SC(═O)—, —$R^a$C(═O)—, —C(═O) $R^a$—, $R^a$C(═O)$R^a$—, —OC(═O)$R^a$— or —$R^a$C(═O)O—, and the other of $L^1$ or $L^2$ is —O(C═O)—, —(C═O)O—, —C(═O)—, —O—, —S(O)$_x$—, —S—S—, —C(═O)S—, SC(═O)—, —$R^a$C(═O)—, —C(═O)$R^a$—, $R^a$C(═O)$R^a$—, —OC(═O)$R^a$— or —N$R^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^1$ is H, $OR^5$, CN, —C(═O)O$R^4$, —OC(═O)$R^4$ or —$R^5$C(═O)$R^4$;

$R^4$ is $C_1$-$C_{12}$ alkyl;

$R^5$ is H or $C_1$-$C_6$ alkyl; and x is 0, 1 or 2.

In some embodiments, the lipid nanoparticle comprises a lipid having the structure:

(XIV-L)

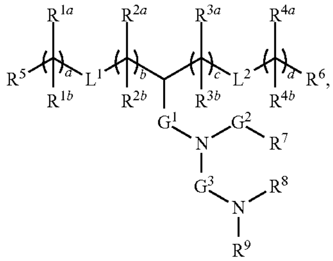

or a pharmaceutically acceptable salt, tautomer, prodrug or stereoisomer thereof, wherein:

$L^1$ and $L^2$ are each independently —O(C═O)—, —(C═O))—, —C(═O)—, —O—, —$S(O)_x$—, —S—S—, —C(═O)S—, —SC(═O)—, —$R^aC$(═O)—, —C(═O) $R^a$—, —$R^aC$(═O) $R^a$—, —OC(═O) $R^a$—, —$R^aC$(═O)O— or a direct bond;

$G^1$ is $C_1$-$C_2$ alkylene, —(C═O)—, —O(C═O)—, —SC(═O)—, —$R^aC$(═O)— or a direct bond;

$G^2$ is —C(═O)—, —(C═O)O—, —C(═O)S—, —C(═O)$NR^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments, the lipid nanoparticle comprises a lipid having the structure:

(XV-L)

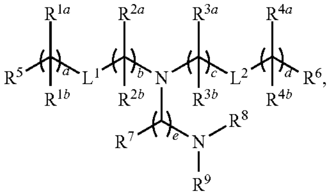

or a pharmaceutically acceptable salt, tautomer, prodrug or stereoisomer thereof, wherein:

$L^1$ and $L^2$ are each independently —O(C═O)—, —(C═O))— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl; $R^8$ and $R^9$ are each independently unsubstituted $C_1$-$C_{12}$ alkyl; or R and $R^9$, together with the nitrogen atom to which they are attached, form a 5, 6 or 7-membered heterocyclic ring comprising one nitrogen atom;

a and d are each independently an integer from 0 to 24; b and c are each independently an integer from 1 to 24; and e is 1 or 2, provided that:

at least one of $R^{1a}$, $R^{2a}$, $R^{3a}$ or $R^{4a}$ is $C_1$-$C_{12}$ alkyl, or at least one of $L^1$ or $L^2$ is —O(C═O)— or —(C═O)O—; and $R^{1a}$ and $R^{1b}$ are not isopropyl when a is 6 or n-butyl when a is 8.

In some embodiments, the lipid nanoparticle comprises a lipid having the structure:

(XVI-L)

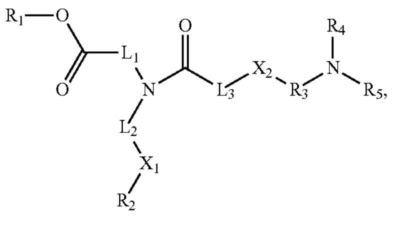

or a pharmaceutically acceptable salt thereof, wherein $R_1$ and $R_2$ are the same or different, each a linear or branched alkyl with 1-9 carbons, or as alkenyl or alkynyl with 2 to 11 carbon atoms, $L_1$ and $L_2$ are the same or different, each a linear alkyl having 5 to 18 carbon atoms, or form a heterocycle with N, $X_1$ is a bond, or is —CG-G- whereby L2-CO—O—$R_2$ is formed, $X_2$ is S or O, $L_3$ is a bond or a lower alkyl, or form a heterocycle with N, $R_3$ is a lower alkyl, and $R_4$ and $R_5$ are the same or different, each a lower alkyl.

In some embodiments, the lipid nanoparticle comprises an ionizable lipid having the structure:

(XVII-L)

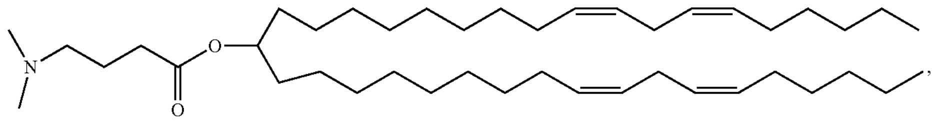

or a pharmaceutically acceptable salt thereof.

In some embodiments, the lipid nanoparticle comprises a lipid having the structure:

(XVIII-L)

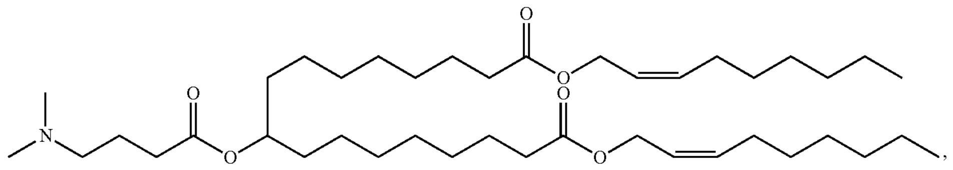

or a pharmaceutically acceptable salt thereof.

In some embodiments, the lipid nanoparticle comprises a lipid having the structure:

(XIX-L)

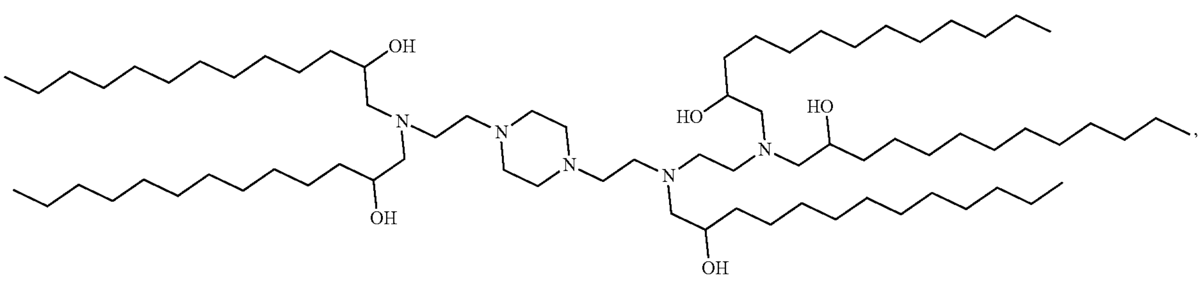

or a pharmaceutically acceptable salt thereof.

In some embodiments, the lipid nanoparticle comprises a lipid having the structure:

(XX-L)

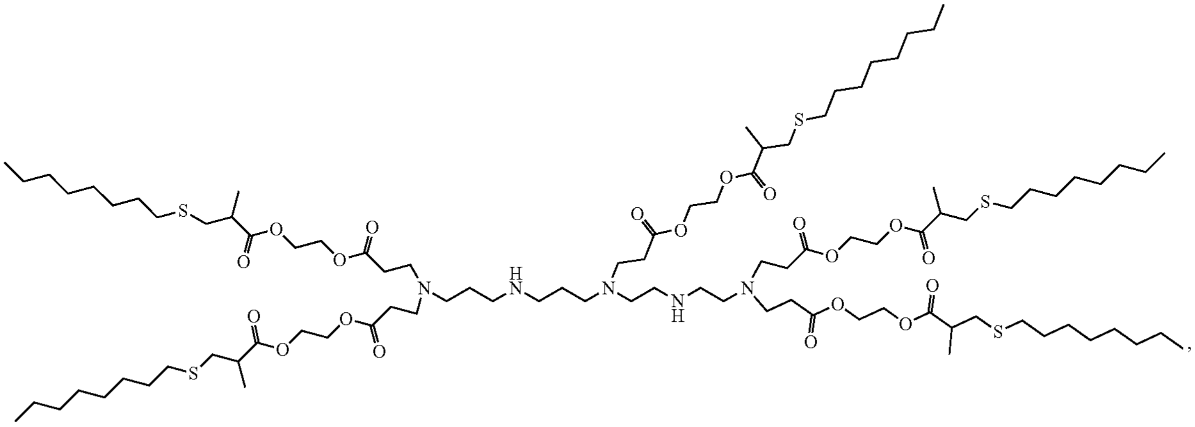

or a pharmaceutically acceptable salt thereof.

In some embodiments, the lipid nanoparticle comprises a lipid having the structure:

(XXI-L)

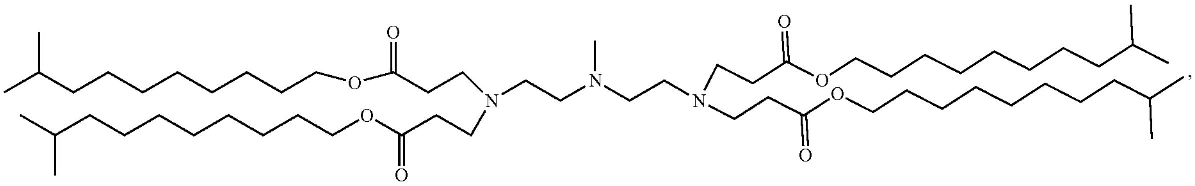

or a pharmaceutically acceptable salt thereof.

In some embodiments, the lipid nanoparticle comprises a lipid having the structure:

(XXII-L)

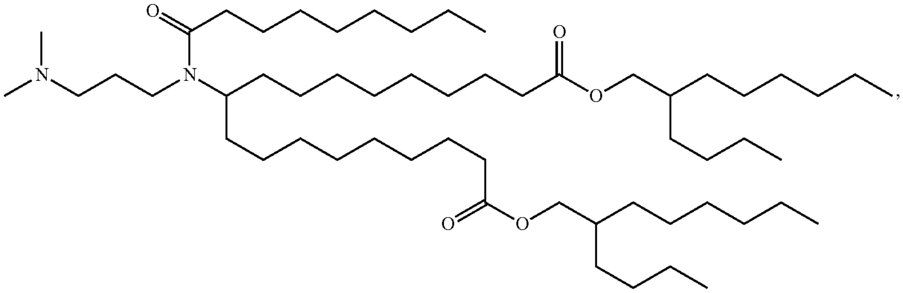

or a pharmaceutically acceptable salt thereof.

In some embodiments, the lipid nanoparticle comprises a lipid having the structure:

(XXIII-L)

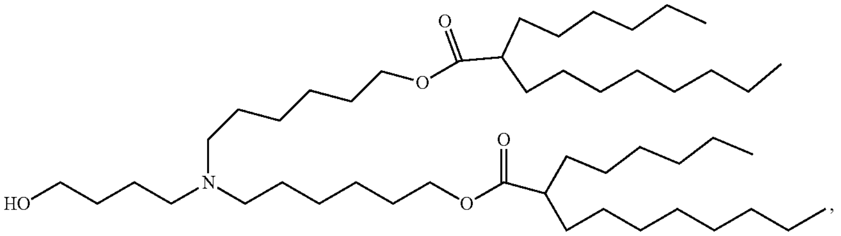

or a pharmaceutically acceptable salt thereof.

In some embodiments, the lipid nanoparticle comprises a lipid having the structure:

(XXIV-L)

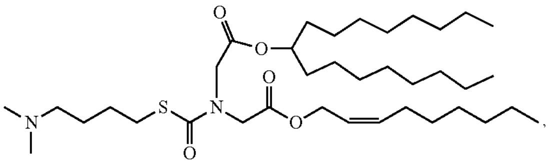

or a pharmaceutically acceptable salt thereof.

In some embodiments, the lipid nanoparticle comprises a lipid having the structure:

(XXV-L)

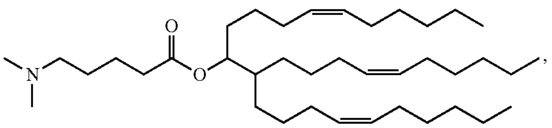

or a pharmaceutically acceptable salt thereof.

In some embodiments, the lipid nanoparticle comprises a lipid having the structure:

(XXVI-L)

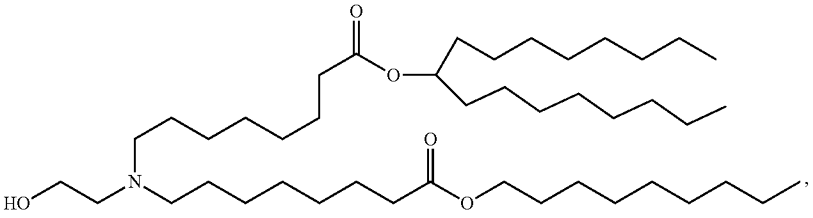

or a pharmaceutically acceptable salt thereof.

In some embodiments, the lipid nanoparticle comprises a lipid having the structure:

(XXVII-L)

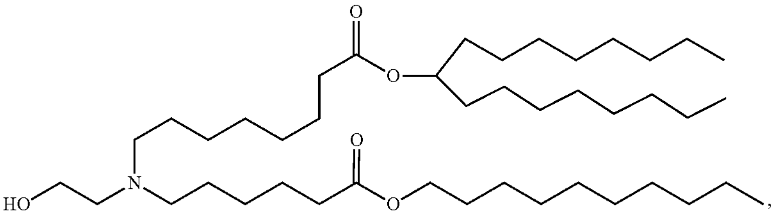

or a pharmaceutically acceptable salt thereof.

Non-Cationic Lipids

In certain embodiments, the lipid nanoparticles provided herein comprise one or more non-cationic lipids. Non-cationic lipids may be phospholipids.

In some embodiments, the lipid nanoparticle comprises 5-25 mol % non-cationic lipid. For example, the lipid nanoparticle may comprise 5-20 mol %, 5-15 mol %, 5-10 mol %, 10-25 mol %, 10-20 mol %, 10-25 mol %, 15-25 mol %, 15-20 mol %, or 20-25 mol % non-cationic lipid. In some embodiments, the lipid nanoparticle comprises 5 mol %, 10 mol %, 15 mol %, 20 mol %, or 25 mol % non-cationic lipid.

In some embodiments, a non-cationic lipid comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18.0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, the lipid nanoparticle comprises 5-15 mol %, 5-10 mol %, or 10-15 mol % DSPC. For example, the lipid nanoparticle may comprise 5, 6, 7, 8, 9, 10, 11, 12, 13, 14, or 15 mol % DSPC.

In certain embodiments, the lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidyl glycerols, and phosphatidic acids. Phospholipids also include phosphosphingolipid, such as sphingomyelin.

In some embodiments, a phospholipid comprises 1,2-distearoyl-sn-glycero-3-phosphocholine (DSPC), 1,2-Distearoyl-sn-glycero-3-phosphoethanolamine (DSPE), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In certain embodiments, a phospholipid is an analog or variant of DSPC. In certain embodiments, a is a compound of Formula (IX):

(IX)

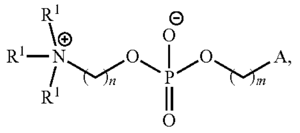

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10; m is 0, 1, 2, 3, 4, 5, 6, 7, 8, 9, or 10;

A is of the formula:

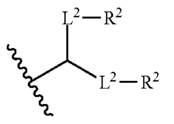

or

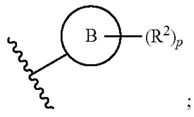

;

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O). $C(O)N(R^N)$, $NR^NC(O)$, C(O)O, OC(O), OC(O)O, $OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), —OC(O)O, $OC(O)N(R^N)$, $NR^NC(O)O$, C(O)S. SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, —OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $—N(R^N)S(O)O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

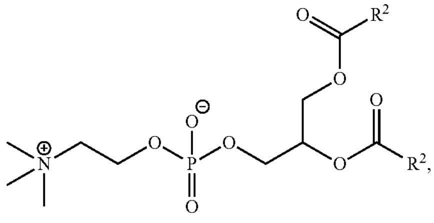

wherein each instance of $R^2$ is independently unsubstituted alkyl, unsubstituted alkenyl, or unsubstituted alkynyl.

In some embodiments, the phospholipids may be one or more of the phospholipids described in PCT Application No. PCT/US2018/037922.

In some embodiments, the lipid nanoparticle comprises a molar ratio of 5-25% phospholipid relative to the other lipid components. For example, the lipid nanoparticle may comprise a molar ratio of 5-30%, 5-15%, 5-10%, 10-25%, 10-20%, 10-25%, 15-25%, 15-20%, 20-25%, or 25-30% phospholipid. In some embodiments, the lipid nanoparticle comprises a molar ratio of 5%, 10%, 15%, 20%, 25%, or 30% non-cationic lipid.

In some embodiments, the lipid nanoparticle comprises a molar ratio of 25-55% structural lipid relative to the other lipid components. For example, the lipid nanoparticle may comprise a molar ratio of 10-55%, 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% structural lipid. In some embodiments, the lipid nanoparticle comprises a molar ratio of 10%, 15%, 20%, 25%, 30%, 35%, 40%, 45%, 50%, or 55% structural lipid.

In some embodiments, the lipid nanoparticle comprises a molar ratio of 0.5-15% PEG lipid relative to the other lipid components. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15% PEG lipid. In some embodiments, the lipid nanoparticle comprises a molar ratio of 0.5%, 1%, 2%, 3%, 4% 5%, 6%, 7%, 8%, 9% 10%, 11%, 12%, 13%, 14%, or 15% PEG-lipid.

In some embodiments, the lipid nanoparticle comprises a molar ratio of 20-60% amino lipid, 5-25% phospholipid, 25-55% structural lipid, and 0.5-15% PEG lipid.

In some embodiments, the lipid nanoparticle comprises a molar ratio of 20-60% amino lipid, 5-30% phospholipid, 10-55% structural lipid, and 0.5-15% PEG lipid.

Structural Lipids

The lipid composition of a pharmaceutical composition provided herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As used herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. application Ser. No. 16/493,814.

In some embodiments, the lipid nanoparticle comprises 30-45 mol % sterol, optionally 35-40 mol %, for example, 30-31 mol %, 31-32 mol %, 32-33 mol %, 33-34 mol %, 35-35 mol %, 35-36 mol %, 36-37 mol %, 38-38 mol %, 38-39 mol %, or 39-40 mol %. In some embodiments, the lipid nanoparticle comprises 25-55 mol % sterol. For example, the lipid nanoparticle may comprise 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises 25 mol %, 30 mol %, 35 mol %, 40 mol %, 45 mol %, 50 mol %, or 55 mol % sterol.

In some embodiments, the lipid nanoparticle comprises 35-40 mol % cholesterol. For example, the lipid nanoparticle may comprise 35, 35.5, 36, 36.5, 37, 37.5, 38, 38.5, 39, 39.5, or 40 mol % cholesterol.

Polyethylene Glycol (PEG)-Liquids

Effective in vivo delivery of nucleic acids represents a continuing medical challenge. Exogenous nucleic acids (i.e., originating from outside of a cell or organism) are readily degraded in the body, e.g., by the immune system. Accordingly, effective delivery of nucleic acids to cells often requires the use of a particulate carrier (e.g., lipid nanoparticles). The particulate carrier should be formulated to have minimal particle aggregation, be relatively stable prior to intracellular delivery, effectively deliver nucleic acids intracellularly, and illicit no or minimal immune response. To achieve minimal particle aggregation and pre-delivery stability, many conventional particulate carriers have relied on the presence and/or concentration of certain components (e.g., PEG-lipid). However, it has been discovered that certain components may decrease the stability of encapsulated nucleic acids (e.g., mRNA molecules). The reduced stability may limit the broad applicability of the particulate carriers. As such, there remains a need for methods by which to improve the stability of nucleic acid (e.g. mRNA) encapsulated within lipid nanoparticles.

The lipid composition of a pharmaceutical composition disclosed herein can comprise one or more polyethylene glycol (PEG) lipids. As used herein, the term "PEG-lipid" or "PEG-modified lipid" refers to polyethylene glycol (PEG)-modified lipids. Non-limiting examples of PEG-lipids include PEG-modified phosphatidylethanolamine and phosphatidic acid. PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated to lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxypropyl-3-amine (PEG-c-DMA).

In some embodiments, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG. PEG-c-DOMG (also referred to as PEG-DOMG), PEG-DSG and/or PEG-DPG.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-$NH_2$, has a size of about 1000, 2000, 5000, 10,000, 15,000 or 20,000 daltons. In some embodiments, the PEG-lipid is $PEG_{2k}$-DMG.

In some embodiments, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

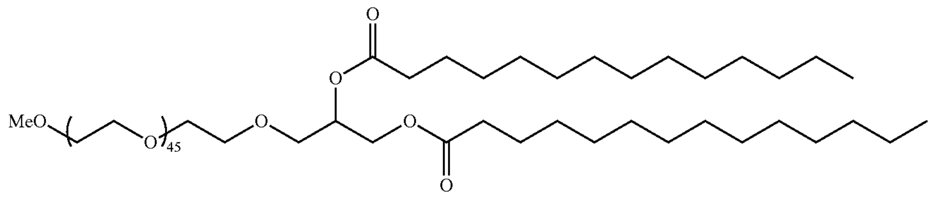

In some embodiments, PEG lipids can be PEGylated lipids described in International Publication No. WO2012099755, the contents of which is herein incorporated by reference in its entirety. Any exemplary PEG lipids may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment.

In certain embodiments, a PEG lipid is a compound of Formula (X):

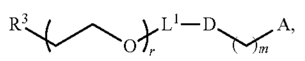

(X)

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), $C(O)N(R^N)$, $NR^NC(O)$, C(O)O, OC(O), OC(O)O, $OC(O)N(R^N)$, $NR^NC(O)O$, or $NR^NC(O)N(R^N)$.

D is a moiety obtained by click chemistry or a moiety cleavable under physiological conditions;

m is 0, 1, 2, 3, 4, 5, 6, 7, 8, 9, or 10;

A is of the formula:

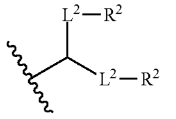 or 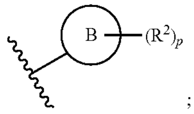 ;

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$ $NR^NC(O)$, C(O)O, OC(O), OC(O)O, $OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), —OC(O)O, $OC(O)N(R^N)$, $NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, —OS(O)O, $OS(O)_2$, $S(O)_2O$, $OS(O)_{2}O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $—N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (X) is a PEG-OH lipid (i.e., $R^3$ is $—OR^O$, and $R^O$ is hydrogen). In certain embodiments, the compound of Formula (X) is of Formula (X-OH):

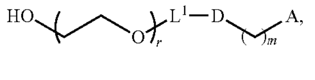

(X-OH)

or a salt thereof.

In certain embodiments, a PEG lipid is a PEGylated fatty acid. In certain embodiments, a PEG lipid is a compound of Formula (XI). Provided herein are compounds of Formula (XI):

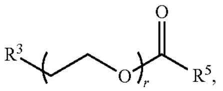

(XI)

or a salts thereof, wherein:

$R^3$ is $—OR^O$;

$R^O$ is hydrogen, optionally substituted alkyl or an oxygen protecting group;

r is an integer between 1 and 100, inclusive;

$R^5$ is optionally substituted $C_{1-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), $C(O)N(R^N)$, $—NR^NC(O)$, $NR^NC(O)N(R^N)$, C(O)O, OC(O), OC(O)O, $OC(O)N(R^N)$, $NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $—NR^NC(S)N(R^N)$, S(O). OS(O), S(O)O, OS(O)O, $OS(O)_2$, $S(O)_{2}O$, $OS(O)_{2}O$, $N(R^N)S(O)$, $—S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $—N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group.

In certain embodiments, the compound of Formula (XI) is of Formula (XI-OH):

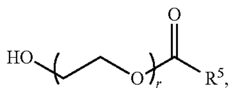

(XI-OH)

or a salt thereof. In some embodiments, r is 40-50.

In yet other embodiments the compound of Formula (XI) is:

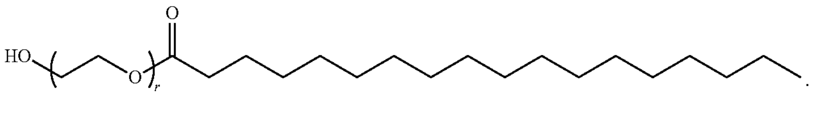

or a salt thereof.

In one embodiment, the compound of Formula (XI) is

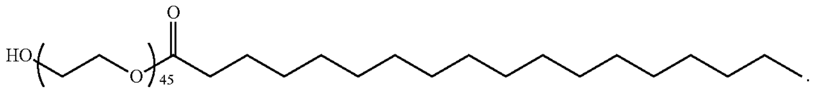

In some embodiments, the lipid composition of the pharmaceutical compositions disclosed herein does not comprise a PEG-lipid.

In some embodiments, the PEG-lipids may be one or more of the PEG lipids described in U.S. application Ser. No. 15/674,872.

In some embodiments, the lipid nanoparticle comprises 1-5% PEG-modified lipid, optionally 1-3 mol %, for example 1.5 to 2.5 mol %, 1-2 mol %, 2-3 mol %, 3-4 mol %, or 4-5 mol %. In some embodiments, the lipid nanoparticle comprises 0.5-15 mol % PEG-modified lipid. For example, the lipid nanoparticle may comprise 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol %. In some embodiments, the lipid nanoparticle comprises 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

In some embodiments, the lipid nanoparticle comprises 20-60 mol % ionizable amino lipid, 5-25 mol % non-cationic lipid, 25-55 mol % sterol, and 0.5-15 mol % PEG-modified lipid.

In some embodiments, a LNP comprises an ionizable amino lipid of Compound 1, wherein the non-cationic lipid is DSPC, the structural lipid that is cholesterol, and the PEG lipid DMG-PEG.

In some embodiments, a LNP comprises an ionizable amino lipid of any of Formula VI, VII or VIIII, a phospholipid comprising DSPC, a structural lipid, and a PEG lipid comprising PEG-DMG.

In some embodiments, a LNP comprises an ionizable amino lipid of any of Formula VI, VII or VIII, a phospholipid comprising DSPC, a structural lipid, and a PEG lipid comprising a compound having Formula XI.

In some embodiments, a LNP comprises an ionizable amino lipid of Formula VI, VII or VIII, a phospholipid comprising a compound having Formula VIII, a structural lipid, and the PEG lipid comprising a compound having Formula X or XI.

In some embodiments, a LNP comprises an ionizable amino lipid of Formula VI, VII or VIII, a phospholipid comprising a compound having Formula IX, a structural lipid, and the PEG lipid comprising a compound having Formula X or XI.

In some embodiments, a LNP comprises an ionizable amino lipid of Formula VI, VII or VIII, a phospholipid having Formula IX, a structural lipid, and a PEG lipid comprising a compound having Formula XI.

In some embodiments, the lipid nanoparticle comprises 49 mol % ionizable amino lipid, 10 mol % DSPC, 38.5 mol % cholesterol, and 2.5 mol % DMG-PEG.

In some embodiments, the lipid nanoparticle comprises 49 mol % ionizable amino lipid, 11 mol % DSPC, 38.5 mol % cholesterol, and 1.5 mol % DMG-PEG.

In some embodiments, the lipid nanoparticle comprises 48 mol % ionizable amino lipid, 11 mol % DSPC, 38.5 mol % cholesterol, and 2.5 mol % DMG-PEG.

In some embodiments, a subject to which a composition comprising a nucleic acid, and a compound of Formula I' or Formula I, or a tautomer, solvate, or salt thereof, is administered is a subject that suffers from or is at risk of suffering from a disease, disorder or condition, including a communicable or non-communicable disease, disorder or condition. As used herein. "treating" a subject can include either therapeutic use or prophylactic use relating to a disease, disorder or condition, and may be used to describe uses for the alleviation of symptoms of a disease, disorder or condition, uses for vaccination against a disease, disorder or condition, and uses for decreasing the contagiousness of a disease, disorder or condition, among other uses.

In some embodiments the nucleic acid is an mRNA vaccine designed to achieve particular biologic effects. Exemplary vaccines feature mRNAs encoding a particular antigen of interest (or an mRNA or mRNAs encoding antigens of interest). In exemplary aspects, the vaccines feature an mRNA or mRNAs encoding antigen(s) derived from infectious diseases or cancers.

The compositions provided herein are also useful for treating or preventing a symptom of diseases characterized by missing or aberrant protein activity, by replacing the missing protein activity or overcoming the aberrant protein activity.

In some embodiments, microbial growth within a composition disclosed herein is inhibited. In some embodiments, microbial growth is inhibited by the compound (e.g., a compound of Formula I' or Formula I, or a tautomer, solvate, or salt thereof). In some embodiments, a composition disclosed herein does not comprise a pharmaceutical preservative. Non-limiting examples of pharmaceutical preservatives include methyl paragen, ethyl paraben, propyl paraben, butyl paraben, benzyl alcohol, chlorobutanol, phenol, meta cresol (m-cresol), chloro cresol, benzoic acid, sorbic acid, thiomersal, phenylmercuric nitrate, bronopol, propylene glycol, benzylkonium chloride, and benzethionium chloride. In some embodiments, a composition disclosed herein does not comprise phenol, m-cresol, or benzyl alcohol. Compositions in which microbial growth is inhibited may be useful in the preparation of injectable formulations, including those intended for dispensing from multi-dose vials. Multi-dose vials refer to containers of pharmaceutical compositions from which multiple doses can be taken repeatedly from the same container. Compositions intended for dispensing from multi-dose vials typically must meet USP requirements for antimicrobial effectiveness. In some embodiments, a composition comprising a stabilizing compound (e.g., a compound of Formula I' or Formula I, or a tautomer, solvate, or salt thereof) has antimicrobial effectiveness, and may be dispensed from a multi-dose vial.

In some embodiments, "administering" or "administration" means providing a material to a subject in a manner that is pharmacologically useful. In some embodiments, a composition is administered to a subject enterally. In some embodiments, an enteral administration of the composition is oral. In some embodiments, a composition is administered to the subject parenterally. In some embodiments, a composition is administered to a subject subcutaneously, intraocularly, intravitreally, subretinally, intravenously (IV), intracerebro-ventricularly, intramuscularly, intrathecally (IT), intracistemally, intraperitoneally, via inhalation, topically, or by direct injection to one or more cells, tissues, or organs.

To "treat" a disease as the term is used herein, means to reduce the frequency or severity of at least one sign or symptom of a disease, disorder or condition experienced by a subject. The compositions described above or elsewhere herein are typically administered to a subject in an effective amount, that is, an amount capable of producing a desirable result. The desirable result will depend upon the active agent being administered. For example, an effective amount of a composition comprising a nucleic acid, a lipid, and a compound of Formula I' or Formula I, or a tautomer, solvate, or salt thereof, may be an amount of the composition that is capable of increasing expression of a protein in the subject. A therapeutically acceptable amount may be an amount that is capable of treating a disease or condition, e.g., a disease or condition that that can be relieved by increasing expression of a protein in a subject. As is well known in the medical and veterinary arts, dosage for any one subject depends on many factors, including the subject's size, body surface area, age, the particular composition to be administered, the active ingredient(s) in the composition, the intended outcome of the administration, time and route of administration, general health, and other drugs being administered concurrently.

In some embodiments, a subject is administered a composition comprising a nucleic acid, a lipid, and/or a compound of Formula I' or Formula I, or a tautomer, solvate, or salt thereof, in an amount sufficient to increase expression of a protein in the subject.

Methods of Formulating

Also provided are methods of formulating nucleic acids. Some embodiments comprise adding a stabilizer compound to a composition comprising a nucleic acid and a lipid. In some embodiments, a method of formulating a nucleic acid comprises adding to a composition comprising a nucleic acid and a lipid, a compound of Formula I' or Formula I, or a tautomer or solvate thereof, to obtain a formulated composition. In certain embodiments, the compound of Formula I' or Formula I is of Formula Ia, Formula Ib, or Formula Ic, or a tautomer or solvate thereof.

In some embodiments, a method of formulating a nucleic acid comprises adding to a composition comprising a nucleic acid and a lipid, a compound of Formula II, or a tautomer or solvate thereof, to obtain a formulated composition. In certain embodiments, the compound of Formula II is of Formula IIa, or a tautomer or solvate thereof.

In some embodiments, the stabilizer compound is added to a composition comprising mRNA, and then the mRNA/stabilizer composition is used in the formation of a LNP. In some embodiments, the mRNA, stabilizer compound, and one or more LNP components are independently mixed together to form a LNP composition comprising mRNA and the stabilizer compound. In some embodiments, the stabilizer compound is added to a mRNA-encapsulated LNP. In some embodiments, the stabilizer compound is added to the LNP in a composition that comprises one or more components of the LNP, such as an ionizable lipid, a non-cationic lipid, and sterol, and/or a PEG-lipid.

In some embodiments, the stabilizer compound is added to a composition (e.g., containing mRNA, mRNA-encapsulated LNPS, or LNP components) at a pH of about 3.5 to about 8.5, such as from about 4 to about 8, about 4.5 to about 7.5, about 4, about 4.5, about 5, about 5.5, about 6, about 6.5, about 7, about 7.4, about 7.5, about 7.6, or about 8.

In some embodiments, the compositions containing the stabilizer compound are formulated under conditions that minimize, inhibit, or prevent exposure of the composition to light (e.g., room light, sunlight, UV light, and/or fluorescent light). In some embodiments, the formulations are prepared in the absence of one or more of room light, sunlight, UV light, and fluorescent light. In some embodiments, compositions containing the stabilizer compound are exposed to light (e.g., room light, UV light, and/or fluorescent light) for a period of 24 hours or less, such as 20 hours or less, 15 hours or less, 10 hours or less, 5 hours or less, 3 hours or less, 2 hours or less, 1 hour or less, 45 minutes or less, 30 minutes or less, 15 minutes or less, 10 minutes or less, or 5 minutes or less.

In certain embodiments, LNP preparations (e.g., populations or formulations) are analyzed for polydispersity in size (e.g., particle diameter) and/or composition (e.g., amino lipid amount or concentration, phospholipid amount or concentration, structural lipid amount or concentration, PEG-lipid amount or concentration, mRNA amount (e.g., mass) or concentration) and, optionally, further assayed for in vitro and/or in vivo activity. Fractions or pools thereof can also be analyzed for accessible mRNA and/or purity (e.g., purity as determined by reverse-phase (RP) chromatography).

Particle size (e.g., particle diameter) can be determined by Dynamic Light Scattering (DLS). DLS measures a hydrodynamic diameter. Smaller particles diffuse more quickly, leading to faster fluctuations in the scattering intensity and shorter decay times for the autocorrelation function. Larger particles diffuse more slowly, leading to slower fluctuations in the scattering intensity and longer decay times in the autocorrelation function.

mRNA purity can be determined by reverse phase high-performance liquid chromatography (RP-HPLC) size based separation. This method can be used to assess mRNA integrity by a length-based gradient RP separation and UV detection of RNA at 260 nm. As used herein "main peak" or "main peak purity" refers to the RP-HPLC signal detected from mRNA that corresponds to the full size mRNA molecule loaded within a given LNP formulation. mRNA purity can also be assessed by fragmentation analysis. Fragmentation analysis (FA) is a method by which nucleic acid (e.g., mRNA) fragments can be analyzed by capillary electrophoresis. Fragmentation analysis involves sizing and quantifying nucleic acids (e.g., mRNA), for example by using an intercalating dye coupled with an LED light source. Such analysis may be completed, for example, with a Fragment Analyzer from Advanced Analytical Technologies, Inc.

Compositions formed via the methods described herein may be particularly useful for administering an agent to a subject in need thereof. In some embodiments, the compositions are used to deliver a pharmaceutically active agent. In some instances, the compositions are used to deliver a prophylactic agent. The compositions may be administered in any way known in the art of drug delivery, for example, orally, parenterally, intravenously, intramuscularly, subcutaneously, intradermally, transdermally, intrathecally, submucosally, sublingually, rectally, vaginally, etc.

Once the compositions have been prepared, they may be combined with pharmaceutically acceptable excipients to form a pharmaceutical composition. As would be appreciated by one of skill in this art, the excipients may be chosen based on the route of administration as described below, the agent being delivered, and the time course of delivery of the agent.

Pharmaceutical compositions described herein and for use in accordance with the embodiments described herein may include a pharmaceutically acceptable excipient. As used herein, the term "pharmaceutically acceptable excipient" means a non-toxic, inert solid, semi-solid or liquid filler, diluent, encapsulating material or formulation auxiliary of any type. Some examples of materials which can serve as pharmaceutically acceptable excipients are sugars such as lactose, glucose, and sucrose; starches such as corn starch and potato starch; cellulose and its derivatives such as sodium carboxymethyl cellulose, methylcellulose, hydroxypropylmethylcellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen free water; isotonic saline; citric acid, acetate salts, Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions can be administered to humans and/or to animals, orally, rectally, parenterally, intracistemally, intravaginally, intranasally, intraperitoneally, topically (as by powders, creams, ointments, or drops), bucally, or as an oral or nasal spray.

Liquid dosage forms for oral administration include pharmaceutically acceptable emulsions, microemulsions, solutions, suspensions, syrups, and elixirs. In addition to the active ingredients (i.e., the particles), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, ethanol, U.S.P., and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are used in the preparation of injectables.

The injectable formulations can be sterilized, for example, by filtration through a bacteria retaining filter, or by incorporating sterilizing agents in the form of sterile solid compositions which can be dissolved or dispersed in sterile water or other sterile injectable medium prior to use.

Compositions for rectal or vaginal administration may be suppositories which can be prepared by mixing the particles with suitable non irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard filled gelatin capsules using such excipients as lactose or milk sugar as well as high molecular weight polyethylene glycols and the like.

The solid dosage forms of tablets, dragées, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also possible.

The ointments, pastes, creams, and gels may contain, in addition to the compositions provided herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the compositions provided herein, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compositions in a proper medium. Absorption enhancers can also be used to increase the flux of the compound across the skin. The rate can be controlled by either providing a rate controlling membrane or by dispersing the compositions in a polymer matrix or gel.

In other embodiments, the stabilized compositions are loaded and stored in prefilled syringes and cartridges for patient-friendly autoinjector and infusion pump devices.

Kits for use in preparing or administering the compositions are also provided. A kit for forming compositions may include any solvents, solutions, buffer agents, acids, bases, salts, targeting agent, etc. needed in the composition formation process. Different kits may be available for different targeting agents. In certain embodiments, the kit includes materials or reagents for purifying, sizing, and/or characterizing the resulting compositions. The kit may also include instructions on how to use the materials in the kit. The one or more agents (e.g., pharmaceutically active agent) to be contained within the composition are typically provided by the user of the kit.

Kits are also provided for using or administering the compositions. The compositions may be provided in convenient dosage units for administration to a subject. The kit may include multiple dosage units. For example, the kit may include 1-100 dosage units. In certain embodiments, the kit includes a week supply of dosage units, or a month supply of dosage units. In certain embodiments, the kit includes an even longer supply of dosage units. The kits may also include devices for administering the compositions. Exemplary devices include syringes, spoons, measuring devices, etc. The kit may optionally include instructions for administering the compositions (e.g., prescribing information).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds provided herein include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, the terms "composition" and "formulation" are used interchangeably.

The following examples are intended to illustrate certain non-limiting embodiments. Without further elaboration, it is believed that one skilled in the art can, based on the above description, utilize the disclosed compositions and methods to the fullest extent. The following specific embodiments are, therefore, to be construed as merely illustrative, and not limitative in any way whatsoever.

Other Definitions

Unless otherwise stated, structures depicted herein are also meant to include compounds that differ only in the presence of one or more isotopically enriched atoms. For example, compounds having the present structures except for the replacement of hydrogen ($^1H$) by deuterium ($^2H$) or tritium ($^3H$), replacement of $^{19}F$ with $^{18}F$, or the replacement of a carbon ($^{12}C$) by a $^{13}C$- or $^{14}C$-enriched carbon are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "pharmaceutically acceptable anion" refers to a negatively charged group that is associated with a positively charged group (e.g., the polycyclic core of Formula I' or Formula I) in order to maintain electronic neutrality. Also referred to as a "counterion," the anion may be monovalent (e.g., including one formal negative charge). The anion may also be multivalent (e.g., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, propanoate, benzoate, glycerate, lactate, tartrate, glycolate, gluconate, and the like). Exemplary counterions which may be multivalent include $CO_3^{2-}$, $HPO_4^{2-}$, $PO_4^{3-}$, $SO_4^{2-}$, and carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like). In certain particular embodiments, the pharmaceutically acceptable anion of the compound of Formula I' or Formula I is chloride.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds provided herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·$0.5H_2O$)), and polyhydrates (x is a number greater than 1, e.g., dihydrates (R·$2H_2O$) and hexahydrates (R·$6H_2O$)).

The term "tautomers" or "tautomeric" refer to isomers of a compound which differ only in the position of the protons and electrons, e.g., two or more interconvertible compounds resulting from at least one migration of a hydrogen atom or electron pair, and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol, amide-to-imide, lactam-to-lactam, enamine-to-imine, and enamine-to-(a different enamine) tautomerizations. Tautomerizations may result from delocalization of electrons (e.g., between heteroatoms and/or pi bonds in conjugated systems).

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds provided herein include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example. Berge et al., describe pharmaceutically acceptable salts in detail in *J. Pharmaceutical Sciences,* 1977, 66, 1-19, incorporated herein by reference. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

EXAMPLES

Example 1. Representative Syntheses 1

Scheme 1A

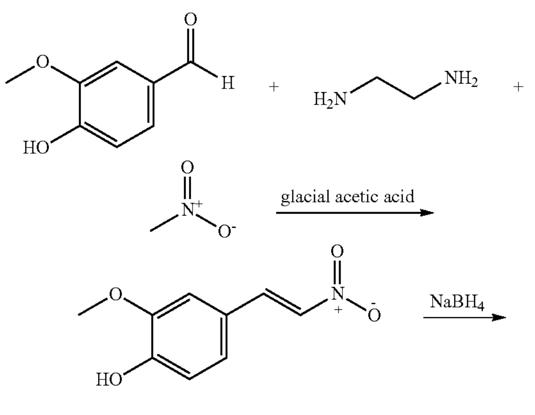

-continued

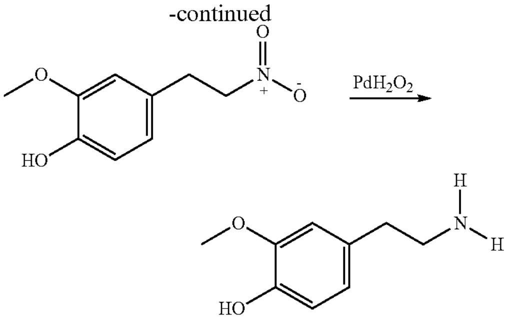

Scheme 1B

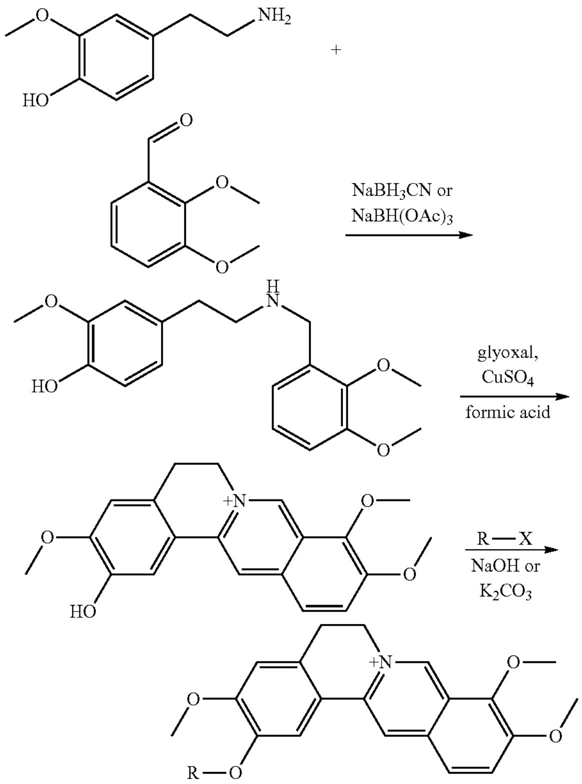

Scheme 1C

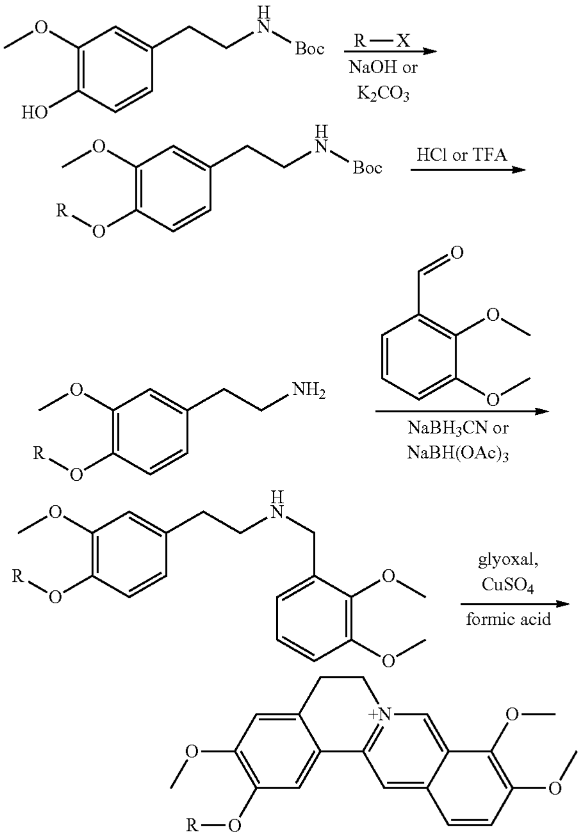

Appropriately substituted phenethylamine and benzaldehyde reagents are reductively coupled, then condensed with glyoxal to afford the tetracyclic core compound. As will be appreciated by those of skill in the art, this reaction sequence can be used to obtain isomeric or analogous products, suitable for the synthesis of all of the compounds disclosed herein, by substituting the appropriate analogous or isomeric phenethylamine and/or benzaldehyde reagents. The hydroxyl-containing compounds are alkylated with appropriate R—X reagents either prior to reductive coupling or subsequent to condensation to afford the corresponding product, as shown in the table below.

| R—X | Product | Example |
|---|---|---|
| none | 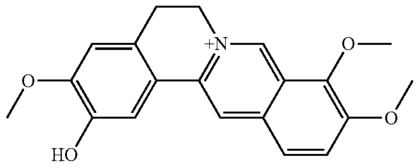 | 1 |
| 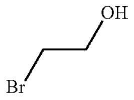 | 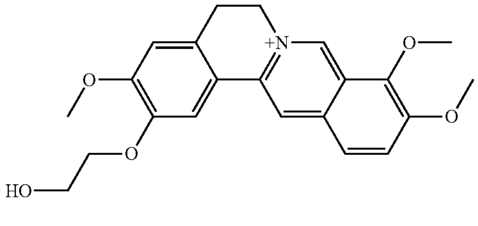 [SMILES: COc1cc2c(cc1OCCO)-c1cc3ccc(OC)c(OC)c3c[n+]1CC2] | 2 |

-continued
| R—X | Product | Example |
|---|---|---|
| 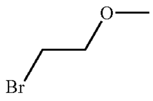 | 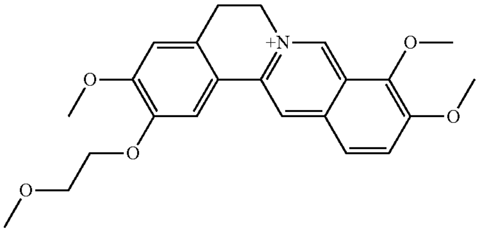 | 3 |
| 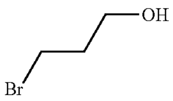 | 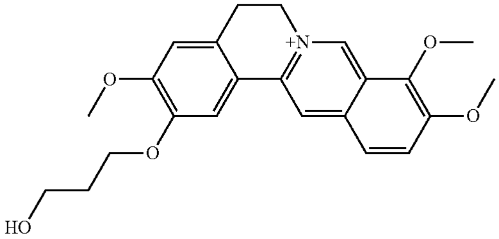 [SMILES: COc1cc2c(cc1OCCCO)-c1cc3ccc(OC)c(OC)c3c[n+]1CC2] | 4 |
| 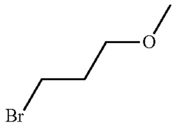 | 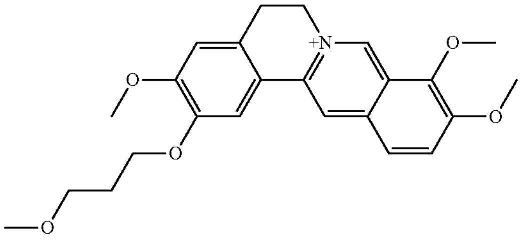 | 5 |
| 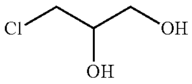 | 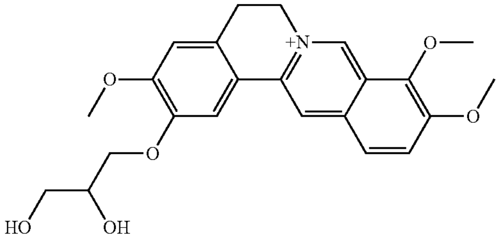 [SMILES: COc1cc2c(cc1OCC(O)CO)-c1cc3ccc(OC)c(OC)c3c[n+]1CC2] | 11 |
| 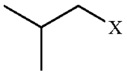 | 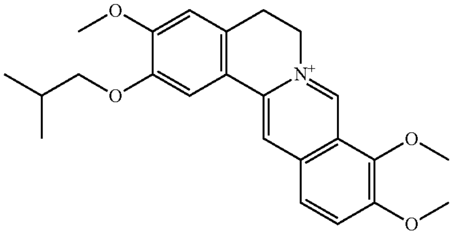 [SMILES: COc1cc2c(cc1OCC(C)C)-c1cc3ccc(OC)c(OC)c3c[n+]1CC2] | 80 |
| 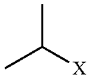 | 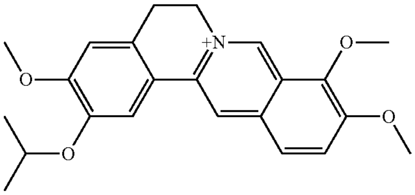 [SMILES: COc1cc2c(cc1OC(C)C)-c1cc3ccc(OC)c(OC)c3c[n+]1CC2] | 81 |

-continued

| R—X | Product | Example |
|---|---|---|
| 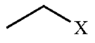 | 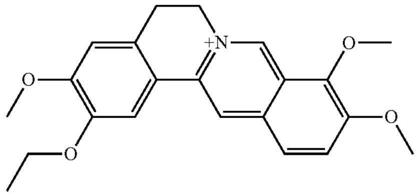 [SMILES: CCOc1cc2c(cc1OC)CC[n+]1cc3c(OC)c(OC)ccc3cc1-2] | 82 |
| 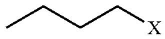 | 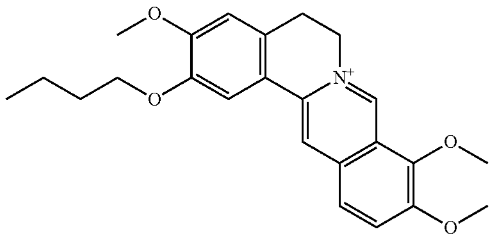 [SMILES: CCCCOc1cc2c(cc1OC)CC[n+]1cc3c(OC)c(OC)ccc3cc1-2] | 83 |
| 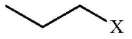 | 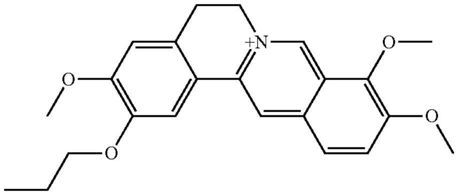 [SMILES: CCCOc1cc2c(cc1OC)CC[n+]1cc3c(OC)c(OC)ccc3cc1-2] | 84 |

2-Hydroxy-3,9,10-trimethoxy-5,6-dihydroisoquinolino[3,2-a]isoquinolin-7-ium (Example 1

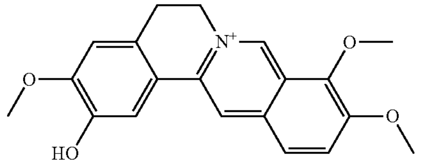

UPLC/ELSD: RT=0.61 min. MS (ES): m/z ($M^+$) 338.21 for $C_{20}H_{20}NO_4^+$. $^1$H NMR (301 MHz, $CD_3OD$) δ 3.28 (m, 2H); 3.99 (s, 3H); 4.13 (s, 3H); 4.23 (s, 3H), 4.95 (m, 2H); 7.05 (s, 1H); 7.60 (s, 1H); 8.07 (m, 2H); 8.68 (s, 1H); 9.77 (s, 1H).

11-(2-hydroxyethoxy)-3,4,10-trimethoxy-7,8-dihydro-6λ$^5$-azatetraphen-6-ylium (Example 2

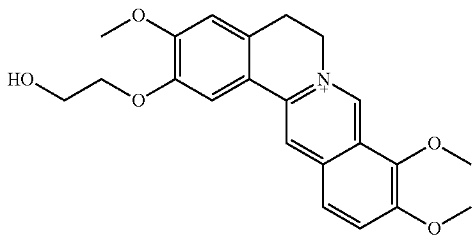

Chemical Formula: $C_{22}H_{24}NO_5^+$

Molecular Weight: 382.44

To a suspension of anhydrous copper(II) sulfate (1.908 g, 11.952 mmol) and 2-[4-(2-{[(2,3-dimethoxyphenyl)methyl]amino}ethyl)-2-methoxyphenoxy]ethanol (1.2 g, 3.32 mmol) in formic acid (16.6 mL). When the temperature reached 100° C., glyoxal (0.963 g, 6.64 mmol) was added. Upon addition, solution turned from blue to green to yellow to brown. The reaction was cooled to room temperature and was allowed to stir at for 18 hours. The solvent was then removed under reduced pressure. The crude product was dissolved in methanol and was left to settle, then was filtered. The residue was purified by silica gel chromatography (20-100% ACN in water) to obtain 11-(2-hydroxyethoxy)-3,4,10-trimethoxy-7,8-dihydro-6λ$^5$-azatetraphen-6-ylium (0.067 g, 3.32 mmol, 4.1% yield). UPLC/ELSD: RT=0.56 min. MS (ES) m/z calcd for $C_{22}H_{25}NO_5^+$ (M+H), 382.17; found, 382.28. $^1$H NMR (301 MHz, MeOD) δ 9.79 (s, 1H), 8.80 (s, 1H), 8.15 (d. J=9.1 Hz, 1H), 8.03 (d, J=9.1 Hz, 1H), 7.74 (s, 1H), 7.10 (s, 1H), 4.96 (t, J=6.3 Hz, 2H), 4.25 (q, J=4.4 Hz, 2H), 4.23 (s, 3H), 4.14 (s, 3H), 3.98 (s, 3H), 4.02-3.93 (m, 2H).

2-(3-Hydroxypropoxy)-3,9,10-trimethoxy-5,6-dihydroisoquinolino[3,2-a]isoquinolin-7-ium (Example 4

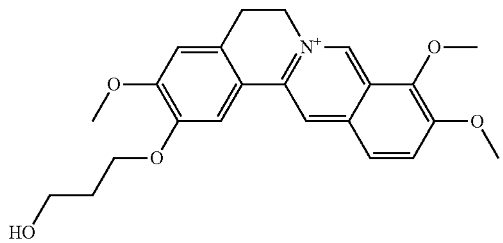 [SMILES: COc1cc2c(cc1OCCCO)-c1cc3ccc(OC)c(OC)c3c[n+]1CC2]

UPLC/ELSD: RT=0.71 min. MS (ES): m/z ($M^+$) 396.23 for $C_{23}H_{26}NO_5$+. $^1$H NMR (301 MHz. $CD_3OD$) δ 2.09 (m, 2H); 3.32 (m, 2H); 3.83 (m, 2H); 3.95 (s, 3H); 4.12 (s, 3H); 4.18-4.35 (m, 5H); 4.95 (m, 2H); 7.06 (s, 1H); 7.69 (s, 1H); 8.06 (m, 2H); 8.42 (m, 1H); 8.76 (s, 1H); 9.77 (s, 1H).

11-(2,3-dihydroxypropoxy)-3,4,10-trimethoxy-7,8-dihydro-6λ$^5$-azatetraphen-6ylium (Example 11

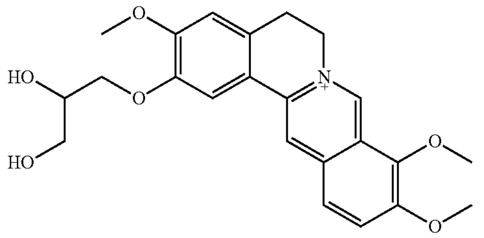

Chemical Formula: $C_{23}H_{26}NO_6^+$
Molecular Weight: 412.46

To a suspension of anhydrous copper(II) sulfate (1.761 g, 11.035 mmol) and 3-[4-(2-{[(2,3-dimethoxyphenyl)methyl]amino}ethyl)-2-methoxyphenoxy]propane-1,2-diol (1.2 g, 3.065 mmol) in formic acid (15.3 mL). When the temperature reached 100° C., glyoxal (0.89 g, 6.131 mmol) was added. Upon addition, solution turned from blue to green to yellow to brown. The reaction was stirred at 100° C. for 2 h. The reaction was then cooled to room temperature and was allowed to stir for 18 hours. The solvent was removed under reduced pressure. The crude product was dissolved in methanol and was left to settle, then was filtered. The residue was purified by silica gel chromatography (20-100% ACN in water) to obtain 11-(2,3-dihydroxypropoxy)-3,4,10-trimethoxy-7,8-dihydro-6λ$^5$-azatetraphen-6-ylium (0.031 g, 0.053 mmol, 1.7% yield). UPLC/ELSD: RT=0.24 min. MS (ES) m/z calcd for $C_{23}H_{27}O_6^+$ (M+H), 412.18; found, 412.40. $^1$H NMR (301 MHz, MeOD) δ 9.72 (s, 1H), 8.73 (s, 1H), 8.11-7.98 (m, 2H), 7.64 (s, 1H), 6.99 (s, 1H), 4.27 (dd, J=9.9, 4.3 Hz, 1H), 4.20 (s, 4H), 4.17-4.11 (m, OH), 4.08 (s, 4H), 3.93-3.68 (m, 6H), 3.27 (t, J=6.4 Hz, 2H), 3,4,10-trimethoxy-11-(2-methylpropoxy)-7,8-dihydro-6?s-azatetraphen-6-ylium (Example 80)

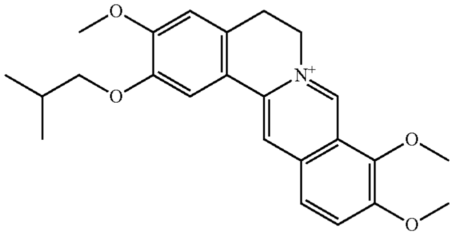

Chemical Formula: $C_{24}H_{28}NO_4^+$
Molecular Weight: 394.49

To a suspension of anhydrous copper(II) sulfate (1.785 g, 11.181 mmol) and [(2,3-dimethoxyphenyl)methyl]({2-[3-methoxy-4-(2-methylpropoxy)phenyl]ethyl})amine (1.16 g, 3.106 mmol) in formic acid (15.529 mL, 0.2 M, 13.387 Vols). When the temperature reached 100° C., glyoxal (0.901 g, 6.212 mmol) was added. Upon addition, solution turned from blue to green to yellow to brown. The reaction was cooled to room temperature and was allowed to stir at for 18 hours. The solvent was then removed under reduced pressure. The crude product was dissolved in methanol and was left to settle, then was filtered. The residue was purified by silica gel chromatography (20-100% ACN in water) to obtain 3,4,10-trimethoxy-11-(2-methylpropoxy)-7,8-dihydro-6λ$^5$-azatetraphen-6-ylium (0.071 mg, 0.171 mmol, 5.49% yield). UPLC/ELSD: RT=2.78 min. MS (ES) m/z calcd for $C_{24}H_{29}NO_4^+$ (M+H), 394.02; found, 394.25. $^1$H NMR (301 MHz, MeOD) δ 9.78 (s, 1H), 8.81 (s, 1H), 8.29 (s, 1H), 8.14 (d, J=9.1 Hz, 1H), 8.03 (d, J=9.2 Hz, 1H), 7.67 (s, 1H), 7.07 (s, 1H), 4.96 (t, J=6.4 Hz, 2H), 4.23 (s, 3H), 4.13 (s, 3H), 3.95 (d, J=8.8 Hz, 5H), 3.37 (s, 1H), 3.29 (d. J=6.2 Hz, 1H), 2.17 (dt, J=13.4, 6.8 Hz, 1H), 1.12 (d, J=6.7 Hz, 6H).

11-butoxy-3,4,10-trimethoxy-7,8-dihydro-6λ$^5$-azatetraphen-6-ylium (Example 83

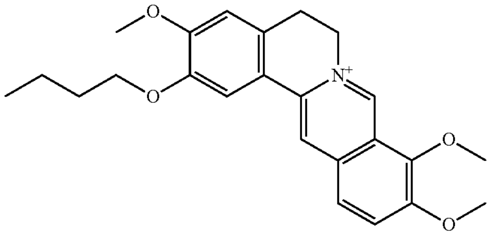

Chemical Formula: $C_{24}H_{28}NO_4^+$
Molecular Weight: 394.49

To a suspension of anhydrous copper(II) sulfate (1.846 g, 11.566 mmol) and [2-(4-butoxy-3-methoxyphenyl)ethyl][(2,3-dimethoxyphenyl)methyl]amine (1.2 g, 3.213 mmol) in Formic acid (16.065 mL, 0.2 M, 13.387 Vols). When the temperature reached 100 dC. Glyoxal (0.932 g, 6.426 mmol) was added. Upon addition, solution turned from blue to green to yellow to brown. The reaction was stirred at 100° C. for 2 h. The reaction was cooled to room temperature and was allowed to stir at for 18 hours. The solvent was then removed under reduced pressure. The crude product was dissolved in methanol and was left to settle, then was filtered. The residue was purified by silica gel chromatography (20-100% ACN in water) to obtain 11-butoxy-3,4,10-trimethoxy-7,8-dihydro-6λ$^5$-azatetraphen-6-ylium (0.11 g, 0.249 mmol, 7.7% yield). UPLC/ELSD: RT=2.19 min. MS (ES) m/z calcd for $C_{24}H_{29}NO_4^+$ (M+H), 394.20; found, 394.42. $^1$H NMR (301 MHz, $CDCl_3$) δ 7.03 (t, J=8.0 Hz, 1H), 6.94-6.79 (m, 3H), 6.73 (s, 1H), 6.65 (d. J=9.3 Hz, 2H), 5.48 (s, 1H), 5.32 (s, 1H), 4.53-4.47 (m, 1H), 4.43 (s, 1H), 4.15 (q, J=7.1 Hz, 1H), 3.85 (d, J=17.5 Hz, 9H), 3.41 (s, 1H), 3.33 (s, 1H), 2.75 (s, 2H), 2.07 (s, 1H), 1.57 (d, J=5.8 Hz, 1H), 1.28 (t, J=7.1 Hz, 1H).

2,3,9,10-Tetramethoxy-5-methyl-5,6-dihydroisoquinolino[3,2-a]isoquinolin-7-ium (Example 87

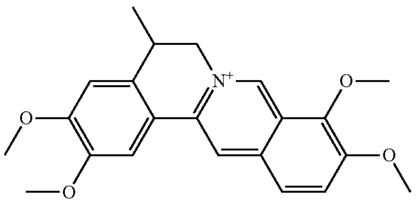

1,2-dimethoxy-4-(1-nitropropan-2-yl)benzene

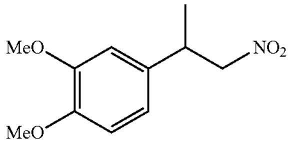 [SMILES: COc1ccc(C(C)C[N+](=O)[O-])cc1OC]

To a solution of 1,2-dimethoxy-4-[(1E)-2-nitroethenyl]benzene (6.71 g, 32.07 mmol) in THF (160 mL) was cooled to −20° C. and added methylmagnesium bromide (21.3 mL, 64.1 mmol, 3 M solution in diethyl ether) while maintaining temp at −20° C. Allowed it to stir for 30 mm. The reaction was quenched with water and solvents evaporated under vac. The residue was dissolved with water and ethyl acetate and extracted with ethyl acetate. The organic layer was separated, washed with brine, dried with $Na_2SO_4$, filtered and evaporated under vacuum. The residue was purified by flash chromatography (ISCO) by 0-50% ethyl acetate in hexanes to obtain the desired product 1,2-dimethoxy-4-(1-nitropropan-2-yl)benzene (3.56 g, 15.805 mmol, Yield 49.2%). UPLC/ELSD: RT=0.64 min. MS (ES): m/z (MH) 225.98 for $C_{11}H_{15}NO_4$. $^1H$ NMR (300 MHz, $CDCl_3$) □: ppm 1.39 (d, 3H); 3.61 (m, 1H); 3.90 (m, 6H); 4.51 (m, 2H); 6.80 (m, 3H).

2-(3,4-dimethoxyphenyl)propan-1-amine

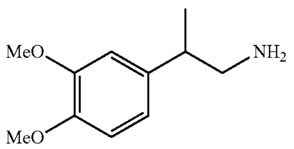

To a stainless steel pressurized vessel containing 1,2-dimethoxy-4-(1-nitropropan-2-yl)benzene (3.57 g, 15.8 mmol) under $N_2$ added Pearlmans Catalyst (995 mg, 7.09 mmol) followed by EtOH (80 mL). The reaction was allowed to stir under $H_2$ at 200 psi for 16 h at rt. The reaction was evacuated and filled with $N_2$. The reaction was filtered through a plug of Celite and washed with EtOH. Solvents were evaporated under vacuum. The residue was purified by flash chromatography (ISCO) by 0-20% MeOH in DCM to obtain 2-(3,4-dimethoxyphenyl)propan-1-amine (2 g, 10.2 mmol, Yield 64.6%). UPLC/ELSD: RT=0.37 min. MS (ES): m/z ($MH^+$) 195.73 for $C_{11}H_{17}NO_2$. $^1H$ NMR (301 MHz, $CD_3OD$) δ 1.28 (d, 3H); 2.75-2.94 (m, 3H); 3.84 (m, 6H); 6.79-6.97 (m, 3H).

N-(2,3-dimethoxybenzyl)-2-(3,4-dimethoxyphenyl)propan-1-amine

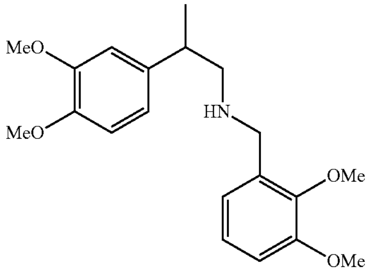 [SMILES: COc1ccc(C(C)CNCc2cccc(OC)c2OC)cc1OC]

To a slurry of 2-(3,4-dimethoxyphenyl)propan-1-amine (2 g, 10.2 mmol) in MeOH (51 mL) added, 2,3-dimethoxybenzaldehyde (1.702 g, 10.2 mmol) and stirred at rt. After few minutes (~5-10 min) the reaction turned clear amber color. Let the reaction stir for another 5 min and added Sodium cyanoborohydride (0.644 g, 10.2 mmol) and let it stir at rt ON. The solvents were evaporated. The residue was dissolved with water and ethyl acetate and extracted with ethyl acetate. The organic layer was separated, washed with brine, dried with $Na_2SO_4$, filtered and evaporated under vacuum. The residue was purified by flash chromatography (ISCO) by 0-6% MeOH in DCM to obtain N-(2,3-dimethoxybenzyl)-2-(3,4-dimethoxyphenyl)propan-1-amine (1.1 g, 3.1 mmol, Yield 31%). UPLC/ELSD: RT=0.69 min. MS (ES): m/z ($MH^+$) 346.23 for $C_{20}H_{27}NO_4$. $^1H$ NMR (301 MHz, $CDCl_3$) δ 1.26 (d, 3H); 2.58-2.89 (m, 4H); 2.97 (m, 1H); 3.75 (s, 3H); 3.88 (m, 10H); 6.66-6.90 (m, 5H); 7.02 (m, 1H).

2,3,9,10-Tetramethoxy-5-methyl-5,6-dihydroisoquinolino[3,2-a]isoquinolin-7-ium

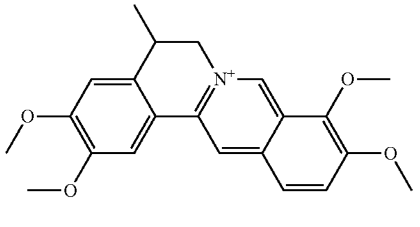

To a suspension of anhydrous Copper(II) sulfate (1.93 g, 12.0 mmol) and [(2,3-dimethoxyphenyl)methyl][2-(3,4-dimethoxyphenyl)propyl]amine (1.16 g, 3.3 mmol) in Formic acid (10 mL) added Glyoxal (0.974 g, 0.77 mL, 6.7 mmol) at 100° C. The reaction was stirred at 100° C. for 3 h. LCMS it to monitor the reaction. The reaction was cooled to rt. The reaction was evaporated under vac and the residue was dissolved in MeOH and evap under vac. The residue was dissolved in water and purified by reversed phase flash chromatography (ISCO) by 5-100% acetonitrile in water. The solid was triturated with IPA (3×) and the solid was dried under vacuum to obtain yellow colored solid as the product 2,3,9,10-Tetramethoxy-5-methyl-5,6-dihydroisoquinolino[3,2-a]isoquinolin-7-ium (99 mg, 0.25 mmol, Yield 12.3%). UPLC/ELSD: RT=1.28 min. MS (ES): m/z (M') 365.99 for $C_{22}H_{24}NO_4$+. $^1$H NMR (301 MHz, $CD_3OD$) δ 1.33 (d, 3H); 3.49 (m, 1H); 3.99 (m, 6H); 4.12 (s, 3H); 4.24 (s, 3H); 4.91 (m, 2H); 7.08 (s, 1H); 7.68 (s, 1H); 8.12 (m, 2H); 8.85 (s, 1H); 9.81 (s, 1H).

5-Cyclopropyl-2,3,9,10-tetramethoxy-5,6-dihydroisoquinolino[3,2-a]isoquinolin-7-ium (Example 86

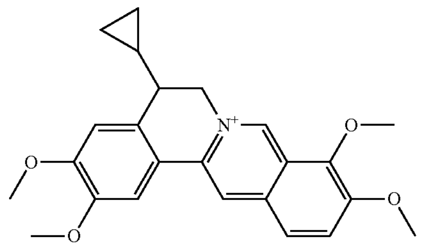

UPLC/ELSD: RT=1.78 min. MS (ES): m/z (M") 392.16 for $C_{24}H_{26}NO_4$+. $^1$H NMR (301 MHz. $CD_3OD$) δ 0.45 (m, 2H); 0.64 (m, 2H); 0.85 (m, 1H); 2.69 (m, 1H); 3.97 (s, 3H); 4.02 (s, 3H); 4.11 (s, 3H); 4.24 (s, 3H); 5.02 (m, 2H); 7.20 (s, 1H); 7.69 (s, 1H); 8.12 (m, 2H); 8.86 (s, 1H); 9.88 (s, 1H).

2-Isopropoxy-3,9,10-trimethoxy-5,6-dihydroisoquinolino[3,2-a]isoquinolin-7-ium (Example 81

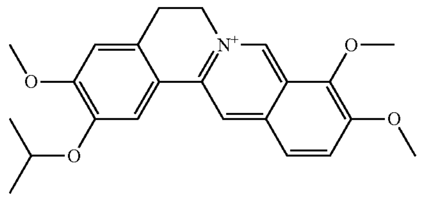 [SMILES: COc1cc2c(cc1OC(C)C)-c1cc3ccc(OC)c(OC)c3c[n+]1CC2]

Tert-butyl (4-isopropoxy-3-methoxyphenethyl)carbamate

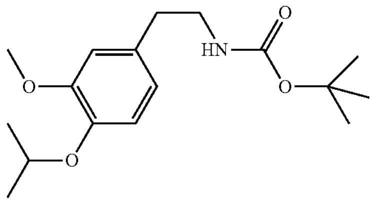 [SMILES: COc1cc(CCNC(=O)OC(C)(C)C)ccc1OC(C)C]

To a solution of tert-butyl N-[2-(4-hydroxy-3-methoxyphenyl)ethyl]carbamate (4 g, 14.96 mmol) in DMF (75 mL) added cesium carbonate (14.63 g, 44.89 mmol) and 2-iodopropane (2.24 mL, 22.45 mmol). The reaction was heated at 80° C. for 16 h. The reaction was cooled to rt, diluted with DCM and extracted with water (5×). The organic layer was separated, washed with brine, dried with $Na_2SO_4$, filtered and evaporated under vacuum. The residue was purified by flash chromatography (ISCO) by 0-20% MeOH in DCM to obtain tert-butyl N-[2-(4-isopropoxy-3-methoxyphenyl)ethyl]carbamate (3.4 g, 10.99 mmol, Yield 73.4%). $^1$H NMR (301 MHz, $CDCl_3$) δ 1.37 (d, 6H); 1.46 (s, 9H); 2.75 (m, 2H); 3.37 (m, 2H); 3.86 (s, 3H); 4.43-4.62 (m, 2H); 6.72 (m, 2H); 6.85 (m, 1H).

N-(2,3-dimethoxybenzyl)-2-(4-isopropoxy-3-methoxyphenyl)ethan-1-amine

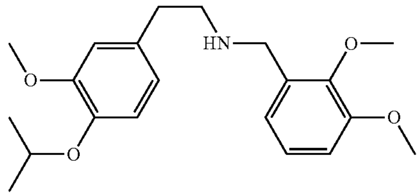 [SMILES: COc1cc(CCNCc2cccc(OC)c2OC)ccc1OC(C)C]

To a solution of tert-butyl N-[2-(4-isopropoxy-3-methoxyphenyl)ethyl]carbamate (3.4 g, 10.98 mmol) in DCM (55 mL) added Trifluoroacetic acid (8.5 mL, 109.89 mmol). The reaction was stirred at rt for 2 h. The reaction was evaporated under vacuum. The residue was diluted with DCM and extracted with sat $NaHCO_3$. The organic layer was separated, washed with brine, dried with $Na_2SO_4$, filtered and evaporated under vacuum. The residue-2-(4-isopropoxy-3-methoxyphenyl)ethan-1-amine (2.06 g, 9.8 mmol) in MeOH (50 mL) added 2,3-dimethoxybenzaldehyde (1.64 g, 9.84 mmol). The reaction was stirred at rt. After 10 min added Sodium cyanoborohydride (0.62 g, 9.84 mmol). Let the reaction stirred at rt for 16 h. Quenched the reaction with few drops of water and evaporated under vacuum. The residue was purified by flash chromatography (ISCO) by 0-100% (a solution of 20% MeOH, 80% DCM, 1% $NH_4OH$) in DCM to obtain the desired product. UPLC/ELSD: RT=0.65 min. MS (ES): m/z ($MH^+$) 360.43 for $C_{21}H_{29}NO_4$. $^1$H NMR (301 MHz, $CDCl_3$) δ 1.36 (d, 6H); 2.03 (bs, 1H); 2.85 (m, 4H); 3.75-4.00 (m, 11H); 4.48 (m, 1H); 6.72 (m, 2H); 6.85 (m, 3H); 7.02 (m, 1H).

2-Isopropoxy-3,9,10-trimethoxy-5,6-dihydroisoquinolino[3,2-a]isoquinolin-7-ium (Example 81

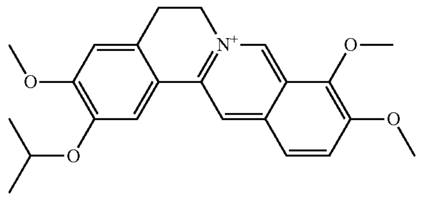 [SMILES: COc1cc2c(cc1OC(C)C)-c1cc3ccc(OC)c(OC)c3c[n+]1CC2]

To a suspension of anhydrous Copper(II) sulfate (2.08 g, 13.02 mmol) and [(2,3-dimethoxyphenyl)methyl][2-(4-isopropoxy-3-methoxyphenyl)ethyl]amine (1.3 g, 3.62 mmol) in Formic acid (18 mL) added Glyoxal (0.83 mL, 7.23 mmol) at 100° C. The reaction was stirred at 100° C. for 3 h. The reaction was monitored by LCMS. The reaction was cooled to rt and the reaction was evaporated under vac and the residue was dissolved in MeOH, filtered and the filtrate was evaporated under vac. The residue was dissolved in water and purified by reversed phase flash chromatography (ISCO) by 0-100% acetonitrile in water to obtain 2-Isopropoxy-3,9,10-trimethoxy-5,6-dihydroisoquinolino[3,2-a]

isoquinolin-7-ium (220 mg, 0.538 mmol, Yield 14.9%). UPLC/ELSD: RT=1.71 min. MS (ES): m/z ($M^+$) 380.31 for $C_{23}H_{26}NO_4$+. $^1$H NMR (301 MHz, $CD_3OD$) δ 1.40 (d, 6H); 3.37 (m, 2H); 3.95 (s, 3H); 4.12 (s, 3H); 4.22 (s, 3H); 4.77 (m, 1H); 4.96 (m, 2H); 7.08 (s, 1H); 7.70 (s, 1H); 8.08 (m, 2H); 8.74 (s, 1H); 9.79 (s, 1H).

2-Ethoxy-3,9,10-trimethoxy-5,6-dihydroisoquinolino[3,2-a]isoquinolin-7-ium (Example 82

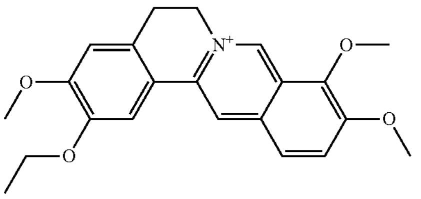 [SMILES: CCOc1cc2c(cc1OC)CC[n+]1cc3c(OC)c(OC)ccc3cc1-2]

UPLC/ELSD: RT=1.20 min. MS (ES): m/z ($M^+$) 366.48 for $C_{22}H_{24}NO_4$+. $^1$H NMR (301 MHz, $CD_3OD$) δ 1.49 (m, 3H); 3.37 (m, 2H); 3.97 (s, 3H); 4.06-4.34 (m, 8H); 4.96 (m, 2H); 7.06 (s, 1H); 7.65 (s, 1H); 8.08 (m, 2H); 8.76 (s, 1H); 9.78 (s, 1H).

3,9,10-Trimethoxy-2-propoxy-5,6-dihydroisoquinolino[3,2-a]isoquinolin-7-ium (Example 84

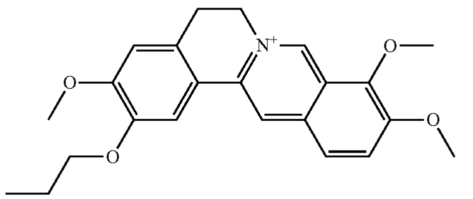 [SMILES: CCCOc1cc2c(cc1OC)CC[n+]1cc3c(OC)c(OC)ccc3cc1-2]

UPLC/ELSD: RT=1.91 min. MS (ES): m/z ($M^+$) 380.31 for $C_{23}H_{26}NO_4$+. $^1$H NMR (301 MHz, $CD_3OD$) δ 1.12 (t, 3H), 1.91 (p, 2H); 3.37 (m, 2H); 3.96 (s, 3H); 4.12 (m, 5H), 4.22 (s, 3H); 4.97 (m, 2H); 7.06 (s, 1H); 7.65 (s, 1H); 8.07 (m, 2H); 8.76 (s, 1H); 9.79 (s, 1H).

Example 2. Representative Syntheses 2

Scheme 2

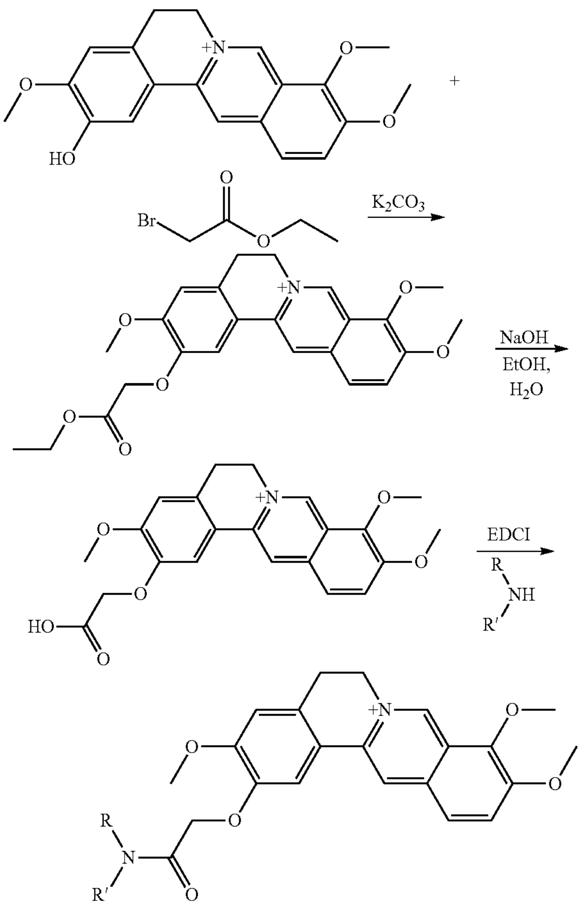

| R(R')NH | Product | Example |
| --- | --- | --- |
| none | 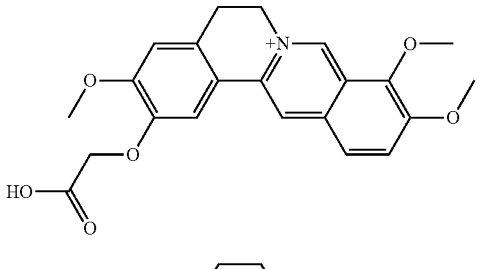 | 6 |
| 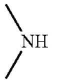 | 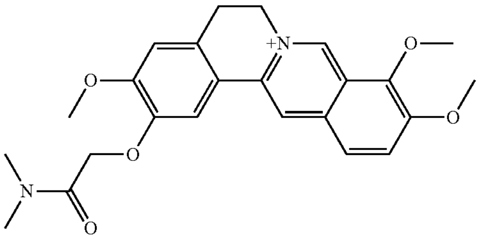 | 7 |

-continued
| R(R')NH | Product | Example |
| --- | --- | --- |
| 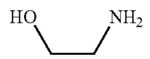 | 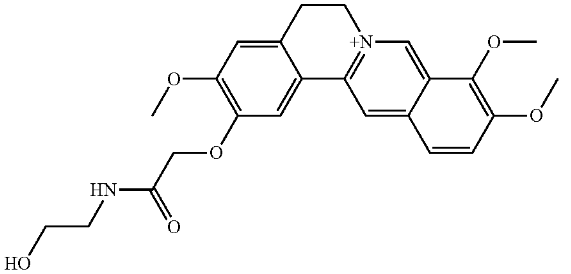 [SMILES: COc1cc2c(cc1OCC(=O)NCCO)-c1cc3ccc(OC)c(OC)c3c[n+]1CC2] | 8 |
| 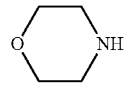 | 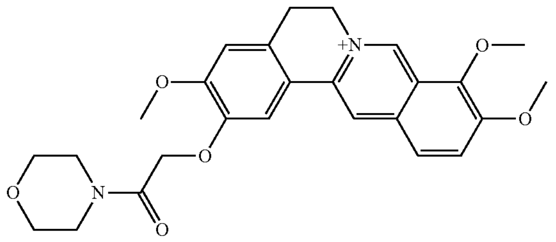 [SMILES: COc1cc2c(cc1OCC(=O)N1CCOCC1)-c1cc3ccc(OC)c(OC)c3c[n+]1CC2] | 9 |
| 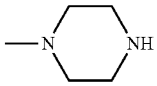 | 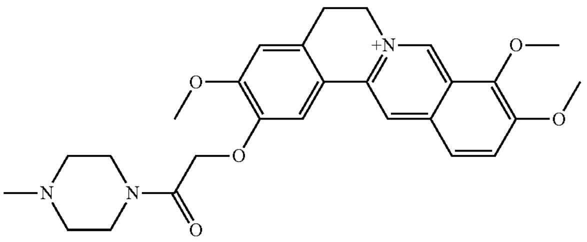 | 10 |
2-(2-(Dimethylamino)-2-oxoethoxy)-3,9,10-trimethoxy-5,6-dihydroisoquinolino[3,2-a]isoquinolin-7-ium (Example 7
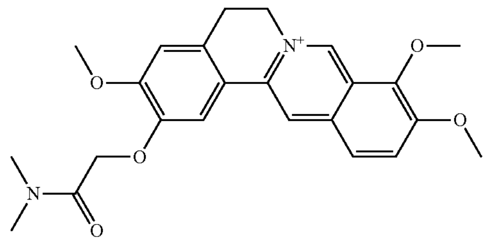
UPLC/ELSD: RT=0.63 min. MS (ES): m/z ($M^+$) 423.75 for $C_{24}H_{27}N_2O_5$+. $^1H$ NMR (301 MHz, $CD_3OD$) δ 2.99 (s, 3H); 3.17 (s, 3H); 3.31 (m, 2H); 3.95 (s, 3H); 4.11 (s, 3H); 4.22 (s, 3H); 4.96 (m, 4H); 7.07 (s, 1H); 7.69 (s, 1H); 8.09 (m, 2H); 8.73 (s, 1H); 9.77 (s, 1H).
Example 3. Representative Syntheses 3
Scheme 3
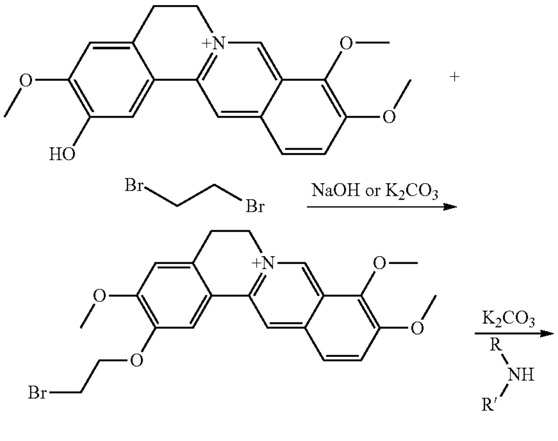

-continued
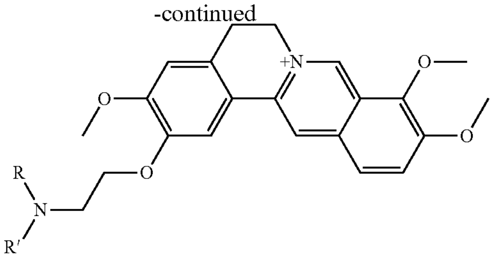
| R(R')NH | Product | Example |
|---|---|---|
| 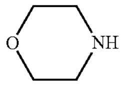 | 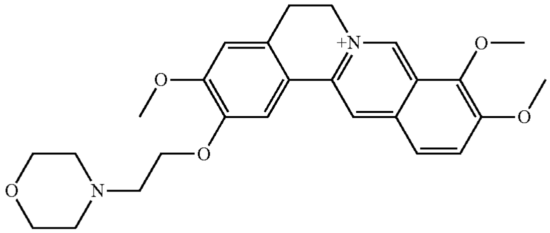 [SMILES: COc1cc2c(cc1OCCN1CCOCC1)-c1cc3ccc(OC)c(OC)c3c[n+]1CC2] | 12 |
| 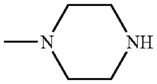 | 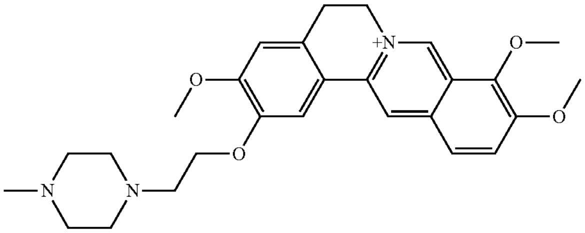 | 13 |
| 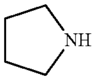 | 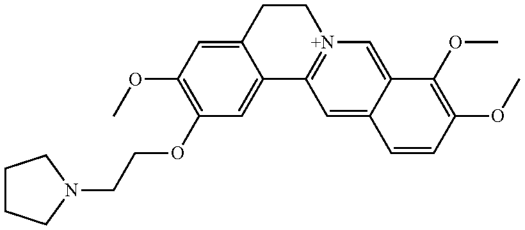 [SMILES: COc1cc2c(cc1OCCN1CCCC1)-c1cc3ccc(OC)c(OC)c3c[n+]1CC2] | 14 |
| 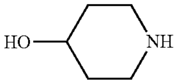 | 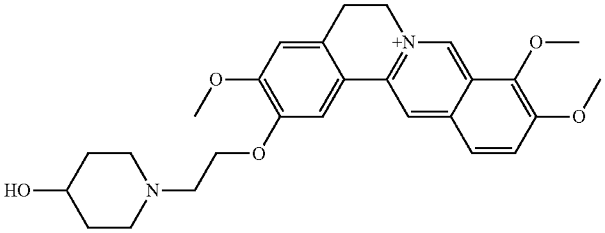 [SMILES: COc1cc2c(cc1OCCN1CCC(O)CC1)-c1cc3ccc(OC)c(OC)c3c[n+]1CC2] | 15 |

Example 4. Representative Syntheses 4
Scheme 4
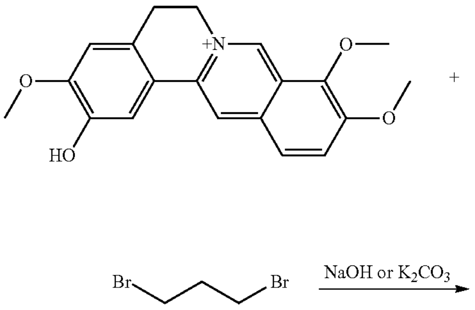
-continued
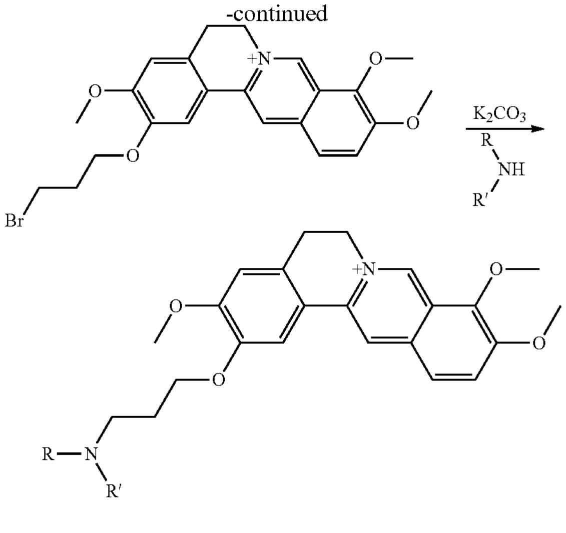
| R(R')NH | Product | Example |
| --- | --- | --- |
| 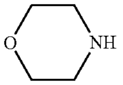 | 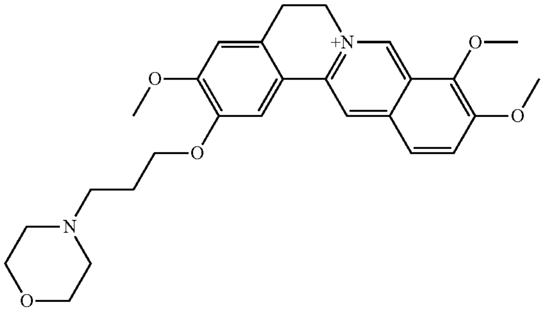 [SMILES: COc1cc2c(cc1OCCCN1CCOCC1)-c1cc3ccc(OC)c(OC)c3c[n+]1CC2] | 16 |
| 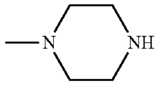 | 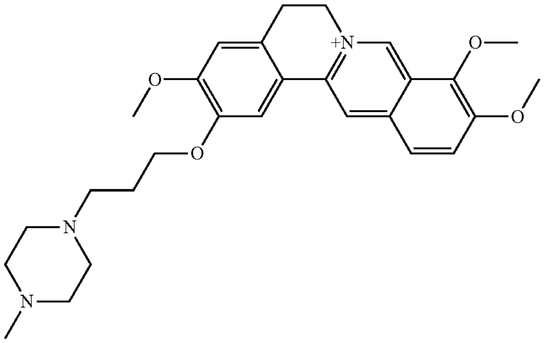 [SMILES: COc1cc2c(cc1OCCCN1CCN(C)CC1)-c1cc3ccc(OC)c(OC)c3c[n+]1CC2] | 17 |
| 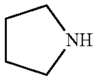 | 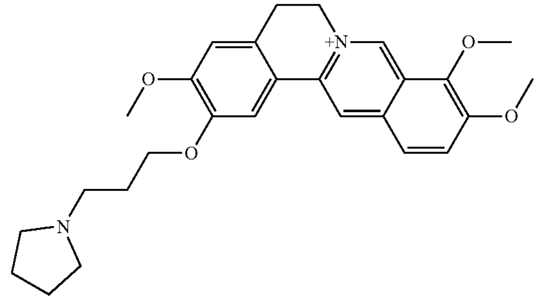 [SMILES: COc1cc2c(cc1OCCCN1CCCC1)-c1cc3ccc(OC)c(OC)c3c[n+]1CC2] | 18 |

-continued

| R(R')NH | Product | Example |
| --- | --- | --- |
| 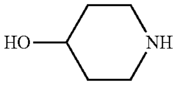 | 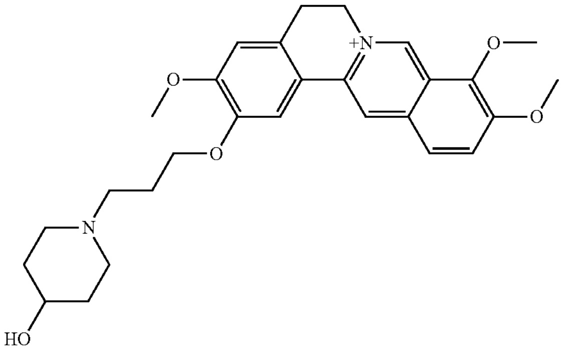 [SMILES: COc1cc2c(cc1OCCCN1CCC(O)CC1)-c1cc3ccc(OC)c(OC)c3c[n+]1CC2] | 19 |

Example 5. Representative Syntheses 5

Scheme 5

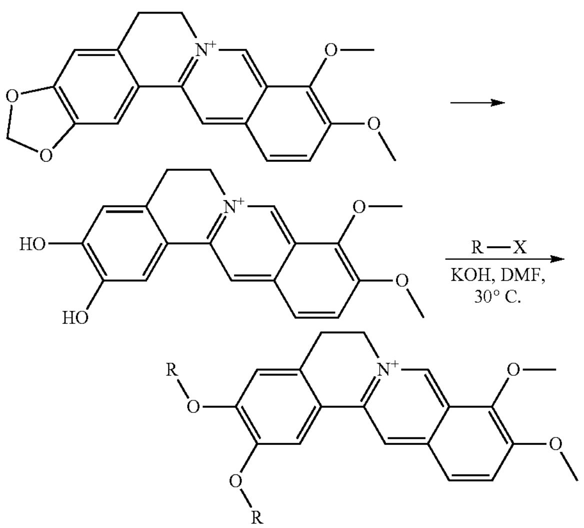

2,3-Dihydroxy-9,10-dimethoxy-5,6-dihydroisoquinolino[3,2-a]isoquinolin-7-ium (Example 88

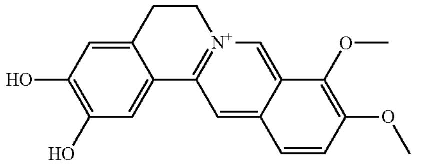 [SMILES: COc1ccc2cc3[n+](cc2c1OC)CCc1cc(O)c(O)cc1-3]

2,3-Dihydroxy-9,10-dimethoxy-5,6-dihydroisoquinolino[3,2-a]isoquinolin-7-ium was synthesized according to the procedure provided in Tao, C. et al. Neurochemistry International (2020), 139, 104807.

2,3-Diisopropoxy-9,10-dimethoxy-5,6-dihydroisoquinolino[3,2-a]isoquinolin-7-ium (Example 78

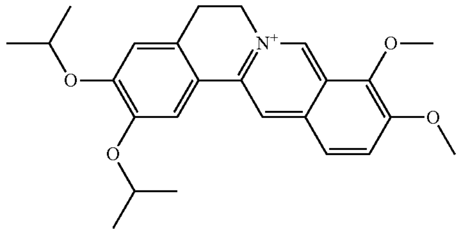 [SMILES: COc1ccc2cc3[n+](cc2c1OC)CCc1cc(OC(C)C)c(OC(C)C)cc1-3]

To a solution of 2,3-dihydroxy-9,10-dimethoxy-5,6-dihydroisoquinolino[3,2-a]isoquinolin-7-ium (0.5 g, 1.5 mmol) in DMF (2 mL) added potassium hydroxide (0.216 g, 3.8 mmol) and 2-iodopropane (0.46 mL, 4.6 mmol) and stirred at 30° C. for 5 h. The reaction was cooled to rt and added with ethyl acetate and hexanes. The solid was filtered and purified by 0-5% MeOH in DCM to obtain the desired product 10,11-diisopropoxy-3,4-dimethoxy-7,8-dihydro-6$\lambda^5$-azatetraphen-6-ylium (57 mg, 0.133 mmol, Yield 8.6%). UPLC/ELSD: RT=2.49 min. MS (ES): m/z ($M^+$) 408.45 for $C_{25}H_{30}NO_4$+. $^1$H NMR (301 MHz, $CD_3OD$) δ 1.40 (m, 12H); 3.30 (m, 2H); 4.13 (s, 3H); 4.23 (s, 3H); 4.75 (m, 2H); 4.96 (m, 2H); 7.09 (s, 1H); 7.75 (s, 1H); 8.09 (m, 2H); 8.78 (s, 1H); 9.78 (s, 1H).

2,3-Diethoxy-9,10-dimethoxy-5,6-dihydroisoquinolino[3,2-a]isoquinolin-7-ium (Example 77

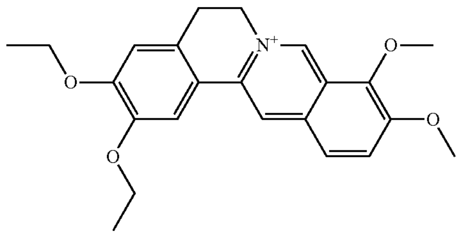 [SMILES: CCOc1cc2c(cc1OCC)-c1cc3ccc(OC)c(OC)c3c[n+]1CC2]

UPLC/ELSD: RT=1.28 min. MS (ES): m/z ($M^+$) 380.18 for $C_{23}H_{26}NO_4$+. $^1$H NMR (301 MHz, $CD_3OD$) δ 1.48 (t, 6H); 3.20 (m, 2H); 3.99-4.32 (m, 10H); 4.71 (m, 2H); 6.99 (s, 1H); 7.58-8.08 (m, 3H); 8.13-8.88 (bs, 1H); 8.94-10.02 (bs, 1H).

Example 6

Scheme 6

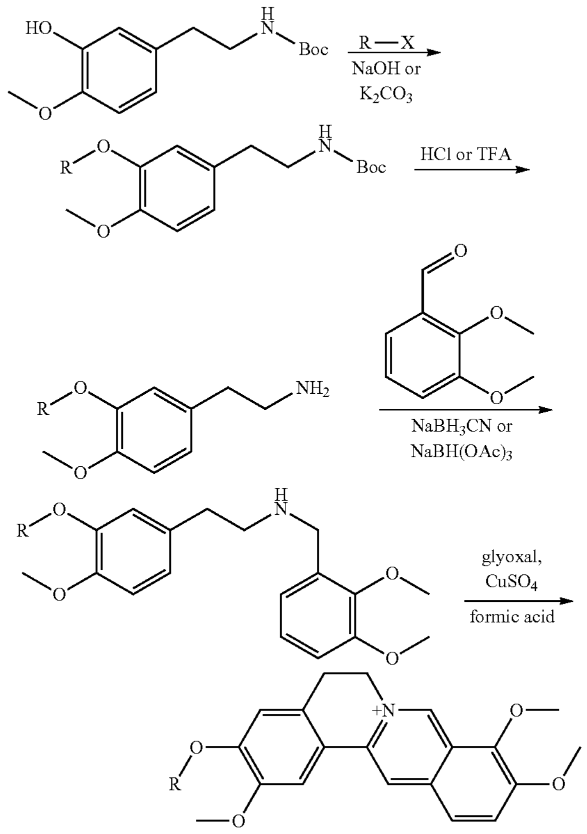

Appropriately substituted phenethylamine and benzaldehyde reagents are reductively coupled, then condensed with glyoxal to afford the tetracyclic core compound. As will be appreciated by those of skill in the art, this reaction sequence can be used to obtain isomeric or analogous products, suitable for the synthesis of the compounds disclosed herein, by substituting the appropriate analogous or isomeric phenethylamine and/or benzaldehyde reagents, and using the methods disclosed herein.

40

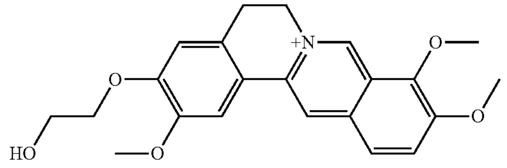

41

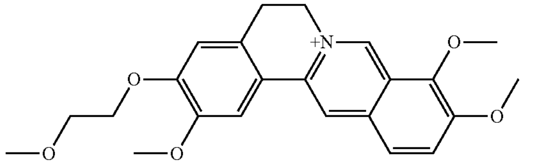

-continued

42

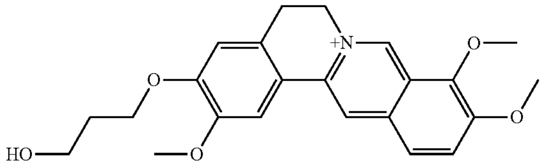

43

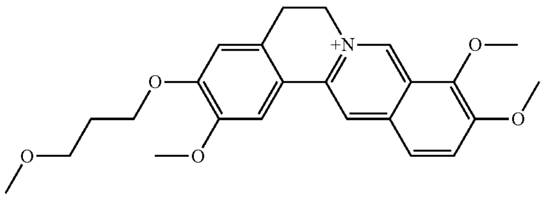

44

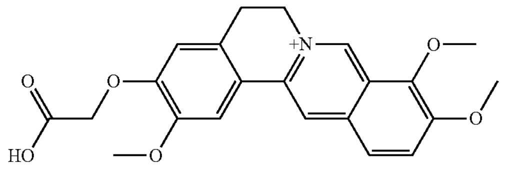

45

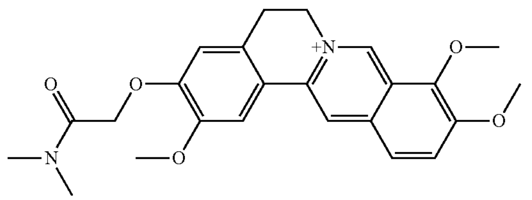

46

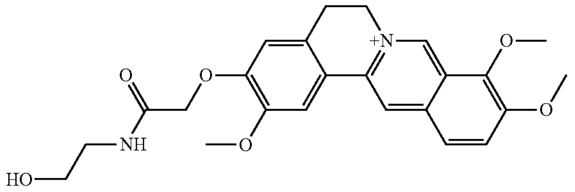

47

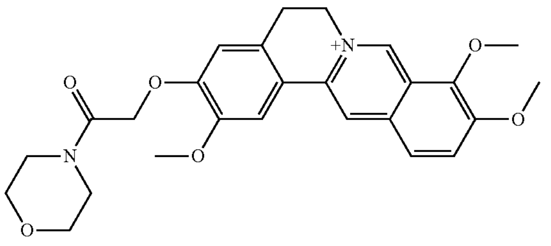

48

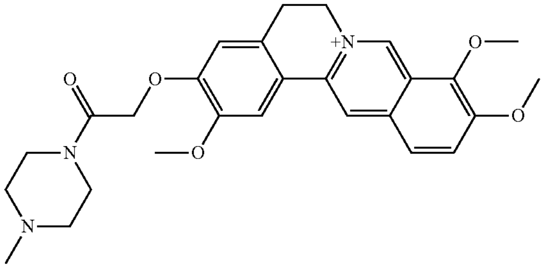

-continued

49

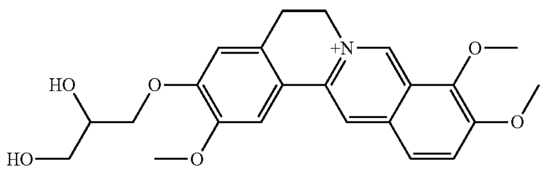

50

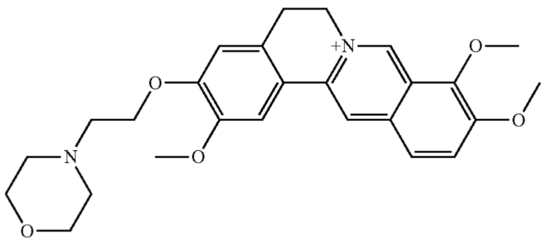

51

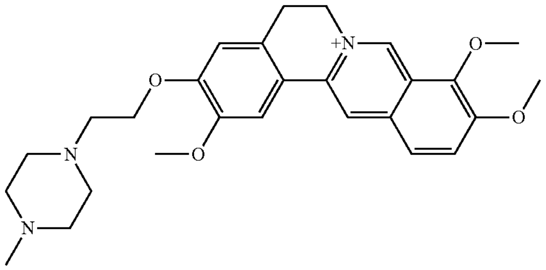

52

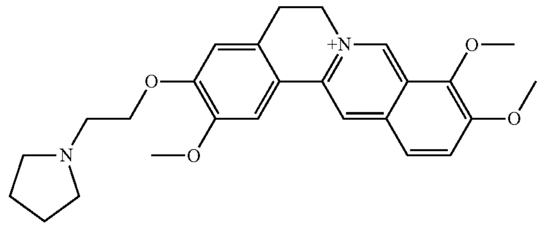

53

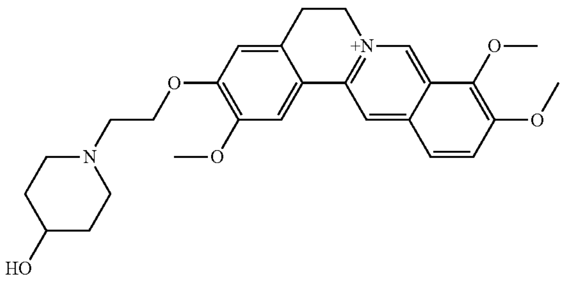

54

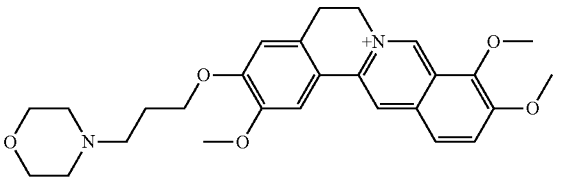

-continued

55

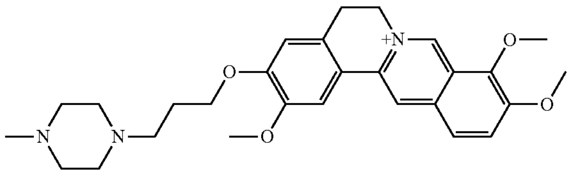

56

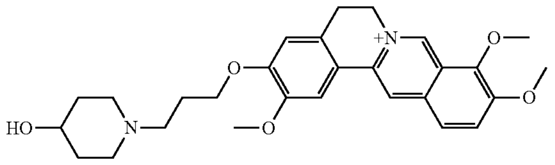

57

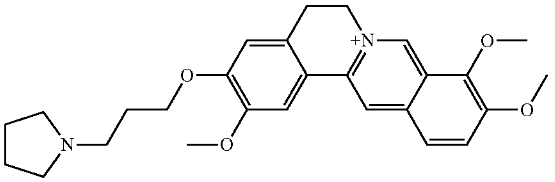

Example 7

Scheme 7

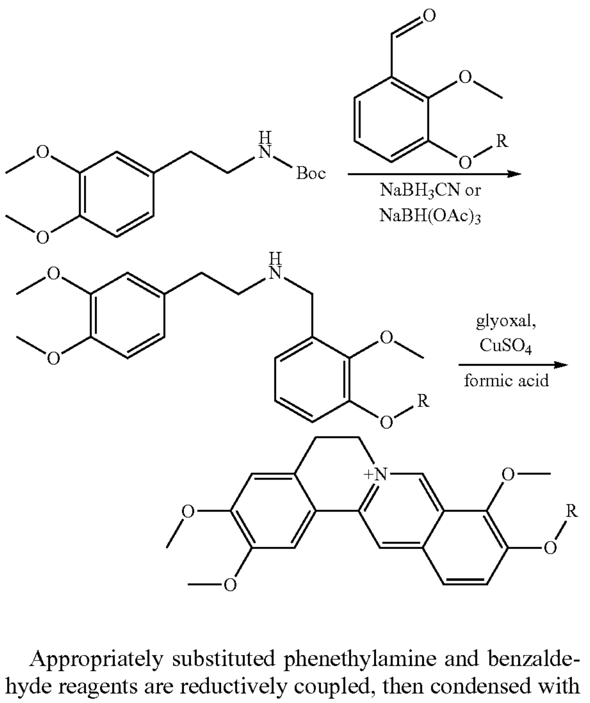

Appropriately substituted phenethylamine and benzaldehyde reagents are reductively coupled, then condensed with glyoxal to afford the tetracyclic core compound. As will be appreciated by those of skill in the art, this reaction sequence can be used to obtain isomeric or analogous products, suitable for the synthesis of the compounds disclosed herein, by substituting the appropriate analogous or isomeric phenethylamine and/or benzaldehyde reagents, and using the methods disclosed herein.

-continued
59
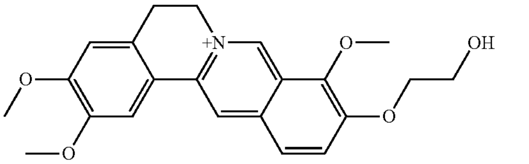
60
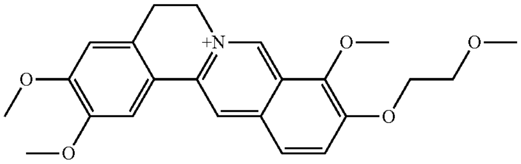
61
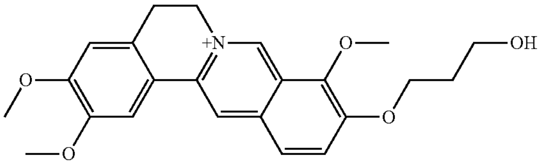
62
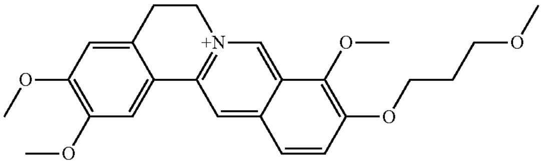
63
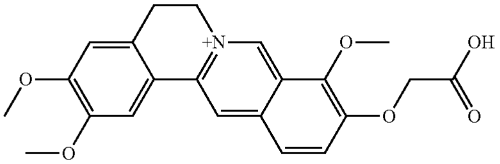
64
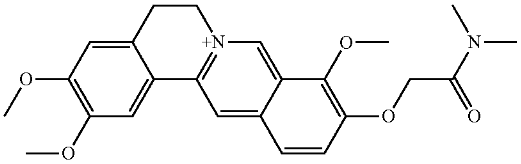
65
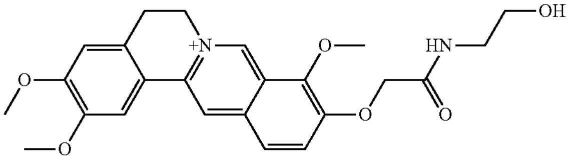
66
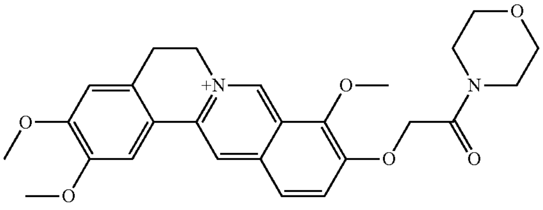
67
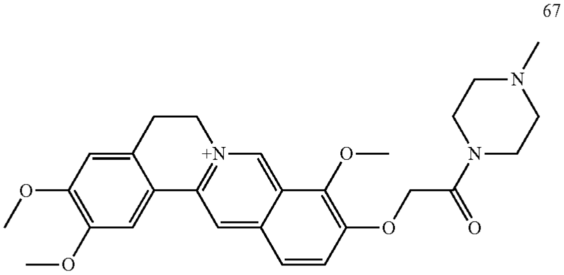
68
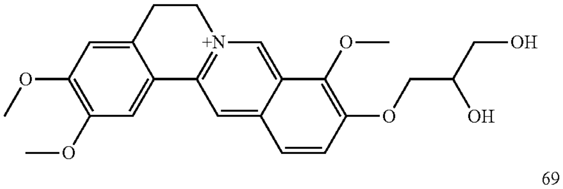
69
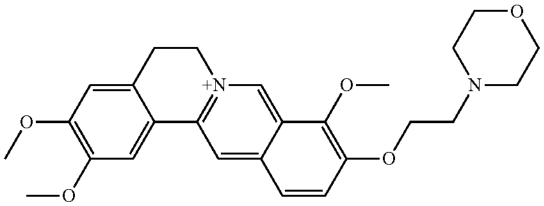
70
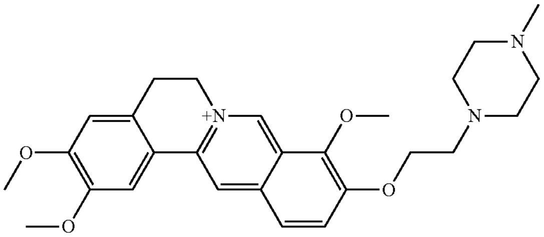
71
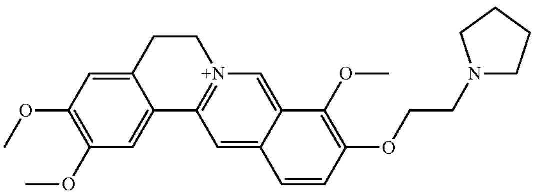
72
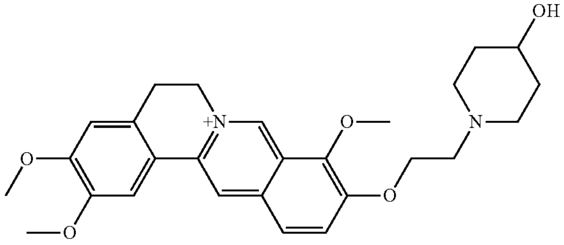
73
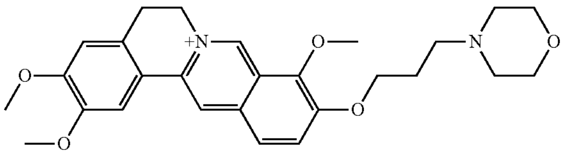

-continued

74

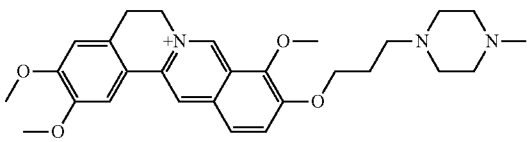

75

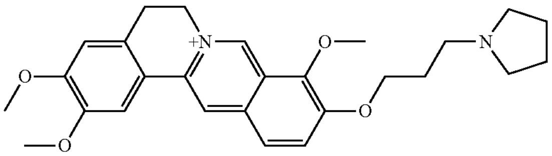

76

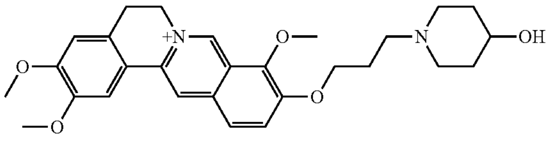

79

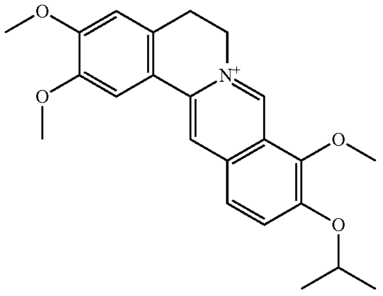

10-Isopropoxy-2,3,9-trimethoxy-5,6-dihydroisoquinolino[3,2-a]isoquinolin-7-ium (Example 79

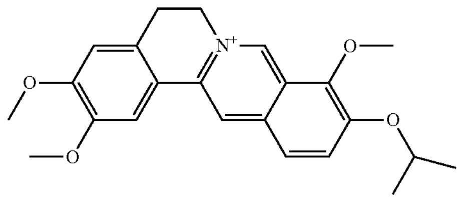 [SMILES: COc1cc2c(cc1OC)-c1cc3ccc(OC(C)C)c(OC)c3c[n+]1CC2]

UPLC/ELSD: RT=1.58 min. MS (ES): m/z (M+) 380.18 for $C_{23}H_{26}NO_4$+. $^1$H NMR (301 MHz. $CD_3OD$) δ 1.47 (d, 6H); 3.31 (m, 2H); 3.99 (m, 6H); 4.24 (s, 3H); 4.95 (m, 3H); 7.08 (s, 1H); 7.69 (s, 1H); 8.05 (m, 2H); 8.82 (s, 1H); 9.77 (s, 1H).

Example 8

Scheme 8

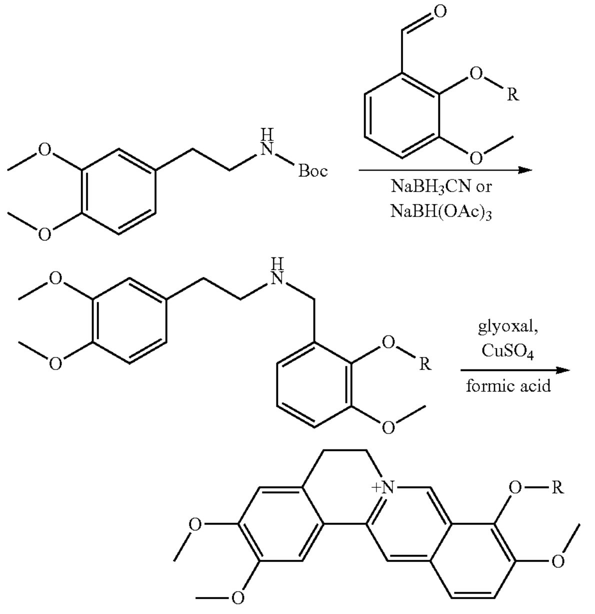

Appropriately substituted phenethylamine and benzaldehyde reagents are reductively coupled, then condensed with glyoxal to afford the tetracyclic core compound. As will be appreciated by those of skill in the art, this reaction sequence can be used to obtain isomeric or analogous products, suitable for the synthesis of the compounds disclosed herein, by substituting the appropriate analogous or isomeric phenethylamine and/or benzaldehyde reagents, and using the methods disclosed herein.

21

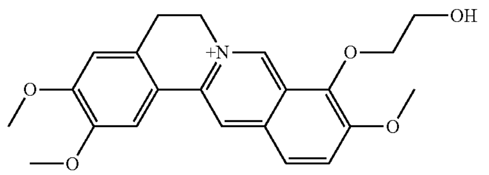

22

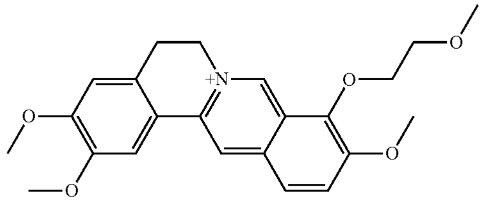

23

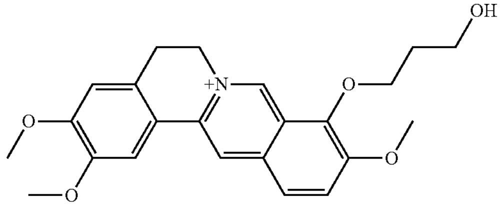

-continued
24
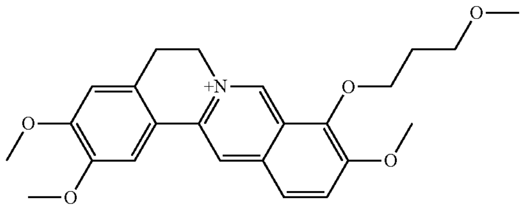
25
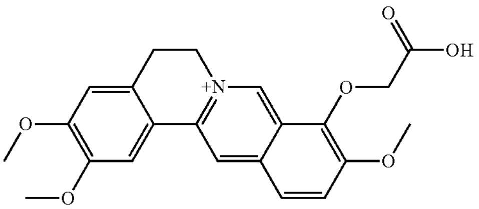
26
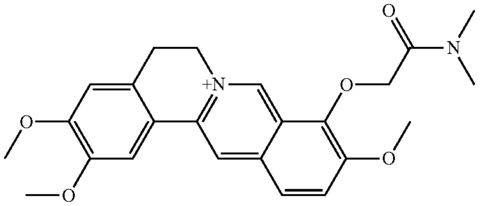
27
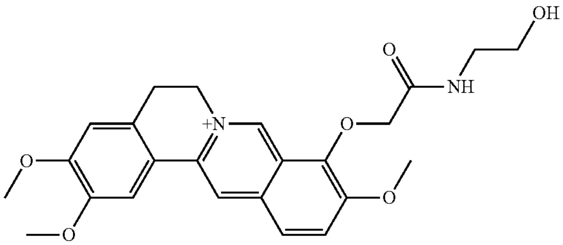
28
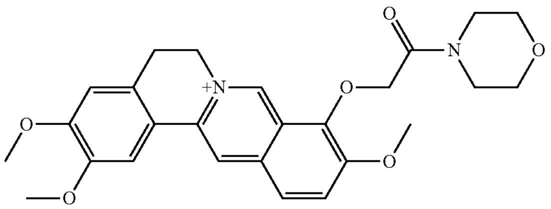
29
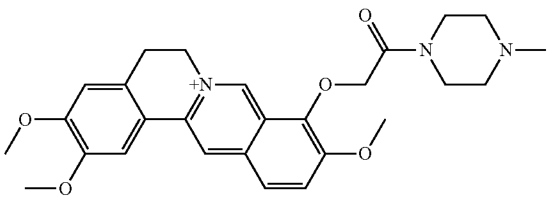
30
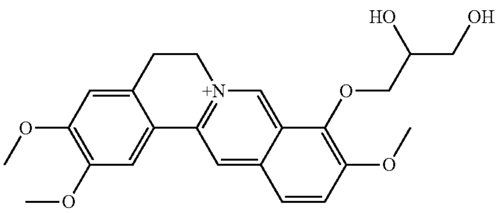
-continued
31
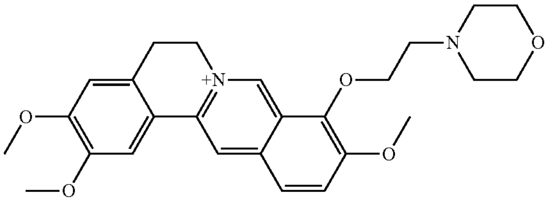
32
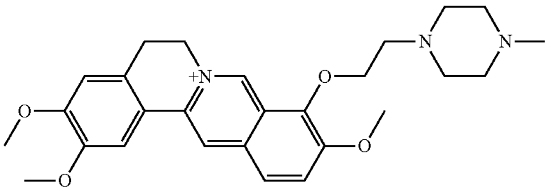
33
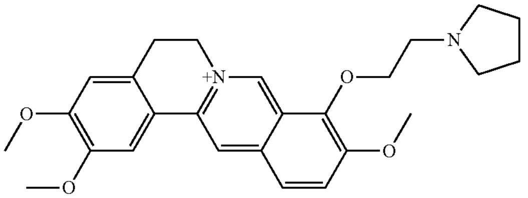
34
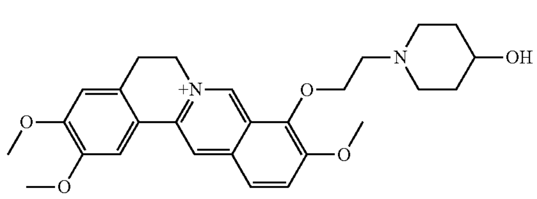
35
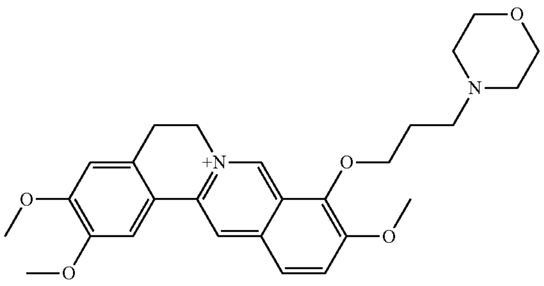
36
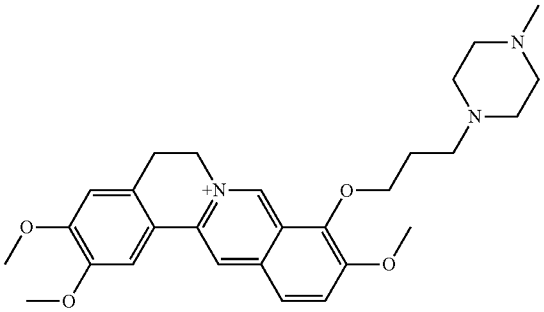

-continued

37

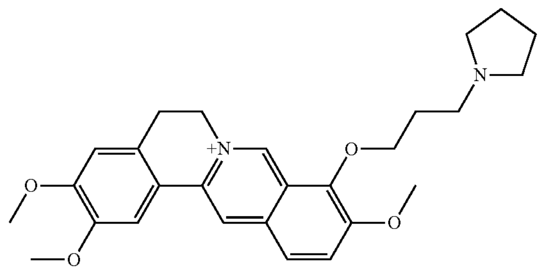

38

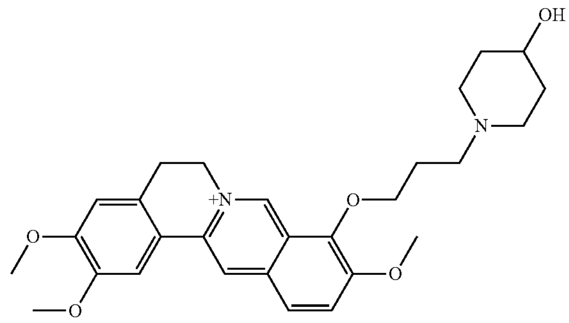

Example 9. Other Compounds Appropriately substituted phenethylamine (e.g., beta-methylphenethylamine or beta-cyclopropylphenthylamine) and benzaldehyde reagents are reductively coupled, then condensed with glyoxal to afford the tetracyclic core compound. As will be appreciated by those of skill in the art, this reaction sequence can be used to obtain isomeric or analogous products, suitable for the synthesis of the compounds disclosed herein, by substituting the appropriate analogous or isomeric phenethylamine and/or benzaldehyde reagents, and using the methods disclosed herein.

9,10-Dimethoxy-5-methyl-5,6-dihydro-[1,3]dioxolo[4,5-g]isoquinolino[3,2-a]isoquinolin-7-ium (Example 85

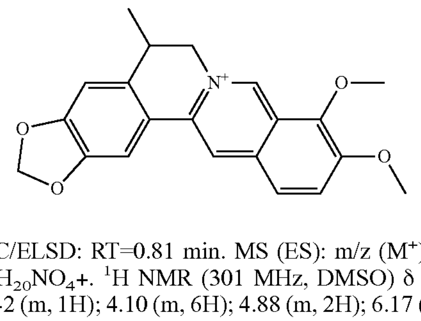

UPLC/ELSD: RT=0.81 min. MS (ES): m/z ($M^+$) 350.18 for $C_{21}H_{20}NO_4$+. $^1H$ NMR (301 MHz, DMSO) δ 1.20 (d, 3H); 3.42 (m, 1H); 4.10 (m, 6H); 4.88 (m, 2H); 6.17 (m, 2H); 7.15 (s, 1H); 7.82 (s, 1H); 8.02 (d, 1H); 8.22 (d, 1H); 8.99 (s, 1H); 9.90 (s, 1H).

Example 10. RNA Instability

This example describes the instability of RNA in lipid nanoparticle formulations when stored as a refrigerated liquid. One of the most formidable barriers to translating the concept of using messenger RNA as a pharmaceutical agent is the inherent instability of the mRNA molecule. RNA is highly susceptible to chemical and enzymatic cleavage as well as adduct formation, which causes a loss of translational potency. Lipid nanoparticle (LNP) formulations of mRNA undergo rapid loss of purity when stored as a refrigerated liquid, as exemplified by the data in FIGS. 1A and 1B.

Figure 1B:
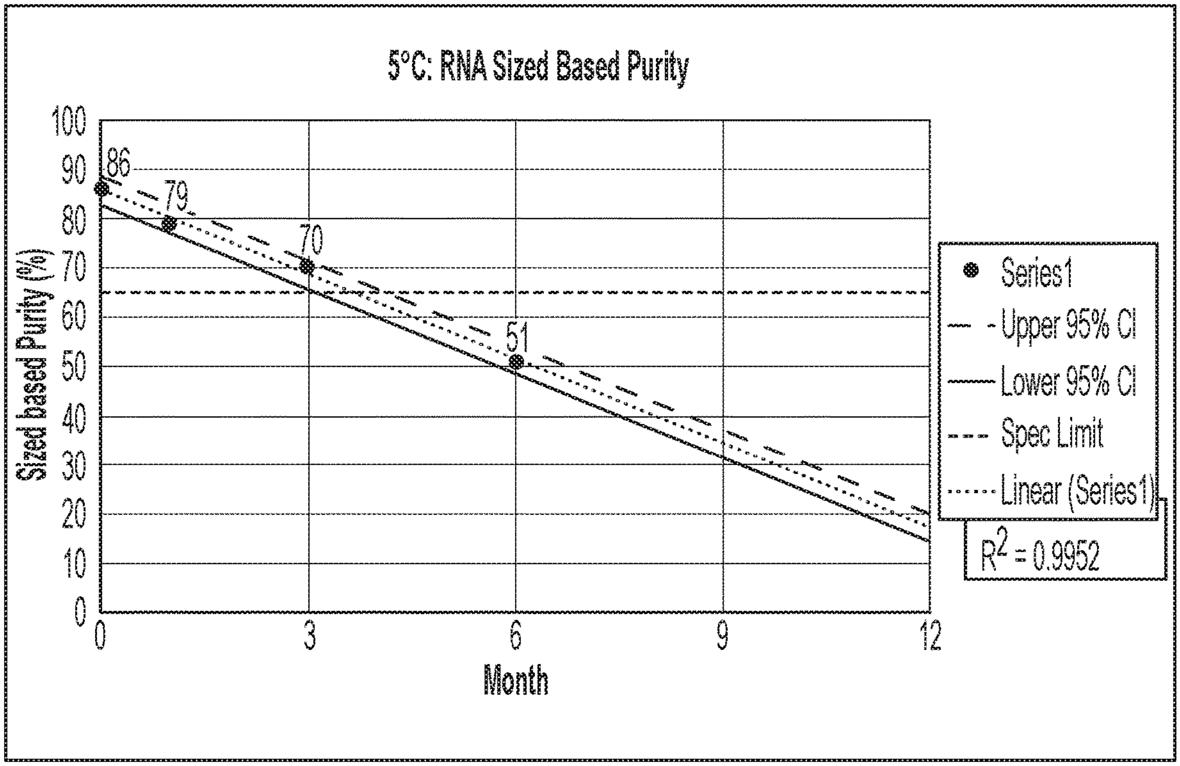

It is evident that the stability of mRNA is poorer when encapsulated in LNP than when stored unformulated as a simple solution in buffer. A two-year shelf-life is generally considered the minimum shelf-life target for a viable pharmaceutical product, or in the case of a poorly stable drug, 18 months at the absolute minimum. FIGS. 1A and 1B demonstrate that the shelf life of LNP-mRNA formulations falls below this minimum. Consequently, most mRNA formulations must be stored frozen at −20° C. or −80° C. Although these storage conditions may be viable in the case of rare disease treatment or highly specialized indications, they are far from ideal. Additionally, refrigerated liquid products are preferred over reconstituted lyophilized powder or −80° C. products as they are more patient-friendly for widespread use. The ability to formulate mRNA drug products in refrigerated liquid compositions would facilitate widespread use of mRNA drugs, such as for vaccine products, which are typically provided as shelf-stable injectables requiring no special reconstitution or storage conditions.

Example 11. mRNA Stabilization with Palmatine

Figure 2:
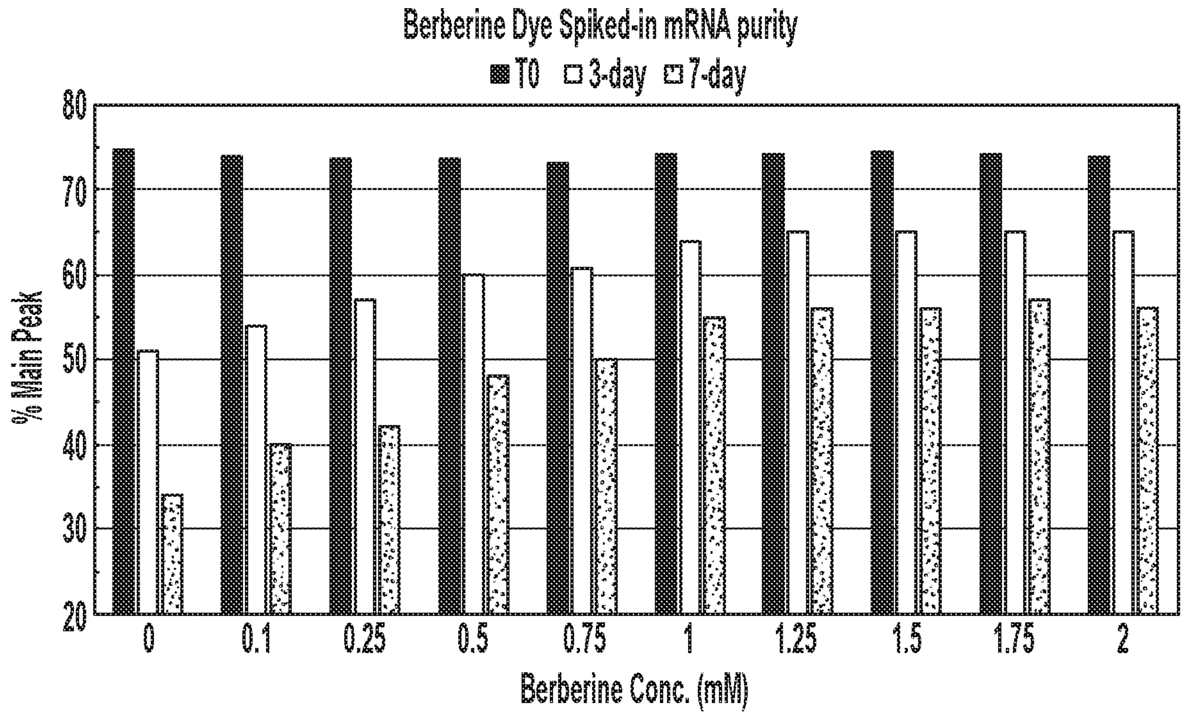
FIG. 2 shows mRNA purity as a function of time and palmatine concentration.

Palmatine USP was combined with an LNP containing mRNA (0.2 mg/mL in buffer) in amounts corresponding to the concentrations reported in FIG. 2. Main peak purity was measured by RP-HPLC at T0, 3-day, and 7-day. See, FIG. 2.

Embodiments Listing

1. A stabilized pharmaceutical composition, comprising: a nucleic acid formulation, comprising a nucleic acid, and a compound of Formula I':

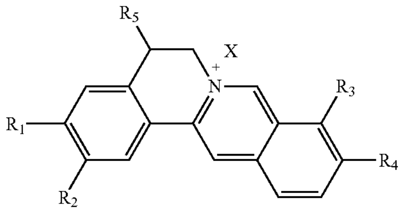

or a tautomer, solvate, or salt thereof, wherein:

each of $R_1$, $R_2$, $R_3$, and R, are independently selected from —OH and —$OC_{1-4}$alkyl, wherein the —$OC_{1-4}$alkyl is optionally substituted with one or more —OH, —C(O)OH, —NR'R", or —C(O)NR'R";

R' is H, or —$C_{1-4}$alkyl, wherein the —$C_{1-4}$alkyl is optionally substituted with one or more —OH;

R" is H, or —$C_{1-4}$alkyl; or

R' and R" taken together can form a 5 to 6 membered heterocycle with O or N heteroatoms, wherein the heterocycle is optionally substituted with one or more —$C_{1-4}$alkyl, or —OH; or $R_1$ and $R_2$ together with the intervening atoms form a 5-membered ring;

$R_5$ is H, —$C_{1-4}$alkyl, or $C_{3-7}$cycloalkyl; and

X is a pharmaceutically acceptable anion.

2. The stabilized pharmaceutical composition of embodiment 1, comprising:

a nucleic acid formulation, comprising a nucleic acid, and a compound of Formula I:

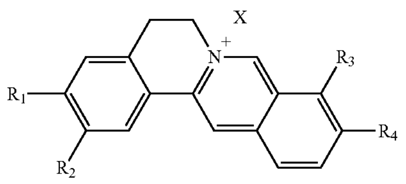

or a tautomer, solvate, or salt thereof, wherein:

each of $R_1$, $R_2$, $R_3$, and $R_4$ are independently selected from —OH, and —$OC_{1-4}$alkyl, wherein the —$OC_{1-4}$alkyl is optionally substituted with one or more —OH, —C(O)OH, —NR'R", or —C(O)NR'R";

R' is H, or —$C_{1-4}$alkyl, wherein the —$C_{1-4}$alkyl is optionally substituted with one or more —OH;

R" is H, or —$C_{1-4}$alkyl; or

R' and R" taken together can form a 5 to 6 membered heterocycle with O or N heteroatoms, wherein the heterocycle is optionally substituted with one or more —$C_{1-4}$alkyl, or —OH; and X is a pharmaceutically acceptable anion.

3. The composition of embodiment 1 or 2, wherein: $R_1$, $R_2$, and $R_3$ are independently —$OC_{1-4}$alkyl; and $R_4$ is —OH or —$OC_{1-4}$alkyl, wherein the —$OC_{1-4}$alkyl is substituted with one or more —OH, —C(O)OH, —NR'R", or —C(O)NR'R".

4. The composition of embodiment 3, wherein: $R_1$, $R_2$, and $R_3$ are —$OCH_3$.

5. The composition of any one of embodiments 3-4, wherein $R_4$ is —OH.

6. The composition of any one of embodiments 3-4, wherein $R_4$ is —$OC_{1-4}$alkyl substituted with one or more —OH, —C(O)OH, —NR'R", or —C(O)NR'R".

7. The composition of embodiment 1 or 2, wherein: $R_1$, $R_2$, and $R_4$ are independently —$OC_{1-4}$alkyl and $R_3$ is —OH or —$OC_{1-4}$alkyl, wherein the —$OC_{1-4}$alkyl is substituted with one or more —OH, —C(O)OH, —NR'R", or —C(O)NR'R".

8. The composition of embodiment 7, wherein: $R_1$, $R_2$, and $R_4$ are —$OCH_3$.

9. The composition of any one of embodiments 7-8, wherein $R_3$ is —OH.

10. The composition of any one of embodiments 7-8, wherein $R_3$ is —$OC_{1-4}$alkyl substituted with one or more —OH, —C(O)OH, —NR'R", or —C(O)NR'R".

11. The composition of embodiment 1 or 2, wherein: $R_1$, $R_3$, and $R_4$ are independently —$OC_{1-4}$alkyl; and $R_2$ is —OH or —$OC_{1-4}$alkyl, wherein the —$OC_{1-4}$alkyl is substituted with one or more —OH, —C(O)OH, —NR'R", or —C(O)NR'R".

12. The composition of embodiment 11, wherein: $R_1$, $R_3$, and $R_4$ are —$OCH_3$.

13. The composition of any one of embodiments 11-12, wherein $R_2$ is —OH.

14. The composition of any one of embodiments 11-12, wherein $R_2$ is —$OC_{1-4}$alkyl substituted with one or more —OH, —C(O)OH, —NR'R", or —C(O)NR'R".

15. The composition of embodiment 1 or 2, wherein: $R_2$, $R_3$, and $R_4$ are independently —$OC_{1-4}$alkyl; and $R_1$ is —OH or —$OC_{1-4}$alkyl, wherein the —$OC_{1-4}$alkyl is substituted with one or more —OH, —C(O)OH, —NR'R", or —C(O)NR'R".

16. The composition of embodiment 15, wherein: $R_2$, $R_3$, and $R_4$ are —$OCH_3$.

17. The composition of any one of embodiments 15-16, wherein $R_1$ is —OH.

18. The composition of any one of embodiments 15-16, wherein $R_1$ is —$OC_{1-4}$alkyl substituted with one or more —OH, —C(O)OH, —NR'R", or —C(O)NR'R".

19. The composition of any one of embodiments 1, 5, 6, 9, or 10, wherein $R_1$ and $R_2$ together with the intervening atoms form a 5-membered ring.

20. The composition of any one of embodiments 1-19, wherein $R_5$ is —H, —$CH_3$, or cyclopropyl.

21. The composition of any one of embodiments 1-20, wherein $R_5$ is —H.

22. The composition of embodiment 1 or 2, wherein the compound is selected from the compounds of Table 1, and tautomers, solvates, and salts thereof, wherein each compound further comprises a pharmaceutically acceptable anion X.

23. The composition of embodiment 1 or 2, wherein the compound is selected from the compounds of Table 2, and tautomers, solvates, and salts thereof: wherein each compound further comprises a pharmaceutically acceptable anion X.

24. The composition of embodiment 1, wherein the compound is selected from the compounds of Table 3, and tautomers, solvates, and salts thereof; wherein each compound further comprises a pharmaceutically acceptable anion X.

25. The composition of any one of the preceding embodiments, wherein X is chloride.

26. The composition of any one of the preceding embodiments, wherein the compound contains fewer than 100 ppm of elemental metals.

27. The composition of any one of the preceding embodiments, wherein the nucleic acid is coding or non-coding.

28. The composition of any one of the preceding embodiments, wherein the nucleic acid is DNA or RNA.

29. The composition of embodiment 28, wherein the DNA is plasmid DNA.

30. The composition of embodiment 28, wherein the RNA is mRNA, siRNA, shRNA, snRNA, snoRNA, or lncRNA.

31. The composition of embodiment 30, wherein the RNA is mRNA.

32. The composition of any one of the preceding embodiments, further comprising an ionizable amino lipid is.

33. The composition of any one of the preceding embodiments, further comprising a PEG-lipid.

34. The composition of any one of the preceding embodiments, further comprising a structural lipid.

35. The composition of any one of the preceding embodiments, further comprising a phospholipid.

36. The composition of any one of the preceding embodiments, further comprising an ionizable amino lipid, a PEG-lipid, a structural lipid, and a phospholipid.

37. The composition of embodiment 36, wherein the composition comprises a ratio of 20-60% ionizable amino lipids, 5-30% phospholipid, 10-55% structural lipid, and 0.5-15% PEG-modified lipid.

38. The composition of embodiment 36, wherein the composition comprises a ratio of 20-60% ionizable amino lipids, 5-25% phospholipid, 25-55% structural lipid, and 0.5-15% PEG-modified lipid.

39. The composition of any one of the preceding embodiments, wherein the nucleic acid is mRNA, and the composition comprises a mRNA purity level of greater than 60%, greater than 70%, greater than 80%, or greater than 90% main peak mRNA purity after at least thirty days of storage.

40. The composition of any one of the preceding embodiments, wherein the nucleic acid is mRNA, and the composition comprises a mRNA purity level of greater than 50% main peak mRNA purity after at least sixty days of storage.
41. The composition of any one of the preceding embodiments, wherein the mRNA comprises intact mRNA and at least one RNA fragment, wherein the composition comprises less than 90%, less than 80%, less than 70%, less than 60%, or less than 50% RNA fragments after at least thirty days of storage.
42. The composition of any one of embodiments 39-41, wherein the storage is at room temperature.
43. The composition of any one of embodiments 39-41, wherein the storage is at greater than room temperature.
44. The composition of any one of embodiments 39-41, wherein the storage is at about 4° C.
45. The composition of any one of the preceding embodiments, wherein the composition comprises lipid nanoparticles (LNP).
46. The composition of any one of embodiments 1-45, wherein the composition comprises liposomes.
47. The composition of any one of embodiments 1-45, wherein the composition comprises a lipoplex.
48. The composition of any one of embodiments 4547, wherein the nucleic acid is encapsulated by the LNP, liposomes, or lipoplex.
49. The composition of any one of embodiments 1-48, wherein the composition is a lyophilized product.
50. The composition of any one of embodiments 1-48, wherein the composition is formulated in an aqueous solution.
51. The composition of embodiment 50, wherein the aqueous solution has a pH of or about 5 to 8, including pH of about 5, 5.5, 6, 6.5, 7, 7.5, or 8.
52. The composition of embodiment 50 or 51, wherein the aqueous solution does not comprise NaCl.
53. The composition of embodiment 50 or 51, wherein the aqueous solution comprises NaCl in a concentration of or about 150 mM.
54. The composition of any one of embodiments 50-53, wherein the aqueous solution comprises a phosphate buffer, a tris buffer, an acetate buffer, a histidine buffer, or a citrate buffer.
55. The composition of any one of the preceding embodiments, wherein the compound is present at a concentration of less than about 10 mM.
56. The composition of any one of the preceding embodiments, wherein microbial growth in the composition is inhibited by the compound.
57. The composition of embodiment 56, wherein the composition does not comprise phenol, m-cresol, or benzyl alcohol.
58. The use of the composition of any one of embodiments 1-57 for the treatment of a disease in a subject.
59. The use according to embodiment 58, wherein the disease is caused by an infectious agent.
60. The use according to embodiment 59, wherein the disease is caused by or associated with a virus.
61. The use according to embodiment 58, wherein the disease is caused by or associated with a malignant cell.
62. The use according to embodiment 61, wherein the disease is cancer.
63. A method of formulating a nucleic acid comprising: adding to a composition comprising a nucleic acid a compound of Formula I, or a tautomer, solvate, or salt thereof, to obtain a formulated composition.
64. A method for producing a protein in a subject, comprising:
administering a composition of any one of embodiments 1-57 to the subject, wherein the nucleic acid is an mRNA and wherein the mRNA encodes for the production of a protein in the subject.
65. A pharmaceutically acceptable method of processing an mRNA-lipid nanoparticle for therapeutic injection, comprising combining an mRNA, a lipid nanoparticle, and a compound of Formula I, or a tautomer, solvate, or salt thereof.
66. The method of embodiment 65, comprising adding the compound of Formula I, or a tautomer, solvate, or salt thereof, to the lipid nanoparticle, and subsequently adding the mRNA to the lipid nanoparticle-compound mixture.
67. The method of embodiment 65, comprising adding the mRNA to the lipid nanoparticle, and subsequently adding the compound of Formula I, or a tautomer, solvate, or salt thereof, to the lipid nanoparticle-mRNA mixture.
68. A pharmaceutically acceptable method of conferring anti-microbial properties to an mRNA-lipid nanoparticle composition, comprising adding a compound of Formula I, or a tautomer, solvate, or salt thereof, to the mRNA-lipid nanoparticle composition.
69. A syringe or cartridge, comprising a composition of any one of embodiments 1-57.
70. The syringe or cartridge of embodiment 69, comprising multiple doses of the composition.
71. An infusion pump, comprising a composition of any one of embodiments 1-57.
72. A photoprotective container comprising the stabilized pharmaceutical composition of any one of embodiments 1-57.
73. The photoprotective container of embodiment 72, wherein the container prevents light from contacting the stabilized pharmaceutical composition, lipid nanoparticle, or composition.
74. The photoprotective container of embodiment 73, wherein the container comprises a film, foil, or coating.

EQUIVALENTS

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed.

Embodiments are provided that are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles “a” and “an.” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc. As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessanly including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example. “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. Each possibility represents a separate embodiment.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

The invention claimed is:

1. A stabilized pharmaceutical composition, comprising: a nucleic acid and a compound of Formula I':

(I')

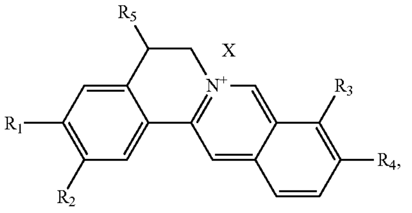

or a tautomer, solvate, or salt thereof, wherein:

each of $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R", and wherein at least one of $R_1$, $R_2$, $R_3$, and $R_4$ is —OH, —$OC_{2-4}$alkyl, or —$OC_{1-4}$alkyl substituted with one or more —OH, —C(O)OH, —NR'R", or —C(O)NR'R";

each instance of R' is independently H or —$C_{1-4}$alkyl, wherein the —$C_{1-4}$alkyl is optionally substituted with one or more —OH;

each instance of R" is independently H or —$C_{1-4}$alkyl;

optionally wherein R' and R" taken together form a 5 to 6 membered heterocycle with one or more O or N heteroatoms, wherein the heterocycle is optionally substituted with one or more —$C_{1-4}$ alkyl or —OH;

optionally wherein $R_1$ and $R_2$ together with the intervening atoms form a 5-membered ring;

$R_5$ is H, —$C_{1-4}$alkyl, or $C_{3-7}$cycloalkyl; and

X is a pharmaceutically acceptable anion.

2. The stabilized pharmaceutical composition of claim 1, wherein the compound of Formula I' is of Formula I:

(I)

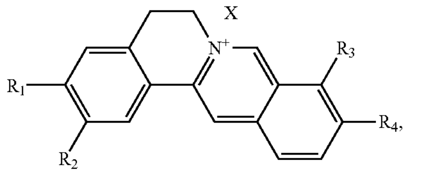

or a tautomer, solvate, or salt thereof.

3. The composition of claim 1, wherein:

$R_1$, $R_2$, and $R_3$ are independently —$OC_{1-4}$alkyl; and $R_4$ is —OH or —$OC_{1-4}$alkyl, wherein the —$OC_{1-4}$alkyl is substituted with one or more —OH, —C(O)OH, —NR'R", or —C(O)NR'R".

4. The composition of claim 3, wherein:

$R_1$, $R_2$, and $R_3$ are —$OCH_3$.

5. The composition of claim 3, wherein $R_4$ is —$OC_{1-4}$alkyl substituted with one or more —OH, —C(O)OH, —NR'R", or —C(O)NR'R".

6. A stabilized pharmaceutical composition, comprising a nucleic acid and a compound selected from:

1

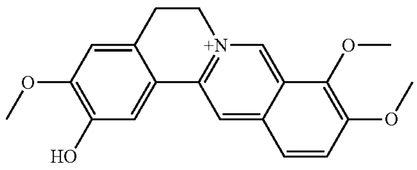

2

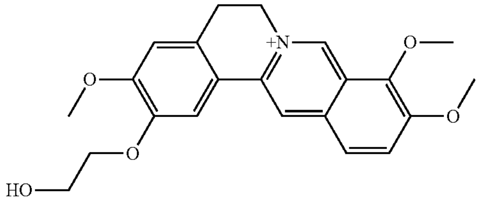

3

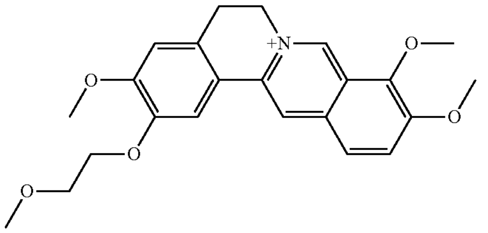

4

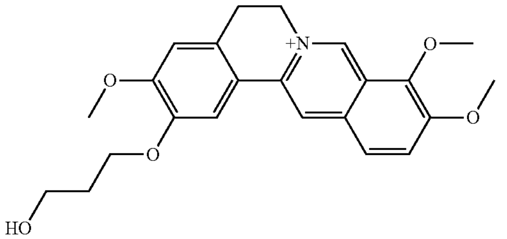

-continued

5

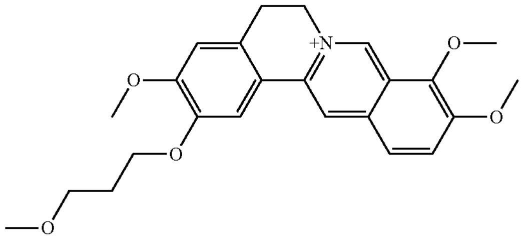

6

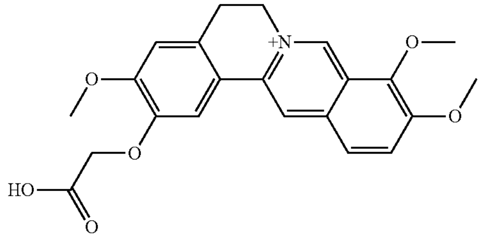

7

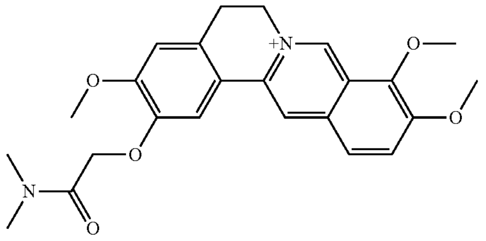

8

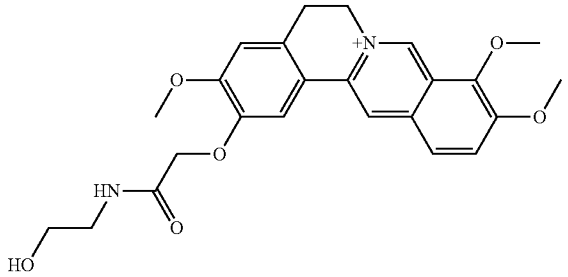

9

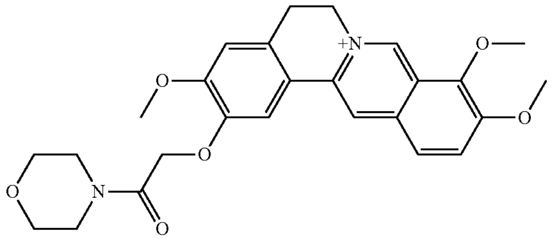

10

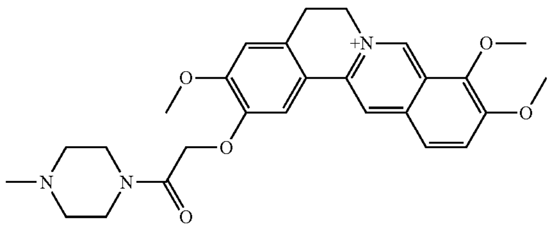

-continued
11
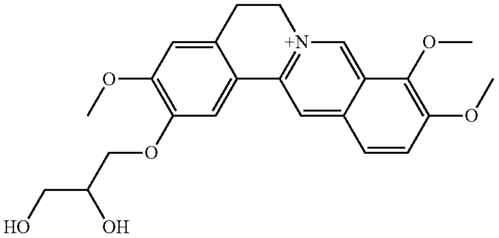
12
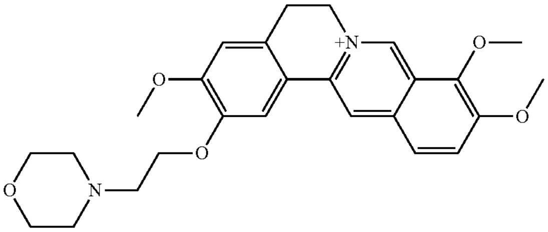
13
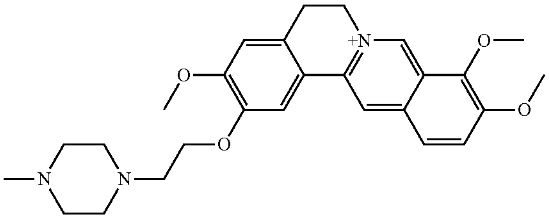
14
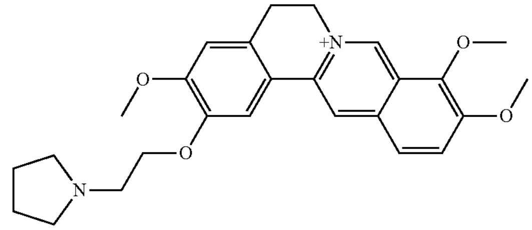
15
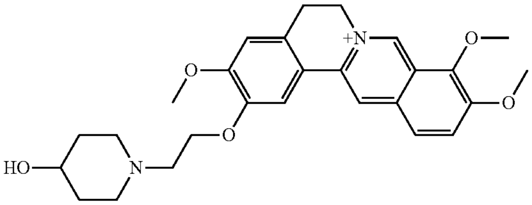
16
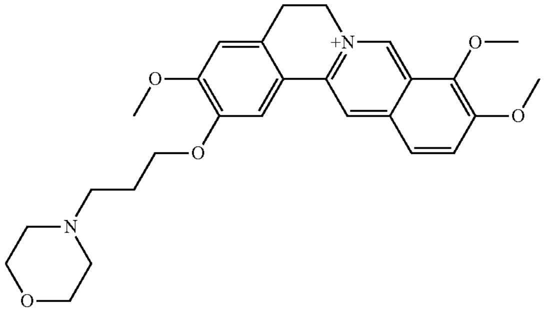
-continued
17
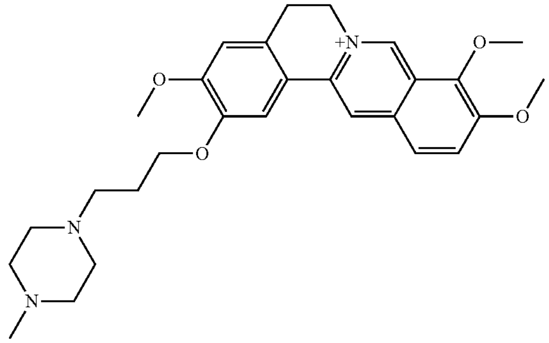
18
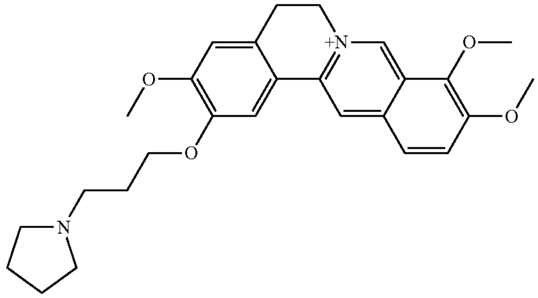
19
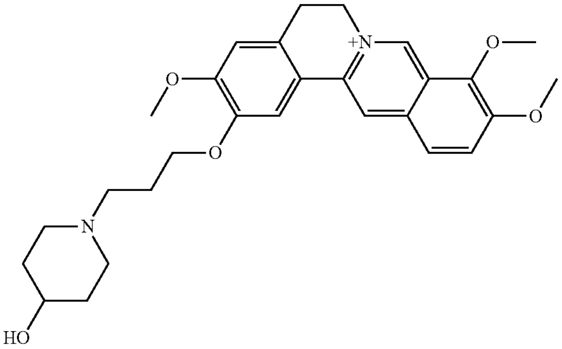
20
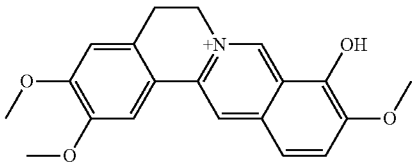
21
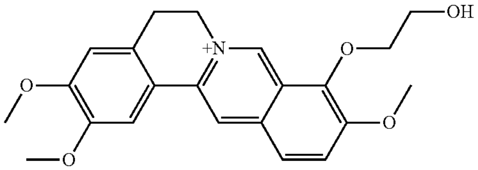
22
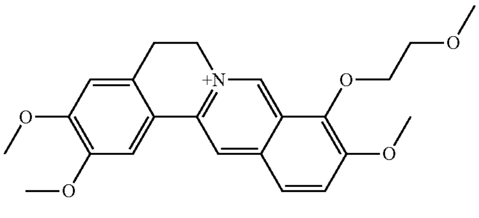

-continued
23
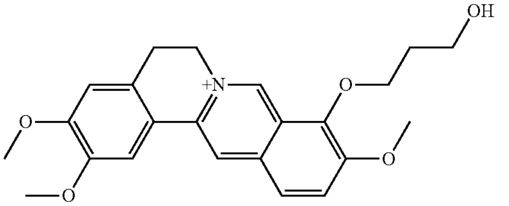
24
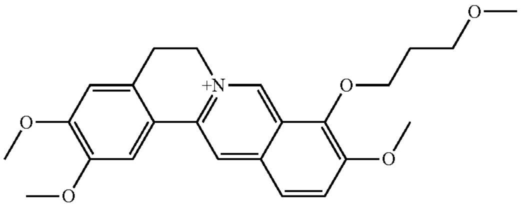
25
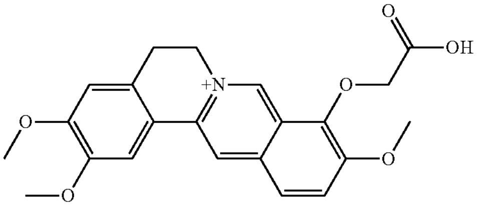
26
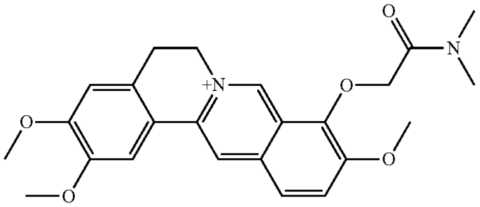
27
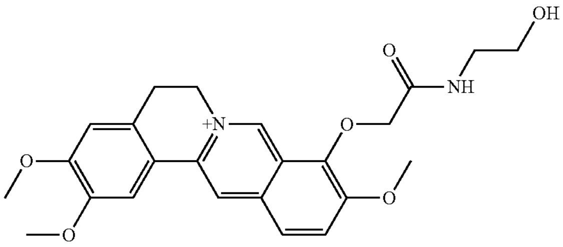
28
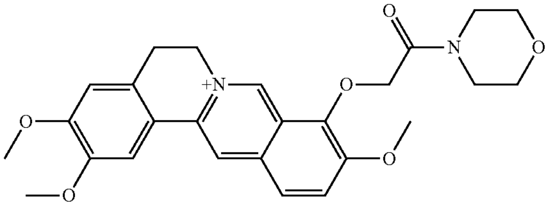
29
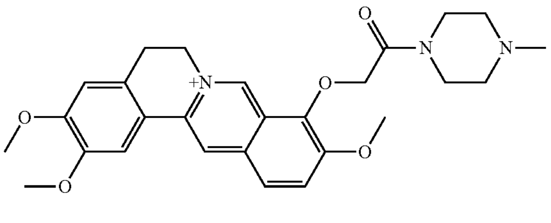
-continued
30
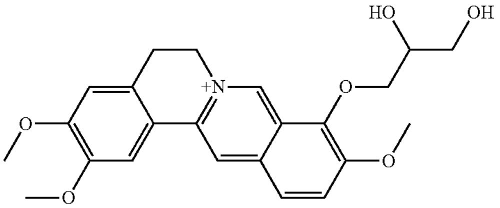
31
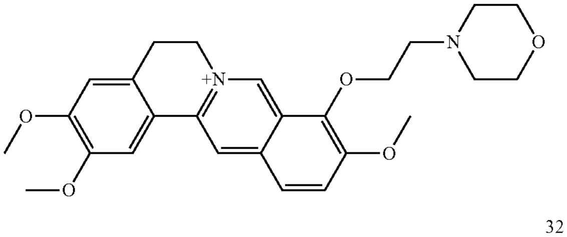
32
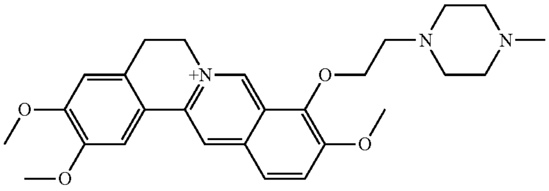
33
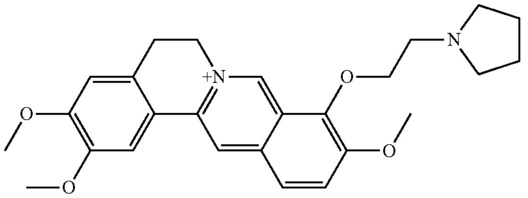
34
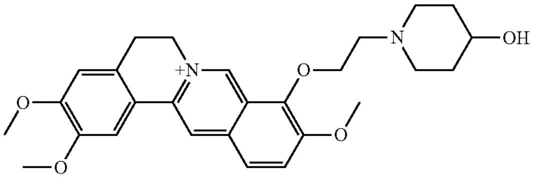
35
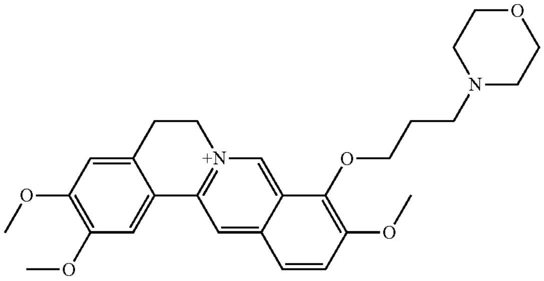

-continued
36
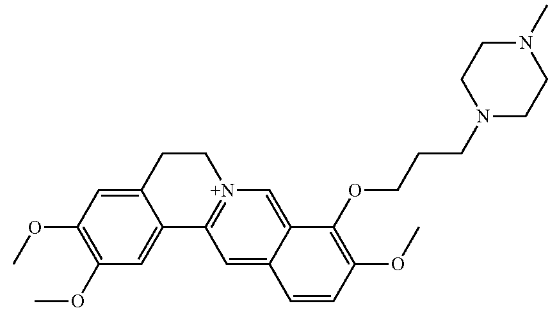
37
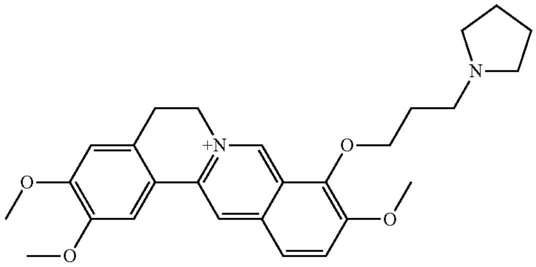
38
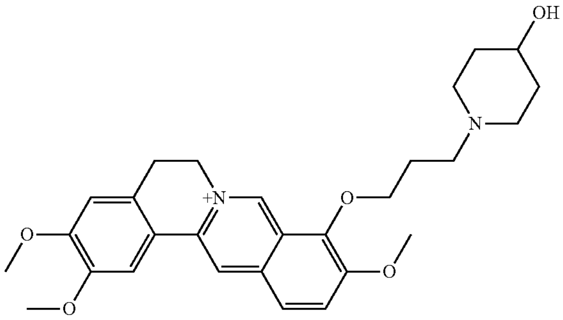
39
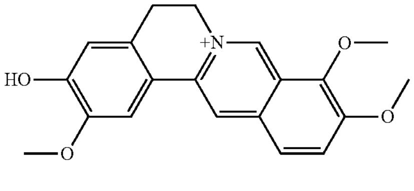
40
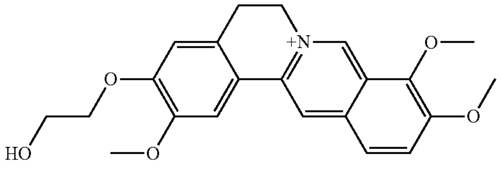
41
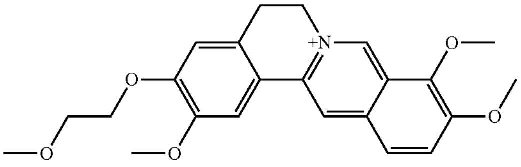
-continued
42
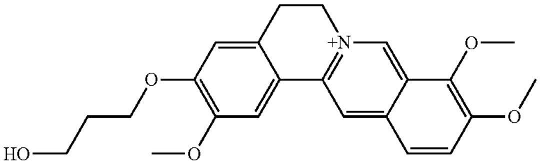
43
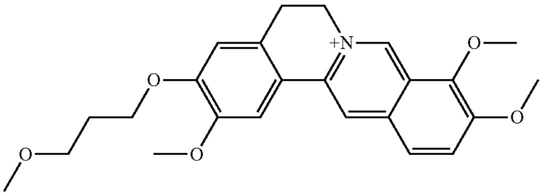
44
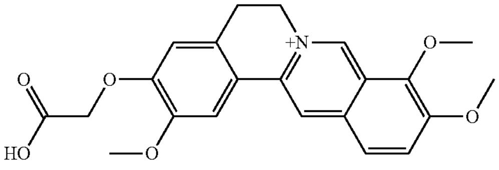
45
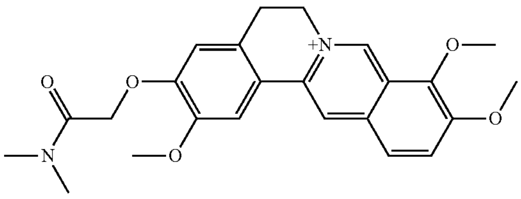
46
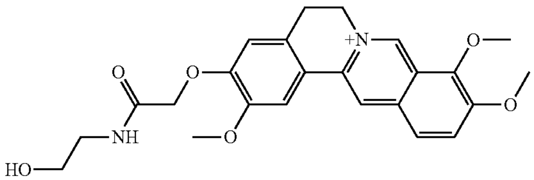
47
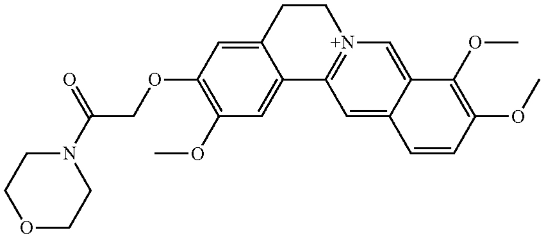
48
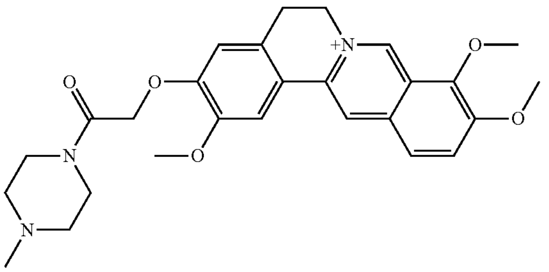

-continued
49
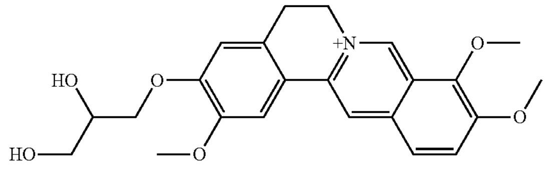
50
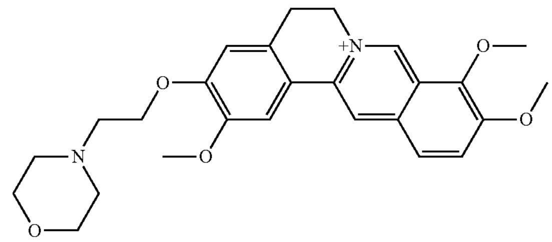
51
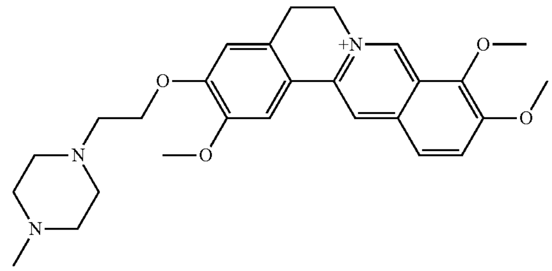
52
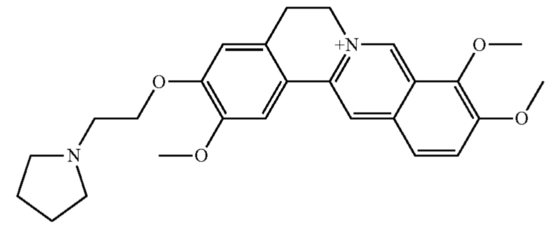
53
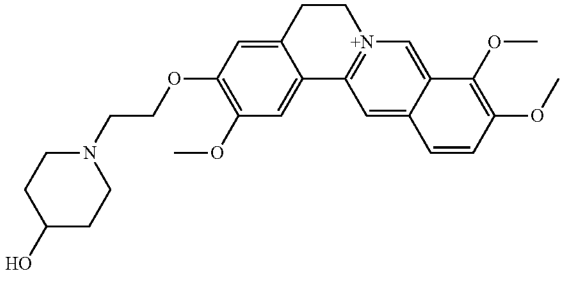
54
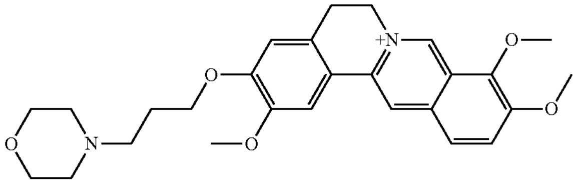
-continued
55
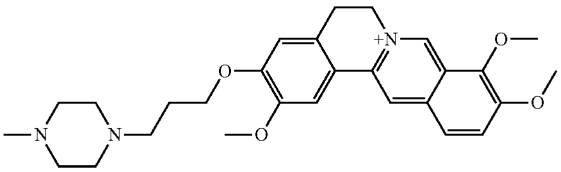
56
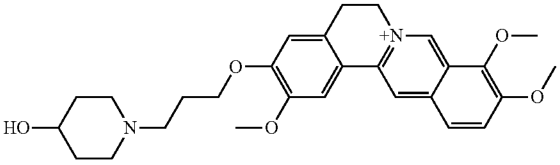
57
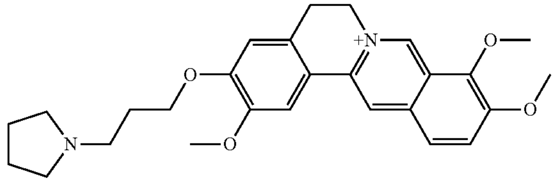
58
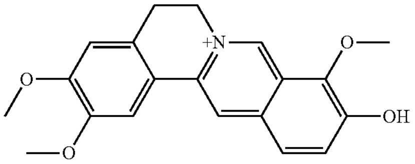
59
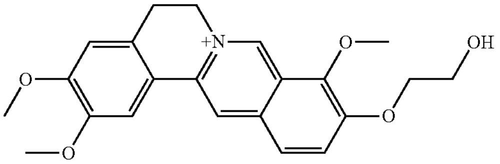
60
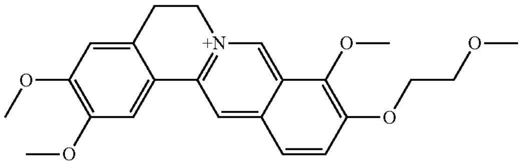
61
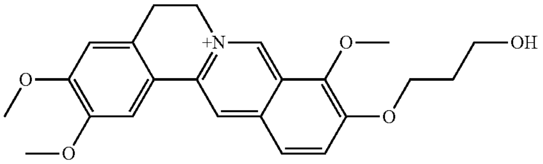
62
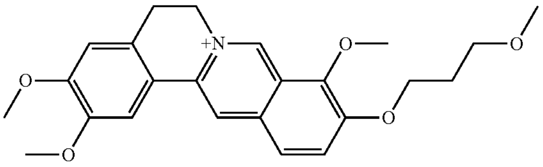

-continued
63
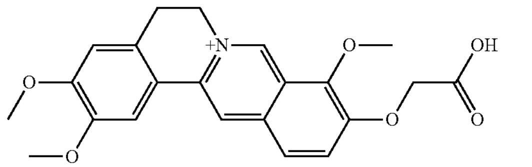
64
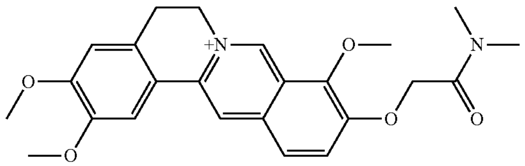
65
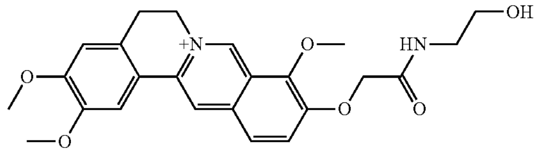
66
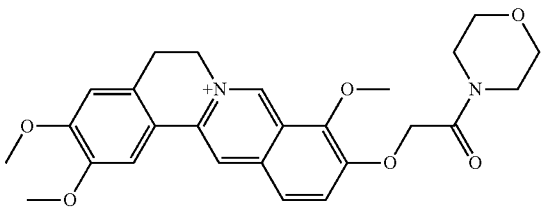
67
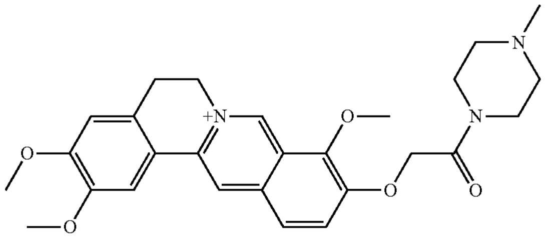
68
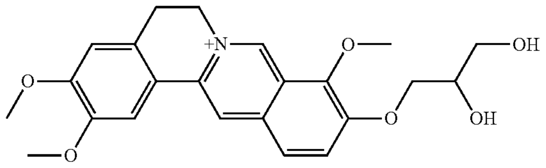
69
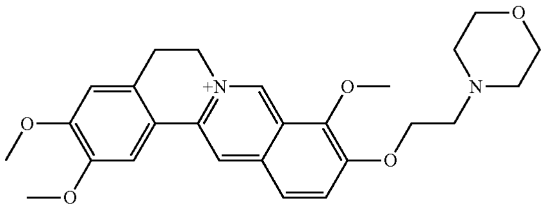
-continued
70
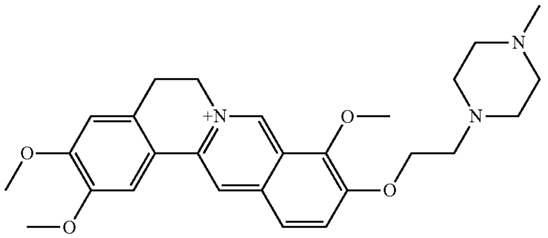
71
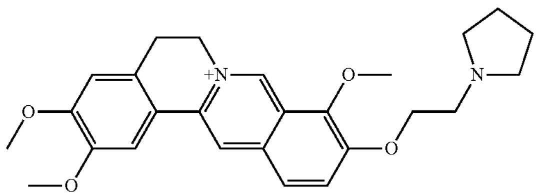
72
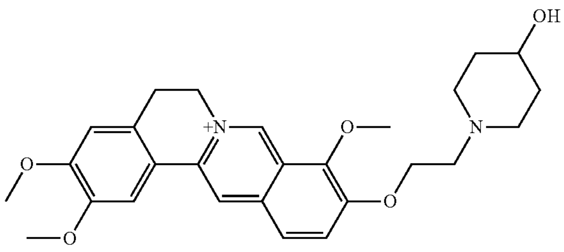
73
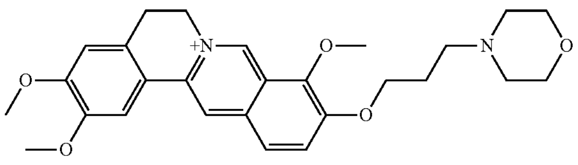
74
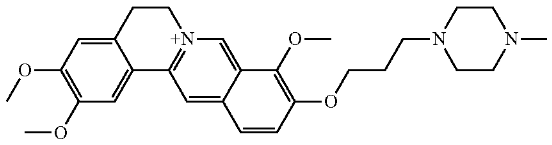
75
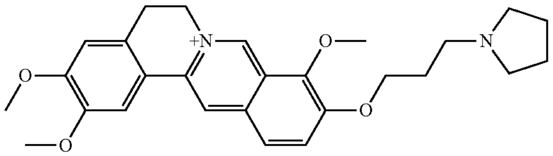
76
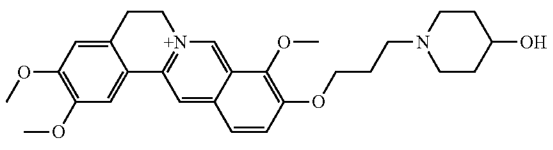

-continued

77

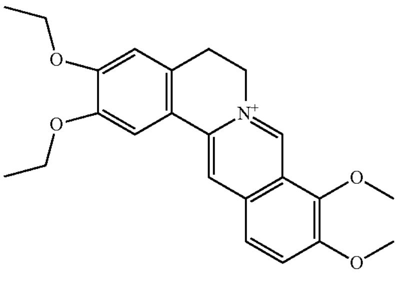

78

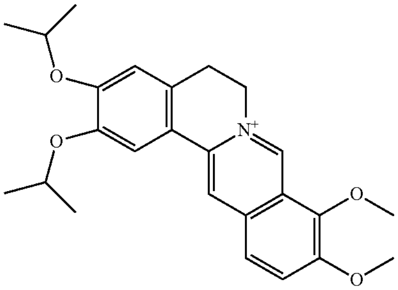

79

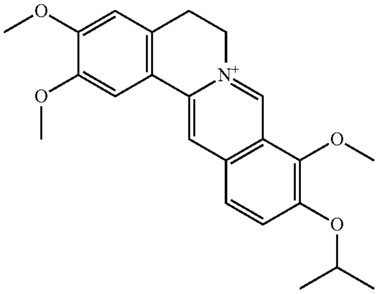

80

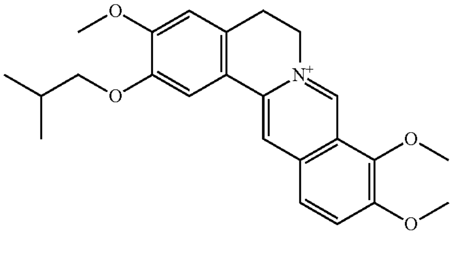

81

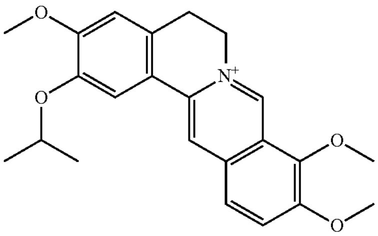

82

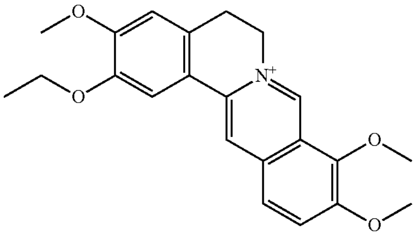

-continued

83

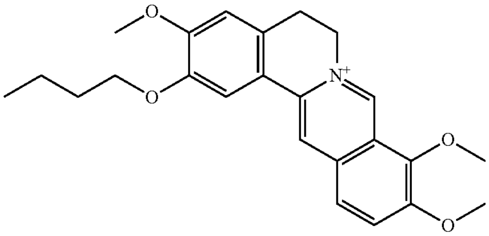

84

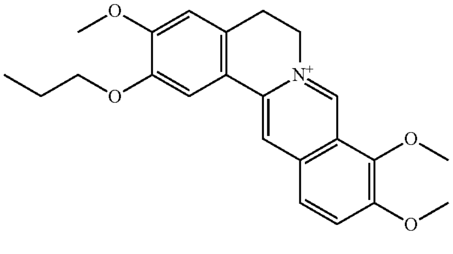

85

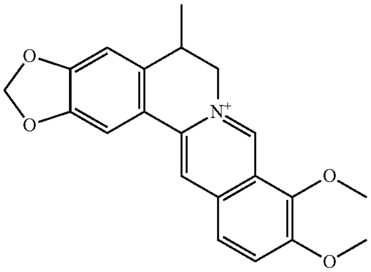

86

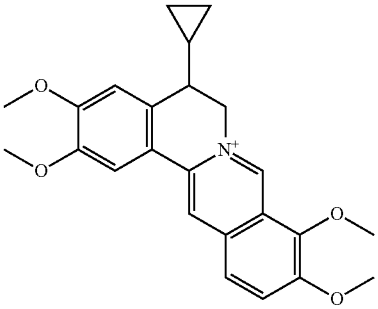

87

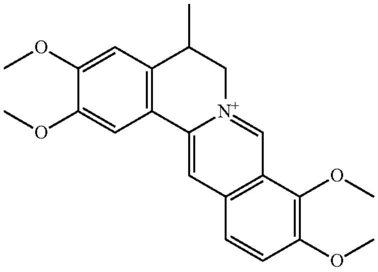

and tautomers, solvates and salts thereof;

wherein each compound further comprises a pharmaceutically acceptable anion x.

7. The composition of claim 1, wherein X is chloride.

8. The composition of claim 1, wherein the compound, or tautomer, solvate, or salt thereof, contains fewer than 100 ppm of elemental metals.

9. The composition of claim 1, wherein the nucleic acid is DNA or RNA.

10. The composition of claim 1, further comprising an ionizable amino lipid, a PEG-lipid, a structural lipid, and/or a phospholipid.

11. The composition of claim 1, wherein the composition comprises lipid nanoparticles (LNPs).

12. The composition of claim 1, wherein the compound, or tautomer, solvate, or salt thereof, is present at a concentration of less than about 10 mM.

13. A method of treating a disease in a subject in need thereof, comprising administering to the subject a composition of claim 1.

14. The method according to claim 13, wherein the disease is caused by an infectious agent, is caused by or associated with a virus, or is caused by or associated with a malignant cell.

15. A method for producing a protein in a subject, comprising:

administering a composition claim 1 to the subject, wherein the nucleic acid is an mRNA and wherein the mRNA encodes for the production of the protein in the subject.

16. A pharmaceutically acceptable method of processing an mRNA-lipid nanoparticle for therapeutic injection, comprising combining an mRNA, a lipid nanoparticle, and a compound of Formula I':

(I')

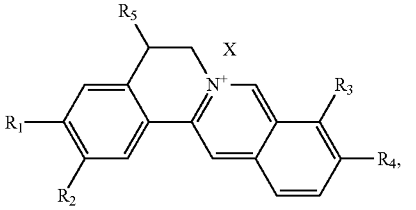

or a tautomer, solvate, or salt thereof, wherein:

each of $R_1$, $R_2$, $R_3$, and $R_4$ are independently selected from —OH and —$OC_{1-4}$alkyl, wherein the —$OC_{1-4}$alkyl is optionally substituted with one or more —OH, —C(O)OH, —NR'R", or —C(O)NR'R", and wherein at least one of $R_1$, $R_2$, $R_3$, and $R_4$ is —OH, —$OC_{2-4}$alkyl, or —$OC_{1-4}$alkyl substituted with one or more —OH, —C(O)OH, —NR'R", or —C(O)NR'R";

each instance of R' is independently H or —$C_{1-4}$alkyl, wherein the —$C_{1-4}$alkyl is optionally substituted with one or more —OH;

each instance of R" is independently H or —$C_{1-4}$alkyl;

optionally wherein R' and R" taken together form a 5 to 6 membered heterocycle with one or more O or N heteroatoms, wherein the heterocycle is optionally substituted with one or more —$C_{1-4}$alkyl or —OH;

optionally wherein $R_1$ and $R_2$ together with the intervening atoms form a 5-membered ring;

$R_5$ is H, —$C_{1-4}$alkyl, or $C_{3-7}$cycloalkyl; and

X is a pharmaceutically acceptable anion.

17. A syringe or cartridge, comprising a composition of claim 1.

18. An infusion pump, comprising a composition of claim 1.

19. A photoprotective container comprising the stabilized pharmaceutical composition of claim 1.

20. The composition of claim 1, wherein at least one of $R_1$, $R_2$, $R_3$, and $R_4$ is —$OC_{1-4}$alkyl substituted with one or more —OH, —C(O)OH, —NR'R", or —C(O)NR'R".

21. The composition of claim 1, wherein the compound is selected from:

1

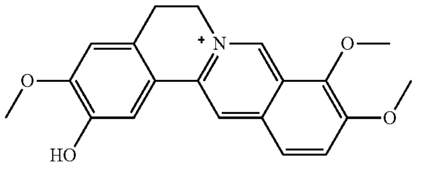

2

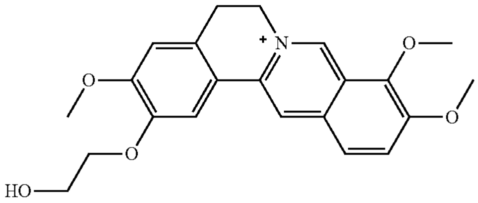

3

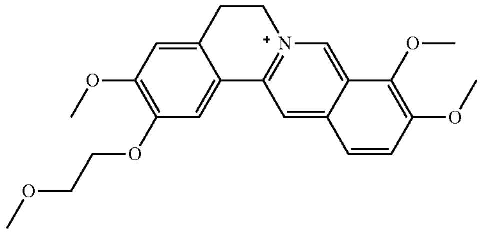

4

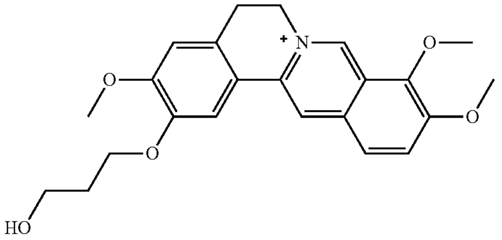

5

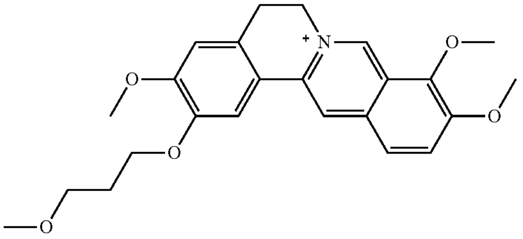

6

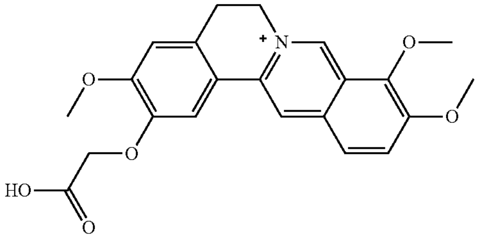

-continued
7
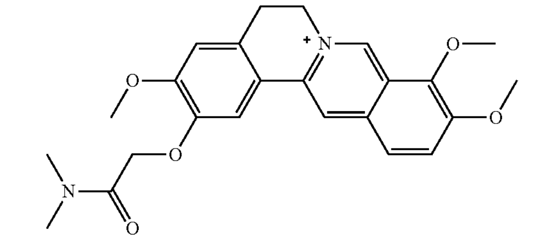
8
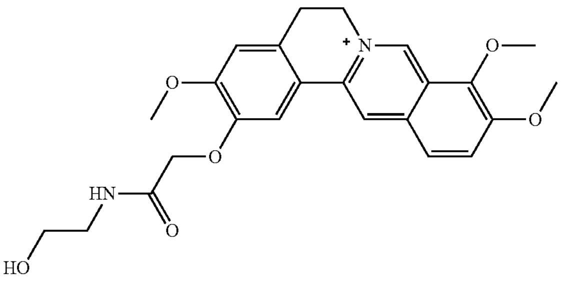
9
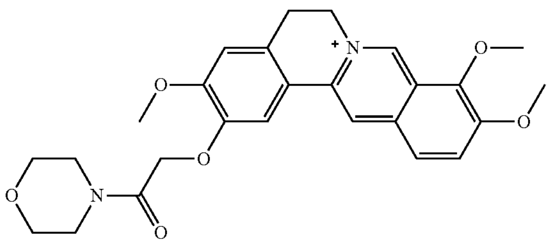
10
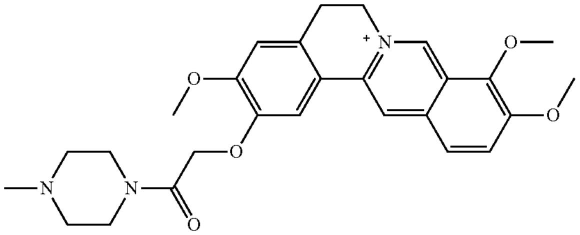
11
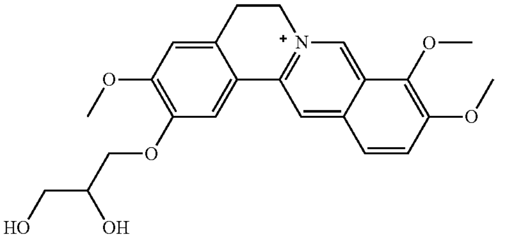
12
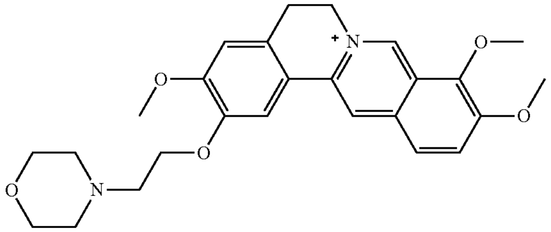
-continued
13
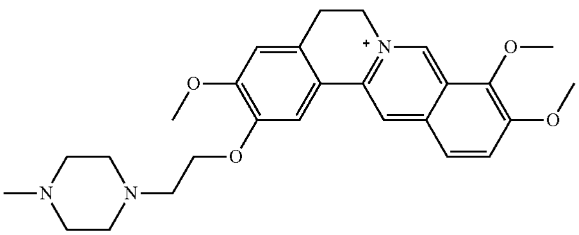
14
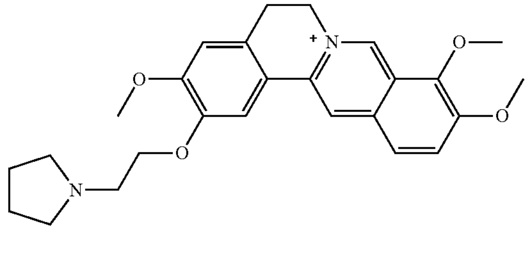
15
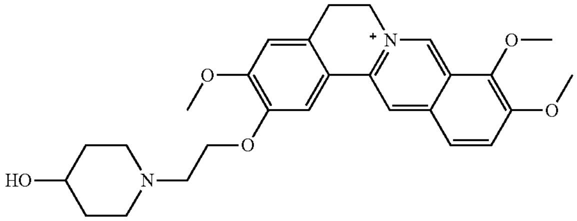
16
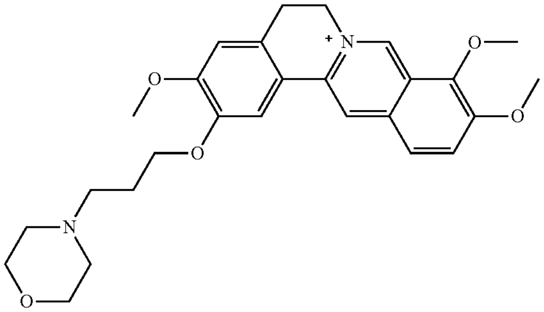
17
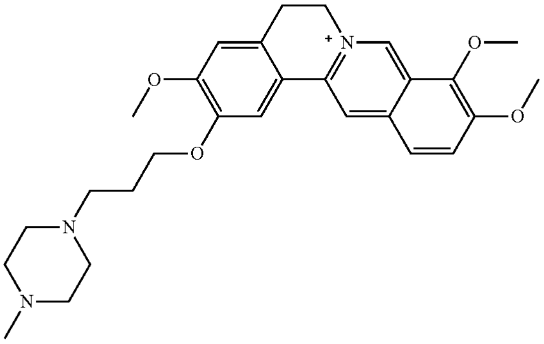

-continued
18
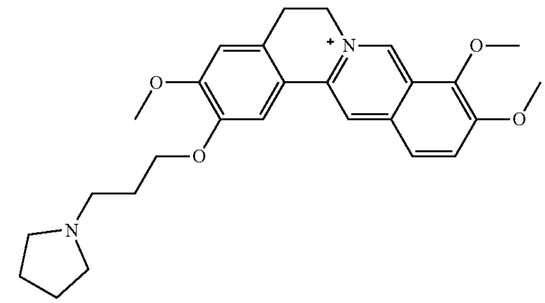
19
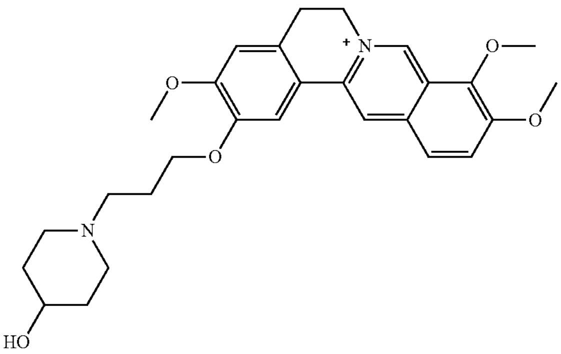
20
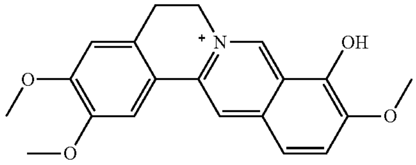
21
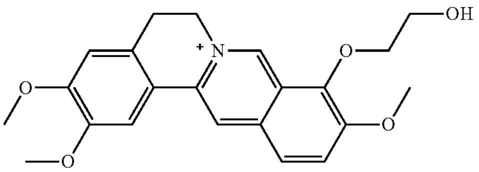
22
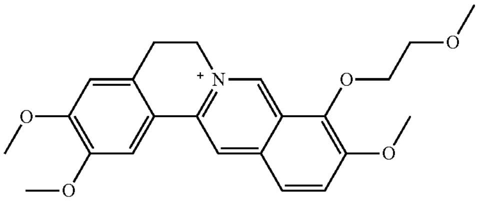
23
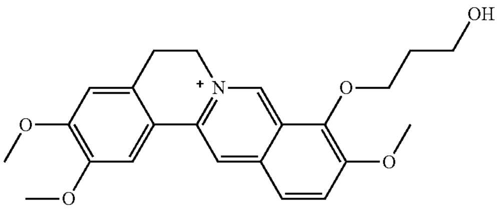
-continued
24
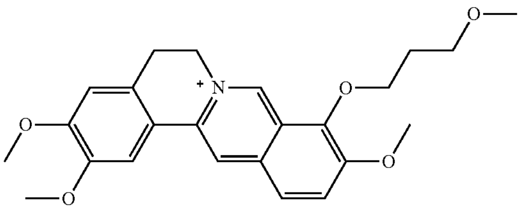
25
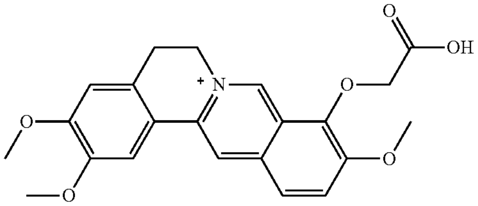
26
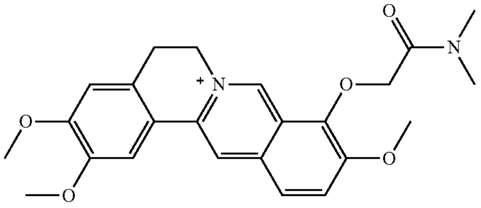
27
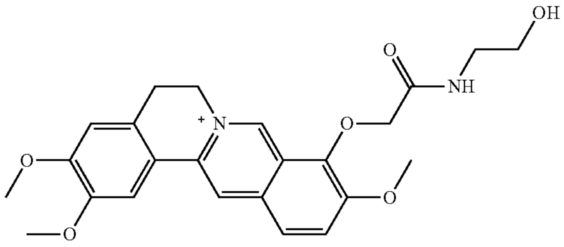
28
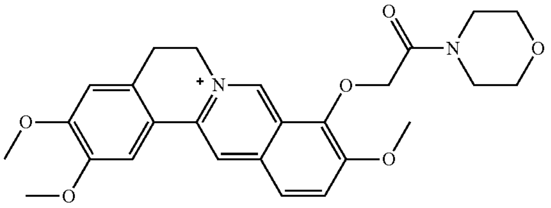
29
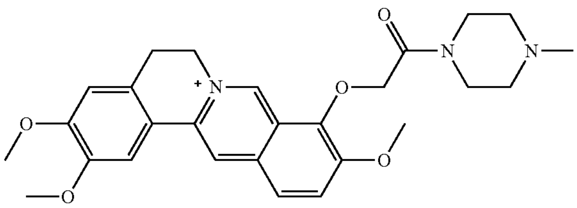
30
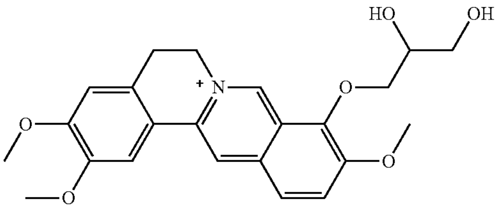

-continued
31
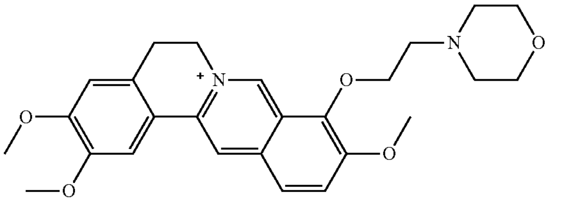
32
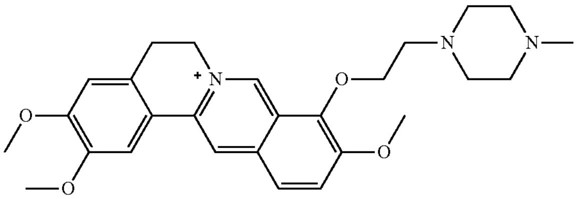
33
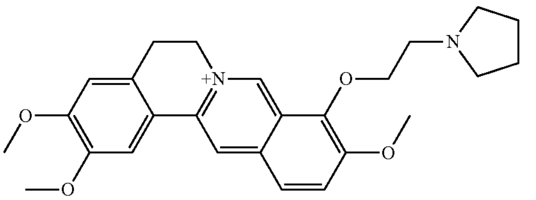
34
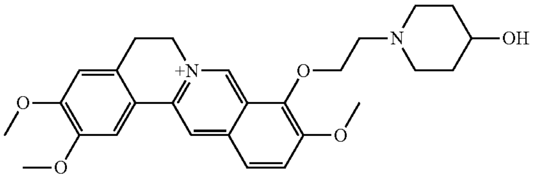
35
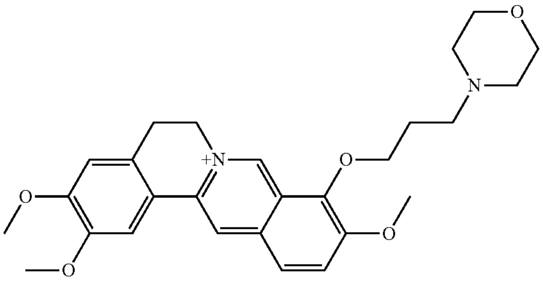
36
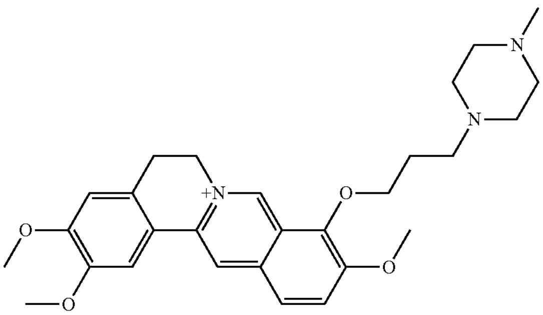
-continued
37
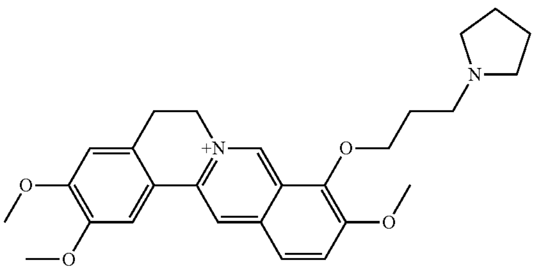
38
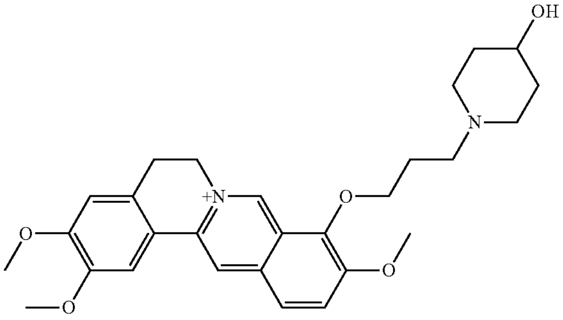
39
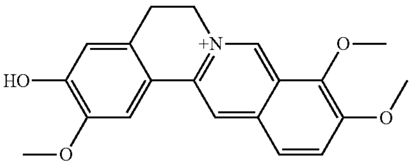
40
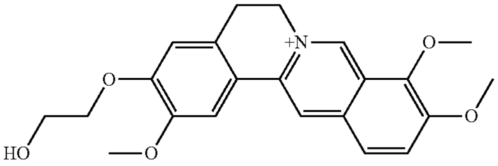
41
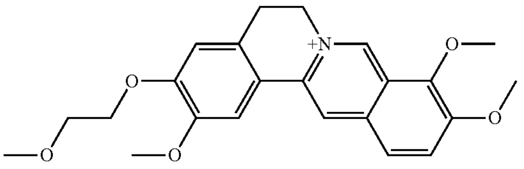
42
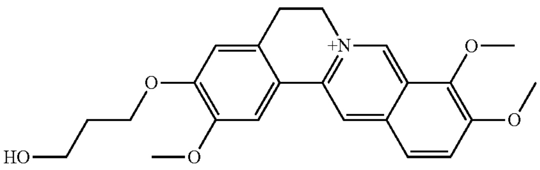
43
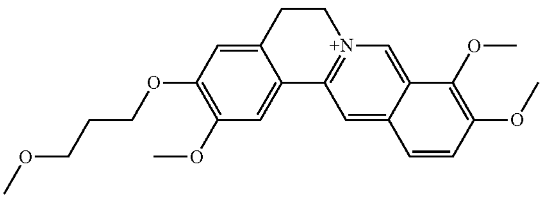

-continued
44
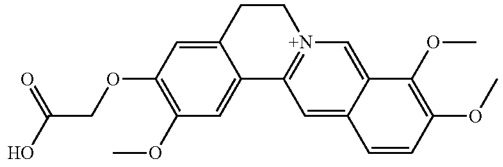
45
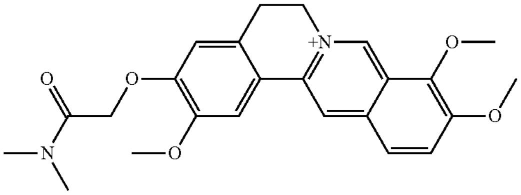
46
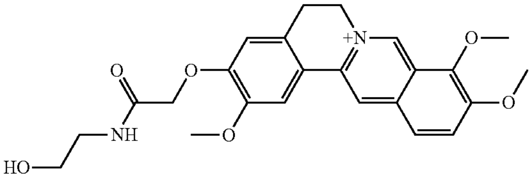
47
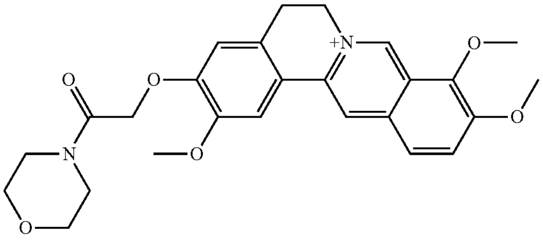
48
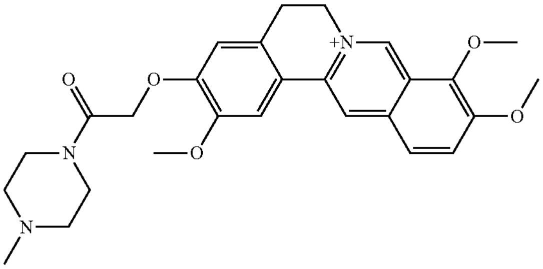
49
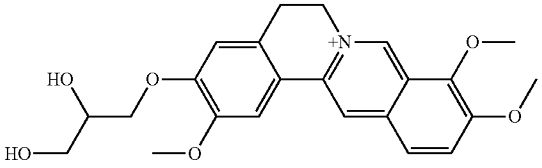
50
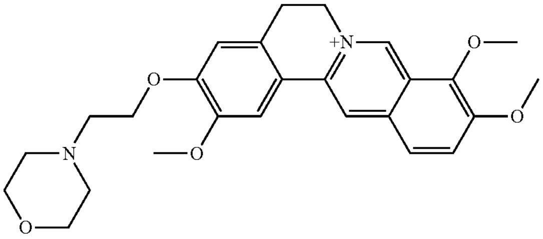
-continued
51
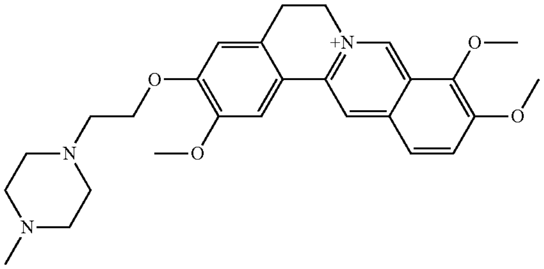
52
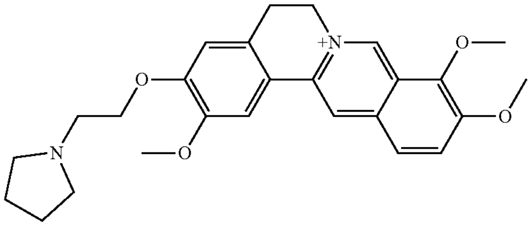
53
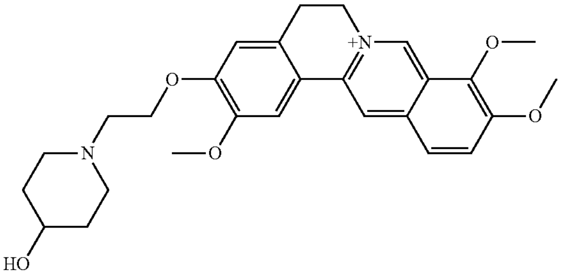
54
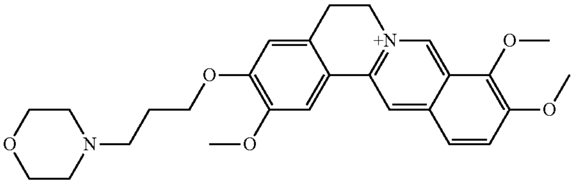
55
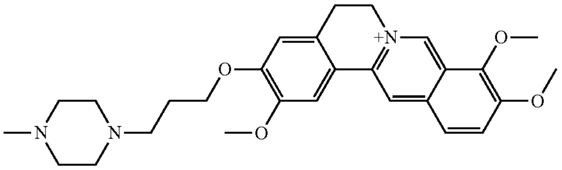
56
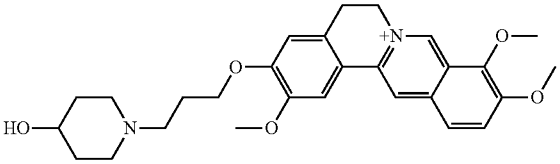
57
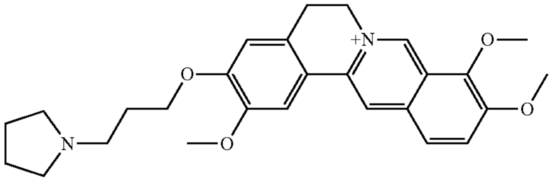

-continued
58
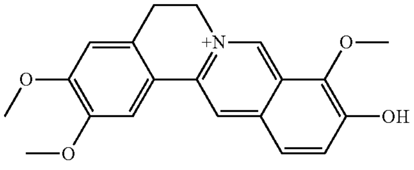
59
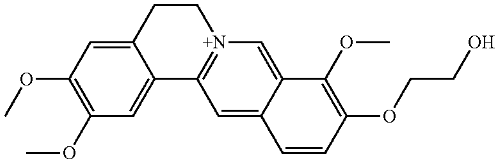
60
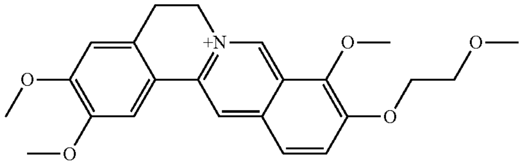
61
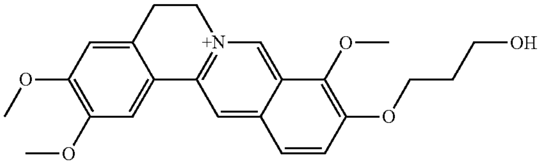
62
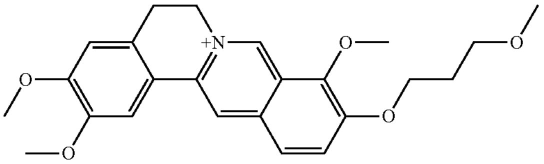
63
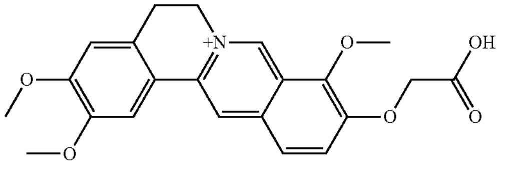
64
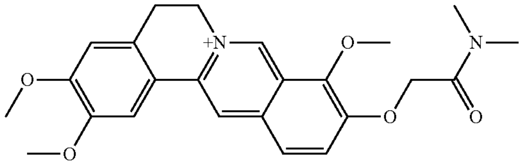
65
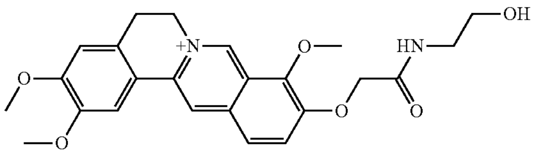
-continued
66
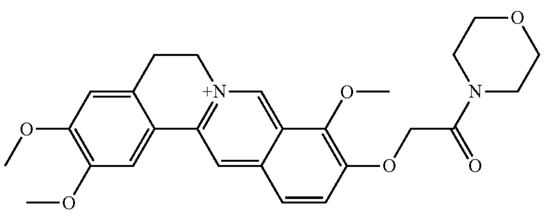
67
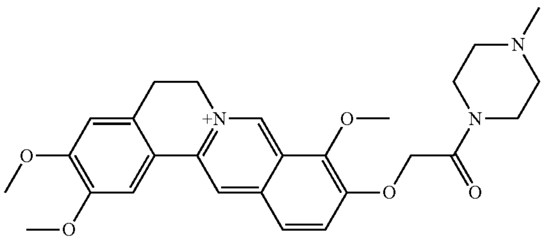
68
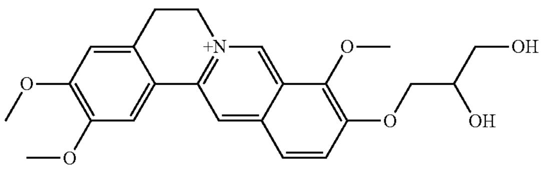
69
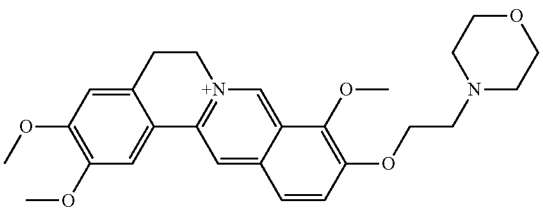
70
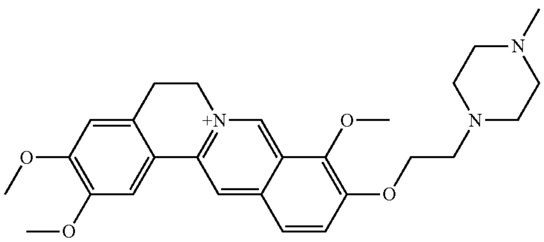
71
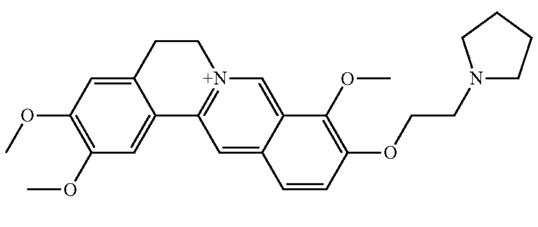

-continued
72
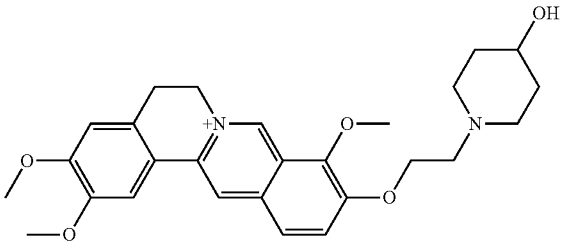
73
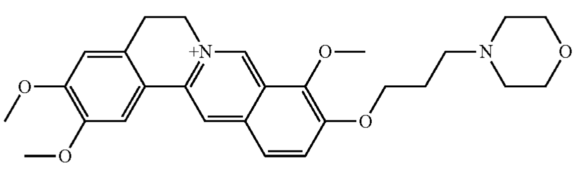
74
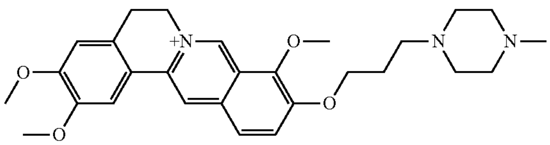
75
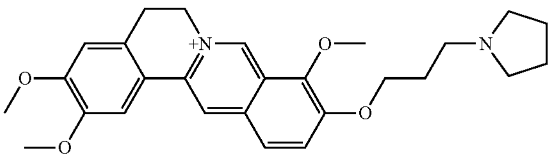
76
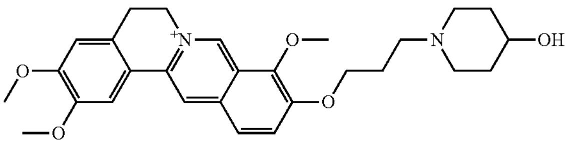
77
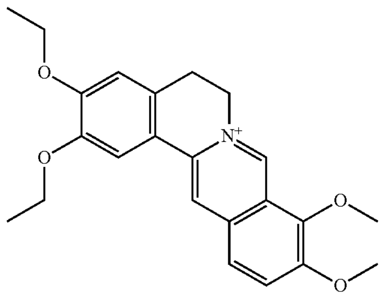
-continued
78
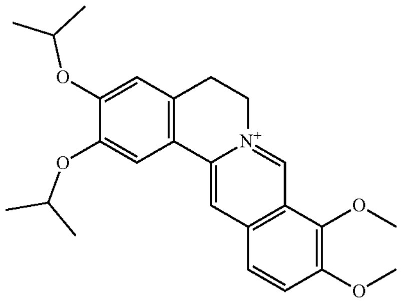
79
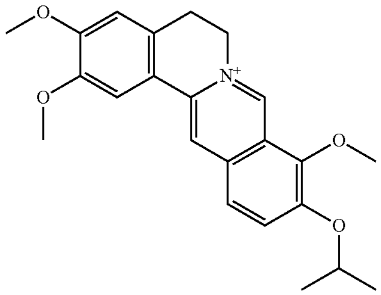
80
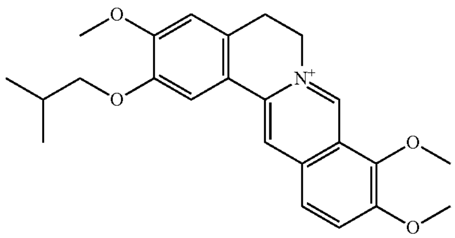
81
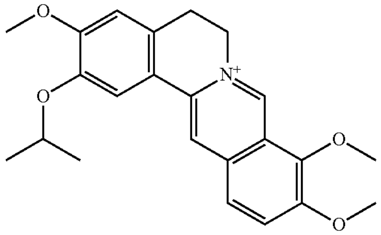
82
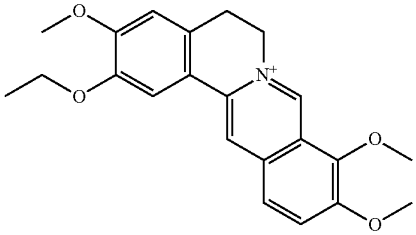
83
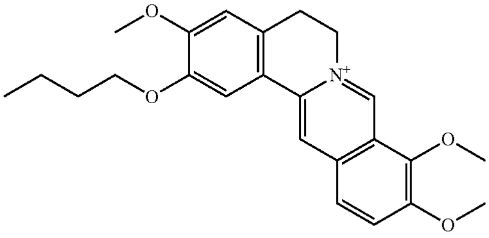

-continued
84
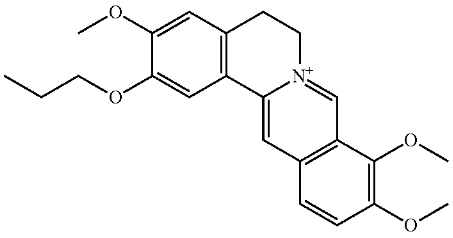
and tautomers, solvates, and salts thereof;
wherein each compound further comprises a pharmaceutically acceptable anion X.
22. The composition of claim 6, wherein X is chloride.
23. The composition of claim 21, wherein X is chloride.
* * * * *